(12) United States Patent
Freije et al.

(10) Patent No.: US 8,546,078 B2
(45) Date of Patent: *Oct. 1, 2013

(54) MATERIALS AND METHOD FOR ASSAYING FOR METHYLATION OF CPG ISLANDS ASSOCIATED WITH GENES IN THE EVALUATION OF CANCER

(75) Inventors: Wadiha Freije, Forest Park, IL (US); Deborah Nusskern, Forest Park, IL (US)

(73) Assignee: Euclid Diagnostics LLC, Crown Point, IN (US)

( * ) Notice: Subject to any disclaimer, the term of this patent is extended or adjusted under 35 U.S.C. 154(b) by 74 days.

This patent is subject to a terminal disclaimer.

(21) Appl. No.: 12/983,738

(22) Filed: Jan. 3, 2011

(65) Prior Publication Data

US 2011/0097728 A1    Apr. 28, 2011

Related U.S. Application Data

(60) Division of application No. 12/115,674, filed on May 6, 2008, now abandoned, which is a continuation of application No. PCT/US2006/060685, filed on Nov. 8, 2006.

(60) Provisional application No. 60/734,577, filed on Nov. 8, 2005.

(51) Int. Cl.
   *C12Q 1/68* (2006.01)

(52) U.S. Cl.
   USPC .......... 435/6.1; 435/6.11; 435/6.12; 435/6.14

(58) Field of Classification Search
   None
   See application file for complete search history.

(56) References Cited

U.S. PATENT DOCUMENTS

| | | | |
|---|---|---|---|
| 6,251,594 B1 | 6/2001 | Gonzalgo et al. | |
| 2003/0198972 A1 | 10/2003 | Erlander et al. | |
| 2005/0064414 A1 | 3/2005 | Hanna | |
| 2005/0196792 A1 | 9/2005 | Fodor et al. | |
| 2005/0214812 A1 | 9/2005 | Li et al. | |
| 2006/0024676 A1 | 2/2006 | Uhlmann et al. | |
| 2007/0026393 A1* | 2/2007 | Berlin et al. | 435/6 |
| 2007/0059720 A9 | 3/2007 | Fuqua et al. | |

FOREIGN PATENT DOCUMENTS

| | | |
|---|---|---|
| WO | WO 97/046705 A1 | 12/1997 |
| WO | WO 00/060085 A1 | 10/2000 |
| WO | WO 00/070090 A1 | 11/2000 |
| WO | WO 02/00928 A2 | 1/2002 |
| WO | WO 03/044232 A1 | 5/2003 |
| WO | WO 2004/067775 A2 | 8/2004 |
| WO | WO 2005/005660 A1 | 1/2005 |
| WO | WO 2005/007830 A2 | 1/2005 |
| WO | WO 2005/042713 A2 | 5/2005 |
| WO | WO 2005/054517 A2 | 6/2005 |

OTHER PUBLICATIONS

Cairns et al., *Clin. Cancer Res.*, 7: 2727-2730 (2001).
Clark et al., *Nucleic Acids Research*, 22(15): 2990-2997 (1994).
Derks et al., *Cellular Oncology*, 26(5/6): 291-299 (2004).
Dunn et al., *Journal of Pathology*, 203: 672-680 (2004).
El-Maarri et al., *Nucleic Acids Research*, 30(6): e25, pp. 1-4 (2002).
Esteller et al., *Cancer Research*, 61: 3225-3229 (2001).
Falls, Douglas, *Experimental Cell Research*, 284(1): 14-30 (2003).
Fernandez et al., #1590, *Proc. of the American Association for Cancer Research*, 47: pp. 375 (Apr. 2006).
Frommer et al., *Proc. Natl. Acad. Sci. USA*, 89: 1827-1831 (Mar. 1992).
Goessl et al., *Ann. N.Y. Acad. Sci.*, 945: 51-58 (2001).
Gonzalgo e al., *Clin. Cancer Res.*, 9: 2673-2677 (2003).
Grossfeld et al., *Epidemiol. Rev.*, 23(1): 173-180 (2001).
Herman et al., *Proc. of the Natl. Acad. Sci. USA*, 93: 9821-9826 (Sep. 1996).
Hesson et al., *Oncogene*, 22: 947-954 (2003).
Huang et al., *Cancer Research*, 64(19): 6840-6844 (Oct. 1, 2004).
Humphrey et al., *J. Urol.*, 155: 816-820 (1996).
Jeronimo et al., *Urology*, 60: 1131-1135 (2002).
Laird, Peter, *Human Molecular Genetics*, 14(Rev. Issue 1): R65-R-76 (2005).
Lerman et al., *Cancer Research*, 60: 6116-6133 (Nov. 1, 2000).
Li et al., *Biochimica et Biophysica Acta*, 1704: 87-102 (2004).
Mettlin et al., *Cancer*, 82(2): 249-251 (1998).
Mettlin et al., *Cancer*, 83(8): 1679-1684 (1998).
Olek et al., *Nucleic Acids Research*, 24(24): 5064-5066 (1996).
Schulz et al., *J. Cell. Mol. Med.*, 10(1): 100-125 (2006).
Singal et al., *Blood*, 93(12): 4059-4070 (1999).
Takai et al., *Proc. Natl. Acad. Sci.*, 99(6): 3740-3745 (2002).
Thompson et al., *N. Engl. J. Med.*, 350: 2239-2246 (2004).
European Patent Office, Extended European Search Report in European Application No. 10153479.0-2402 (Dec. 20, 2010).
European Patent Office, International Search Report for International Patent Application No. PCT/US2006/060685 (Nov. 16, 2007).

* cited by examiner

*Primary Examiner* — Hong Sang
(74) *Attorney, Agent, or Firm* — Leydig, Voit & Mayer, Ltd.

(57) ABSTRACT

Provided are methods, reagents, and kits for evaluating cancer, such as prostate cancer, in a subject. Disclosed methods of evaluating cancer include methods of diagnosing cancer, methods of prognosticating cancer and methods of assessing the efficacy of cancer treatment. The methods include assaying a biological sample for methylation of a CpG island associated with specified genes. Provided reagents and kits include primers suitable for amplifying at least a portion of a target CpG islands associated with specified genes.

24 Claims, 67 Drawing Sheets

FIG 1A

GAGTTTATTTTCGTTTGCGTGCGATAGGGTTTTTGTATTTAAGTGAGTTAA
GGAATGAATTTCGAATTTTTTGGGAAAGTTATTAACGTTTTTTTCGTATTT
TTTTTAGGGTTTTTGATTACGGAGATTTTGTTTGGGGTATAGGTGTGGGAG
TCGTAAATTTTTTTTGCGTCGTTTTTTTTCGCGTGGAATGGGACGGAGTA
GTTTTTTTAGGCGTTGTTTGGTTGCGGAGGGGAGCGGGTAGCGAGAGTTT
CGGGTTTTCGTTTGGGTTTTCGGGTTTTCGGGGCGTTGGTTTCGGTTTTCGC
GTAGCGTTAGCGATTTTGTCGGGGGTTTTCGGTAGTCGCGTCGTTATTT
TTCGTTCGGTTAGCGCGGGAGGAAAAGGGGTTGCGTTCGGGAGCGTCGAG
TTTAGGTTTTTTCGGTGGCGTGTTCGCGTTTCGGGGTGGGGTGTGGTGG
GGAAGAGGGAGGGGGCGAGGTTAGGGGAGGGTGCGAAGGAGGCGTTTGT
TTTTAATTTGCGGGCGGGAGGTGGGTGGTTGCGGGGTAATTGAAAAAGAG
TCGGCGAGGAGTTTTCGAAATTTGTTGGAATTTCGGGTTCGCGCGGAGG
TTAGGAGTTGAGCGGCGGCGGTTGTCGGACGATGGGAGCGTGAGTAGGA
CGGTGATAATTTTTTTTCGATCGGGTTGCGAGGGCGTCGGGTAGAGGTTA
GGACGCGAGTCGTTAGCGGTGGGATTTATCGACGATTTTCGGGGCGATA
GGAGTAGTTTCGAGAGTTAGGGCGAGCGTTCGTTTTAGGTGGTCGGATCG
TTCGTCGCGTTCGCGTCGCGTTTTTGTAGGTAACGGGAGACGTTTCGCG
TAGCGCGAGCGTTTTAGCGCGGTCGTTCGTTTTTTTTTCGAGGGATAAAT
TTTTTTAAATTCGATTCGAGTTTTGGATTAAATTCGTTTGCGTCGAGAGT
CGTTCGCGTAGAGCGTTTCGTTTTCGGCGAGATGTTCGAGCGTAAAGAAG
GTAGAGGTAAAGGGAAGGGTAAGAAGAAGGAGCGAGGTTTCGGTAAGAA
GTCGGAGTTCGCGGCGGGTAGTTAGAGTTTAGGTGGGTGCGTAGCGCGGT
TCGGGTTTTACGATTTTTTTTTGTTTTTTTATTTTTTTTTTTTCGGATGT
CGTGGTTTTTTTTTTTTTTTTTTCGTTCGTTTTTTCGTTTGCGTTTTGA
GCGTTCGTTGAGTCGCGCGGTGTTTTTTTTTTGGGGTCGTCGTTTATTTG
GGCGTCGAGTTTTATCGGGCGTTTACGTTTAGAGTTTAGGGTAAGGGATA
GTAGTTTCGGTCGTATTTTTTAGAGTTTCGGGAGCGTTTCGTTTTTGGTA
CGGTTTTTTTTAGCGTTTAGCGGTTGAGTTTAGTTCGGGAGTGGGATTT
GGGTTATAGGAGTCGAGGTTGCGTGCGCGTGTTTCGCGTTATAAGCGT
TTTGTACGGGGGTCGTGTGTTTTTAGCGGGAAACGTTGGAATGGGTCGTT
TGGAGGGAGAGTCGGTTTTTTCGGTGTGTTTGGTAGCGTAGAAGTGGGTG
GTCGAGTAAGAGGTCGCGTGGGAAGT

[SEQ ID NO: 1]

FIG 1B

ATTTTTTACGCGGTTTTTTGTTCGATTATTTATTTTTGCGTTGTTAGGTATA
TCGAGGGGATCGGTTTTTTTTTAGGCGGTTTATTTTAGCGTTTTTCGTTAG
AGGGTATACGGTTTTCGTGTAAAGCGTTTATGGCGCGGGGTACGCGCGTA
CGTAGTTTCGATTTTTATAGTTTAGGTTTTATTTTCGGGTTGGGTTTAGTCG
TTAAGGCGTTGGGGAGGGGTCGTGTTAGGGAGCGAAGCGTTTTCGGGATT
TTGGGAGGGTGCGGTCGGGATTGTTGTTTTTGTTTGAGTTTTGGGCGTA
GGCGTTCGGTAGGATTCGGCGTTTAGGTGAGCGGCGGTTTTAGGAGGGG
AAGTATCGCGCGATTTAACGGGCGTTTAGAGCGTAGGGCGAAGAGGACG
GGCGAGGGAGAGGGGGAGGGAGAGGTTACGGTATTCGAGGAGGAGGAG
GAGTAGGAGGAGTAGGAGGAGGATCGTGGGGTTCGGGTCGCGTTGCGTA
TTTATTTGGGTTTTGGTTGTTCGTCGCGGATTTCGGTTTTTTGTCGGAGTTT
CGTTTTTTTTTTTGTTTTTTTTTTGTTTTGTTTTTTTGCGTTCGGATATT
TCGTCGGAGACGGAGCGTTTTACGCGGACGGTTTTCGGCGTAGGCGAGTT
TGGTTTAAGGGTTCGGATCGGGTTTGGGAAAAGTTTGTTTTTCGAGGGGG
AGAGCGAGCGGTCGCGTTGAGGCGTTCGCGTTGCGCGGGGGCGTTTTCG
TTGTTTGTAGGGAGCGCGGCGCGGACGCGGCGGGCGGTTCGGTTATTTGG
AACGGGCGTTCGTTTTGGTTTTCGGGGTTGTTTTTGTCGTTTCGGGAAGTC
GTCGATGGGTTTTATCGTTGGCGGTTCGCGTTTGGTTTTGTTCGGCGTTT
TCGTAATTCGATCGGGGAGAGGTTATTATCGTTTTGTTTACGTTTTTATCG
TTCGGTAGTCGTCGTCGTTTAGTTTTTGGTTTTCGCGCGAGTTCGGAGTTTT
AATAAGTTTCGGGGAATTTTTCGTCGGTTTTTTTTAATTGTTTCGTAGTTA
TTTATTTTCGTTCGTAGGTTGGAGGTAGGCGTTTTTTCGTATTTTTTTT
GGTTTCGTTTTTTTTTTTTTTTATTATATTTTTATTTCGAGGCGCGGATAC
GTTATCGGGAGGAGTTTGGGTTCGGCGTTTTCGGGCGTAGTTTTTTTTTTT
TCGCGTTGGTCGGGCGGGGGTGGCGGCGCGGTTGTCGGGAATTTTCGAT
AGGGGTCGTTGGACGTTGCGCGGAGATCGAGGTTAGCGTTTCGGAGATTC
GGGAATTTAGGCGGAGATTCGAGGTTTTCGTTGTTCGTTTTTTTCGTAGT
TAGGTAGCGTTTGGGAGGGTTGTTTCGTTTTATTTTACGCGGAAAAGGAC
GGCGTAGAGAAAGTTTGCGATTTTTATATTTGTGTTTTAAGTAGAGTTTT
CGTGGTTAGGAATTTTGGGAGGGGTGCGGGGGGAACGTTGGTGGTTTTTT
TAGAAGAGTTCGGGGTTTATTTTTTAATTTATTTAAGTATAAAAGTTTTGT
CGTACGTAGGCGAAAATAAATTT
[SEQ ID NO: 2]

FIG 1C

ATTTTGGCGTTTAATATCGTTAATATTAGTGGGTTGTTAGGGGTTTCGTGG
GAGGCGGTTTTAGTCGGGGTTTTGTTGGCGTTGGCGGTGTTGGTTATCGTG
GGAGGTAATTTGTTGGTTATCGTGGTTATCGTTTGGATTTCGAGATTTTAG
ATTATGATTAACGTGTTCGTGATTTCGTTGGTCGTAGTCGATTTGGTGATG
GGATTTTTGGTGGTGTCGTCGGCGGTTATTTGGCGTTGATTGGTTATTGG
TCGTTGGGCGTTATTGGTTGCGAGTTGTGGATTTCGGTGGACGTGTTGTGT
GTGATCGTTAGTATCGAAATTTTGTGCGTTTGGTCGTGGATCGTTATTTG
GTTGTGATTAATTCGTTGCGTTACGGCGTATTGGTTATTAAGCGTTGCGTT
CGGATAGTTGTGGTTTTGGTGTGGGTCGTGTCGGTCGCGGTGTCGTTTGCG
TTTATTATGAGTTAGTGGTGGCGCGTAGGGGTCGACGTCGAGGCGTAGCG
TTGTTATTTTAATTCGCGTTGTTGTGTTTTCGTTTTAATATGTTTTACGTGT
TGTTGTTTTTTTCGTTTTTTTTATTTTTTTTTTCGTGATGTTTTCGTTT
ACGCGCGGGTTTTCGTGGTGGTTACGCGTTAGTTGCGTTTGTTGCGCGGGG
AGTTGGGTCGTTTTTCGTTCGAGGAGTTTTCGTCGGCGTCGTCGCGTTTTTT
GGTTTCGGTTTCGGTGGGGACGTGCGTTTCGTTCGAAGGGGTGTTCGTTTG
CGGTCGGCGGTTCGCGCGTTTTTTGTTTTTCGGGAATATCGGGTTTTGTG
TATTTTGGGTTTTATTATGGGTATTTTTATTTTTTGTTGGTTGTTTTTTTTTT
TGGTTAACGTGTTGCGCGTTTGGGGGGTTTTTTTTAGTTTCGGGTTCGGT
TTTTTTTGTTTTGAATTGGTTAGGTTATGTTAATTTTGTTTTTAATTCGTTTA
TTTATTGTCGTAGTTCGGATTTTCGTAGCGTTTTCGTCGTTTTTGTGTCG
TTGCGGTCGTCGTTTGTTTTCGGAGTTTTGCGTCGTCGTTCGTTCGGTTTTT
TTTTTTTCGGGCGTTTTGCGGTTCGGAGTAGTTTAGCGTAGTTTAGGTTTT
GTTAACGGTTCGACGGGTAGGTAATCGGGGTAGAGGGATCGGCGGTTTAG
GGTCGGGAAGTATGCGATGTGTTCGTGGGTTAATTTTTTGAGTGTGGAGTT
TATTAAGAGAAGGTGGGATGGTTTTGTTTGGAGAGAAAAGGGAACGAGG
AGTAGCGAATTAAAATGGGATTTAGGGTTTTTTTTTTTCGGATTTAGTTA
TTAGGGTAGAAGTA

[SEQ ID NO: 3]

FIG 1D

TGTTTTTATTTTAGTGATTGGATTCGGAAAGAAAAGGATTTTGGGTTTTAT
TTTGGTTCGTTATTTTCGTTTTTTTTTTTTTAAGTAAAGTTATTTTATTT
TTTTTAATAAATTTTATATTTAAAAAGTTGATTTACGGATATATCGTATG
TTTTTCGATTTTGAGTCGTCGGTTTTTTTGTTTCGGTTATTTATTCGTCGAG
TCGTTGGTAAAGTTTGGGTTGCGTTGGGTTGTTTCGGGTCGTAGGAACGTT
CGAGGGGAAGAGGGTCGGGCGGGCGGCGGCGTAGGGTTTCGGAGGTAGG
CGACGGTCGTAGCGGTATAGAAGACGGCGGAAGGCGTTGCGAAAGTTCG
GGTTGCGGTAGTAGATGAGCGGGTTGAAGGTAGAATTGGTATAATTTAGT
TAGTTTAGGGTAAGGAAAGTCGGGTTCGGGATTAGAGAGGGGTTTTTTAG
GGCGCGTAGTACGTTGGTTAGAAAGAAGGGTAATTAGTAGAGAGTGAAG
GTGTTTATGATGAGATTTAAGGTGTATAGGGTTCGGTGTTTTCGGAGAGGT
AGGAGGCGCGCGGGTCGTCGGTCGTAGGCGGGTATTTTTCGGGCGGAGC
GTACGTTTTATCGGGGTCGGGGTTAGAGAGCGCGACGGCGTCGGCGGAG
ATTTTTCGGGCGGAAAGCGGTTTAGTTTTTCGCGTAGTAAGCGTAGTTGGC
GCGTAGTTATTACGAAAATTCGCGCGTAGACGAAGAGTATTACGAGAAGA
GGAAGGTAGAAGGAGACGGAGGAGGATAGTAGTACGTAGGGTATGTTGG
AGGCGAAGGTATAGTAGCGCGGGTTGGAGTGGTAGCGTTGCGTTTCGGCG
TCGGTTTTACGCGTTATTATTGGTTTATGATGGGCGTAAACGATATCGCG
GTCGATACGATTTATATTAGGATTATAGTTGTTCGGGCGTAGCGTTTGGTG
ATTAGTGCGTCGTAACGTAGCGGGTTGGTTATAGTTAGGTAGCGGTTTAC
GGTTAGGGCGTATAGGGTTTCGATGTTGGCGGTTATATATAGTACGTTTAT
CGAGGTTTATAGTTCGTAGTTAGTGGCGTTTAACGGTTAGTGGTTAGTTAG
CGTTAAGGTGGTCGTCGGCGGTATTATTAGGAGTTTTATTATTAGGTCGGT
TGCGGTTAGCGAAGTTACGAATACGTTGGTTATGGTTTGGAGTTTCGGAG
TTTAGGCGATGGTTACGATGATTAGTAGGTTGTTTTTACGGTGGTTAGTA
TCGTTAGCGTTAGTAGGGTTTCGGTTAGGGTCGTTTTTTACGGAATTTTTG
GTAGTTTATTGGTGTTGGCGGTATTGGGCGTTAGGGT

[SEQ ID NO: 4]

FIG 1E

```
CGAAAAGTTTTTGAGGCGTTGCGTGTATTTTATTTTAGGATATCGTGTGTG
CGCGTCGAGTTGAGTGCGAGGAACGTGGCGCGAGGGTCGGGGGATGTCG
GGTTGCGTGGGTGTGAGTTTTCGCGCGATCGCGATTTCGCGTTTTTTCGT
TTTCGTCGGAACGTGATCGTAGTCGTATTTTTTTTTAGTTTTTTTTAGTT
AGACGTTTTTTTTAGGTTTTTTGGGCGTTTATTGTAAATTTGCGATTAA
AATACGTCGGTGAGTTCGGTTTATCGATAGATGGATTAATCGTTTTTTTT
CGGTTAGGGGAGGAGGAATTTTTTAATTTCGGAGTTTAGGGAGTCGGGAG
TTGTTTCGGGACGAGTTTTTCGGAGTTTAGTCGGTTGCGGAGTTTCGGTTC
GGGTCGGTTTCGGGGTTTTTTGTCGGGGTGGGGTGCGAGTTTTGTTCGA
TTTTTTGGGGCGGTTTAGGTAGGTTTGTCGGTTTTCGAGGAGGTGGTTAG
GGCGTTTTGGTTTAGTAGGTTTTTTTCGAGTCGGGGGGAGGGGAGATCG
GTTGGGGAAGGGGTATTTCGAAGGGGTGGAGGTCGGGGCGGGCGGGAGG
TAAGCGCGTCGCGGGCGTGAGGGTAAAGTTTTCGAGGTTCGCGCGGAGAG
TATACGTGTATGTGCGCGCGGGGTTAGGTCGGGGTCGGTAGGATGCGTTG
GGTTCGGGGGCGCGCGGGGTCGGCGTCGAAGGGGATAATTTTTTTTTTG
GTATTATCGGGGAGACGTTTTGTCGGTTTCGGTTTTTGGGCGTAGGGACGT
TTTAGTTTACGGAGGGTGGAGTTTTTTTTAGATTCGGGTTATCGGTTGGGG
TTTTTTTAACGTTTTGTTTTTCGAGTTTTCGGATGGTTCGGGTTTTACGGAT
TTCGCGTTTTTAGTTTTAGTTTAGTTTTTAGGTTTTTAGATTTAGCGGC
GTAGGGGCGGGGGTAGGGGTAGTGGGGGTTGGAGGGCGTAGTCGGTTT
TTAGGGTGGGGAGAGTTGCGGGGGGAGGAGGAGGAGGGTGTCGACGTTT
GAGTGGGTTCGAGTTCGAGTCGTAGTCGGGGGAGTTAGTTAGTTTTCGGT
TAAGGTAGTAGGTTAGTTTTAGGAAGGGCGGGCGATTGAGTCGAGGGAGT
CGGCGGTTGGGTTTTTTTTTCGGTTCGCGATTTTCGGCGTCGTCGTCGTCGT
TATCGTTATCGTTATCGTTTCGTTTGTCGTCGTCGTCGTTGTAGAGTATC
GTAGTTTCGTCGCGTTTTCGCGTTTCGCGTTTCGCGTCGTTAGTCGTTTGGG
AGTTCGAGCGTCGAGTTCGGGGCGGAGGAGAGGGGCGTTGGCGCGAGAG
TTCGGGCGAGGGAGTCGCGAAGGGAGAAGGGGGCGGGCGGAGGGAGGA
GTAGGGAGAGTGGGAGAAGGGGGAGGGAGAGGAGAGCGAGGGAGAG
TTGGAGAGAGCGAGAGTAAAGAGCGAGCGAGGGAGAGGAGAGAGAGAG
AGAGGAGAGAGAAAGATATACGTACGTAGAGATATACGGTTATTGGAAT
TTTATTAGAAAAAAGTGAGTCGAGTAAGGGTTAGCGGGAG
```
[SEQ ID NO: 5]

FIG 1F

TTTTCGTTAATTTTTGTTCGGTTTATTTTTTTTAATGGAATTTTAGTGATC
GTGTGTTTTGCGTGCGTGTGTTTTTTTTTTTTTTTTTTTTTTTTTTTTTTT
TTCGTTCGTTTTTGTTTTCGTTTTTTTAGTTTTTTTTCGTTTTTTTTTTTT
GCGGTTTTTTCGTTCGGGTTTTCGCGTTAGCGTTTTTTTTTTCGTTTCGGG
TTCGGCGTTCGGGTTTTTAGGCGGTTGGCGGCGCGGGGCGCGGGGCGCGG
GAGCGCGGCGGAGTTACGATGTTTTGTAGCGGCGGCGGCGATAAGGCGA
AGGCGGTGGCGGTGGCGGTGGCGGCGGCGGCGGCGTCGGGGATCGCGGG
TCGAGAGGAGAGTTTAGTCGTCGGTTTTTTCGGTTTAATCGTTCGTTTTTT
TGGGATTGATTTGTTGTTTTGGTCGGAAATTGATTGGTTTTTTCGGTTACG
GTTCGGGTTCGAATTTATTTAAGCGTCGGTATTTTTTTTTTTTTTTTTTCGT
AGTTTTTTTTATTTTGGGGATCGGTTGCGTTTTTAATTTTTATTGTTTTTGT
TTTCGTTTTTTGCGTCGTTGGGTTTGGGAAGTTTGGGGAGTTGAGTTGAGG
TTGGAGGGCGCGGAGTTCGTGGGGTTCGAGTTATTCGGGGGTTCGGGGGG
TAGGGCGTTAGAAAAATTTTAGTCGGTGGTTCGGGTTTGAGGGGGGTTTT
ATTTTTCGTGGGTTAAGGCGTTTTGCGTTTAGGAGTCGAGGTCGATAAAG
CGTTTTTTCGATGGTGTTAGGGAAAGGAATTATTTTTTTCGGCGTCGGTTT
CGCGCGTTTTCGAATTTAACGTATTTTGTCGGTTTCGGTTTAGTTTCGCGC
GTATATACGTGTGTTTTCGCGCGGATTTCGGGAATTTTGTTTTTACGTT
CGCGGCGCGTTTGTTTTTCGTTCGTTTCGGTTTTTATTTTTCGAGATGTTT
TTTTTTAGTCGGTTTTTTTTTTTTCGGTTCGGGAAGAAGTTTGTTGGGTT
AGGGCGTTTTGATTATTTTTCGGAGGTCGGTAAATTTGTTTGAATCGTTT
TAGAGGAATCGGGTAGGGGTTCGTATTTTATTTCGGTAGGAGGGTTTCGA
GATCGATTCGGGTCGGGGTTTCGTAGTCGGTTGGGTTTCGAGGAGTTCGTT
TCGAGGTAGTTTTCGGTTTTTTAGGTTTCGGGGTTGGGGGGTTTTTTTTTT
TTAGTCGGGAAGGGGGCGATTGATTTATTTGTCGGTGGGTCGGGTTTATC
GGCGTGTTTTAGTCGTAGAATTTATAATAAACGTTTAGAAGGATTTAAAA
GGAAGCGTTTGGTTGGGAAAGGGTTGGAGGAGAGGTGCGGTTGCGGTTA
CGTTTCGGCGAGAGCGGGAGAGGCGCGGGGTCGCGGTCGCGCGAGGGTT
TATATTTACGTAGTTCGGTATTTTTCGGTTTTCGCGTTACGTTTTTCGTATT
TAGTTCGGCGCGTATATACGGTGTTTTGGGGTGGGGTATACGTAGCGTTTT
AGAAATTTTTCG
[SEQ ID NO: 6]

FIG 1G

GAGGTATTAGTTTTTGAAGGTTTATTTTTAATATTGGTTGCGAGAGTAAG
AATGGTGTGTAATTTATAAAAGTCGTTATTGTTGTAGGTAAGTTGTAGTAA
ACGATTCGCGTTCGAGTATTTTCGTTTTCGTTTTCGTTGCGGTTTCGTTTAC
GACGATTTTGGGGAATTATAAGTTTCGTTATATAGCGGGGAGCGTTCGGA
GTTCGCGTCGGTTTCGTTTTTAGTTCGGTTTTTATTTTCGGTTTCGTTTTCG
GTTTTTTTTCGTCGGGTTAATTTCGAAGAGTCGTCGGTGGTCGCGGTAGAC
GGAAGTCGAACGAGTTTTTCGGCGGTTGTAGGATGGGGGATTTTAAAGTG
AAAGTGGCGGTGCGGATACGATTTATGAATCGGCGAGGTGAGAGTCGAG
TTTTTTGGGTCGTCGGGGCGGAGGCGGTAGGTGTTTGGCGCGTTTTTTTT
TCGGTCGTCGTGGGGGGTTCGGCGGTTTCGTTTTATAGTTAGCGGCGGGG
CGCGAGGAGGGGTTCGGGGATTTTGAAATTCGTTTCGCGTTGAGACGTT
CGGTTTTTTTTTTTTTTTTTTTTTTTTTGGTTAGTTTCGTTTTTGGCGTCG
TCGGGTTTTTCGTGTCGGTTTCGTTGTTTTTTCGTTTGCGTTCGTTTCGTTT
TTGCGTTTTTTTGTTTTTTCGTTTTTTTCGGAGGTTTTCGAGGGCGTTTTCG
GTTTTCGCGTTTAGTTTCGTTTTGGTTTTTTAGTTTCGTTTTTTTTCGTTAG
TTGTTATCGTCGTTTTCGCGCGCGGGTCGTTAGTTTTTGTAGTTCGTTTCGG
GATCGTTCGGGATTTTTCGGGATTTCGCGTTTCGTTCGGGTCGTTTAAGTT
TGTATCGTTTTGGTTCGCGGCGGGAAGAAGGGTAGGGGGTTAGGCGGGTG
TTTCGCGGCGAGTTTTTTTATTTGGGCGTTTTGAGATTGGGGTTAGGTGG
AGGAGATGTTTTTTCGTTGTTTTGGATAGTTGAGAAAGTTTTGGTTTTGT
TTGAAGTTTTATTTATTATTTTTAATAAATAGTTAAAGTGTTAAGATTTTT
GTGGAATTGTATTTTTTTGATA
[SEQ ID NO: 7]

TGTTAGAAAGATATAATTTTATAAGAATTTTGGTATTTTAGTTATTTATTG
AGAGATGATGAATGAGATTTTAGGTAAAATTAAAATTTTTTAATTGTTTA
AAAATAACGAAAAGGGTATTTTTTTATTTGATTTTAATTTTAGGACGTTT
AGGTGGAAGGAATTCGTCGCGGGTATTCGTTTGGTTTTTTGTTTTTTTTT
CGTCGCGGGTTAAGGCGGTGTAGGTTTGGGCGATTCGGGCGAGACGCGGG
GTTTCGGGGGGTTTCGGGCGGTTTCGAGGCGGGTTGTAGGGGTTGGCGAT
TCGCGCGCGGGGGCGACGATGATAGTTGGCGGGGAAGGAGCGAGGTTGA
GGGGTTAGGACGAGGTTGGGCGCGAGGGTCGAGGGCGTTTTCGGGAATTT
TCGGGGGAGACGAGAGGGTAAAAGGGCGTAGGGGCGGGGCGGGCGTAG
GCGGAAGGGGTAGCGGGGTCGGTACGAGGGGTTCGACGGCGTTAGGGAC
GGGGTTGGTTAGGGGGGAAGGGAGGGGAGAAGAGGGAGTCGGGCGTTTT
AGCGCGGGAGCGGGTTTTAGGGTTTTCGGGTTTTTTTCGCGTTTCGTCGT
TGATTATAGGGGCGGGGTCGTCGGATTTTTTACGGCGGTCGAGGGAAGGG
CGCGTTAGGTATTTGTCGTTTTCGTTTCGGCGGTTTAGGAGGGTTCGGTTT
TTATTTCGTCGGTTTATGGGTCGTATTCGTATCGTTATTTTATTTTGGAGT
TTTTTATTTTGTAGTCGTCGAGGAATTCGTTCGGTTTTCGTTTGTCGCGGTT
ATCGGCGATTTTTCGGGGTTGATTCGGCGGGAGGGGGTCGGGGGCGGAGT
CGGGGGTGGGGATCGGTTGGGGCGGGGTCGGCGCGAGTTTCGGGCGT
TTTTCGTTGTATGGCGGGATTTGTAGTTTTTAGGGTCGTCGTGGGCGGGG
TCGTAGCGAAGGCGGGGGCGGGAATGTTCGGGCGCGAGTCGTTTGTTATA
ATTTATTTATAGTAATGACGGTTTTTGTAAATTATATATTATTTTTGTTTTC
GTAGTTAGTATTGAGAAGTAAGTTTTTAAGAGTTGATATTTT
[SEQ ID NO: 8]

FIG 1H

TTGTGGAGCGGAGGAGGGGAGGTTTGGGGTCGCGGCGGTGTGCGTTTCGT
TTTGATCGTAGAGTTTTTTTTCGAGGAAAGCGGTTGGTTCGGTTTCGGTT
GGTGATTACGCGGGGTTTTTGTTTGTTTGGTGCGTAGGTGAGGGTTTGTTT
TTTCGTTGCGTTTCGGATAGTTTGGAGGTGAGTACGCGTTGGGTTTTGGAT
CGCGAGTAGCGGGAGAAGTACGAGTTGGTGGTCGTGTGTATCGTGTACGT
CGGCGCGCGCGAGGAGGTGGTGATGGTGTTTTTTTCGGTGATCGTGTACG
ACGAGGACGATTCGGCGTTTATTTTTTCGCGGGCGTCGATATCGTTAGCG
TCGTGGTGGAGTTTAAGCGGAAGGAGGTGTTTGTTCGCGCGTGTTGTGGT
TTATTTAGTGTTTGTTTTCGGTTATAGTTCGTTTTCGGTCGGTTTAGTGTT
CGTGTAGTTATTTAATCGTGTGGTCGATTATTCGCGTTTTTATTTGTTTTTC
GTTTTCGTTTGCGTCGTTTGTTTTAGGGGGAGGGGAAGGGGGAGTTTTGTT
AGTATTTAGTTGGGTTTTGTTTCGGGAGGTAAGGATTAGGACGAGGTTCG
AGGGTTCGCGTTTGGGGTATATTTGTGTCGTTGTAGGCGGGCGCGGCGCG
TTGTTCGGGCGGGGAGTATTTGTCGGGAGGGTATTTTTTTTATTAGTAGT
TAGTTTTTAACGGGAGGGTTTTTGAGTGATTACGAGTAGAGTCGGGGATT
GGAGAAGGACGGGAAGGCGGATTATTTTCGGCGTCGTTCGTTTCGTTTTTT
TTCGGTTCGCGTTGGTGGAGCGCGATCGTTATTTGTTGG
[SEQ ID NO: 9]
TTAGTAGGTGGCGGTCGCGTTTTATTAGCGCGAGTCGGAGAAGGGCGGGG
CGGGCGGCGTCGGAGGTGATTCGTTTTTTCGTTTTTTTTAATTTTCGGTTT
TGTTCGTGGTTATTTAAGGGTTTTTCGTTGGGGGTTAATTGTTGGTGGGA
GGGAGTGTTTTTCGGTAGATGTTTTTCGTTCGGGTAGCGCGTCGCGTTCG
TTTGTAGCGGTATAAGTATGTTTTAGACGCGAGTTTTCGGGTTTCGTTTTG
TTTTTTTTTTTAGGATAGACGGCGTAGACGGAGGCGAAGGATAAATGAAA
GCGCGAATGGTCGGTTATACGGTTGGGTGGTTATACGGATATTAAATCGA
TCGAGAAACGAATTGTGGTCGGAGATAGATATTGGGTAGATTATAGTACG
CGCGGATAAGTATTTTTTTCGTTTGAATTTTATTACGGCGTTGGCGGTGT
CGACGTTCGCGGGGAAGGTGGGCGTCGAGTCGTTTTCGTCGTATACGGTT
ATCGGGAAGGGTATTATTATTATTTTTCGCGCGCGTCGGCGTGTACGGTG
TATACGGTTATTAGTTCGTATTTTTTCGTTGTTCGCGGTTTAGGGTTTAGC
GCGTGTTTATTTTAGGTTGTTCGGGGCGTAGCGGAAGGGTAGATTTTTAT
TTGCGTATTAAGTAGATAGGGGTTTCGCGTGATTATTAGTCGGGATCGGG
TTAGTCGTTTTTTTCGGGAAGGGGGTTTTGCGGTTAGAGCGGGGCGTATAT
CGTCGCGGTTTTAGGTTTTTTTTTTTTCGTTTTATAG
[SEQ ID NO: 10]

FIG 1I

ATCGTTTTTTCGTAGGGGTTTTAGGATTTATTTAGATTTCGTTTGTTTTTTT
TTTCGCGGTAGGTTTCGTTGTATCGTGTATTTTTTCGCGAGAAGTTGATTT
TGCGGAAGGCGTTCGTTATTATCGTCGTTATTTGGGTTTTGGCGTTGTTTA
TTATGTGTTTTCGGTCGTTACGTTGATCGTTATTCGTGAGGAGTATTATTT
TATGGTGGACGTTCGTAATCGTTTTTATTCGTTTTATTTTGTTGGGAGGTT
TGGTTCGAGAAGGGTATGCGTAGGGTTTATATTATTGTGTTTTTTCGTAT
ATTTATTTGGCGTCGTTGGCGTTTATCGTGGTTATGTACGTTCGTATCGCG
CGTAAGTTTTGTTAGGTTTCGGGTTCGGTTTTCGGGGGCGAGGAGGTTGCG
GATTCGCGAGTATCGCGGCGTAGAGCGCGCGTGGTGTATATGTTGGTTAT
GGTGGCGTTGTTTTTACGTTGTTTTGGTTGTCGTTTTGGGCGTTGTTGTTG
TTTATCGATTACGGGTAGTTTAGCGCGTCGTAGTTGTATTTGGTTATCGTT
TACGTTTTTTTTTCGCGTATTGGTTGGTTTTTTTAATAGTAGCGTTAATT
TTATTATTTACGGTTATTTTAACGAGAATTTTCGTCGCGGTTTTTAGGTCGT
TTTTCGCGTTCGTTTTGTTCGCGTTCGTCGGGGAGTTATAAGGAGGTTTA
TTTCGAGCGGTTCGGCGGGTTTTTGTATAGGCGGGTTTTCGTGGTGGTGCG
GTTTAGCGATTTCGGGTTGTTTTTTGAGTCGGGTTTTAGTAGTGGGGTTTTT
AGGTTCGGTCGTTTTTCGTTGCGGAAT
[SEQfIDNO: 11]

ATTTCGTAGCGGGAGGCGGTCGGGTTTGGGGGTTTTATTGTTAGGGTTCG
ATTTAGAGGGTAGTTCGGAGTCGTTGGGTCGTATTATTACGAAGATTCGTT
TGTGTAGAAGTTCGTCGGGTCGTTCGGAGTAGGTTTTTTGTGGTTTTTCG
ACGGGCGCGGGTAGAGGCGGGCGCGGAAGGCGGTTTGGAAGTCGCGGCG
GAAGTTTTCGTTGAAGTAGTCGTAGATGATGGGGTTGGCGTTGTTGTTGA
AGAAGGTTAGTTAGTGCGCGAAGGGGAAGGCGTAGACGGTGATTAGGTG
TAGTTGCGGCGCGTTGAGTTGTTCGTAGTCGATGAGTAGTAGTAGCGTTTA
GAGCGGTAGTTAGGATAGCGTGAAGAATAGCGTTATTGATTAGTATGT
GTATTACGCGCGTTTTGCGTCGCGATGTTCGCGGGTTCGTAGTTTTTTCGT
TTTCGGGGGTCGGGTTCGGGGTTTGGTAGAGTTTGCGCGCGATGCGGGCG
TATATGATTACGATGAGCGTTAGCGGCGTTAGGTAGATGTGCGAGAAGAG
TATAGTGGTGTAGATTTTGCGTATGTTTTTTCGGGTTAGGTTTTTAGTAG
GAGTAGAGCGGGTAGGAGCGGTTGCGGCGTTTATTATGAAGTGGTGTTT
TTTACGGGTGACGGTTAGCGTGACGGTCGAGGGATATATGATGAGTAGCG
TTAGGGTTTAGATGACGGCGATGGTGACGAGCGTTTTTCGTAGGGTTAGT
TTTTCGCGGAAAGGGTGTACGATGTAGCGGAATTTGTCGCGGGGAGAGAG
ATAGGCGGGATTTGGGTGGGTTTTAGGGTTTTTGCGAGGGGACGGT
[SEQ ID NO: 12]

FIG 1J

TTTAGTTTCGGAATCGCGGATTGCGTTTAGTGACGGATTTAAATTTATTTT
TTTTTTTGATTTCGTCGTAGGATGACGTTTTAATTTTCGGGTGCGTTTATTG
TTTAAGTGATTCGTGAGACGGAGCGGTTTTTTTTAGAGTTTCGGAAGACG
AAGTGATTTGTTTTACGTTCGTTCGTTTAGTTTTATTCGTATACGGGGGA
ATTGCGTAGAGGCGGAAGAGGGAGGTTGTCGAGGGGTTTCGAGGAAGTT
TCGGGTACGGCGCGGGGACGTAGTCGGTTTAAGAGCGAGTTGGTATTGA
GTAAGTAGCGACGGAGTCGGCGAAAGAAGGTTAACGATCGCGAGCGTAA
TCGAATGTATAATTTTAATTCGGTATTGGACGTTTTGCGCGGTGTTTTGTTT
ATTTTTTAGACGACGCGAAGTTTATTAAGATCGAGACGTTGCGTTTCGTT
TATAATTATATTTGGGCGTTGATTTAAACGTTGCGTATAGCGGATTATAGT
TTGTACGCGTTGGAGTCGTCGGCGTCGTATTGCGGGAGTTGGGTAGTTT
AGGCGGTTTTTCGGGGATTGGGGGTTTTTTTATTTTTTAGTT
[SEQ ID NO: 13]

GATTGGGGAGTAGAGGGATTTTTAGTTTTCGGGGGAATCGTTTGGGTTGTT
TAGTTTTTCGTAGTGCGGCGTCGGCGGTTTTAGCGCGTATAAGTTGTGGTT
CGTTATGCGTAGCGTTTGAGTTAGCGTTTAGATGTAGTTGTGGGCGAAGC
GTAGCGTTTCGATTTGGTGAGTTTCGCGTCGTTTGGGAAGGTGGGTAGG
ATATCGCGTAGGGCGTTTAGTGTCGAGTTGAGGTTGTGTATTCGATTGCGT
TCGCGGTCGTTGGTTTTTTTCGTCGATTTCGTCGTTGTTTGTTTAGTGTTA
ATTCGTTTTAGGTCGGTTGCGTTTTCGCGTCGTGTTCGGAGTTTTTCGG
GGTTTTTCGGTAGTTTTTTTTTTCGTTTTGCGTAGTTTTTCGTGTGCGA
GTGGGGTTGGGCGGGGCGGACGTGGGGTAGGTTATTTCGTTTTCGAGGT
TTTGGGGAAGGATCGTTTCGTTTTACGGGTTATTTGGATAGTGGGCGTATT
CGAGGGTTGAGGCGTTATTTTACGGCGGGGTTAGAGGGAAGGGTAAGTTT
GAGTTCGTTATTGGGCGTAGTTCGCGATTTCGAGGTTAGG
[SEQ ID NO: 14]

TTAGTTTCGGTCGTATTGTATAGCGAGGTCGGTTCGGAGTTCGGATGTTGG
GTTCGGTTTCGTCGAGGTTCGGTTTGGTTGTAAAGTAGAGGGGGGCGAGG
GAAGTCGGGTTAGCGGGTGTCGCGGGTAGTCGGCGTTCGGGACGGGGTGT
GGCGTTTAGAGCGTTGTTGTTTTCGTAGTTAGGAGGTTGGATGTCGGGTT
TGGGTGTTTTTTAGAAGGAGTCGTATTAGCGACGAGGGAAGAGGAATTGG
TTTTTCGGGTAGTTTTTTTCGTTTTAAATTTTTTTTTTCGCGGAGGGTGGG
CGGGCGGAGGGAGGAAGCGTAGTCGGGGAACGTGGCGTTCGCGTTTTTT
CGTTCGGGGGTTGCGGTTGGGTTGAGTGTGTTTTAAATTTGAGTTTTTCG
TTTTTCGCGGTGGGTCGGGATTCGCGGTCGGGCGGGGCGGGCGCGGT
GATTGGCGGTCGGGTCGGGTTCGTTTTCGGCGTTGGGTAGCGGGGCGTT
GGGGAGTAGCGCGGCGCGTACGGGTCGGGCGCGTAGGTTTCGTCGTCGG
TGAGTACGGGTTTTTTTCGCGTGGTTTCGTCGGGTTCGTTGGTTTGTTTA
TTTTCGGAGTTATTTTTGTTTTCGTATGGGTTGGCGAAGTTGGGAGGAGCG
AGTTGGAGTTAGAGCGCGCGTCGGGCGCGTTTCGTCGTTGTTTGATTCGGC
GTTCGTAGTTCGGGCGTAGTACGTCGGTCGTAGGAGTACGGATGTTTTCG
GAGTCGCGGGTTGGTAGGTATCGAAGTGTTTGTTTGGGGTTGGCGAGG
GGAGGGTAAATTTGGAATTTTCGGGTATTTTTAGTTCG
[SEQ ID NO: 15]

FIG 1K

CGGGTTGGGGGGTGTTCGGGGGATTTTAGATTTGTTTTTTTTCGTTAGTTT
TAGGGTAGGATATTTCGGTATTTGTTAGTTCGCGGTTTCGGGGGGTATTCG
TGTTTTTGCGGTCGGCGTGTTGCGTTCGAATTGCGGGCGTCGAGTTAGGTA
GCGACGGGGCGCGTTCGGCGCGCGTTTTGGTTTTAGTTCGTTTTTTTTAAT
TTCGTTAGTTTATGCGGGGGTAGAGGTGGTTTCGGAGGTGGGTAGGTTAG
GCGGATTCGGCGAGGTTACGCGAGAGGGAGTTCGTGTTTATCGGCGACGG
GATTTGCGCGTTTCGGTTCGTGCGCGTCGCGTTGTTTTTAGCGTTTCGTTA
TTTAACGTCGAGGGGCGGATTCGATTCGGTCGTTAATTATCGCGTTCGTTT
TCGTTCGGATCGCGAGTTTCGGTTTTATCGCGAGGGGCGGGGGGTTTAGA
TTTAAAGATATATTTAGTTTAGTCGTAGTTTCGGGCGGGAGGAACGCGG
GCGTTACGTTTTCGGTTGCGTTTTTTTTTCGTTCGTTTATTTTCGCGAG
GAGGAAAAGTTTGGGGCGGGGGAGATTGTTCGGGAAGTTAGTTTTTTTTT
TTTCGTCGTTAGTGCGGTTTTTTTGGAAGATATTTAAATTCGATATTTAGT
TTTTTGGTTGCGAGAGGTAGTAGCGTTTGGGCGTTATATTTCGTTTCGGA
CGTCGGTTATTCGCGATATTCGTTGGTTCGGTTTTTTCGTTTTTTTTGTTT
TATAGTTAGGTCGAGTTTCGGCGGGATCGAGTTTAGTATTCGGGTTTCGGG
TCGGTTTCGTTGTGTAGTGCGGTCGGAGTTGG
[SEQ ID NO: 16]

TTTTGTATAGGAGTAGTGATTTTAGTATTTATTTAATTTTTTTCGGCGTCG
AGTTTAGTTGGAGAGGTTAGGGGTGGTAGTGATTGGTAGGAGGTCGGGGC
GGGGGGAATTTTTAAGTTCGGCGTTTGGGGTTGCGGGTTCGATTCGAGAT
TCGTTTTTTTTGTAAGTTTCGAGTCGTTGGTTAGGTTCGTTATTGCGTATTA
GTCGTATTCGCGAGCGTTGGTTTTGTCGGTTTGAGTTAGGGTGGGTAGGGT
CGGGATTTACGGCGGAGGTGGGGTCGGGTCGAGTAGTTTCGGGGGATTTT
CGAAGTTATAGCGTTTTGTTTTTTGTACGTTTCGCGTTTTCGGTTTTCGAT
TGGTTGTCGGGTTTAGAGTTCGTTTAGAATTGGATCGTTCGTTTGTCGTTC
GGGTTTGGTTTTATTTTAGAGGGAGTTTAGAATTTGGTCGTAGTTTTTAG
AGATTATTTTTATTTCGTGGTTTGCGTCGAAGTTGGGCGGAGGATAGTGGG
TGGTTAGGTTTTTTCGGGTTAGAATTCGGGATTTTTGTTAGTTATTCGTGTT
AGGATAGATTTAAGTTTTTAAAACGCGGATGGATGTAT
[SEQ ID NO: 17]

GTATATTTATTCGCGTTTTGGGGGTTTGAGTTTGTTTTGGTACGGGTAGTT
GGTAGGGGTTTCGAGTTTTGGTTCGGAAGGGTTTGGTTATTTATTGTTTTT
CGTTTAATTTCGGCGTAGGTTACGGGGTGAGGGTAGTTTTAAAAATTGC
GATTAGGTTTTAGGTTTTTTTGGGGGTGGAGTTAGATTCGAGCGATAAGC
GAACGGTTTAATTTTGGGCGGGTTTTAGGTTCGATAGTTAATCGGAGGTC
GGGGGCGCGGAGCGTGTAGGGAGGTAAGGCGTTGTAGTTTCGGGGATTTT
TCGAGGTTGTTCGGTTCGGTTTTATTTTCGTCGTGGGTTTCGGTTTTATTTA
TTTTAGTTTAGGTCGGTAGAGTTAGCGTTCGCGGATGCGGTTGGTGCGTAG
TAGCGGGTTTGGTTAGCGGTTCGGGGTTTGTAGGGAGGGCGGATTTCGGG
TCGGATTCGTAGTTTTAGACGTCGGGTTTGGGGTTTTTTCGTTTCGGTTT
TTTGTTAGTTATTATTATTTTTAGTTTTTTTAATTGAGTTCGGCGTCGGGAG
AGGATTAAGTAAGTGTTGAGGTTATTGTTTTGTGTAAGA
[SEQ ID NO: 18]

FIG 1L

ATCGTTTTTTCGTAGGGGTTTTAGGATTTATTTAGATTTCGTTTGTTTTTTT
TTTCGCGGTAGGTTTCGTTGTATCGTGTATTTTTTCGCGAGAAGTTGATTT
TGCGGAAGGCGTTCGTTATTATCGTCGTTATTTGGGTTTTGGCGTTGTTTA
TTATGTGTTTTTCGGTCGTTACGTTGATCGTTATTCGTGAGGAGTATTATTT
TATGGTGGACGTTCGTAATCGTTTTTATTCGTTTTATTTTTGTTGGGAGGTT
TGGTTCGAGAAGGGTATGCGTAGGGTTTATATTATTGTGTTTTTTTCGTAT
ATTTATTTGGCGTCGTTGGCGTTTATCGTGGTTATGTACGTTCGTATCGCG
CGTAAGTTTTGTTAGGTTTCGGGTTCGGTTTTCGGGGGCGAGGAGGTTGCG
GATTCGCGAGTATCGCGGCGTAGAGCGCGCGTGGTGTATATGTTGGTTAT
GGTGGCGTTGTTTTTACGTTGTTTGGTTGTCGTTTGGGCGTTGTTGTTG
TTTATCGATTACGGGTAGTTAGCGCGTCGTAGTTGTATTTGGTTATCGTT
TACGTTTTTTTTTCGCGTATTGGTTGGTTTTTTTAATAGTAGCGTTAATT
TTATTATTTACGGTTATTTTAACGAGAATTTTCGTCGCGGTTTTTAGGTCGT
TTTTCGCGTTCGTTTTTGTTCGCGTTCGTCGGGGAGTTATAAGGAGGTTTA
TTTCGAGCGGTTCGGCGGGTTTTGTATAGGCGGGTTTTCGTGGTGGTGCG
GTTAGCGATTTCGGGTTGTTTTTTGAGTCGGGTTTTAGTAGTGGGGTTTTT
AGGTTCGGTCGTTTTTCGTTGCGGAAT
[SEQ ID NO: 11]

ATTTCGTAGCGGGAGGCGGTCGGGTTTGGGGGTTTTATTGTTAGGGTTCG
ATTTAGAGGGTAGTTCGGAGTCGTTGGGTCGTATTATTACGAAGATTCGTT
TGTGTAGAAGTTCGTCGGGTCGTTCGGAGTAGGTTTTTTGTGGTTTTTCG
ACGGGCGCGGGTAGAGGCGGGCGCGGAAGGCGGTTTGGAAGTCGCGGCG
GAAGTTTTCGTTGAAGTAGTCGTAGATGATGGGGTTGGCGTTGTTGTTGA
AGAAGGTTAGTTAGTGCGCGAAGGGGAAGGCGTAGACGGTGATTAGGTG
TAGTTGCGGCGCGTTGAGTTGTTCGTAGTCGATGAGTAGTAGTAGCGTTTA
GAGCGGTAGTTAGGATAGCGTGAAGAATAGCGTTATTATGATTAGTATGT
GTATTACGCGCGTTTTGCGTCGCGATGTTCGCGGGTTCGTAGTTTTTTCGT
TTTCGGGGGTCGGGTTCGGGGTTTGGTAGAGTTTGCGCGCGATGCGGGCG
TATATGATTACGATGAGCGTTAGCGGCGTTAGGTAGATGTGCGAGAAGAG
TATAGTGGTGTAGATTTTGCGTATGTTTTTTCGGGTTAGGTTTTTAGTAG
GAGTAGAGCGGGTAGGAGCGGTTGCGGGCGTTTATTATGAAGTGGTGTTT
TTTACGGGTGACGGTTAGCGTGACGGTCGAGGGATATATGATGAGTAGCG
TTAGGGTTTAGATGACGGCGATGGTGACGAGCGTTTTTCGTAGGGTTAGT
TTTTCGCGGAAAGGGTGTACGATGTAGCGGAATTTGTCGCGGGGAGAGAG
ATAGGCGGGATTTGGGTGGGTTTTAGGGTTTTTGCGAGGGGACGGT
[SEQ ID NO: 12]

FIG 1M

TGGTTACGAAGAATCGGTTGGTTACGTCGAAGATGTTTATTACGTTTCGTT
TTACGGGCGAGAGTTTTAGTAGGTTTGGGGGCGGGGCGTAGGTTATTGCG
GGGTAGGTGATTTTTGGTTTATTTCGTTTTTCGGTTTGTTCGTTTTCGGGGA
TTTTATTTTTGGGGTGGGGTTGGGGATAAAGGGTTAGGGTTTTCGGCGTAG
TCGTTTTAAGGGTTTTTAGAGTTTAAGTTGTTTTTTAGGGTTTTCGGAGTT
TAAGTTTGCGTTAGTTTAGATTAGTTTGTTTGTGTAGGGGATTTTCGGCGG
TCGTATTTAGTTTCGGATTTTTAGACGCGAGTTCGATTTTAGCGGTTTTTA
GTTTGGGTTAGGTCGGGGCGCGTGTTTCGGGTTTTTTGTGGTTGTATCGCG
CGTTTTGTGTTTACGGGCGAAGGCGTTGGAATTCGGCGTTCGGAGTTCGA
GTTTTTGAAGGCGGGAGGCGGCGTTCGATTTAGGGGTTGCGTTGGGTTG
TCGGAGTTAAGAGTGTTTGCGTTTTAGTTTCGCGTTAGAAGGGATCGGA
GTTCGAGTTCGTTTCGGTTTTCGGGGTTTTCGAGTAGGTGTTCGTCGAGGG
TTTTAGAGTGTGATTGAGCGGGTTGGTTCGGCGGTCGTTGTTTTCGTTTT
CGTTTTTTCGCGTTTGGTCGCGTTATTTATTGTCGCGGGTGTTCGCGTGCGC
GTCGTCGATGCGGTCGTCGGGGAGCGTTTGGAGGTGGAAGTCGATGTTTA
CGTTGTAGTAGAGTCGTCGTAGTCGTTTGATGTTTAGTAGGTAGTCGTCGG
CGTCGTTTTGGACGGTCGTTTTTTTGGGTTGCGTTGTTATCGGTAGGCGCG
TTAACGAGAGCGTTATTAGGTTTTTTAGCGGCGTTTTAGTTCGGTTTTTA
GCGTGTCGTTGGGTGTAGTGGGTGCGGCGGCGTTTTTTCGGTTCGTTTAGG
GCGTTAGTAAGGTTAGTAGGATCGTCGGGAGTAGCGTTATCGCGGTCGTT
TCGGGTTTCGATATTTCGGTTCGAGGGTCGTGCGTCGGTTAGGCGGTTAGT
GCGTTCGGGAAGTTGGGGGGTAGAGTTGCGTTTGTGGCGTTTCGCGGGAG
CGTACGGTCGATTTCGGGTAGGAGTGCGTAATCGAGGAGGTGCGGGAGGT
AAGCGACGGGGTTTTCGGGCGTCGGGTTTTATTTCGGTTGTATGGAGCGG
CGAGTCGGGCGGAAAGCGCGCGGTTGGAGTTGGGATTTTGAGGAGTAGT
GCGCGTTTTTTTGAGCGTTAGGTTCGTTCGAGGTCGAGTCGTTATATATAT
AGTTCGGCGTTTTTTTTATTCGTTCGTTTTCGCGGGGGGTCGTTCGCGTTT
TTTTGGGCGTTCGGGGCGTTGTGGCGTTCGCGGTTGGTCGTAGGTCGTTTG
TTAATTAGGGTCGGGGGAAGGGAGGAGGTTGGGGATTAGCGTCGCGAGT
GTTATTTGGAGGGATTTCGGTTTTTATTTTTGGTTTCGTTCGGTTTACGGAT
TTGTTCGTTTCGTTTTTTGGCGGTTTTTATATTTTTGTTTTTTAGTTAGTTTT
GTTTTTTGTATTTTGTTTTTGTTT

[SEQ ID NO: 20]

FIG 1N

AGGGTGAAGTTTGAGAGTTTAAATGGTTAATTTTATAGGGTTGAACGTTTT
AGAAGTCGTAGGTTCGTTGGGGTTGATTTTGGTAGTTGTCGTGGAGGTGG
GGGTATTGTTGGGTAACGGCGCGTTGTTGGTCGTGGTGTTGCGTACGTCG
GGATTGCGCGACGCGTTTTATTTGGCGTATTTGTGCGTCGTGGATTTGTTG
GCGGTCGTTTTTATTATGTCGTTGGGTTTGTTGGTCGTATCGTCGTTCGGGT
TGGGTCGCGTGCGTTTGGGTTTCGCGTTATGTCGCGTCGTTCGTTTTTTTT
CGTCGTTTTGTTGTCGGTTTGTACGTTCGGGGTGGTCGTATTTGGTTTGGT
ACGTTATCGTTTATCGTGTATTCGTTGCGGTTAGGTTCGCGGTCGTCGTTT
GTGTTCGTGTTTATCGTCGTGGGTCGCGGCGGGATTGTTGGGCGCGTTT
TTTTTGTTCGGTACGTCGTTCGTATCGTTTTTGTTTTGTTCGTTGTTCGGT
TTTGGTTGGGGGTTTCGGGTTTTTTCGGTCGTTTGGGTTTTGTTGGTTTTC
GCGTTGTTCGTTTTTTGTTGTTCGGCGTTTACGGCGGTATTTCGTGGTGG
CGCGTCGCGTTGTTTGAGGTTTTACGGTCGGCGCGCGGGTTTCGATTTT
ATTCGGATTTTTTGGATAGTCGTTTTTTTATTTGTCGTCGTTTCGGTTTCG
TTTGTTCGGGGGTAAGGCGGTTTTGGTTTTAGCGTTGGTCGTGGGTTAATT
TGTAGTTTGTTGGTTGTTTTATGGTTGCGCGTGTTTGGCGTTCGTAGCGCG
GGTCGCGGAAGTCGAAGCGGTTGTTATTTGGGTCGTTTATTCGGTTTTCGC
GGTTTATTTTTTTTGTACGGGTTGTTGTAGCGTTTCGTGCGTTTGGTATTG
GGTCGTTTTTTCGTCGTGTATTGTTTGGATTTGTGCGGGTTTGTATTTCGT
AAGTTTGGTATTCGCGGGTATTTTGTAATGTTTTAGAGATTTTTAGAGG
GTTTTGTCGTAGGTTTTTTTGAGGTTTTAGAATAGATTTTCGAGTTGGTAG
GAGGGCGGAGTTTCGTATATT
[SEQ ID NO:21]

GGTATGCGGGGTTTCGTTTTTTTGTTAATTCGGGGGTTTGTTTTGGAGTTTT
AGAAGGGTTTACGGTAGGGTTTTTGGGGGTTTTTGGAGGTATTGTAAGA
GTGTTCGCGGGTGTTAGGTTTGCGGAGTGTAGGTTCGTATAGGTTTAGGTA
GTGTACGGCGAGAGAGGCGGTTTAGTGTTAAGCGTACGGGGCGTTGTAGT
AGTTCGTATAGGAAGGGGTGAGTCGCGAAGGTCGAGTAGGCGATTAGGT
GATAGTCGTTTCGGTTTTCGCGGTTCGCGTTGCGGGCGTTAGGTACGCGTA
GTTATAAGGTAGTTAGTAGGTTGTAAATTGGTTTACGGTTAGCGTTGGGGT
TAGGGTCGTTTTGTTTTCGGGTAGGCGAGGTCGGAGCGGCGGTAAGATGG
AAAGGCGGTTATTTAGAGAGTTCGAGTGGAGTCGGGATTCGCGCGTCGGT
CGTGGGGGTTTTAGGGTAGCGCGACGCGTTATTACGAAGATGTCGTCGTA
GGCGTCGAGTAGTAGGAGGGCGGGTAGCGCGAAGGTTAGTAGGGTTTAG
AGCGGTCGGAAGGGTTCGAGGTTTTTAGTTAGGATCGAGTAGCGAGTAGG
AGTAGGGGGCGGTGCGGGCGGCGTGTCGAGTAGGGAGAGCGCGTTTAGT
AGTTTCGTCGCGGTTTATACGGCGGTGAGTACGAGTATAGGCGGCGGTCG
CGAGTTTGGTCGTAGCGGGTGTACGATGAGGCGGTAGCGTGTTAGGTTAA
GTGCGGTTATTTCGAGCGTGTAGGTCGGTAGTAGAGCGGCGGAGAGGAA
GCGAGCGGCGCGGTATGGCGCGGGGTTTAGGCGTACGCGGTTTAGTTCGG
GCGGCGGTGCGGTTAGTAGGTTAGCGGTATGATGGAGGCGGTCGTTAGT
AGGTTTACGACGTATAGGTGCGTTAGGTAGAGCGCGTCGCGTAGTTTCGG
CGTGCGTAGTATTACGATTAGTAGCGCGTCGTTGTTTAGTAGTGTTTTTAT
TTTTACGATAGTTGTTAGGATTAATTTTAACGAGTTTGCGATTTTTGAGGC
GTTTAGTTTTGTGGAGTTGGTTATTTGGGTTTTTAGGTTTTATTTT
[SEQ ID NO: 22]

FIG 10

GGTGTCGGTGTTGGTGTTGTTTATGGTCGCGTTGTATTAGGTGTTTAATAA
GTGGATATTGGGTTAGGTAATTTGCGATTTGTTTATCGTTTCGACGTGTT
GTGTTGTATTTTATTTATTTTGTATTTGTGCGTTATCGCGTTGGATAGGTAT
TGGGTTATTACGGATTTTATCGATTACGTGAATAAGAGGACGTTTCGGCG
CGTCGTTGCGTTTATTTCGTTTATTTGGTTTATTGGTTTTTTTATTTTTATTT
CGTTTATGTTGGGTTGGCGTATTTCGGAAGATCGTTCGGATTTCGACGTAT
GTATTATTAGTAAGGATTATGGTTATATTATTTATTTTATTTTGGAGTTTT
TTATATTTCGTTGTTGTTTATGTTGGTTTTTATGGGCGTATATTTCGAGTT
GCGCGTTTTCGTATTCGTAAGACGGTTAAAAAGGTGGAGAAGATCGGAGC
GGATATTCGTTATGGAGTATTTTCGTTTCGTAGTTTAAGAAGAGTGTGAA
TGGAGAGTCGGGGAGTAGGAATTGGAGGTTGGGCGTGGAGAGTAAGGTT
GGGGGTGTTTTGTGCGTTAATGGCGCGGTGAGGTAAGG
[SEQ ID NO: 23]

TTTTGTTTTATCGCGTTATTGGCGTATAGAGTATTTTTAGTTTTGTTTTTTA
CGTTTAGTTTTTAGTTTTTGTTTTTCGATTTTTTATTTATATTTTTTTGGGT
TGCGGGGCGGGAGATGTTTTATGGCGGGTGTTCGTTTCGGTTTTTTTTATT
TTTTTGATCGTTTTGCGGATGCGGAAGCGCGTAGTTCGGAATATGCGTTTA
TAGAGAATTAGTATGAGTAGTAGCGGGATGTAGAAAGTTTTAAAGGTGGA
ATAGATAGTGTAGTTATGATTTTTGTTAATGGTGTATGCGTCGGGGTTCGA
GCGGTTTTTCGGGGTGCGTTAGTTTAGTATGGGCGGGATAGAGATGAGGA
AGTTAATAAGTTAAGTGAGCGAGATGAGCGTAGCGGCGCGTCGGGGCGTT
TTTTTGTTTACGTAGTCGATGGGGTTCGTGATGGTTTAGTATTTGTTTAGC
GCGATGGCGTATAGGTGTAAGATGGATGAGGTGTAGTATAGTACGTCGAG
GGCGATGAATAGGTCGTAGGTTATTTGGTTTAGTGTTTATTTGTTGAGTAT
TTGATATAGCGCGGTTATGGGTAGTATTAATATCGATATT
[SEQ ID NO: 24]

GGGATGATAAGGGAGAAAAATTTTTTTACGGTTTCGTTTGGTTCGCGGCG
TTTGTTTGTTTGCGCGGGGTTAAAGTTCGGCGTCGTTTACGCGCGGTTCGG
GTGGGAATTCGTAGACGTGGGGCGAGTAGGGTCGTTGGTTGTGGCGGGCG
AGCGTCGGGGCGTTACGTTCGAGGTCGCGGGGTCGGGGTTGTAGGTATAG
TTCGAGCGTTTTCGCGGGGTTTGGTTTTGTCGTTTTCGTTTCGTCGAAT
CGGTATCGTCGTCGTCGGAGTCGTAGCGAGTTTTAGAGTTTGGTTGTTGG
CGGTCGGGAGCGTCGGGACGGGGCGCGAAGTCGGAGGTTTCGGGACGTG
GATATAGGTAAAGGTCGGCGGGTCGGAGTCGGGCGGGGCGCGGCGGCGG
CGTTTTTCGGAGGGATTTGGTTTCGGTCGGGTTTTATTTAGTCGCGGTGGT
TCGGGTTTTTACGTTGGTTTAGGCGGGGACGTGTTAAGGGGTTGGGTTAG
GGTTGTCGTTGGTTTGGTCGTTTTTCGTTCGGCGGGTTTTAGGTGACGCGG
TCGCGGTTTAATTTTCGTATTTGAGGTTTTCGGAGCGGTTTCGGGGCGCGT
TTATTTGGAGGTTGGAATTATATAGGGTCGAAAAAGTTGAGTTTTGGAGG
CGAGGCGTTGTAGGTGTGGCGGAGGAGGTCGGGGAAGGTGGGGTGGGTG
TTAGGGGTTTAGTATTGAATTTTTTTAGGTTTGAGGTGGGGAATTGCGTT
TTGTTTAATTTCGGAGTTTGTGGGGATTATATAGTTTTTTTTACGGTCGATT
TTTTTTGTACGGTTTTATTTTTTTTTGTTTAGTTTATTTTAGT
[SEQ ID NO: 25]

FIG 1P

ATTGAAATGGGTTAGATAAAGGAAAGTGGAATCGTGTAGAGGGAATCGG
TCGTGGAAGGGGTTGTGTGGTTTTTATAAGTTTCGAAATTAAATAAGACG
TAGTTTTTTATTTTAGATTTGGAGAGGGTTTAGTATTGGATTTTGGTATTT
ATTTTATTTTTTTCGGTTTTTTTCGTTATATTTATAGCGTTTCGTTTTTAGGA
TTTAGTTTTTTCGATTTTGTGTAATTTTAATTTTTAGGTGGGCGCGTTTCGA
GGTCGTTCGAGAGTTTTAGGTGCGAAAGTTAAGTCGCGGTCGCGTTATTT
GAGGTTCGTCGGGCGAGAGGCGGTTAGGTTAGCGGTAATTTTAGTTTAGT
TTTTTGGTACGTTTTCGTTTGGGTTAACGTGGGGGTTCGGGTTATCGCGGT
TGGGTAGGGTTCGGTCGAGGTTAGGTTTTTTCGAGAGGCGTCGTCGTCGC
GTTTCGTTCGATTTCGATTCGTCGGTTTTTATTTGTATTTACGTTTCGGAGT
TTTCGGTTTCGCGTTTCGTTCGGCGTTTTCGGTCGTTAGTAGTTAGGTTTT
GAGGATTCGTTGCGGTTTCGGCGGCGGCGATGTCGGTTCGGCGAGACGGG
AAGCGATAGGAGTTAAATTTCGCGGAAAGCGTTCGAGTTGTGTTTGTAGT
TTCGATTTCGCGGTTTCGGACGTGGCGTTTCGGCGTTCGTTCGTTATAGTT
AGCGGTTTTGTTCGTTTTACGTTTGCGGGTTTTTATTCGAGTCGCGCGTGG
GCGGCGTCGGGTTTTGATTTCGCGTAGGTAGATAAGCGTCGCGGGTTAGA
CGGAATCGTGGGAAAGTTTTTTTTTTTGTTATTTT
[SEQ ID NO: 26]

TGAGGTGTGGGGATTATTTATTTCGGTGGGTTTTTTATTTTAGGTCGGTT
TTTTTATTACGCGTGGGTGTGGGGGTATTGTTTTCGTTGCGCGTAGGAATA
GCGGGGAGAGTTAGGAGCGGAGCGGTTTCGGGATGTTAGATTGAGTAGT
GGGTTCGTTTGCGGTTATTTTTAGGGAATAAGTTTTTTTCGCGGAGATT
TTGTTTTTTTAAAAGTTTTTTTGGGTTTAGTTTAGGGCGATAGGACGATTT
TTTTTGGGAAGGGAGAGTTTGTTAGTTTTTTTTTATTCGTTAGGCGGTGT
AGTTTTTTTTTCGTTCGGGGCGCGCGTATTTTAGCGTCGCGGGTTTAGCG
TTTAGTAGTCGCGTTTTAGGTCGGGTTTCGGGTTTCGGGAGTTCGTAGGCG
CGCGTTCGGTCGGGCGTGTCGGGAGCGCGCGGCGGTCGGGGGCGGAGCG
TAGTTAGGGTTGCGCGGCGCGTTTCGGTTTTCGTTCGTTTTAGTCGGGTT
TTTTAGCGGTCGGCGGGACGGTTTTCGGTTGTAGTTTGTTCGTTCGTTTCG
CGCGGGGGTCGAGTCGCGAAGCGCGTTTGCGATTCGGCGTTCGGGCGCGT
TGGAGAGGACGCGAGGAGTTATGAGGCGTTAGTTTGCGAAGGTGGCGGC
GTTGTTGTTCGGGTTGTTTTTGGAGGTAGGGGTCGGGGATCGGGTGTTGTC
GGAGGCGCGGCGTTTATTATGTTGGCGGTTGGGGGCGCGTAGTTTCGAGG
CGTTTTAGAGGATTTTGTTTGGGAGCGTAGACGGTGGAGCGACGGGGAGT
TATAGTTTTGCGCGTTTTTCGGAGTTGGGAGGTGCGGGATTTTGGTGACGG
GGAGGTTTTCGTTTCGGTTCGCGTTTTTCGTCGTTTTTCGGTTTTCGTATT
TCGTTTTTATTTTGCGGGTGAGCGCGTTTTTCGCGTCGATCGTTTTCGTTAG
TTCGGGGTGATTTTTGTGTATCGTTCGTTTTTTTTTTCGTCGTAGAGGGTC
GAGGATCGGATGGATTCGGGGTTGGGCGGGGTGGTTTCGGGCGCGGCG
TAGGCGCGGAGAGTTCGGGGCGTCGGGTAGTTTGGGGTTAGGAAAGGAT
GGGTGTCGAGTCGGGGTGAGGGAGCGGGCGGAGGGGATTGTGGGAAG
TGTCGCGGGAGTGTCGGGAGTTGTGGAGGTGAGTAGCGGGAGGAGGCGT
TTTCGCGTGTGAAAATGAAGTGTAGTTTTTAGGTGCGGGAGGAAATTTT
GCGGAGAGTTTGGTTGGGTGGGGTGCGGAGTCGAAGTCGGCGGGGAAT
TTGTTGAGCGGTTTTCGGGTGCGAGCGTTCGTGATCGT
[SEQ ID NO: 27]

FIG 1Q

GCGGTTACGGGCGTTCGTATTCGGAAGTCGTTTAATAAGTTTTTCGTCGGT
TTCGGTTTCGTATTTTTATTTAGTTAGGTTTTTCGTAGAATTTTTTTTCGTA
TTTAAAGGTTGTATTTTATTTTTATACGCGGGAACGTTTTTTTTCGTTGTTT
ATTTTTATAATTTTCGGTATTTTCGCGATATTTTTTATAGTTTTTTTCGTTC
GTTTTTTTTATTTCGGTTCGGTATTTATTTTTTTTAATTTTAAATTGTTCGG
CGTTTCGGGTTTTTCGCGTTTGCGTCGCGTTCGAGGATTATTTTCGTTTAAT
TTCGGGTTTATTCGATTTCGGTTTTTTGCGGCGGGGAGAGGGGGCGGAC
GGTGTATAAAGGTTATTTCGAGTTAACGGAGGCGGTCGGCGCGGGAAACG
CGTTTATTCGTAGGGTGGGGCGGGGTGCGAAAATCGAAGGAACGACGG
AAGGCGCGGATCGGGGCGGGAGTTTTTTCGTTATTAGGGTTTCGTATTTTT
TAGTTTCGGGAGGCGCGTAGGGTTGTGGTTTTTCGTCGTTTTATCGTTTGC
GTTTTTAGGTAAGGTTTTTTGGGGCGTTTCGGAATTGCGCGTTTTTAGTCG
TTAGTATGGTGGGCGTCGCGTTTTCGGTAGTATTCGGTTTTCGGTTTTTATT
TTTAAGAGTAGTTCGAGTAGTAGCGTCGTTATTTTCGTAGGTTGGCGTTTT
ATGGTTTTTCGCGTTTTTTTTAGCGCGTTCGGACGTCGGGTCGTAGGCGCG
TTTCGCGATTCGGTTTTCGCGCGGGCGGGCGGGTAGATTGTAGTCGGGA
GTCGTTTCGTCGATCGTTGGGGGGTTCGGTTGGGAGCGGGCGGGAGTCGG
GGCGCGTCGCGTAGTTTTGGTTGCGTTTCGTTTCGGTCGTCGCGCGTTTT
CGATACGTTCGGTCGGGCGCGCGTTTGCGGGTTTTCGGAATTCGAGGTTC
GGTTTGGGGCGCGGTTGTTGGGCGTTAGGTTCGCGACGTTGAGGTGCGCG
CGTTTCGGGCGGGAGGAGGGGTTGTATCGTTTGGCGAATGGGAGGGGGAT
TGGTAGGTTTTTTTTTTTAAGGGAGGTCGTTTGTCGTTTAGATTAAATT
TAGGAAGGTTTTTAAAAGAAGTAGAGTTTTCGCGGGGGGAAGTTTGTTTT
TTGAGAGGTGGTCGTAGACGAATTTATTGTTTAGTTTGGTATTTCGAAGTC
GTTTCGTTTTTGGTTTTTTTCGTTGTTTTTGCGCGTAGCGGGGGTAGTGTTT
TTATATTTACGCGTGATGGGAAGGTCGGTTTGGGGGTGGGAAGGTTTATC
GAAATAGATGGTTTTTATATTTTA

[SEQ ID NO: 28]

FIG 1R

AATTTAGAAATAAATAAATATATATGTATACGTATATAAATATATTTTAA
ATTAAAAAATATTTTTAGATAGTGGTATGTATTATATTTAGAAATTAATAA
CGAAGTAAATTATGGGATGTTATTTACGTTTGTTTTAAAGGTATCGAATTT
ATAAATTATTTTAGGTGCGGAGTAGGATAGGTTGAAAATAGGAATGATAT
GAATTCGCGCGGAATAGTTGTCGGCGCGGTGTTTAGGGCGGTATTTCGTT
CGGTTTCGGTTTTTTAGTTTTGGGTTCGATTTTATTACGTTTTGTTTCG
ACGCGAACGCGGAGTTCGAGCGCGCGTTACGTCGTGTGGGGTCGAAGAG
GTTGTTATTTAGAGGCGGAGTGCGGGTTCGCGAGGGTTTTATTCGATTTT
CGTTTTCGTTAGTATTTACGGATTCGCGTTTTCGTCGCGCGTCGATTCGGG
AGTAGTATCGTTTTCGGTATAGGAGTTTTACGCGTTTTTTATTTAATAGGA
AGTTGGGTGGAAGTAGCGCGGATTTACGGTATATCGAACGTATTTTAATA
GAATTCGACGTAGATACGCGTTTTTAATCGGCGGAGATATTGGTAGGGTT
AGAAACGCGCGTAGCGGGGGCGGGAGGTCGGTAAGTTTTCGTTTTGTT
CGAGATTTCGTTTCGGTTCGGTTTCGTTTTTTTTTTGTTTTTTTTTTTGTA
CGTACGGGTTTCGTTTTCGCGCGACGTTTTTGTTGATTCGGAAACGGAT
TTTTCGGAGTCGAGGTTCGTTCGGGTGAGTGTTTTCGTTTTTGTGGTTAA
ATTTAGTTACGTAGTTTTTTTTTGCGGCGTTTTTATATTCGGGGTTTGTT
GGTTTTCGCGGATGTTATAGGTTCGGTAATCGTTTTTTGTCGGCGGGGAG
TTTCGCGACGTTCGGAAATGTTTCGAAGTTTGTCGTTTAGTTGTTAGATTT
GCGTTTGTGTTCGGTTTCGTTATTGAGGTCGTTTTGTTCGGTTTTTTATT
TTAGTTTTTTTTATCGTTCGTTTATTTATCGCGCGCGGTTTTAGGTTTCGA
TTCGGTATGTGGTTTGTTTTTATCGTTTT
[SEQ ID NO: 29]

GGGACGATGGAAGATAAGTTATATGTCGAATCGGGATTTGAGGTCGCGCG
CGATAGGATGGGCGGACGGTGAAGAGAATTAGGGTGGAAGGGTCGGATA
GGGGCGATTTTAGTGACGGAATCGGATATAGACGTAGATTTGGTAGTTGG
GCGATAGGTTTCGGAGTATTTTCGGGCGTCGCGGGATTTTCGTCGATAGG
AGGGCGGTTGTCGAGTTTGTGATATTCGCGGAGATTAGTAGATTTCGGGT
GTGGAGGACGTCGTAGGAAGGGAATTGCGTGGTTGGGTTTGGTTATAAAA
AGCGGAGGGTATTTATTCGAGCGGATTTCGGTTTCGGAGAATTCGTTTTCG
GGTTAATAAAAAACGTCGCGCGAGGGGCGGGGTTCGTACGTGTAGGGAG
GGGAGGTAGAGAAAAAGGCGGGGTCGGGTCGGGCGGGGTTTCGGGTAG
GGGCGGGGAGTTTATCGATTTTTCGTTTTCGTTGCGCGCGTTTTGGTTTTG
TTAGTGTTTTCGTCGGTTGAAAGCGCGTGTTTGCGTCGGGTTTTGTTGGAG
TGCGTTCGGTGTGTCGTGGGTTCGCGTTGTTTTTATTTAATTTTTTGTTAGG
TAAGAGGCGCGTGAGGTTTTTGTGTCGGGGCGGTGTTGTTTTCGAGTCG
GCGCGCGGCGGGGACGCGAGTTCGTAGGTGTTGGCGGGAGCGAGAGTCG
GGTGGGATTTTCGCGAGTTCGTATTCGTTTTGGGTAGTAGTTTTTTCG
GTTTTATACGGCGTGACGCGCGTTCGGGTTTCGCGTTCGCGTCGAGGTAG
AGGCGTAGTAGGGGTCGGGTTTAGGGTTGGAGGGGTCGGGATCGGGCGG
GGTGTCGTTTTGGATATCGCGTCGGTAGTTGTTTCGCGCGGGTTTATGTTA
TTTTTATTTTTAATTTGTTTTGTTTCGTATTTGAGATGATTTATAAATTCGG
TATTTTGGGATAGGCGTGGATGATATTTTATAATTTATTTCGTTATTAATT
TTTAAATGTAATATATATTATTATTTAAAAGTATTTTTTAATTTGAAATAT
ATTTGTATACGTATATATGTATATTTATTTATTTTTGAATT
[SEQ ED NO: 30]

FIG 1S

```
TGCGCGTTGTTGCGTTGAGGTCGAATGAAGCGTAGTACGGTGCGGGTAGT
TCGAGGTTTCGAGGTTGGGTTTTGTTTGTTTGGGATTGCGTCGTGTTTAGT
TTCGGTTTTTTTTTGTGGGTAAGGATGGTTGAGTTTAGTTTTTACGGTAGC
GGTTTTTTGTGTTATTAGTAGTTTTTTTTTGCGTTTTTCGTTTTTTTTTTT
AGATTGGATTTTTTTTTTTTTCGCGTTTTTTTTTCGTATTTTTTATTCGTT
GGTTTTTTTTTAGTTGTTTTTTTTTAGGTTTTTTTGGTTGCGCGCGTTTT
TTTTTTCGTTTTTTTTTTTTCGTAGTTTCGTCGTTTTGGTGTTTTTTGTTCG
GTTCGGTCGGCGTTCGTTTTCGGTTTCGGTTTCGTTAGTTCGGGTTTTCGCG
TTCGGAGTAGTTTAGTTTTGTAGTGGTTCGGGATTCGATGTTATGAGAGGG
AAGCGAGTCGGGCGTTTAGATTTTTAGGAGGCGTCGGATGCGCGGCGGGT
TTTGGGATCGGGTTTTTTTTCGGTTCGTTTTGTTTTCGGGTGATTATTTGG
TTTCGTTTATAGTTTTGTTTTTTTCGGAGGAGTTATCGGTGTCGCGTGCGTG
TGGAGTATTTGTAGATATGATTGCGTGGAGGAGATTTTAGTCGTTGTTTTT
GTTTTTCGGGTTGTTGGTGTTGTGCGCGAGGTTTTTTATTGTAGCGAAGGG
TAAGACGGATTTGTTTTTGGTCGGGGAGGCGGTAGAGTTTTCGGAGGTTT
CGTGTGCGGACGCGAGTGTGCGTTTTGGGGATCGTAGGGTACGGAGTGGT
CGTTTTTGTTCGGCGTTGTTTATCGTCGAAGTTCGGGGAACGCGATGTAC
GGGAGGGAGTTTTTATCGCGTTTTTTTAGTTTTTTGGGTTTTCGTTTTAT
TTCGTTATTTTTTTTTTTTTGGGTTTATAGGAGAGATTTTTTTTTTTCG
GTAGTATAGGGTGTTAAGGAGAAAGGAATTTAATACGAGTTGGGTTGGAA
TTGTGTTTCGTCGGGCGGTGTTGTTTTTTCGAGACGTGGATTTTACGGG
TCGGGGTGGTTGAGGGGTAGTTTTAGGATTTTTTTTCGGATTCGACGCG
TTTGGGAAAGCGTTTCGGGTGAAGTCGGTTTGGAAAGTTCGGGTTTTTAC
GGGGGTTTTGGTATTAATAGGTAAAGGTTTTCGTCGGTTCGGTTTTTTCGT
ATTTATATATTTTATTTTTTTTTTTTTTTTTTTTTTTAACGTTTTTAGTCGG
CGAGGAGTAGTTGTTTTAGAAGGTCGTTTTCGTTTTTTTTTTTTCGGATT
TCGTTTTTT
```
[SEQ ID NO:31]

FIG 1T

AAGGAGCGAAGTTCGGGGGAGAGGAAAGCGGGGGCGATTTTTTAGAGGT
AGTTATTTTTCGTCGGTTGAGGACGTTGGAGAGGGAAGGAGGAGAGGAG
GAATGGGGTGTATGGGTGCGAGGAGGTCGGGTCGGCGGAGATTTTTGTTT
ATTGGTATTAAAATTTTCGTAGAGAGTTCGAATTTTTTAGGTCGGTTTTAT
TCGGGACGTTTTTTTAGGCGCGTCGGGTTCGGGGAGAAAGTTTTGGGAAT
TGTTTTTTAGTTATTTCGATTCGTGGAGTTTACGTTTCGGAGGAGGTAATA
TCGTTTCGGCGGAGTATAGTTTTAGTTTAATTCGTATTGGGTTTTTTTTTTT
TTGATATTTTGTATTGTCGAGAAAAGAGATTTTTTTTGTGAGTTTAAGAG
AGGGGGAAGGAATGGCGGGGTGGGGCGGGGGTTTAGGAGGGTTGGGGAG
AGCGCGATGGAAGTTTTTTTTCGTGTATCGCGTTTTTCGAGTTTCGGCGAT
GGAGTAGCGTCGGGTAGAGGCGGTTATTTCGTATTTTGCGGTTTTAAAAC
GTATATTCGCGTTCGTATACGGGGTTTTCGAGGGTTTTATCGTTTTTTCGGT
TAGGAGTAAGTTCGTTTTATTTTTCGTTGTAGTGAGGAGTTTCGCGTATAG
TATTAGTAGTTCGAGAAGTAGGAGTAGCGATTGGAATTTTTTTACGTAGT
TATGTTTGTAGATATTTTATACGTACGCGATATCGATGGTTTTTTCGAGGA
AGGTAGGGTTATGAGCGGAGTTAAATAATTATTCGAGGGTAAGGCGAGTC
GGAGAGAGAGTTCGGTTTTAAGATTCGTCGCGTATTCGACGTTTTTTGAAG
GTTTGGGCGTTCGGTTCGTTTTTTTTTATAGTATCGGGTTTCGAGTTATTG
TAGGGTTGAGTTGTTTCGAGCGCGGAGATTCGGGTTGGCGGGGTCGGGGT
CGGGGACGAGCGTCGGTCGAGTCGGGTAGGAAGGTATTAAGGCGGCGAG
GTTGCGGGAGGGGGAGAAGCGGGGAGAGGAGCGCGCGTAGTTAGGAGA
GATTTGGAGAGGAGGTAGTTGGAGAGAGAGTTAGCGAGTGGGAGATGCG
GGGAGGGGGGCGCGGGGGGGAGGAGAGATTTAGTTTAGAGAGAAAAGG
CGGAGAGCGTAGAAGAAGGGTTGTTAGTGGTATAAGGAGTCGTTGTCGTG
GAGGTTGGATTTAATTATTTTTATTTATAGAGAGGGGATCGAGGTTGGGT
ACGGCGTAGTTTTAGATAGATAGAGTTTAGTTTCGGGGTTTCGGGTTGTTC
GTATCGTGTTGCGTTTTATTCGGTTTTAGCGTAGTAGCGCGTA
[SEQ ID NO: 32]

GATTTTTTGGGTTAGGATATGTGAGAGTTGCGTAGGTTTGGGTTCGGCGTG
GCGGAGGTGCGCGAGAGCGGTTAGAAGAGGGCGTTAGAGAGTTAGGCGC
GGTTCGCGGAGGAGTTCGCGTCGGTTTTTATATTTAGTTTCGCGTCGCGCG
GATTTATCGAGTTCGCGTTTAGACGTTTTAGTTTTATCGAGAGGTCGTTCG
GGTCGTGTTTTTTTTTTTTTAGGTGTAGGTAGAGTTTTCGAGTTATGGTT
AGTTTTTTCGGTAGTTTCGAAGTTATTGGTAAGTTTCGAGGTAGGGATGGT
CGGTTAGGAGGGAGGAGGACGACGTTTTTTCGAAGAGAAGAGGTTGG
GGTTGTAGTTGGAGGGGGGAAGCGTATAGTTCGAGGATTGCGAGAACGG
GGAGGACGCGTCGCGGTTAGGTAGGGAGGAGATCGGTATTTAGATAGGT
GGCGATCGTAGAGGAGTAAGTGACGCGGGCGTTGGGGTTCGGGGGTGTC
GGGGGCGTCGGTAGGGCGGCGGGAGGTTTCGTGGTCGGTTTCGGGTTGA
AGTTGGTATTTTAGCGGTAATTTCGAAGGGCGCGGAGTGATAGCGCGTGA
CGGTTTTCGAGACGTTAGTTGTCGTTTTTCGGTTGTGTGGTTTTGATTTTTT
GATTTTTTTACGACGTCGTTGGTTGGGAGATTTATTGGATTTTGCGGTTGG
TTAAAAAGAGAGGGGTAGTTTCGCGTTTTGGGGGTTTTTAGTAGGGGAAG
TGGCGGGTGTTGCGTTGGGTATTTTGTTTGGGGTATTTGTTTGGGATTTTG
TTGGTGTTTTTTATTTGGCGAGGGGTTAGTGGTGGGGGTAGGGGG
[SEQ ID NO: 33]

FIG 1U

TTTTTTATTTTTATTATTGGTTTTTCGTTAGGTGAGAGGTATTAATAGGGTT
TTAGATAGATGTTTTAGATAGGATGTTTAGCGTAATATTCGTTATTTTTTT
GTTAGGGGTTTTTAGGACGCGGGGTTGTTTTTTTTTTTGGTTAGTCGTAG
AGTTTAGTGGGTTTTTAGTTAGCGACGTCGTGGGAGAATTAGGAAGTTA
AAGTTATATAGTCGAGAAGCGGTAGTTGGCGTTTCGGAGGTCGTTACGCG
TTGTTATTTCGCGTTTTTCGGAGTTGTCGTTAAAATATTAATTTTAATTCGG
GGTCGGTTACGGAGTTTTTCGTCGTTTTATCGGCGTTTTCGGTATTTTCGG
ATTTTAGCGTTCGCGTTATTTATTTTTTGCGGTCGTTATTGTTTGGGTGT
CGGTTTTTTTTTGTTTGGTCGCGGCGCGTTTTTTCGTTTCGTAGTTTTCG
GGTTGTGCGTTTTTTTTTTTAGTTATAGTTTTAGTTTTTTTTTTCGGGAGG
GACGTCGTTTTTTTTTTTTTGGGTCGGTTATTTTTGTTTCGGGGTTTGTTA
GTGGTTTCGGAGTTGTCGGAAGGGTTGGTTATGGTTCGGGGGTTTTGTTTG
TATTTGGAGAAGAGGAAGGATACGGTTCGAGCGGTTTTTCGGTGGAGTTG
GGGCGTTTGAGCGCGGGTTCGGTGGGTTCGCGCGGCGCGGAGTTGGGTAT
AGGGGTCGGCGCGGGTTTTTTCGCGGGTCGCGTTTGGTTTTTTGGCGTTTT
TTTTTGGTCGTTTTCGCGTATTTTCGTTACGTCGGGTTTAGGTTTGCGTAGT
TTTTATATGTTTTGGTTTAGGAGGTT
[SEQ ID NO: 34]

TCGGCGTTTAGGTGACGTTGATTTTGTTGGTTTATCGTTTTGGGGGTTATTT
AATTTTTTAGCGATGTTTTTAGTTGGGGAGGTTAAGAAGTGTTTCGTTTA
AGGTTTTTTAATATTCGATTTTTAGATTTTTAATTTTGGGTTAGTTATATCG
TAAATTTTTTTAGTTGTTTTTTTTGCGTTTTGCGTTTTTTTTTTACGTTATTT
GTTAGGGAGTCGTTAAATAGTAAGATCGCGCGTTTTGCGGTTTTAGAGTG
CGGATTTCGGTCGCGTGCGGTTTTGATCGCGTCGTTTTATTTTGGCGGGG
TTACGTACGGACGTTATGGTTGGCGTCGCGGAGTCGGGCGATGCGCGCGG
ATTTTTTCGGGGTTTTGATTGTTTTTGAGTTTTTTTGCGGGGGGCGTGCGC
GGTTCGTTTTTCGCGGCGTTACGCGGTTTTTTTTCGGTCGGGGATTGGTGC
GTCGGGCGGGGCGGGGCGGGGCGGGATAAAGGCGCGGGGTTTGGTTGCG
CGGGGTTTGCGGGTAGTTTTAATTTTGGGTTCGTAGTTTGCGTTGGGTGCG
TAGGAAGGTTAGTGTGGGGGTCGTTCGATATTTTTTTTCGCGGAGGTGGG
AGTCGAGTTATATTTTGGAGTGGGGATTGGTCGCGGAGCGGGTTGTTTAG
GGTCGGTCGAGGTCGGGGCGAGTTTTGCGCGGCGTTGGAGATTTTGTATT
TTCGGGCGCGCGTAGGGTTTTCGGTCGTGGTCGTAGAGTTAGGAGGGGCG
GTTTCGGAGTTCGGCGCGGGGAGGGTTTAGGCGTAGTCGGGGTTGGTAGG
GCGCGATATTCGTTTTTTTTATTTTGAAAGGGTTTTTTACGTCGAGAAG
AGGGGCGGGTATGGTCGGTTCGGCGAAATCGGTTTGTATAGATTTTGGGA
AGTTATCGTTTGCGGAGGGTGGGATTTTATAGTTTGTTTATTTGTTTAGGT
TGAGATTTCGTGTTTTAGTTTTGGATGTTTTACGGGTTTTTCGTTCGGGTA
GCGGCGTACGGGAGGAGAAGATTTTCGGTTTGTAGTTAGATTTTTTTTGA
GATTTTTTTTAGTTTAGGTTTAGAGTTTTGGG
[SEQ ID NO: 35]

FIG 1V

TTTAAAGTTTTAAGTTTGAGTTAGGGAGGGTTTTAGAGGGAGGTTTGATTG
TAGATCGGGAGTTTTTTTTTTCGTGCGTCGTTGTTCGGGACGAGAAATTC
GTGGGGTATTTAGGATTAGGATACGAGGTTTTAGTTTGGGTAGGTGGATA
AGTTGTGGGGTTTTATTTTCGTAGGCGATGGTTTTTAAAGTTTGTATAA
ATCGGTTTCGTCGGGTCGGTTATGTTCGTTTTTTTTTCGGCGTGGGAAGTT
TTTTTAAAAGTGGAGGGGAGCGAGTGTCGCGTTTTGTTAATTTCGATTGCG
TTTGGGTTTTTTTCGCGTCGGGTTTCGGAGTCGTTTTTTTTGATTTTGCGAT
TACGGTCGGGGATTTTGCGCGCGTTCGGGAATGTAGAGTTTTTAGCGTCG
CGTAGGGTTCGTTTCGATTTCGGTCGGTTTTGGGTAATTCGTTTCGCGGTT
AGTTTTTATTTTAAGATGTGGTTCGGTTTTTATTTTCGCGGGGGGGAAATG
TCGGGCGATTTTTATATTGATTTTTTTGCGTATTTAGCGTAAATTACGAATT
TAGAGTTGGAGTTGTTCGTAGATTTCGCGTAGTTAGATTTCGCGTTTTTAT
TTCGTTTCGTTTCGTTTCGTTCGGCGTATTAATTTTCGGTCGAGGAGGGGT
CGCGTGGCGTCGCGGGGGGCGGGTCGCGTACGTTTTCGTAGGGAGGATT
TAGGGATAGTTAGGGTTTCGGGAGAGTTCGCGCGTATCGTTCGGTTTCGC
GGCGTTAGTTATGGCGTTCGTGCGTGGTTTCGTTAGGGATGGGGCGACGC
GGTTAGAGTCGTACGCGATCGAAATTCGTATTTTGGAGTCGTAGAGCGCG
CGGTTTTGTTGTTTAGCGGTTTTTTGGTAAGTGACGTGGGGAAGAAACGTA
GGGCGTAGGAGAGATAGTTGGAAAGGTTTGCGGTGTAGTTGGTTTAGGAT
TGAGGGTTTGGAGGTCGGGTGTTGGAAGATTTTGAGCGAGGTATTTTTG
GTTTTTTTAGTTGGGAGGTATCGTTGAAAAATTAGGTGATTTTTAAGACGG
TAGATTAGTAGAGTTAGCGTTATTTGGGCGTCGG
[SEQ ID NO: 36]

AAAGTTAAGCGTCGTCGTTATTTAAGGTATTGCGTTGATGCGTTGCGGGTC
GATTAGGTGTTTTCGTCGGGGCGTTTTTTTTTACGTAGGAAGGGTTACGTC
GAGAGAGGTAGGTAATAAGGGTACGGTTGGAGGTCGGAAGGTTATTTCGT
TTTCGGCGGGGCGGGCGCGGTTTAGTTTTATTTTCGGGTACGTTCGGGCG
GGGCGATTGTAGGGAACGGGGCGGGGAGGCGATAGTTTTCGGTTTCGTCG
CGCGTTAGTTCGTTTTCGTTGTTCGGAGGCGTCGTAGGTTTGGGTTTTCGG
ATAGTTGAGTTCGAGCGTCGTTTTTCGAAAGGTGAAGGCGGTTCGGGGAG
GCGGGGACGGTGACGGGGGCGGGGGTCGCGGGCGGTTTTCGACGGTTGT
CGCGGGGTTAGTTTAAAGTTTTCGATTTTCGGTAGTTGCGTTTTTCGCGCG
GGGCGTCGGAGTAGGGCGGGTTAAGTTGGTTTGCGGTCGCGGCGGGAAG
AAGGGTTAGCGAAGTATTTTCGATCGGGTTTAGGCGTCGGACGTCGGGGG
GCGTTTCGTTGTAATTTTTTTTTGGAAGTTTCGATACGAGTTTCGGTTCGCG
CGCGCGTTTTTTTTACGGTTACGCGCGTATTTTGTCGTTCGTATTTTCGCGCG
TTTTTCGTTTATTTTTTTTTTTTTTTTATTTTTATATTTTAAAATAGGTTA
AGGGGTGGAAGTTATATTTGGTGTAGTTTTCGGTTTTGATGTAAAAGTAGT
TTTTGTTTTTGGTTGCGGGATAGCGTTGTGATTATTCGTAACGGGAGAGTT
GTTGTTAGTCGTTATATCGTGCGGAAAGCGTCGGCGATCGGAGTATTGAT
AATGGTTTGTATAGGGGAGCGGAGAGAAGTTTTTGTTGCGTTTTAGATTC
GTTGTTTCGGCGTTCGTTCGTAGGGAGGAGGGGGCGCGATAGGTCGTTTA
GCGCGTGTTTCGGAGTTCGCGTTCGGGTTTGGTCGTTTGGGTGAGTTTTTG
TTCGTTTTTTGTTTTTTAGTAGTTCGGGGTGGTTGTTTATTTTGTAAATAG
TTTTGTAATACGATTAAAATAGGCGAGATAGTTA
[SEQ ID NO: 37]

FIG 1W

TGGTTGTTTCGTTTGTTTTGATCGTATTGTAAGGTTGTTTGTAAGGTAAAT
AGTTATTTCGGGTTATTGGAAAGGTAGGGGACGAGTAGGAATTTATTTAG
GCGGTTAGATTCGGGCGCGGGTTTCGGGGTACGCGTTAGACGATTTGTCG
CGTTTTTTTTTTTTGCGGGCGGGCGTCGAGGTAGCGGATTTAGGGCGTAA
TAGAAGTTTTTTTCGTTTTTTATGTAGATTATTGTTAGTGTTTCGGTCGT
CGGCGTTTTCGTACGGTGTGGCGATTGGTAGTAGTTTTTCGTTGCGAGT
AGTTATAGCGTTGTTTCGTAGTTAGGGGTAAAAGTTGTTTTGTATTAGAG
TCGAGGGTTGTATTAGGTGTAATTTTTATTTTTGATTTATTTTAGAGTGTG
AGGATGAAAGGAAGAGGAAAAAATAGACGGAGGGCGCGCGGGGGTGCG
GGCGGTAGGGTGCGCGCGTGGTCGTGGGGGAGCGCGCGCGGGTCGGG
GTTCGTGTCGGGGTTTTTAAAGAGAAGTTGTAGCGAGGCGTTTTCGGCGT
TCGGCGTTTGGGTTCGGTCGGGGGTGTTTCGTTAGTTTTTTTTTCGTCGCG
GTCGTAGGTTAGTTTGGTTCGTTTATTTCGGCGTTTCGCGCGGGAAGCGT
AGTTATCGGGGATCGGGGGTTTTGGGTTGGTTTCGCGATAGTCGTCGGGA
GATCGTTCGCGGTTTTCGTTTTCGTTATCGTTTTCGTTTTTCGGGTCGTTT
TTATTTTTCGGGAGGCGGCGTTCGGGTTTAGTTGTTCGGGAATTTAGGTTT
GCGGCGTTTTCGGGTAGCGAAGGCGGGTTGGCGCGCGGCGGAGTCGGGG
ATTGTCGTTTTTTCGTTTCGTTTTTGTAATCGTTTCGTTCGAACGTGTTCG
GGAAGTGAGGTTGGGTCGCGTTCGTTCGTCGGGGACGGGGTGATTTTTC
GGTTTTTAGTCGTGTTTTGTTGTTTGTTTTTTCGGCGTGGTTTTTTTGCG
TAGGAGAAGACGTTTCGGCGGGAGTATTTGGTCGGTTCGTAGCGTATTAG
CGTAGTATTTTGGGTGACGACGACGTTTGGTTTT
[SEQ ID NO: 38]

GCGATTTTAGAGGAGTAATCGGGTTTTAATTTTTTGCGTTCGTTTTGTTAT
AATTTTTTTTATTTATTTTTATTTTATTTTTATAATATTTTTATTGGGGGG
GTTTTTTGTGTTTCGGATTTTTTTTTTATGGTTTTTTTAGTCGAAGTCGGG
GGTTTTTTGGGCGGTTTGGAGGGTTTGGGTTAGTAGGTGGGTTCGTATTTT
TTGTTGTTTTTGTCGGGGAGCGGTCGTCGTTGTTGGGCGAGCGTAGGAGC
GCGGCGGAGCGGAGCGCGCGCGGCGGGTCGGGGGTTGCGTAGTTGGCGT
ATTTGTACGGTATTTTGCGTCGTCGGTAGTTTTATTGTCGTATCGGTTTTTA
TTTGTAGATTTTGTTCGACGGTAGCGTGTAGGGTATTCGGTAGGATTATAG
TTTTTTCGGTACGTATTAGTATTTCGATTTTATTTTTATTTGCGTTTTAGTTC
GGTTTTTCGTTTTTTTTTTGTATTTTTTTTTTGTTTGTTAAGGGCGTTAT
CGTCGCGCGGAGTTCGGAGTTTTTTGGATTTATTCGGTGTAAGACGTAGG
TTGGGGTTGAAGGGTTGGTTAGAGTAGTCGCGG
[SEQ ID NO: 39]

FIG 1X

TCGCGGTTGTTTTGGTTAGTTTTTTAGTTTTAGTTTGCGTTTTGTATCGGAT
GGGTTTAGGGGAGTTTCGGGTTTCGCGCGGCGATGACGTTTTGGTAGGT
AAAGAGGGAGGTGTAAGGGGAGGGAACGAGGAGTCGAGTTGGGGCGTA
GATGGGGGTGGGGTCGGGATGTTAGTACGTATCGAAGAGGTTGTGGTTTT
GTCGGGTGTTTTGTACGTTGTCGTCGGGTAGGATTTGTAGGTGGAAGTCG
GTGCGGTAATAGAGTTGTCGGCGGCGTAGGATGTCGTGTAGGTGCGTTAG
TTGCGTAGTTTTCGGTTCGTCGCGCGCGTTTCGTTTCGTCGCGTTTTTGCGT
TCGTTTAGTAGCGGCGGTCGTTTTTCGGTAGGAGGTAATAGGAAATGCGA
ATTTATTTGTTGGTTTAAGTTTTTTAGGTCGTTTAGAAAGTTTTCGATTTCG
GTTAAGGGAGTTATGGAGGGGGAGATTCGGAATATAAAAGATTTTTTTAG
TAAAGAGTGTTGTGGGGGTGGGATGGAGGTGGATAGAGAAAAATTATAG
TAAAACGAGCGTAAAAAGTTAAGGTTCGGTTATTTTTTGAGGTCGT
[SEQ ID NO: 40]

TATATTTTATTTGTGTCGTATATGTGAAGATATAATTGTAAATCGTTTACG
ATTTGAGTTAAGATTTGAGTTTTTGAGGTTAGGAGATCGTTAGGGAAT
GTGAGTGTTTAGACGGGCGTTGAGTTTAGTTCGGAGATTTATTTCGTTCG
TAGTAGCGGCGCGGGTTTTAGAGAGTTTCGTATTCGGTCGCGTTTTAGTTA
CGTTGATTCGGTTGTGTTCGTAGTGTCGCGTTGTCGCGTAGTTAGGTGTCG
TCGGGTTGGCGCGGTTATTTATGATTGCGTGGTTGGTTGGGGGTTCGGG
GTCGGGGAGTAGTCGGGATTCGTCGTTTTTTTATGATTTTTTCGGGTCGA
ATTACGGGATCGTTACGTTGAAGGTGGCGTCGCGGGTTTTCGGGGTCGCG
CGAGTGTAGGGGTCGTTTTCGGTCGGTCGCGAAGTTCGCGGTATCGATTTT
TCGCGAGATTTCGGCGATTTTTTTTTCGTTTTCGTTTTTTCGTTTTTGTTT
TTTTTTAGTTTTGGTGTGGGCGGTTTTCGTTATGGTTGCGTTGCGAAGGTTT
TTGTGGTCGTTATTTCGGGTGTTTTTTTATTTTGCGTTTATTAGTTTTTTT
TGGGTCGTGGGGGCGGTTTGCGGTGATTATTTGGGTTTTTTTGGTCGGTT
TTTTTTTTTCGAGAGGATGAGGAGAGGGTTGTGGCGGAGGCGGTATGGA
GGCGGCGGCGGCGTTGGGGGGAGTTGAGCGTGGCGGCGGCGGTCGGCGG
GGGGTTGGTCGGTTTGGTATGTTATTAGTTGTACGGGGATTTAGGGTCGG
TTCGTCGGCGATCGGGCGATTTTTAAAGAGCGCGGTTACGGAGTTCGAGG
ATTCGTTTCGCGGTCGGGGGATGTTGTTTATTTTAGTGGCGGTTGTTAAGG
AGACGGTGAGTGCGCGAGCGCGCGTTATATTTGCGCGGGGGATGTGATTT
TCGTGTCGGGTACGTAGGATTTTGGAGGTTGTGGGACGGTGTAAGCGTT
GTGGTCGCGGGTGAGGAATTTTTCGTGAGCGAGGTTGATATTTAGGTCGG
ATAGTTTAGGATTCGGTTATTTACGTATTGGGA
[SEQ ID NO: 41]

FIG 1Y

TTTTAATACGTGGGTGATCGGATTTTAGGTTGTTCGGTTTAGGTGTTAGTT
TCGTTTACGGGAAGTTTTTATTCGCGGTTATAGCGTTTGTATCGTTTTTAT
AGTTTTTAGGGTTTTGCGTATTCGGTACGAAGGTTATATTTTTCGCGTAGG
TGTGACGCGCGTTCGCGTATTTATCGTTTTTTTGGTAGTCGTTATTGGGAT
GGGTAGTATTTTTCGGTCGCGGGGCGGGTTTTCGGGTTTCGTGGTCGCGTT
TTTTGAGGGTCGTTCGGTCGTCGGCGAGTCGGTTTTGGGGTTTTCGTATAG
TTGGTAGTATATTAGGTCGATTAGTTTTTCGTCGGTCGTCGTCGTTACGTTT
AGTTTTTTTAGCGTCGTCGTCGTTTTATGTCGTTTCGTTATAGTTTTTTT
TTTATTTTTCGGGAGGAGAAGGGTCGGTTAGGAAGGTTTAGGGTGGTTA
TCGTAGGTCGTTTTACGGTTTAAGGAGGGGTTGGTGAGCGTAGAGTGGA
GGAGATATTCGGGGTGGCGGTTATAAGAGTTTTCGTAGCGTAGTTATAGC
GGAGGTCGTTTATATTAGAGTTGGGAGGGGGTAGAGAACGGAGGGGCGG
GGGCGGGGGGGGGGTCGTCGAAATTTCGCGAGAAGTCGGTGTCGCGAG
TTTCGCGGTCGGTCGAGAGCGATTTTATATTCGCGCGGTTTCGGGGATTC
GCGACGTTATTTTAGCGTAGCGGTTTCGTGGTTCGGTTCGGGAAGATTAT
GGAAGAGGCGGCGGATTTCGGTTGTTTTCGGTTTCGAATTTTTAGTTTAA
TTACGTAGTTATAAATAATCGCGTTAGTTCGGCGATATTTGGTTACGCGAT
AGCGCGATATTGCGGGTATAGTCGAGTTAGCGTAATTGAGGCGCGGTCGA
GTGCGGGGTTTTTGGGGTTCGCGTCGTTGTTACGGGCGGGGTGGGTTTTC
GAGTTGGGTTTAGCGTTCGTTTGGGATATTTATATTTTTAACGGTTTTTTG
ATTTTAGGAAATTTAAGGTTTTGATTTAAGGTCGTGAACGATTTGTAATTG
TATTTTTATATATACGATATAAATGAGGTATA
[SEQ ID NO: 42]

GTTTGGGTACGCGGGATAGGTTGTATTCGTTTGTTAGAGGCGTTTTATCGA
GGCGTTACGGGTGAAGTTTTCGGTTTTATTTACGGGGCGGGGTTTCGGTTC
GGTTCGATTATTGTTCGCGGTGGGGGAGGGGGATGGATTACGTTACGCGT
TAAAGGCGATCGCGATTTTTTTTTGTAGGTAGTTTGGAAGGTTTTTTTTT
TTTTTACGTTATTTTTTCGTGGTATTGAAAAGTTTCGTTTTTTTTTTTAG
TTTCGTTTTTTCGAGCGTTTTTTTATTGTTTGGAATGGTGCGGTTTTAGG
TCGCGGGTTACGCGGCGGAGGGGCGTGGTTTGTTTTCGGTTTAGTCGGTT
TTTTTTTGTTTTTGTTGGAGTTCGGGGAGTGGCGTTGGTTGTTAGAGCGAT
GTCGGGTCGGAGTTGCGTCGTTTTAGTTTTTTTGGTTGTCGTCGTTAGTTGT
GTCGTCGCGTAGTACGCGTCGTCGGTGAGTGAGTTTGAGTCGAGGCGTAG
AGAGGGGCGTGTAGGTGCGGGCGCGGATGGAGGCGTAGGTGTGGCGGCG
CGAGCGGGTATAAGGAATATTTCGTGTTGGGTAGTTTT
[SEQ ID NO: 43]

FIG 1Z

GAAGTTGTTTAGTACGAGGTGTTTTTTGTATTCGTTCGCGTCGTTATATTTG
CGTTTTTATTCGCGTTCGTATTTGTACGTTTTTTTTGCGTTTCGGTTTAAG
TTTATTTATCGGCGGCGCGTGTTGCGCGACGGTATAGTTGACGGCGGTAG
TTAGGAGGATTAAGGCGACGTAATTTCGGTTCGGTATCGTTTTAGTAGTTA
ACGTTATTTTTCGGATTTTAGTAGAGGTAAAGAAGAGTCGGTTGGGTCGG
GGGTAGGTTACGTTTTTTTCGTCGCGTGATTCGCGATTTGGGATCGTATTA
TTTTAGGTAGTAGGGGGAACGTTCGGAGGAGGCGGGATTGGGAGGAGAG
GACGGGGTTTTTTAGTGTTACGAAAAGGGTGGCGTAGAGAAAGAGAGAG
AGTTTTTTAGGTTATTTGTAGAAGGAGAGTCGCGATCGTTTTGGCGCGTG
GCGTGATTTATTTTTTTTTTTATCGCGGGTAATAGTCGGATCGAGTCGGA
GTTTCGTTTCGTAGGTGGGGTCGGGAGTTTTATTCGTGGCGTTTCGATGGG
GCGTTTTAGTAGGCGGGTGTAGTTTGTTTCGCGTATTTAGGT
[SEQ ID NO: 44]

GGTAGTGTAGTTGTGGGAATTTTTTTACGCGTACGAATTTAGTTAACGATT
TTTGATAGATTTTTGGGAGTTTGATTAGAGATGTAAGGGGTGAAGGAGCG
TTTTTATCGTTAGGGAATTTTGGGGATAGAGCGTTTCGGTCGTTTGATGG
TCGAGGTAGGGTGCGATTAGGATTAGGACGGCGTCGGGAATTATATTA
TGGTTCGGATTTTTAAGATTTTAAAGTTCGTCGTCGTTATCGTCGCGGTTTT
GTTGTTAGTGAGTTTCGGTCGCGGTTTTGGTTGGGGAAGAGCGTATTTGG
CGTCGGGAGGGGGTAGGGAGACGGGGATACGGTAGGGATGTTTGGTTTT
GGTTATTTGCGGTCGGGTATGTTCGGGTAGGACGAATTCGTCGTCGGAGT
TAGGGGAAGAATTGGGTTTTCGGGTTGGGTAGGAGGGATTCGGTCGCGAG
GGAGTAGAGAGGCGGTTTTTTGGTTGTTCGAGTTCGCGAAGGGAGGGA
AGTTTTAGAATCGAGAGAGGGAGGGAGTTAAGGTGGAATTTATAGAGTG
AGTTTTTTGAAGATATAGAGCGGTTGTTTTTTTATTAATTAATTAA
[SEQ ID NO: 45]

TTAATTAATTAATGAGAGAGGTAATCGTTTGTGTTTTAGGAGGTTTATT
TTATGGGTTTTATTTTGATTTTTTTTTTTTCGATTTTGGAATTTTTTTTTT
TCGCGGGTTCGGGGTAGTTAGGGGGATCGTTTTTTTGTTTTTCGCGGTCG
GGTTTTTTTTGTTTAGTTCGGGGATTTAGTTTTTTTTTTGATTTCGACGGCG
AGTTCGTTTTGTTCGGATATGTTCGGTCGTAGGTGATTAGGGTTAGGTATT
TTTGTCGTGTTTTCGTTTTTTGTTTTTTTCGGCGTTAGGTGCGTTTTTTTT
TAGTTAGGGATCGCGGTCGGGATTTATTGGTAGTAGGATCGCGACGATGA
CGACGACGAATTTTAGGGTTTTGGGGATTCGGGTTATGGTATGGTTTTCGA
CGTCGTTTTGGGTTTTGGGTCGTATTTTGTTTCGGTTATTAGGCGGTCGGG
GCGTTTTGTTTTAGAGTTTTTAACGGTAGGAAGCGTTTTTTTATTTTTTG
TATTTTTGGTTAAATTTTTAAAAATTTATTAGAAATCGTTGGTTGAGTTCG
TGCGCGTGGAGAGGTTTTTATAGTTGTATTGTT
[SEQ ID NO: 46]

FIG 1AA

CGTTTGCGGAGGATTGCGTTGACGAGATTTTATTTATTGTTATTAATTTG
TGGTGGAATTTGTAGTTGTATATTGGATTTGATTCGTTTCGTTTCGAATGA
CGTTTGTTCGGAGGTAGTGAAAGTATAGTCGCGTCGTTTTAAGTTAGTTTG
GATATATAAATTAGTACGCGGTCGGAGAATTTCGTAATTTTTGCGTTTATA
AAATATATCGACGATGTTCGATTTATTTTAAGGGTTGAAATTTACGGGTTT
GAGAGATTATAAGAGCGTTTTTTATCGTTATGGAATAACGGGGATAGAAC
GTTTCGGTCGTTCGGGGGTTCGGAAAAGGTACGGTTTAGGATTTAGGGA
GGCGCGGGGAGTTAGGTTTGGGTTTCGGGTTTTTAAGATTTTTGTGTTCGT
TGTCGTCGCGGTTTTGTTGTTGGTGAGTTTCGTCGCGGTTTTTGGTTGGG
GAAGAGCGTGTTTGGCGTTTGGAGAGGGTAGGGAGAGAGGGGGATACGG
CGGGGGTGCGTGGTTCGGGTCGTTTGCGGTCGGGTATGTTCGGGTAAGAC
GTATTAGTCGTCGGAGTCGGGGGAAGAGATGGGTTTTCGGGTTGGGTAGG
AGCGATTTGGGTCGTTAGGGAATAGAGCGCGCGTTTTATTTGGTGTAAAT
TTTCGAATTTAGTGGGGGAGGGCGATAAGGAGGGAATTTTCGAGTAAGTT
GCGTGAAGTTACGGAGAGGTCGTCGGATTTTGATTTTGTTTTTTTTTTTAT
TTTTTGTTTTTTTTTTTTTTTTTTTTTTTTTTTTTTTTTTTTTTTTTTTTC
GTTTAGTTTTTGTTTAATTTTTTTTTTTTTGCGTTTTCGAATGAATTTTTA
AAGGCGTTTATTGTAGATCGTTTTGAATTTGCGGTCGGCGAAGAATTTTT
TGTGGTCGTTGCGGTTTAGTGGTTTCGTTTCGTGCGCGGGAGTCGTCGCGG
GCGTAGTTGGAGAGGTTTTTTTTTTTTTAGCGGTTGCGTTTTACGCGTG
CGGGGTCGTTTATCGTTAATGTTATTGTTTGGGGTTTTTTGGGAAAACGAG
ATTTAGGAGAAGGGAGTTGTGGTATTTG
[SEQ ID NO: 47]

TAAGTGTTATAATTTTTTTTTTTAAATTTCGTTTTTTTAAGGAATTTTAAA
TAATGGTATTGGCGATGAGCGGTTTCGTACGCGTAGGGGCGTAGTCGTTA
AGGAGGGGAAGGGGTTTTTTTAGTTGCGTTCGCGACGATTTTCGCGTACG
GAACGGAATTATTGGGTCGTAGCGATTATAGGGGAGTTTTTCGTCGGTCG
TAGGTTTAAAGCGATTTGTAATGAGCGTTTTAGGAATTTATTCGAAGGCG
TAAAAGAAAAAGAAATTAAGGTAGGAATTGAGCGAGGAAGGAAGGGAG
GGAAAGAAAGGAAGAAAGAGAAAAAGAGAAAGAAATAGAAAGTAAGGA
AAGAAAATAAAATTAAAGTTCGACGATTTTTCGTGGTTTTACGTAGTTTA
TTCGGGAATTTTTTTTTTGTCGTTTTTTTTATTGGATTCGGGAATTTATAT
TAAGTGGAGCGCGCGTTTTGTTTTTTGGCGGTTTAGGTCGTTTTGTTTAAT
TCGGGGATTTATTTTTTTTTCGATTTCGACGATTGGTGCGTTTTGTTCGGA
TATGTTCGGTCGTAGGCGATTCGGGTTACGTATTTTCGTCGTGTTTTTTTTT
GCGGGGATTTATTAATAGTAGGATCGCGGCGATAACGAGTATAAGGGTTT
TGGGGATTCGGGGTTTAGGTTTGGTTTTCGCGTTTTTTGGGTTTGGGTC
GTGTTTTTTTCGGGTTTTCGAAGCGGTCGGGGCGTTTGTTTTCGTTGTTTT
ATGGCGGTAGGGAACGTTTTTATAGTTTTTAGGTTCGTGGGTTTTAGTTT
TTAAAGTAGATCGGGTATCGTCGGTGTATTTTGTGGGCGTAGAGATTGCG
GGGTTTTTCGGTCGCGTGTTGATTTATGTGTTTAGGTTGATTTGGGGCGGC
GCGGTTGTATTTTTATTGTTTTCGGGTAGGCGTTATTCGGGGCGGGGCGAA
TTAGATTTAATGTGTAATTGTAAATTTTATTATAGGTTGGTGATAATAAAT
AAGAGTTTCGTTAACGTAATTTTTCGTAAGCG
[SEQ ID NO: 48]

FIG 1BB

TGTACGTTTATTGTTTGTTTTTTTTTGTACGTTTGGTGGGTTTTATTTTAG
GCGGGTGTTGCGACGGTGGTTATTGCGTTTTGCGTACGCGGGGGTAGTTT
TCGTCGTTATTTTTTTGGCGTATATGTTGAGTTTTTATCGCGATTCGTTGT
CGAGGGTAGATATTATTCGTAGTTTATAGGTAGAAGGTAGGTAGTGTCGC
GTGTCGCGTTTTGTTGGGTATTTTCGGGGCGTTTTCGTCGCGTTTAGTTAG
CGGATTCGGGAAGTGTTGTGGGTTGGGGGTTGCGGTTTCGAGTCGGGTTT
GTAGTCGTTCGGGCGTTTCGAGTTTAGGGTTTAGTTTTGCGGGTGTTTTCG
CGTTAGTAGGTTCGGGGTGTAGCGTTGGTGGTTGGGGGCGTATTTACGGT
CGAGTCGGGAAGGGATTTTAGCGTTTAGGGTGTGTTTTCGACGGGGATTA
TTGTTTTTGGGTTTTGGTTTGGGATTGCGCGGAGCGTAGCGCGGAAGGGT
GGGAGTTTTTAATTTTTAGTTTTGTGAAGTTGTTTATTTCGGAGTTTGGGTT
TGCGTATTTGTAGGATAGGTGTAATAAATAATATTTCGTTTATTAGATTGT
GGAAAGCGCGAGATGATAATGCGCGCGAAACGTTTAGCGTAGTATTCGGT
ATAGTTATAGTTAACGGTCGTTGGTATTATTGTAATGGTTTGGTTTTGGCG
CGGGAGTATCGGTAGTTGAGTTGGTAATATCGGGGATTCGGGTTTACGGT
TCGGAGATTAGGGATGGGTTGTTTCGAAGTCGCGAATTGTGGTAGTTTTG
GGTTTTTTAGTCGCGTCGGGGAAGTGTTAAGTGTTTCGTTTAATTTCGGGT
TCGGGGTTATGATTTGTAGGGGAGTGGGTGTTAAGGACGGTAGGGATTTG
AGGGTATCGTTTTCGAGGATTTGGTAGCGCGTTTTGGGTATTTAGCGCGGC
GAGTAGGTGGGTGTTGCGGAGAGGGAGTTTTTTTCGCGTTTTAATTTATAT
TTTGTCGTTTGGGTAGTCGCGGTCGTTTACGTTTTTTTTCGTTTGCGGGGGT
TAGACGGTTTTTTTTGGGGTCGGGGCGTAATTTATAAACGTTAATTTGATT
CGATTTGTCGTTTGTTCGTTTTTGTGATTTGGTGTCGGGGGTTTTTCGTTT
TCGCGTTTGGGGTTAGATAGTCGGTGATTTTTTCGGAAGGGTTATTTGGG
GATTAGTTAGATTAGGGGATATTTTCGGGGGCGGGGTAATGAGAAATTTG
TTGGAGTGTTCGGTTTTTTAATCGAAAA

[SEQ ID NO: 49]

FIG 1CC

TTTTCGGTTGAGGGGTCGAGTATTTTAGTAAATTTTTTATTGTTTCGTTTTC
GAGGGTGTTTTTGGTTTGGTTGGTTTTAGATGATTTTTCGGAGAGGGT
TATCGGTTGTTTGATTTTAGGCGCGGGAGCGAAGGGTTTTCGGTATTAGGT
TATAAGGGGCGGGTAGGCGGTAGGTCGGATTAGATTAGCGTTTGTGGATT
GCGTTTCGGTTTTAGGGAGGGTCGTTTGGTTTTCGTAGGCGGAGGGAGGC
GTGGGCGGTCGCGGTTGTTAGGCGGTAGAATGTGGATTGAGGCGCGGAA
GGGGTTTTTTTTCGTAGTATTTATTTGTTCGTCGCGTTGGGTGTTTAGAAC
GCGTTGTTAGGTTTTCGAGGGCGATATTTTAGATTTTGTCGTTTTTGATA
TTTATTTTTTGTAAATTATGGTTCGAATTCGGGGTTAAGCGAGATATTT
GATATTTTTCGGCGCGGTTGGAGGATTTAAGGTTGTTATAGTTCGCGATT
TCGGGATAGTTTATTTTTGATTTTCGGGTCGTGAGTTCGAATTTTCGATGTT
ATTAGTTTAGTTGTCGATATTTTCGACGTTATATTTCGGGATTTATTTATTT
TTATTCGTAGAAAGAAAAAAAAATCGTTAAGATTAAATTATTATAGTAAT
ATTAACGATCGTTGATTGTGGTTGTGTCGGGTATTGCGTTGAGCGTTTCGC
GCGTATTGTTATTTCGCGTTTTTTATAGTTTGATAGGCGAGGTGTTATTTAT
TATATTTATTTTATAGATGCGTAGATTTAGGTTTCGGGATAAGTAATTTTA
TAAGATTGGAGATTAGAAGTTTTATTTTTCGCGTTGCGTTTCGCGTAAT
TTTAAATTAAAATTTAGAGATAATGGTTTTCGTCGAGGATATATTTTGAAC
GTTAGAATTTTTTTCGATTCGGTCGTGGATACGTTTTAGTTATTAACGTT
GTATTTCGAGTTTGTTGACGCGGAGATATTCGTAGAGTTAGGTTTTGGGTT
CGGGACGTTCGGGCGGTTGTAAATTCGGTTCGGAGTCGTAGTTTTAATTT
ATAGTATTTTCGAGTTCGTTGGTTGGACGCGGCGGAGGCGTTTCGGGGG
TGTTTAGTAGGGCGCGGTACGCGGTATTGTTTATTTTTGTTTGTAGGTTG
CGGATGATGTTTGTTTTCGGTAGCGGGTCGCGGTAGAGGTTTAGTATGTAC
GTTAGAGGGGATGGCGACGAGGGTTGTTTTCGCGTACGTAGGAGCGTAGT
GGTTATCGTCGTAGTATTCGTTGGAGTAGGGTTTATTAGGCGTGTAGAAG
GAAGGGTAGGTAGTGGGCGTGTA
[SEQ ID NO: 50]

TTTTGAAGGGCGGCGGATTTTAGGGTTATGTTGGTTGTTTTAGAAAGTAG
GAGTTCGAAATCGCGGGGTTAACGAACGTTTATATTTTTTGTTATAATTTC
GTTATTTTTTGCGTTTTTTTTTTGTTTTTTGTTTTTATAGGTAACGTTTAG
AACGAGTGTTTTTTCGGTGGGGTATTGAGGAGTTTGGGTTGTAGTTGTCG
AGTCGTTATAGTTACGTTGAGTTCGGTTTGGTTTGTATATTGGCGTTATCG
TTTGGCGGGGAGCGGGATTGACGCGTTTTTTTTTTTTTTTTAGTTTAGAT
TACGGAGGCGCGGAGTTTATTTTTTGTTTGGGCGAGGGG
[SEQ ID NO: 51]

TTTTTCGTTTAGGGTAGGAGATGGAGTTTCGCGTTTTCGTGATTTGGGTTG
GAGGAGAGGGAGAGGAGCGCGTTAGTTTCGTTTTTCGTTAGGCGGTGGCG
TTAGTGTGTAGGTTAGGTCGGGTTTAGCGTGGTTGTGGCGGTTCGGTAGTT
GTAGTTTAGGTTTTTTAGTATTTTATCGGGAGAAGTATTCGTTTTGGGCGT
TATTTGTGGGGGTAGGGGGTAAGGGGAGAGGCGTAGGGGAGTGGCGAGG
TTGTAGTAGAGAATGTGGGCGTTCGTTGGTTTCGCGGTTTCGGGTTTTGT
TTTTTGGGGATAGTTAGTATGGTTTTGAAGTTCGTCGTTTTTAGAG
[SEQ ID NO: 52]

FIG 1DD

TAATTAGGGTTGGTTTATTTTTTTTTAGTTAATTTTTTTTTATTTTTAGTTTT
TAATTTAATTTATTTCGTTTATTAGTTTTTGGATTTTTATTATTTTTTCGTA
TTTTCGGTAGTTTTGGGGAAGTTTCGTGACGTTATAGGTTTCGTTTTTAGTT
TCGGTCGGGGTTAGTGCGTGTTGACGTTATGTTGCGTGCGGGTCGGTGCG
GAATCGTTTTTTTAATTTCGCGGGGTAGTAGGAGTTAGTTAGTAAAGAGTC
GAGGTCGGGCGCGCGATTTTCGTTTTTTTGTTTTTGGTCGTATATTTTGCGT
ATATTTTTTTTTTGTATGGTGGATATTATTTTTATT
[SEQ ID NO: 53]

AATGAAAAATAATATTTATTATGTAGAAAAAGAGATGTGCGTAAAGTGTG
CGGTTAGGGGTAGAAGGACGAGGGTCGCGCGTTCGGTTTCGGTTTTTTGT
TAATTAATTTTTATTGTTTCGCGGAGTTGAAGGAGCGATTTCGTATCGGTT
CGTACGTAGTATGACGTTAATACGTATTAGTTTCGGGTCGGAGTTGGGGG
CGGGATTTGTGGCGTTACGAAGTTTTTTAGAATTGTCGGGGATGCGGGG
GAGGTGATGGGGATTTAGGGGTTGATGGGCGGGGTGGGTTGGGTTGGAG
GTTGGGGGTGAAGGGAGATTGGTTGGGAGGAAGTGGGTTAATTTTGATTG
[SEQ ID NO: 54]

FIG 2A

```
GTCAGGTGGGCTACTCCACCAGGGAGGCCTTCTCCCCACCCCTGGCCCAGGGCCCTTCCG
GATTTCCAGAGAATTCTGGAACCAAGACCTTCCCCTTTCTCACCAGGGACCTCCTTGCTC
CAGGGCCTCCCGAGCGCCTGGCCGTGAGGCAGGGCCCAGAAGGCCAGGGCGGGATCCAGG
TGGCTGGCCTCACCCACTGGGACGTGCCCAACCTGGAGACATTGCACCAGGTAGGGCTGC
ACCGCTCTCCGAGACCCCGCCCCGTGCTTCCACTTGGGGGCGGGGACCCTGCACCTGACC
AGCCCTTCGCCCCGCCTTCCAGATGCTGAAACTGGGGAGGAGCAACCGGGCCACCGCCGC
CACCGCCATGAACCAGCGCAGCTCCCGCTCGCATGCCCTGGTCACGCTGACGCTGCGCGC
GGCGTCTCCACCGCGCGCTCCAGGCACCGCAGGTACCACGGCCGGTGCCTGAGCCCTGCG
GAGTCTCCAGAGCACCCGAGGCCCGGCCTTCCCCCATGTCGGGCTCGCTCGCCCCTCTAG
GCACGCTGCACCTGGTGGACCTGGCGGGATCCGAACGCGCACGGAAGGCAGGGGCGGCCG
GCCCGCCGCGGGGAGACCCAGACGGCGCCCGGCGCCTGCGGGAGGCCCAGACCATAAACC
GCTCGCTGCTGGCGCTAGGAGGCGTGATGGCCGCACTGCGGGCCCACCGGCCGCACGTGC
CCTTCCGCGACTCGCAGCTCACGCGACTGCTGCAGCCGGCGCTGGGCCCAGGCACCACCG
CGGTGCTGCTGCTGCAGGTGGGCGCCGGGGCGGGGCAGGTGTGTGCGTGCCGGTCGCCGC
CCACCCGGGCCCGCCCACCCGCGCCTCTTGCCCGCAGATCTCCACGCGGCCGGAGGATCT
CGGGGAGACAGTCTGCTCCCTCAAGTTCGCCGACCGAGTGGGTCAAGTGGAGCTGGGGCC
AGCCCGGCGCCGCAGGGTCCCGCGCTCCTCCGGGACGCCTTCTTCCCTCAGCACCGACAC
TCCGCTCACCGGGACCCCCTGCACCCCTACGCCGTCCCCTGGCAGTCCTCCATGCCCCAG
TCCCGACAACGGCTCGGGCTCGGCTCTCGCGCCCGCAGAGGGCCTGCCCCTCTAGTCCTG
GGTCGCGGCCCTGCCCATGGGGTCTCAGGCCAGGTCTCTGCTGGCAGAGGCGGTAGTAAA
GTCCCTGTACCCCGTCTCCCAGGGCACAAGCTCCCTAGCCTCTTTGGATCCATTGCCCCT
GAGCTCCCAGAGTCACCCCTCCACCTCCGCAGCCAGTGAA
[SEQ ID NO: 119] - KIFC2

TTCACTGGCTGCGGAGGTGGAGGGGTGACTCTGGGAGCTCAGGGGCAATGGATCCAAAGA
GGCTAGGGAGCTTGTGCCCTGGGAGACGGGGTACAGGGACTTTACTACCGCCTCTGCCAG
CAGAGACCTGGCCTGAGACCCCATGGGCAGGGCCGCGACCCAGGACTAGAGGGGCAGGCC
CTCTGCGGGCGCGAGAGCCGAGCCCGAGCCGTTGTCGGGACTGGGGCATGGAGGACTGCC
AGGGGACGGCGTAGGGGTGCAGGGGGTCCCGGTGAGCGGAGTGTCGGTGCTGAGGGAAGA
AGGCGTCCCGGAGGAGCGCGGGACCCTGCGGCGCCGGGCTGGCCCCAGCTCCACTTGACC
CACTCGGTCGGCGAACTTGAGGGAGCAGACTGTCTCCCCGAGATCCTCCGGCCGCGTGGA
GATCTGCGGGCAAGAGGCGCGGGTGGGCGGGCCCGGGTGGGCGGCGACCGGCACGCACAC
ACCTGCCCCGCCCCGGCGCCCACCTGCAGCAGCAGCACCGCGGTGGTGCCTGGGCCCAGC
GCCGGCTGCAGCAGTCGCGTGAGCTGCGAGTCGCGGAAGGGCACGTGCGGCCGGTGGGCC
CGCAGTGCGGCCATCACGCCTCCTAGCGCCAGCAGCGAGCGGTTTATGGTCTGGGCCTCC
CGCAGGCGCCGGGCGCCGTCTGGGTCTCCCGCGGCGGGCCGGCCGCCCCTGCCTTCCGT
GCGCGTTCGGATCCCGCCAGGTCCACCAGGTGCAGCGTGCCTAGAGGGGCGAGCGAGCCC
GACATGGGGGAAGGCCGGGCCTCGGGTGCTCTGGAGACTCCGCAGGGCTCAGGCACCGGC
CGTGGTACCTGCGGTGCCTGGAGCGCGCGGTGGAGACGCCGCGCGCAGCGTCAGCGTGAC
CAGGGCATGCGAGCGGGAGCTGCGCTGGTTCATGGCGGTGGCGGCGGTGGCCCGGTTGCT
CCTCCCCAGTTTCAGCATCTGGAAGGCGGGGCGAAGGGCTGGTCAGGTGCAGGGTCCCCG
CCCCCAAGTGGAAGCACGGGGCGGGGTCTCGGAGAGCGGTGCAGCCCTACCTGGTGCAAT
GTCTCCAGGTTGGGCACGTCCCAGTGGGTGAGGCCAGCCACCTGGATCCCGCCCTGGCCT
TCTGGGCCCTGCCTCACGGCCAGGCGCTCGGGAGGCCCTGGAGCAAGGAGGTCCCTGGTG
AGAAAGGGGAAGGTCTTGGTTCCAGAATTCTCTGGAAATCCGGAAGGGCCCTGGGCCAGG
GGTGGGGAGAAGGCCTCCCTGGTGGAGTAGCCCACCTGAC
[SEQ ID NO: 120] - KIFC2
```

FIG 2B

```
AACACGTGTAGGTTGTTGGAATTACATTAACGAATGAATGAGCAAAACCTTCTAAACCAC
CGACCAATGAAACCCCGATACAGAAAATCGCTGTCATGAGTAAGTTAGCACTCCTGAAGA
GTTTGAATACTGAACTGGCCAGAGTCTGCGCGCCGACGCCCCCAGGTGGCCGGAGTGAC
CCGGAGCAGGCGTGGCTGTCTCTCAGACCCGCGCGTTGGGCCCGAACAGTTTGTCCCCAC
GCAGCTCCCATATAAGGCGGGCCCCTCCCCTGCCCCAGCCAGCTAGGTCGCCGCGCTGGC
TCCCTGGCGGCTTCTCAAACCAACCCGCCGCTACTGCGCATGCTTGGCAAGCTCGCCCGC
TCCTTAATATCCTGCTCCGGCTGTTCCTGCCACCCGTTGGTCAAATTCGCACCCAGCTCT
GCTCCAGACAGAGGGAAAACCCAGTGATTTCCGGGCTCTAGAAACAAAGGGAGGCTATGA
TTCCCTGCTGGCCCTAGGGGTCCAGGGAAGGTTATGGAAAGATAATTCTTTGTGTAAGCG
GGTTGCGTAC
```
[SEQ ID NO: 121] - c20orf23

```
GTACGCAACCCGCTTACACAAAGAATTATCTTTCCATAACCTTCCCTGGACCCCTAGGGC
CAGCAGGGAATCATAGCCTCCCTTTGTTTCTAGAGCCCGGAAATCACTGGGTTTTCCCTC
TGTCTGGAGCAGAGCTGGGTGCGAATTTGACCAACGGGTGGCAGGAACAGCCGGAGCAGG
ATATTAAGGAGCGGGCGAGCTTGCCAAGCATGCGCAGTAGCGGCGGGTTGGTTTGAGAAG
CCGCCAGGGAGCCAGCGCGGCGACCTAGCTGGCTGGGGCAGGGGAGGGGCCCGCCTTATA
TGGGAGCTGCGTGGGGACAAACTGTTCGGGCCCAACGCGCGGGTCTGAGAGACAGCCACG
CCTGCTCCGGGTCACTCCGGCCACCTGGGGGCGTCGGCGCGCAGACTCTGGCCAGTTCA
GTATTCAAACTCTTCAGGAGTGCTAACTTACTCATGACAGCGATTTTCTGTATCGGGGTT
TCATTGGTCGGTGGTTTAGAAGGTTTTGCTCATTCATTCGTTAATGTAATTCCAACAACC
TACACGTGTT
```
[SEQ ID NO: 122] - c20orf23

```
CAGCCGAGGGGCGCGCCTGGCTGATGTGTGGTTGAATGGAGAGCGGCCCAACCCTCCTCC
TTCCTCCTCTTCTTCTCCCCGCCCTGACACCCGGGCCTCAAACTTCAACCAAAGCCCGTG
CCCTTTTCAATTTACCCCCCTCGATCAAAATGAGCCATTCTTGTCTGTCCTCCGCGGCGG
CCCATTGTCTGGCGTGATAGGTTTGCAGATTTGACAGCTGGGCGCACGCAGATTTGATTC
AAACTCGGTCTCCCCGAGAGATGAACTTGGACATCAGCAAAGATCCCGAGCACTGCCGGC
TGGCTCCTAGACCGGTCTCCCGACCCAGTGTAGACTTCGGTGCCCCGGGCGCCCCCGGC
GTGCGGGAAGGGGAGCGTGTGTCAGGCGTGGGGGCGGGGGGTGAGCAGCACGACTGGGA
ACCAGCGGTCCCAGGGGTTGGGGCGAAGGGCTGTGTACATGTTAGGCTTTTTTTGTTGTT
GTTAATTTACTCTCGAAACAGCCAAAATGGAGGTCAGCTTATAAATTTTCTAAAGCCAGG
TCTGGCCGGG
```
[SEQ ID NO: 123] - GFRA1

```
CCCGGCCAGACCTGGCTTTAGAAAATTTATAAGCTGACCTCCATTTTGGCTGTTTCGAGA
GTAAATTAACAACAACAAAAAAAGCCTAACATGTACACAGCCCTTCGCCCCAACCCCTGG
GACCGCTGGTTCCCAGTCGTGCTGCTCACCCCCCGCCCCCACGCCTGACACACGCTCCC
CTTCCCGCACGCCGGGGGCGCCCGGGGCACCGAAGTCTACACTGGGTCGGGAGACCGGT
CTAGGAGCCAGCCGGCAGTGCTCGGGATCTTTGCTGATGTCCAAGTTCATCTCTCGGGGA
GACCGAGTTTGAATCAAATCTGCGTGCGCCCAGCTGTCAAATCTGCAAACCTATCACGCC
AGACAATGGGCCGCCGCGGAGGACAGACAAGAATGGCTCATTTTGATCGAGGGGGTAAA
TTGAAAAGGGCACGGGCTTTGGTTGAAGTTTGAGGCCCGGGTGTCAGGGCGGGAGAAGA
AGAGGAGGAAGGAGGAGGGTTGGGCCGCTCTCCATTCAACCACACATCAGCCAGGCGCGC
CCCTCGGCTG
```
[SEQ ID NO: 124] - GFRA1

FIG 2C

```
AGAAACTGAGGTCGGAGTGGGGGCGTGACCAGGCCAGCCTAAGGCCGCTGCACTAATGAG
AAGCTGAGCTCTCAGATTTTGCCTCCCTGTCCCTGCCAAGTCGCTGTTTCCTGGGACAA
GAGGGAGCCTCACTGAAACGAACTCCGGTCTCAGGGGACAGAATCCTGAAACCCTGGCTC
TGGGGTCCGGGGCAGGGGTGCGCTGCCTCAGGACAGACGGTGAAACTGAGGTCCAGAGCC
GGACATCCACCGCCTGCGGAGGGAACGAGAACGCGGCGCGTCCTGCCTTGCGGGCCGAGC
GGCGCCAGAGCCGCCTCCTCCCGCCCCCGCGCTAGATCCCCCGCCCCGTCTTTGCCCT
CGCGACGCCGCCACCTCCGGAACAAGCCATGGTGGCGGCGACGGTGGCAGCGGCGTGGCT
GCTCCTGTGGGCTGCGGCCTGCGCGCAGCAGGAGCAGGACTTCTACGACTTCAAGGCGGT
CAACATCCGGGGCAAACTGGTGTCGCTGGAGAAGTACCGCGGATCGGTGAGTGCGCGGGG
TCTGGCGGCGCCGCTGGGCCCGGCCTCGCCCTGGCGGGCCTGCTGGGGACGCCCCGCAG
CCCGGTCCCCGCGCGGTGTGGCTCCGAGGACGCTCCAGCCGCGCGGCCGCCAAACCCCG
GCCCCCGCCCCGCTCGGCCGTGACCTCTGGCGCGGCGCCCCATCCCGCGCCCGGCCCGG
CCCGGCCCGCGGCTACGTGGCACGGCCTTGGCGCGGAGGAACCCGAAGCGCTCGCAGTCG
GCGCCCACTTCGCTACCGGCACCTTTGGGCAGCGGGGTCCAGACCTTCGCCGGGAGGCCG
GGCACCACTGCCCAGCCTTTGCCATTCACGGGTGAAAAAAGTAACCGTAGCATCGTGCGG
CCTTTCCCTCTCCCGTCCTCATTTTCTGCATCTGGAACGGGGAGTGGCTGATTCGGAGTC
CAGTGAAGAACACTGTGGAGATCAATGTGCAGGGCAGAGAGAGAGTTATTTCAGATGCAC
GGAGACCTCACACGGATCATCCCTGGGAGA
[SEQ ID NO: 125] - GPX7

TCTCCCAGGGATGATCCGTGTGAGGTCTCCGTGCATCTGAAATAACTCTCTCTCTGCCCT
GCACATTGATCTCCACAGTGTTCTTCACTGGACTCCGAATCAGCCACTCCCCGTTCCAGA
TGCAGAAAATGAGGACGGGAGAGGGAAAGGCCGCACGATGCTACGGTTACTTTTTTCACC
CGTGAATGGCAAAGGCTGGGCAGTGGTGCCCGGCCTCCCGGCGAAGGTCTGGACCCCGCT
GCCCAAAGGTGCCGGTAGCGAAGTGGGCGCCGACTGCGAGCGCTTCGGGTTCCTCCGCGC
CAAGGCCGTGCCACGTAGCCGCGGGCCGGGCCGGGCCGGGCGCGGGATGGGGCGCCGCG
CCAGAGGTCACGGCCGAGCGGGGCGGGGGCCGGGGTTTGGCGGCCGCGCGGCTGGAGCGT
CCTCGGAGCCACACCGCGCGGGGGACCGGGCTGCGGGGCGTCCCAGCAGGCCCCGCCAG
GGCGAGGCCGGGCCCAGCGGCGCCGCCAGACCCCGCGCACTCACCGATCCGCGGTACTTC
TCCAGCGACACCAGTTTGCCCCGGATGTTGACCGCCTTGAAGTCGTAGAAGTCCTGCTCC
TGCTGCGCGCAGGCCGCAGCCCACAGGAGCAGCCACGCCGCTGCCACCGTCGCCGCCACC
ATGGCTTGTTCCGGAGGTGGCGGCGTCGCGAGGGCAAAGACGGGCGGGGGATCTAGCG
CGGGGGGCGGGAGGAGGCGGCTCTGGCGCCGCTCGGCCCGCAAGGCAGGACGCGCCGCGT
TCTCGTTCCCTCCGCAGGCGGTGGATGTCCGGCTCTGGACCTCAGTTTCACCGTCTGTCC
TGAGGCAGCGCACCCCTGCCCCGGACCCCAGAGCCAGGGTTTCAGGATTCTGTCCCCTGA
GACCGGAGTTCGTTTCAGTGAGGCTCCCTCTTGTCCCAGGAAACAGCGACTTGGCAGGGA
CAGGGAGGCAAAAATCTGAGAGCTCAGCTTCTCATTAGTGCAGCGGCCTTAGGCTGGCCT
GGTCACGCCCCACTCCGACCTCAGTTTCT
[SEQ ID NO: 126] - GPX7

TTCTCTTACGATCTGGCTTTACTCTCACGCGCACAGCCGAGTCCCTGGGGACCCAGCAGA
GGTCCGAAGCGGAGCGGGGCGGGGCGGGCTACGGAAGCTGGCGAGGCCGAGCCCCTCCT
AGTGCTTCCGGACCTTGCTCCCTGAACACTCGGAGGTGGCGGTGGATCTTACTCCTTCCA
GCCAGTGAGGATCCAGCAACCTGCTCCGTGCCTCCCGCGCCTGTTGGTTGGAAGTGACGA
CCTTGAAGATCGGCCGGTTGGAAGTGACGACCTTGAAGATCGGCGGGCGCAGCGGGGCCG
AGGGGGCGGGTCTGGCGCTAGGTCCAGCCCCTGCGTGCCGGGAACCCCAGAGGAGGTCGC
AGTTCAGCCCAGCTGAGGCCTGTCTGCAGAATCGACACCAACCAGCATCATGTCCATGAC
ACTGGGGTACTGGGACATCCGCGGGGTGAGTGAGGGTCCGCTGCACTGTGGGACCGGGCG
CGTGGGCGGGAAGTGCCGAGCGGCTGGGACCGGCTCTAGGGACGGTTCCCTCCTTAGGG
CTATCTCTCA
[SEQ ID NO: 127] - GSTM4
```

FIG 2D

```
TGAGAGATAGCCCTAAGGAGGGAACCGTCCCTAGAGCCGGTCCCCAGCCGCTCGGCACTT
CCCGCCCACGCGCCCGGTCCCACAGTGCAGCGGACCCTCACTCACCCCGCGGATGTCCCA
GTACCCCAGTGTCATGGACATGATGCTGGTTGGTGTCGATTCTGCAGACAGGCCTCAGCT
GGGCTGAACTGCGACCTCCTCTGGGGTTCCCGGCACGCAGGGGCTGGACCTAGCGCCAGA
CCCGCCCCCTCGGCCCCGCTGCGCCCGCCGATCTTCAAGGTCGTCACTTCCAACCGGCCG
ATCTTCAAGGTCGTCACTTCCAACCAACAGGCGCGGGAGGCACGGAGCAGGTTGCTGGAT
CCTCACTGGCTGGAAGGAGTAAGATCCACCGCCACCTCCGAGTGTTCAGGGAGCAAGGTC
CGGAAGCACTAGGAGGGGCTCGGCCTCGCCAGCTTCCGTAGCCCCGCCCCGCCCCGCTCC
GCTTCGGACCTCTGCTGGGTCCCCAGGGACTCGGCTGTGCGCGTGAGAGTAAAGCCAGAT
CGTAAGAGAA
[SEQ ID NO: 128] - GSTM4

TCTTGAATTGGGGGCGGAGGTAAAAAAAAAAAAAAAAGTCCTCACTGTGGGAAGCTATAAA
AAGCAAAGAGGACTGGGGAGAGAGCAGAGAGAGAGAAAGCGGGAGCCCGCGGCGAGCGTA
GCGCAAGTCCGCTCCCTAGGCATCGCTGCGCTGGCAGCGATTCGCTGTCTCTTGTGAGTC
AGGGGACAACGCTTCGGGGCAACTGTGAGTGCGCGTGTGGGGGACCTCGATTCTCTTCAG
ATCTCGAGGATTCGGTCCGGGGACGTCTCCTGATCCCCTACTAAAGCGCCTGCTAACTTT
GAAAAGGAGCACTGTGTCCTGCAAAGTTTGACACATAAAGGATAGGAAAAGAGAGGAGAG
AAAAGCAACTGAGTTGAAGGAGAAGGAGCTGATGCGGGCCTCCTGATCAATTAAGAGGAG
AGTTAAACCGCCGAGATCCCGGCGGGACCAAGGAGGTGCGGGGCAAGAAGGAACGGAAGC
GGTGCGATCCACAGGGCTGGGTTTTCTTGCACCTTGGGTCACGCCTCCTTGGCGAGAAAG
CGCCTCGCAT
[SEQ ID NO: 129] - DKK2

ATGCGAGGCGCTTTCTCGCCAAGGAGGCGTGACCCAAGGTGCAAGAAAACCCAGCCCTGT
GGATCGCACCGCTTCCGTTCCTTCTTGCCCCGCACCTCCTTGGTCCCGCCGGGATCTCGG
CGGTTTAACTCTCCTCTTAATTGATCAGGAGGCCCGCATCAGCTCCTTCTCCTTCAACTC
AGTTGCTTTTCTCTCCTCTCTTTTCCTATCCTTTATGTGTCAAACTTTGCAGGACACAGT
GCTCCTTTTCAAAGTTAGCAGGCGCTTTAGTAGGGGATCAGGAGACGTCCCCGGACCGAA
TCCTCGAGATCTGAAGAGAATCGAGGTCCCCCACACGCGCACTCACAGTTGCCCCGAAGC
GTTGTCCCCTGACTCACAAGAGACAGCGAATCGCTGCCAGCGCAGCGATGCCTAGGGAGC
GGACTTGCGCTACGCTCGCCGCGGGCTCCCGCTTTCTCTCTCTGCTCTCTCCCCAGTC
CTCTTTGCTTTTTATAGCTTCCCACAGTGAGGACTTTTTTTTTTTTTTTACCTCCGCCCC
CAATTCAAGA
[SEQ ID NO: 130] - DKK2

CGATTGGCTGCAAGGGTCTCGGCTTGGCCGCGGATTGGTCACACCCGAGGGCTTGAAAGG
TGGCTGGGAGCGCCGGACACCTCAGACGGACGGTGGCCAGGGATCAGGCAGCGGCTCAGG
CGACCCTGAGTGTGCCCCCACCCCGCCATGGCCCGGCTGCTGCAGGCGTCCTGCCTGCTT
TCCCTGCTCCTGGCCGGCTTCGTCTCGCAGAGCCGGGACAAGAGAAGTCGAAGGTGAGT
GAGCCTCCGGGCCGGGGCCGGGAGAAAAAACCTAGCCCCTCGGTGTCCAGCGCTCAGTG
CAATGCACCCCTTTTCCCAGGCTCCCCGCCAGATGGGCAATCCCCAGGTGCGAGAGACCT
CCTGAACCCCTTTTGCCGCCCCTCCGCCGCGGGACCCCGCCCCGACCGTCGTCGTCT
CGTAGTTCCATCTGTTGGAGAGCCGAGACCTGGTGCTTCAGGCGGGCAGAATGACTAAGG
GAGGAAGGTCTCTCTCCCCGAGCTCGCACTTTCTCCCCACTGCCACCTCGAGGGTCGCCT
TGCTACATCT
[SEQ ID NO: 131] - GPX3
```

FIG 2E

```
AGATGTAGCAAGGCGACCCTCGAGGTGGCAGTGGGGAGAAAGTGCGAGCTCGGGGAGAGA
GACCTTCCTCCCTTAGTCATTCTGCCCGCCTGAAGCACCAGGTCTCGGCTCTCCAACAGA
TGGAACTACGAGACGACGACGGTCGGGGCGGGGTCCCGGCGGCGGAGGGGGCGGCAAAA
GGGGTTCAGGAGGTCTCTCGCACCTGGGGATTGCCCATCTGGCGGGGAGCCTGGGAAAAG
GGGTGCATTGCACTGAGCGCTGGACACCGAGGGGCTAGGTTTTTTCTCCCGGCCCCCGGC
CCGGAGGCTCACTCACCTTCGACTTCTCTTGTCCCGGCTCTGCGAGACGAAGCCGGCCA
GGAGCAGGGAAAGCAGGCAGGACGCCTGCAGCAGCCGGGCCATGGCGGGGTGGGGGCACA
CTCAGGGTCGCCTGAGCCGCTGCCTGATCCCTGGCCACCGTCCGTCTGAGGTGTCCGGCG
CTCCCAGCCACCTTTCAAGCCCTCGGGTGTGACCAATCCGCGGCCAAGCCGAGACCCTTG
CAGCCAATCG
```
[SEQ ID NO: 132] - GPX3

```
AGGGGAACTGGTATCTCCACAGTAATTACTAGAGCAGCTCTGGGGAACGGAGGGTTGGCT
AAGGAAGAAAAGCTCCCCCAACCCTTGGGGCGAGGGAGCGTTCTCTCAATGGAGCCCCCC
CAACTCCCCTCCACCCCCCACCAGTCTTCCAGGAAAGAGGAATACCCTACCCGGCAGGGC
TGCGAAGGAAGGGGAAATCCAACCAGAGCGAAAGTCGCACGCGGACAGCTCTGCCAGCCC
TTGGAGGCATCCGGCGGTCACCCACGGGACAAAGCGCGGCTGCGGGAGCGCGCGCGGGGC
ATTCCGGACCCGCGTCGAGCTCCGCTCTAGAGGGGGCGGCGGGCGGCGACAAGCCGGAGA
GAGGAAGGGCCAAGGAGCACGGCCCTCCTGTCGGCACCATCAGCGGGAGAGTGGCGAGCG
GACGCCTAGACGGAGGGGCCCTACTCAGACCCCATCGAGCCAGTTCCCAAGCTTTTCCCT
CCGACCTGCTCCCTCCCGGGGCGCGTGAGGGTGCGGGTCGGGGGTGAACCTGGTGTTGGG
GAAAGTGATT
```
[SEQ ID NO: 133] - RASSF5

```
AATCACTTTCCCCAACACCAGGTTCACCCCCGACCCGCACCCTCACGCGCCCCGGGAGGG
AGCAGGTCGGAGGGAAAAGCTTGGGAACTGGCTCGATGGGGTCTGAGTAGGGCCCCTCCG
TCTAGGCGTCCGCTCGCCACTCTCCCGCTGATGGTGCCGACAGGAGGGCCGTGCTCCTTG
GCCCTTCCTCTCTCCGGCTTGTCGCCGCCCGCCGCCCCTCTAGAGCGGAGCTCGACGCG
GGTCCGGAATGCCCCGCGCGCGCTCCCGCAGCCGCGCTTTGTCCCGTGGGTGACCGCCGG
ATGCCTCCAAGGGCTGGCAGAGCTGTCCGCGTGCGACTTTCGCTCTGGTTGGATTTCCCC
TTCCTTCGCAGCCCTGCCGGGTAGGGTATTCCTCTTTCCTGGAAGACTGGTGGGGGTGG
AGGGGAGTTGGGGGGGCTCCATTGAGAGAACGCTCCCTCGCCCCAAGGGTTGGGGGAGCT
TTTCTTCCTTAGCCAACCCTCCGTTCCCCAGAGCTGCTCTAGTAATTACTGTGGAGATAC
CAGTTCCCCT
```
[SEQ ID NO: 134] - RASSF5

FIG 2F

```
CGGGCAAAAATGGAGAGCAGGCAGAGGTCACATCCTCCTCCTCTTCCTCACGCTCCCGGG
CTGCGTGCCCACAGGGGCACAGCCCTGTGCGCGGTGCCACCGGGGGCCATCAGGCTGGGT
TAGAGGAAGGCCCGACCTCCGCGCAGCAAAGAAAACAAACACAGATGTGTTTGGCTGGGA
CCGGGAGGGAGAAAGTGGCCCCCTTCCCCCGCCCGCGCGCTCCCCGGGCGTGAGGCTCT
CCGGGCGGCGCGGGGCGCGGGCGAGGCTGACAGTCCCCGGCGGCCCCTCCTCCCCACGG
GGTGCGCGCCTGGCCCGGCCCAGCCCCCTCTCCGGGGTTTCCCCGGGTGCTCTCCTCGCT
TTCTCTTTGTCTCTGCTGTTCTTTCTCGGGCTCCCGGGTTCCCACCCGCCTGTGCTCTCC
CTCTCGGGCGTCCGGGCCGGTTCCCTTTAACTTTCTTCTTTCCGGGGTGAAAACTTTGC
TCGGAGCTGGCGGCAGCTCGCGGACGTTATTGGCCGGCGCCCCGCCCGGCGGCCCCGCCC
CCCGCCCCCGCGCTCCCCTCCGCCCCTCACTCCCAGCGCGAGTGGCGGCGGCGGCGGAGC
CTTCGGGGGCGAGCGCGCGTGTGTGAGTGCGCGCCGGCCAGCGTGAGTGTGTGTGCGC
CCCGGGCGCGGGCAGGGCAGCACTCCGAGCTCGGCGGGAGCGGCGGGAGCCGGGCGGCCG
CGTAGTCACTCGGGCGAGAGAGGCGGCGGCGGGGCCGGGACCGGGGCTGGGGCTGGGGCA
GCGGCGGCCGCGCCGGGCATGGAGCTGGCAAGCCCGCGCTGAGGCGGGACGCGCCTGCTA
GCAGCGAGCGAGAGGCTCTCCGGCGACCGGCGCGCGGGCTCCCCGGAGGGGCCAGGCAAA
CTTTTCTTTCTCTTTTGCCCCCTCCAGAGGTAAAGTCCCGAACGCGGACTTTCCGGCGGG
GACGCGATCGGGGGGCATCTGAGAGGGACCCCGGGCTGCGAGACGAAGGGGCGCGGGCCG
TGCAGAGTCGGGGTCCCCCAGCTCTCCTGCGCCCGAAACTTGGGGTGCGAGGGGGCTGG
TCGCGGACGGGGAGACCGGCTCAGGCATGCCCCTCGGGCGGCGTGGGGCGGCGGTGGCG
GGGAAGCAGAGCGTTCTCCCGCCGGGCGGGGAAGAAGGGGCGCGAGCGGTGCGGACTTGG
AGGGCCCCGGCTTCGCCGCCCGCGGGACTTTGGGGGAGAGAGGCGGGCAGTCGGCTGCGG
GGTGGGTGCCCAGGAAGCCGGGCGTTCTCCCGCATCTCCGCTCGCCACCCCGCCGAGAGC
TGGAGGGCGCGGGGCGGGCTGGCTGAGCGCAGCTCCCTTCTCTCCGCAGGCGCCTTCTGC
GGCAGGCGGACAGATCCTCGGCGCGGCAGGGCCGGGGCAAGCTGGACGCAGCATGATGCG
CGCAGTGTGGGAGGCGCTGGCGGCGCTGGCGGCGGTGGCGTGCCTGGTGGGCGCGGTGCG
CGGCGGGCCCGGGCTCAGCATGTTCGCGGGCCAGGCGGCGCAGCCCGATCCCTGCTCGGA
CGAGAACGGCCACCCGCGCCGCTGCATCCCGGACTTTGTCAATGCGGCCTTCGGCAAGGA
CGTGCGCGTGTCCAGCACCTGCGGCCGGCCCCGGCGCGCTACTGCGTGGTGAGCGAGCG
CGGCGAGGAGCGGCTGCGCTCGTGCCACCTCTGCAACGCGTCCGACCCCAAGAAGGCGCA
CCCGCCCGCCTTCCTCACCGACCTCAACAACCCGCACAACCTGACGTGCTGGCAGTCCGA
GAACTACCTGCAGTTCCCGCACAACGTCACGCTCACACTGTCCCTCGGCAAGAAGTTCGA
AGTGACCTACGTGAGCCTGCAGTTCTGCTCGCCGCGGCCCGAGTCCATGGCCATCTACAA
GTCCATGGACTACGGGCGCACGTGGGTGCCCTTCCAGTTCTACTCCACGCAGTGCCGCAA
GATGTACAACCGGCCGCACCGCGCGCCCATCACCAAGCAGAACGAGCAGGAGGCCGTGTG
CACCGACTCGCACACCGACATGCGCCCGCTCTCGGGCGGCCTCATCGCCTTCAGCACGCT
GGACGGGCGGCCCTCGGCGCACGACTTCGACAACTCGCCCGTGCTGCAGGACTGGGTCAC
GGCCACAGACATCCGCGTGGCCTTCAGCCGCCTGCACACGTTCGGCGACGAGAACGAGGA
CGACTCGGAGCTGGCGCGCGACTCGTACTTCTACGCGGTGTCCGACCTGCAGGTGGGCGG
CCGGTGCAAGTGCAACGGCCACGCGGCCCGCTGCGTGCGCGACCGCGACGACAGCCTGGT
GTGCGACTGCAGGCACAACACGGCCGGCCCGGAGTGCGACCGCTGCAAGCCCTTCCACTA
CGACCGGCCCTGGCAGCGCGCCACAGCCCGCGAAGCCAACGAGTGCGTGGGTGAGTGGGG
TGCGGCGGCGGAGCCGGCGGCGGGTGGGGCCGCGGGCGGGAGCTGCTGGGCCTCGCAGCG
GCGAGTTCATAGGAGCGCGGGTCGAGGGAACGGCGGGAGGCGCGTTCGCCGATGCCCGGG
ACCCGGGAGGGCTCAGAGCAGGTCCACTCGCTCGCGTGGCGCTCGTGGTGGACGCCCGAA
TTTGCGCCCAGTGCTCTCTGCGAAGCCAAGAAGCAGCAGGAGAAATGTTCCCGGGAGGGG
GTTTGGCAGAACATTTGCAGATAGGTCTCCGCTAACCCTGGATCCAAACGCAAACATTCA
TTGCCTTCCCCCTCGTTGGGTTGGACGCTGGGATTCACCT
```
[SEQ ID NO: 135] - NTN1

FIG 2G

```
AGGTGAATCCCAGCGTCCAACCCAACGAGGGGGAAGGCAATGAATGTTTGCGTTTGGATC
CAGGGTTAGCGGAGACCTATCTGCAAATGTTCTGCCAAACCCCCTCCCGGGAACATTTCT
CCTGCTGCTTCTTGGCTTCGCAGAGAGCACTGGGCGCAAATTCGGGCGTCCACCACGAGC
GCCACGCGAGCGAGTGGACCTGCTCTGAGCCCTCCCGGGTCCCGGGCATCGGCGAACGCG
CCTCCCGCCGTTCCCTCGACCCGCGCTCCTATGAACTCGCCGCTGCGAGGCCCAGCAGCT
CCCGCCCGCGGCCCCACCCGCCGCCGGCTCCGCCGCCGCACCCCACTCACCCACGCACTC
GTTGGCTTCGCGGGCTGTGGCGCGCTGCCAGGGCCGGTCGTAGTGGAAGGGCTTGCAGCG
GTCGCACTCCGGGCCGGCCGTGTTGTGCCTGCAGTCGCACACCAGGCTGTCGTCGCGGTC
GCGCACGCAGCGGGCCGCGTGGCCGTTGCACTTGCACCGGCCGCCCACCTGCAGGTCGGA
CACCGCGTAGAAGTACGAGTCGCGCGCCAGCTCCGAGTCGTCCTCGTTCTCGTCGCCGAA
CGTGTGCAGGCGGCTGAAGGCCACGCGGATGTCTGTGGCCGTGACCCAGTCCTGCAGCAC
GGGCGAGTTGTCGAAGTCGTGCGCCGAGGGCCGCCCGTCCAGCGTGCTGAAGGCGATGAG
GCCGCCCGAGAGCGGGCGCATGTCGGTGTGCGAGTCGGTGCACACGGCCTCCTGCTCGTT
CTGCTTGGTGATGGGCGCGCGGTGCGGCCGGTTGTACATCTTGCGGCACTGCGTGGAGTA
GAACTGGAAGGGCACCCACGTGCGCCCGTAGTCCATGGACTTGTAGATGGCCATGGACTC
GGGCCGCGGCGAGCAGAACTGCAGGCTCACGTAGGTCACTTCGAACTTCTTGCCGAGGGA
CAGTGTGAGCGTGACGTTGTGCGGGAACTGCAGGTAGTTCTCGGACTGCCAGCACGTCAG
GTTGTGCGGGTTGTTGAGGTCGGTGAGGAAGGCGGGCGGGTGCGCCTTCTTGGGGTCGGA
CGCGTTGCAGAGGTGGCACGAGCGCAGCCGCTCCTCGCCGCGCTCGCTCACCACGCAGTA
GCGCGCCGGGGGCCGGCCGCAGGTGCTGGACACGCGCACGTCCTTGCCGAAGGCCGCATT
GACAAAGTCCGGGATGCAGCGGCGCGGGTGGCCGTTCTCGTCCGAGCAGGGATCGGGCTG
CGCCGCCTGGCCCGCGAACATGCTGAGCCCGGGCCCGCCGCGCACCGCGCCCACCAGGCA
CGCCACCGCCGCCAGCGCCGCCAGCGCCTCCCACACTGCGCGCATCATGCTGCGTCCAGC
TTGCCCCGGCCCTGCCGCGCCGAGGATCTGTCCGCCTGCCGCAGAAGGCGCCTGCGGAGA
GAAGGGAGCTGCGCTCAGCCAGCCCGCCCCGCGCCCTCCAGCTCTCGGCGGGTGGCGAG
CGGAGATGCGGGAGAACGCCCGGCTTCCTGGGCACCCACCCCGCAGCCGACTGCCCGCCT
CTCTCCCCCAAAGTCCCGCGGGCGGCGAAGCCGGGGCCCTCCAAGTCCGCACCGCTCGCG
CCCCTTCTTCCCCGCCCGGCGGGAGAACGCTCTGCTTCCCCGCCACCGCCGCCCCCACGC
CGCCCGAGGGGCATGCCTGAGCCGGTCTCCCCGTCCGCGACCAGCCCCCCTCGCACCCCA
AGTTTCGGGCGCAGGAGAGCTGGGGGACCCCGACTCTGCACGGCCCGCGCCCCTTCGTCT
CGCAGCCCGGGGTCCCTCTCAGATGCCCCCGATCGCGTCCCCGCCGGAAAGTCCGCGTT
CGGGACTTTACCTCTGGAGGGGGCAAAAGAGAAAGAAAAGTTTGCCTGGCCCCTCCGGGG
AGCCCGCGCGCCGGTCGCCGGAGAGCCTCTCGCTCGCTGCTAGCAGGCGCGTCCCGCCTC
AGCGCGGGCTTGCCAGCTCCATGCCCGGCGCGGCCGCCGCTGCCCCAGCCCCAGCCCCGG
TCCCGGCCCCGCCGCCGCCTCTCTCGCCCGAGTGACTACGCGGCCGCCCGGCTCCCGCCG
CTCCCGCCGAGCTCGGAGTGCTGCCCTGCCCGCGCCCGGGGCGCACACACACTCACGCTG
GCCGGCGCGCACTCACACACGCGCGCTCGCCCCGAAGGCTCCGCCGCCGCCGCCACT
CGCGCTGGGAGTGAGGGGCGGAGGGGAGCGCGGGGGCGGGGGCGGGGCCGCCGGGCGGG
GCGCCGGCCAATAACGTCCGCGAGCTGCCGCCAGCTCCGAGCAAAGTTTTCACCCCGGGA
AGAAGAAAGTTAAAGGGAACCGGCCCGGACGCCCGAGAGGGAGAGCACAGGCGGGTGGG
AACCCGGGAGCCCGAGAAAGAACAGCAGAGACAAAGAGAAAGCGAGGAGAGCACCCGGGG
AAACCCCGGAGAGGGGCTGGGCCGGGCCAGGCGCGCACCCCGTGGGGGAGGAGGGGCCG
CCGGGGACTGTCAGCCTCGCCCGCGCCCCGCGCCGCCCGGAGAGCCTCACGCCCGGGGA
GCGCGCGGGCGGGGAAGGGGGCCACTTTCTCCCTCCCGGTCCCAGCCAAACACATCTGT
GTTTGTTTTCTTTGCTGCGCGGAGGTCGGGCCTTCCTCTAACCCAGCCTGATGGCCCCCG
GTGGCACCGCGCACAGGGCTGTGCCCCTGTGGGCACGCAGCCCGGGAGCGTGAGGAAGAG
GAGGAGGATGTGACCTCTGCCTGCTCTCCATTTTTGCCCG
[SEQ ID NO: 136] - NTN1
```

FIG 2H

```
GCAGTCCTGTGTGACTGGTGAGACTCTTGTAGGGGCGTTTCTACAACGACGAAACCCTTC
CTAGGCACTCACTCCAACAGAATAACAAGCCCATTTTATTAGTATTTCGTTTTCCATGTA
AAGTTCTGCTCATACGAATATATTTATAATTCTGATTTTTTTACGGCATTGGGGAGCACA
CCGACAGGCTGCTGAACGGTGGCTGGAGATTCGAGGGAAAACGAAGTTCGCCGAGGCGGC
CTCGGGCGGGCAGGTCCCGGGCTCCATCACAGGGCACACGCGGCTACCAGGGACGCAGCC
CCCCAACACACACACACACACACACACACACACACACACACACACACACCCTCTCCCA
CTCATGCCTGGCAACCCAGCAGAAACTTCGGACTGGGGCAAAACAAGCCCGGGCCCCGGC
GGCACGCGGGGCTAGGCGCGTTCCCGCCAGTACCTGGTCGCGAGGCCGCTCGCGGGGTGC
CCTGCGTGCCCCCCACTCCCGCAGCCCGCGCCCTGCTCGCTCACTGTGGGGCGCAGCGG
CCAGGCTTCTCTGTTTGTTGTTTAAAGAAATCCTAGGGCGGGCGAGCGGCGGCATCTAGG
GGAGGGGGCGCAGCCAGAATTCCCTTCCAGCAAGCGCGTGAGGGGCATTCTCAACGCAAA
ACCAGACCCAGAAAGTAGTGACCAGCCCTCCTCGGATTACCCTTCATTGGCTCCTCCCTT
GCTCCCCCCACCCTCCAGATTTGCATAAAAAAGGCCAAGAAAACTCTGGCTGTGCCCCAG
CAACGGCTCATTCTGCTCCCCGGGTCGGAGCCCCCGGAGCTGCGCGCGGGCTTGCAGC
GCCTCGCCCGCGCTGTCCTCCCGGTGTCCCGCTTCTCCGCGCCCCAGCCGCCGGCTGCCA
GCTTTTCGGGGCCCCGAGTCGCACCCAGCGAAGAGAGCGGGCCCGGGACAAGCTCGAACT
CCGGCCGCCTCGCCCTTCCCCGGCTCCGCTCCCTCTGCCCCCTCGGGGTCGCGCGCCCAC
GATGCTGCAGGGCCCTGGCTCGCTGCTGCTGCTCTTCCTCGCCTCGCACTGCTGCCTGGG
CTCGGCGCGCGGGCTCTTCCTCTTTGGCCAGCCCGACTTCTCCTACAAGCGCAGCAATTG
CAAGCCCATCCCTGCCAACCTGCAGCTGTGCCACGGCATCGAATACCAGAACATGCGGCT
GCCCAACCTGCTGGGCCACGAGACCATGAAGGAGGTGCTGGAGCAGGCCGGCGCTTGGAT
CCCGCTGGTCATGAAGCAGTGCCACCCGGACACCAAGAAG
[SEQ ID NO: 137] - SFRP2

CTTCTTGGTGTCCGGGTGGCACTGCTTCATGACCAGCGGGATCCAAGCGCCGGCCTGCTC
CAGCACCTCCTTCATGGTCTCGTGGCCCAGCAGGTTGGGCAGCCGCATGTTCTGGTATTC
GATGCCGTGGCACAGCTGCAGGTTGGCAGGGATGGGCTTGCAATTGCTGCGCTTGTAGGA
GAAGTCGGGCTGGCCAAAGAGGAAGAGCCCGCGCGCCGAGCCCAGGCAGCAGTGCGAGGC
GAGGAAGAGCAGCAGCAGCGAGCCAGGGCCCTGCAGCATCGTGGGCGCGCGACCCCGAGG
GGGCAGAGGGAGCGGAGCCGGGGAAGGGCGAGGCGGCCGGAGTTCGAGCTTGTCCCGGGC
CCGCTCTCTTCGCTGGGTGCGACTCGGGGCCCCGAAAAGCTGGCAGCCGGCGGCTGGGGC
GCGGAGAAGCGGGACACCGGGAGGACAGCGCGGGCGAGGCGCTGCAAGCCCGCGCGCAGC
TCCGGGGGGCTCCGACCCGGGGGAGCAGAATGAGCCGTTGCTGGGGCACAGCCAGAGTTT
TCTTGGCCTTTTTTATGCAAATCTGGAGGGTGGGGGAGCAAGGGAGGAGCCAATGAAGG
GTAATCCGAGGAGGGCTGGTCACTACTTTCTGGGTCTGGTTTTGCGTTGAGAATGCCCCT
CACGCGCTTGCTGGAAGGGAATTCTGGCTGCGCCCCCTCCCCTAGATGCCGCCGCTCGCC
CGCCCTAGGATTTCTTTAAACAACAAACAGAGAAGCCTGGCCGCTGCGCCCCCACAGTGA
GCGAGCAGGGCGCGGGCTGCGGGAGTGGGGGGCACGCAGGGCACCCGCGAGCGGCCTCG
CGACCAGGTACTGGCGGGAACGCGCCTAGCCCCGCGTGCCGCCGGGGCCCGGGCTTGTTT
TGCCCCAGTCCGAAGTTTCTGCTGGGTTGCCAGGCATGAGTGGGAGAGGGTGTGTGTGTG
TGTGTGTGTGTGTGTGTGTGTGTGTGTGTGTGTTGGGGGGCTGCGTCCCTGGTAGCCG
CGTGTGCCCTGTGATGGAGCCCGGGACCTGCCCGCCCGAGGCCGCCTCGGCGAACTTCGT
TTTCCCTCGAATCTCCAGCCACCGTTCAGCAGCCTGTCGGTGTGCTCCCAATGCCGTAA
AAAAATCAGAATTATAAATATATTCGTATGAGCAGAACTTTACATGGAAAACGAAATACT
AATAAAATGGGCTTGTTATTCTGTTGGAGTGAGTGCCTAGGAAGGGTTTCGTCGTTGTAG
AAACGCCCCTACAAGAGTCTCACCAGTCACACAGGACTGC
[SEQ ID NO: 138] - SFRP2
```

FIG 2I

```
GCTGCCTTTGTTCTTTGACTACTCAGCCAATTCAGGTCTGAGCTGTTCTTCGACGCCGCC
CTAGATGCGATGATGAAGGTCAGGTGCCCGCATCCCACCCACCGTCCCCTCGCAGGGGCC
CTAGGACCCACCCAGATCCCGCCTGTCTCTCTCCCCGCGGCAGGTTCCGCTGCATCGTGC
ACCCTTTCCGCGAGAAGCTGACCCTGCGGAAGGCGCTCGTCACCATCGCCGTCATCTGGG
CCCTGGCGCTGCTCATCATGTGTCCCTCGGCCGTCACGCTGACCGTCACCCGTGAGGAGC
ACCACTTCATGGTGGACGCCCGCAACCGCTCCTACCCGCTCTACTCCTGCTGGGAGGCCT
GGCCCGAGAAGGGCATGCGCAGGGTCTACACCACTGTGCTCTTCTCGCACATCTACCTGG
CGCCGCTGGCGCTCATCGTGGTCATGTACGCCCGCATCGCGCGCAAGCTCTGCCAGGCCC
CGGGGCCCGGCCCCGGGGGCGAGGAGGCTGCGGACCCGCGAGCATCGCGGCGCAGAGCGC
GCGTGGTGCACATGCTGGTCATGGTGGCGCTGTTCTTCACGCTGTCCTGGCTGCCGCTCT
GGGCGCTGCTGCTGCTCATCGACTACGGGCAGCTCAGCGCGCCGCAGCTGCACCTGGTCA
CCGTCTACGCCTTCCCCTTCGCGCACTGGCTGGCCTTCTTCAACAGCAGCGCCAACCCCA
TCATCTACGGCTACTTCAACGAGAACTTCCGCCGCGGCTTCCAGGCCGCCTTCCGCGCCC
GCCTCTGCCCGCGCCCGTCGGGGAGCCACAAGGAGGCCTACTCCGAGCGGCCCGGCGGGC
TTCTGCACAGGCGGGTCTTCGTGGTGGTGCGGCCCAGCGACTCCGGGCTGCCCTCTGAGT
CGGGCCCTAGCAGTGGGGCCCCCAGGCCCGGCCGCCTCCCGCTGCGGAATGGGCGGGTGG
CTCACCACGGCTTGCCCAGGGAAGGGCCTGGCTGCTCCCACCTGCCCCTCACCATTCCAG
CCTGGGATATCTGA
[SEQ ID NO: 139] - GPR147

TCAGATATCCCAGGCTGGAATGGTGAGGGGCAGGTGGGAGCAGCCAGGCCCTTCCCTGGG
CAAGCCGTGGTGAGCCACCCGCCCATTCCGCAGCGGGAGGCGGCCGGGCCTGGGGCCCC
ACTGCTAGGGCCCGACTCAGAGGGCAGCCCGGAGTCGCTGGGCCGCACCACCACGAAGAC
CCGCCTGTGCAGAAGCCCGCCGGGCCGCTCGGAGTAGGCCTCCTTGTGGCTCCCCGACGG
GCGCGGGCAGAGGCGGGCGCGGAAGCGGCCTGGAAGCCGCGGCGGAAGTTCTCGTTGAA
GTAGCCGTAGATGATGGGGTTGGCGCTGCTGTTGAAGAAGGCCAGCCAGTGCGCGAAGGG
GAAGGCGTAGACGGTGACCAGGTGCAGCTGCGGCGCGCTGAGCTGCCCGTAGTCGATGAG
CAGCAGCAGCGCCCAGAGCGGCAGCCAGGACAGCGTGAAGAACAGCGCCACCATGACCAG
CATGTGCACCACGCGCGCTCTGCGCCGCGATGCTCGCGGGTCCGCAGCCTCCTCGCCCCC
GGGGGCCGGGCCCGGGGCCTGGCAGAGCTTGCGCGCGATGCGGGCGTACATGACCACGAT
GAGCGCCAGCGGCGCCAGGTAGATGTGCGAGAAGAGCACAGTGGTGTAGACCCTGCGCAT
GCCCTTCTCGGGCCAGGCCTCCCAGCAGGAGTAGAGCGGGTAGGAGCGGTTGCGGGCGTC
CACCATGAAGTGGTGCTCCTCACGGGTGACGGTCAGCGTGACGGCCGAGGGACACATGAT
GAGCAGCGCCAGGGCCCAGATGACGGCGATGGTGACGAGCGCCTTCCGCAGGGTCAGCTT
CTCGCGGAAAGGGTGCACGATGCAGCGGAACCTGCCGCGGGGAGAGAGACAGGCGGGATC
TGGGTGGGTCCTAGGGCCCTGCGAGGGACGGTGGGTGGGATGCGGGCACCTGACCTTC
ATCATCGCATCTAGGGCGGCGTCGAAGAACAGCTCAGACCTGAATTGGCTGAGTAGTCAA
AGAACAAAGGCAGC
[SEQ ID NO: 140] - GPR147
```

FIG 2J

```
AGAAAGGTAATATTTGGAGGCCTCCGAGGGACGGGCAGGGGAAAGAGGGATCCTCTGACC
CAGCGGGGGCTGGGAGGATGGCTGTTTTTGTTTTTTCCCACCTAGCCTCGGAATCGCGGA
CTGCGCCCAGTGACGGACTCAAACTTACCCTTCCCTCTGACCCCGCCGTAGGATGACGCC
TCAACCCTCGGGTGCGCCCACTGTCCAAGTGACCCGTGAGACGGAGCGGTCCTTCCCCAG
AGCCTCGGAAGACGAAGTGACCTGCCCCACGTCCGCCCCGCCCAGCCCCACTCGCACACG
GGGGAACTGCGCAGAGGCGGAAGAGGGAGGCTGCCGAGGGGCCCCGAGGAAGCTCCGGGC
ACGGCGCGGGGACGCAGCCGGCCTAAGAGCGAGTTGGCACTGAGCAAGCAGCGACGGAG
TCGGCGAAAGAAGGCCAACGACCGCGAGCGCAATCGAATGCACAACCTCAACTCGGCACT
GGACGCCCTGCGCGGTGTCCTGCCCACCTTCCCAGACGACGCGAAGCTCACCAAGATCGA
GACGCTGCGCTTCGCCCACAACTACATCTGGGCGCTGACTCAAACGCTGCGCATAGCGGA
CCACAGCTTGTACGCGCTGGAGCCGCCGGCGCCGCACTGCGGGGAGCTGGGCAGCCCAGG
CGGTTCCCCCGGGGACTGGGGGTCCCTCTACTCCCCAGTCTCCCAGGCTGGCAGCCTGAG
TCCCGCCGCGTCGCTGGAGGAGCGACCCGGGCTGCTGGGGGCCACCTTTTCCGCCTGCTT
GAGCCCAGGCAGTCTGGCTT
[SEQ ID NO: 141] - NEUROG3

AAGCCAGACTGCCTGGGCTCAAGCAGGCGGAAAAGGTGGCCCCCAGCAGCCCGGGTCGCT
CCTCCAGCGACGCGGCGGGACTCAGGCTGCCAGCCTGGGAGACTGGGGAGTAGAGGGACC
CCCAGTCCCCGGGGGAACCGCCTGGGCTGCCCAGCTCCCCGCAGTGCGGCGCCGGCGGCT
CCAGCGCGTACAAGCTGTGGTCCGCTATGCGCAGCGTTTGAGTCAGCGCCCAGATGTAGT
TGTGGGCGAAGCGCAGCGTCTCGATCTTGGTGAGCTTCGCGTCGTCTGGGAAGGTGGGCA
GGACACCGCGCAGGCGTCCAGTGCCGAGTTGAGGTTGTGCATTCGATTGCGCTCGCGGT
CGTTGGCCTTCTTTCGCCGACTCCGTCGCTGCTTGCTCAGTGCCAACTCGCTCTTAGGCC
GGCTGCGTCCCCGCGCCGTGCCCGGAGCTTCCTCGGGCCCCTCGGCAGCCTCCCTCTT
CCGCCTCTGCGCAGTTCCCCGTGTGCGAGTGGGCTGGGCGGGCGGACGTGGGGCAGG
TCACTTCGTCTTCCGAGGCTCTGGGGAAGGACCGCTCCGTCTCACGGGTCACTTGGACAG
TGGGCGCACCCGAGGGTTGAGGCGTCATCCTACGGCGGGGTCAGAGGGAAGGGTAAGTTT
GAGTCCGTCACTGGGCGCAGTCCGCGATTCCGAGGCTAGGTGGGAAAAAACAAAACAGC
CATCCTCCCAGCCCCGCTGGGTCAGAGGATCCCTCTTTCCCCTGCCCGTCCCTCGGAGG
CCTCCAAATATTACCTTTCT
[SEQ ID NO: 142] - NEUROG3
```

FIG 2K

```
TAAAGCTTCCCCAGAGGGAGGAAAGGTGGGGGCGGGGCGGCTGCTGAGGCCCAGGATATA
AGGGCTGGAGGTGCTGCTTTCAGGCCTGGCCAGCCCACCATGCACGCCCACTGCCTGCCC
TTCCTTCTGCACGCCTGGTGGGCCCTACTCCAGGCGGGTGCTGCGACGGTGGCCACTGCG
CTCCTGCGTACGCGGGGGCAGCCCTCGTCGCCATCCCCTCTGGCGTACATGCTGAGCCTC
TACCGCGACCCGCTGCCGAGGGCAGACATCATCCGCAGCCTACAGGCAGAAGGTAGGCAG
TGCCGCGTGCCGCGCCCTGCTGGGCACCCCGGGGCGCCTCCGCCGCGTCCAGCCAGCGG
ACTCGGGAAGTGCTGTGGGTTGGGGCTGCGGCTCCGAGCCGGGTTTGCAGCCGCCCGGG
CGTCCCGAGCCCAGGGCCTAGCTCTGCGGGTGTCTCCGCGTCAGCAGGCTCGGGGTGCAG
CGTTGGTGGCTGGGGGCGTATCCACGGCCGAGTCGGGAAGGGATTCTAGCGTTCAGGGTG
TGTCCTCGACGGGGACCATTGTCTCTGGGTTTTGGTTTGGGATTGCGCGGAGCGCAGCGC
GGAAGGGTGGGAGCTTCTAATCTCCAGTCTTGTGAAGTTGCTTATCCCGGAGCCTGGGTC
TGCGCATCTGTAGGATAGGTGTAATAAATAACACCTCGCCTATCAGACTGTGGAAAGCGC
GAGATGACAATGCGCGCGAAACGCTCAGCGCAGTACCCGGCACAGCCACAGTCAACGGTC
GTTGGTATTACTGTAATGGTTTGGTCTTGGCGATTTTTTTTCTTTCTGCGAGTGAGGGT
GAATGGGTCCCGGGGTGTGACGTCGGGAGTATCGGCAGCTGAGCTGGTAACATCGGGGAT
TCGGGCTCACGGCCCGGAGATCAGGGATGGGCTGTCCCGAAGTCGCGAACTGTGGCAGCC
TTGGGTCCTCCAGCCGCGCCGGGGAAGTGTCAAGTGTCTCGCTTAACCCCGGGTTCGGGG
CCATGATTTGCAGGGGAGTGGGTGTCAAGGACGGCAGGGATCTGAGGGTATCGCCCTCGA
GGACCTGGCAGCGCGTTCTGGGCACCCAGCGCGGCGAGCAGGTGGGTGCTGCGGAGAGGG
AGCCCCTTCCGCGCCTCAATCCACATTCTGCCGCCTGGGCAGCCGCGGCCGCCCACGCCT
CCCTCCGCCTGCGGGGGCCAGACGGCCCTCCCTGGGGCCGGGGCGCAATCCACAAACGCT
AATCTGATCCGACCTGCCGCCTGCCCGCCCTTGTGACCTGGTGCCGGGGGCCCTTCGCT
CCCGCGCCTGGGGTCAGACAGCCGGTGACCCTCTCCGGAAGGGTCATCTGGGGACCAGCC
AGACCAGGGACACCCTCGGGGCGGGGCAATGAGAAATTTGCTGGAGTGCTCGGCCCCT
CAACCGAAAAGCGGCCGGGGATGGGAGGGGGCAAAGAAGGGAGGGAGCGCTTTTCCAGTT
CACTCCCTTCTGGAAAGTTCGAGATGTGTGCGGTGATGGACAGGCATCTG
```
[SEQ ID NO: 143] - NODAL

FIG 2L

```
CAGATGCCTGTCCATCACCGCACACATCTCGAACTTTCCAGAAGGGAGTGAACTGGAAAA
GCGCTCCCTCCCTTCTTTGCCCCCTCCCATCCCCGGCCGCTTTTCGGTTGAGGGGCCGAG
CACTCCAGCAAATTTCTCATTGCCCCGCCCCGAGGGTGTCCCCTGGTCTGGCTGGTCCC
CAGATGACCCTTCCGGAGAGGGTCACCGGCTGTCTGACCCCAGGCGCGGGAGCGAAGGGC
CCCCGGCACCAGGTCACAAGGGGCGGGCAGGCGGCAGGTCGGATCAGATTAGCGTTTGTG
GATTGCGCCCCGGCCCCAGGGAGGGCCGTCTGGCCCCCGCAGGCGGAGGGAGGCGTGGGC
GGCCGCGGCTGCCCAGGCGGCAGAATGTGGATTGAGGCGCGGAAGGGGCTCCCTCTCCGC
AGCACCCACCTGCTCGCCGCGCTGGGTGCCCAGAACGCGCTGCCAGGTCCTCGAGGGCGA
TACCCTCAGATCCCTGCCGTCCTTGACACCCACTCCCCTGCAAATCATGGCCCCGAACCC
GGGGTTAAGCGAGACACTTGACACTTCCCCGGCGCGGCTGGAGGACCCAAGGCTGCCACA
GTTCGCGACTTCGGGACAGCCCATCCCTGATCTCCGGGCCGTGAGCCCGAATCCCCGATG
TTACCAGCTCAGCTGCCGATACTCCCGACGTCACACCCCGGGACCCATTCACCCTCACTC
GCAGAAAGAAAAAAAATCGCCAAGACCAAACCATTACAGTAATACCAACGACCGTTGAC
TGTGGCTGTGCCGGGTACTGCGCTGAGCGTTTCGCGCGCATTGTCATCTCGCGCTTTCCA
CAGTCTGATAGGCGAGGTGTTATTTATTACACCTATCCTACAGATGCGCAGACCCAGGCT
CCGGGATAAGCAACTTCACAAGACTGGAGATTAGAAGCTCCCACCCTTCCGCGCTGCGCT
CCGCGCAATCCCAAACCAAAACCCAGAGACAATGGTCCCCGTCGAGGACACACCCTGAAC
GCTAGAATCCCTTCCCGACTCGGCCGTGGATACGCCCCAGCCACCAACGCTGCACCCCG
AGCCTGCTGACGCGGAGACACCCGCAGAGCTAGGCCCTGGGCTCGGGACGCCCGGGCGGC
TGCAAACCCGGCTCGGAGCCGCAGCCCCCAACCCACAGCACTTCCCGAGTCCGCTGGCTG
GACGCGGCGGAGGCGCCCCGGGGTGCCCAGCAGGGCGCGGCACGCGGCACTGCCTACCT
TCTGCCTGTAGGCTGCGGATGATGTCTGCCCTCGGCAGCGGGTCGCGGTAGAGGCTCAGC
ATGTACGCCAGAGGGGATGGCGACGAGGGCTGCCCCGCGTACGCAGGAGCGCAGTGGCC
ACCGTCGCAGCACCCGCCTGGAGTAGGGCCCACCAGGCGTGCAGAAGGAAGGGCAGGCAG
TGGGCGTGCATGGTGGGCTGGCCAGGCCTGAAAGCAGCACCTCCAGCCCTTATATCCTGG
GCCTCAGCAGCCGCCCCGCCCCCACCTTTCCTCCCTCTGGGGAAGCTTTA
[SEQ ID NO: 144] - NODAL

ACCCCGGGGCGTGGGAGAAGCCCCTGCTTGGGGGGACCGTCTGCTGTTTAGGGGCTCCCC
TTCGACACGTGGGAGGCAAAAGTGCAGAGCGCACCATCATCCAGCTCCGGCCGCACTGCA
CAGCGAGGCCGGCCCGGAGCCCGGATGCTGGGCTCGGTCCCGCCGAGGCTCGGCCTGGCT
GTAAAGCAGAGGGGGCGAGGGAAGCCGGGCCAGCGGGTGTCGCGGGTAGCCGGCGTCCG
GGACGGGTGTGGCGCCCAGAGCGCTGCTGCCTCTCGCAGCCAGGAGGCTGGATGTCGGG
TTTGGGTGTCTTCCAGAAGGAGCCGCACTAGCGACGAGGGAAGAGGAACTGGCTTCCCGG
GCAGTCTCCCCCGCCCCAAACTTTTCCTCCTCGCGGAGGGTGGGCGGGCGGAGGGAGGAA
GCGCAGCCGGGGAACGTGGCGCCCGCGTTCCTCCCGCCCGGGGGCTGCGGCTGGGCTGAG
TGTGTCTTTAAATCTGAGCCCCCGCCCCTCGCGGTGGGGCCGGGACTCGCGGTCCGGGC
GGGGGCGGGCGCGGTGATTGGCGGCCGGGTCGGGTCCGCCCCTCGGCGTTGGGTAGCGGG
GCGCTGGGGAGCAGCGCGGCGCGCACGGGCCGGGGCGCGCAGGTCCCGTCGCCGGTGAGC
ACGGGCTCCCTCTCGCGTGGCCTCGCCGGGTCCGCCTGGCCTGCCCACCTCCGGAGCCAC
CTCTGCCCCGCATGGGCTGGCGAAGTTGGGAGGAGCGAGCTGGAGCCAGAGCGCGCGCC
GGGCGCGCCCCGTCGCTGCCTGACTCGGCGCCCGCAGTTCGGGCGCAGCACGCCGGCCGC
AGGAGCACGGATGCCCCCCGGAGCCGCGGGCTGGCAGGTACCGAAGTGTCCTGCCCTGGG
GCTGGCGAGGGGAGGGCAAATCTGGAATCCCCGGGCACCCCCAGCCCGAGGCTGCTCC
AGACACCAACTCCCCATCCTTTGGAGAGGTGAGGTCCTGGGCCTTCACCCCACACCCGCT
CAGGATTGGTCCCTGGGAGGCAAGAGGGAC
[SEQ ID NO: 145] - PALD
```

FIG 2M

```
GTCCCTCTTGCCTCCCAGGGACCAATCCTGAGCGGGTGTGGGGTGAAGGCCCAGGACCTC
ACCTCTCCAAAGGATGGGGAGTTGGTGTCTGGAGCAGCCTCGGGCTGGGGGTGCCCGGG
GGATTCCAGATTTGCCCTCCCCTCGCCAGCCCCAGGGCAGGACACTTCGGTACCTGCCAG
CCCGCGGCTCCGGGGGGCATCCGTGCTCCTGCGGCCGGCGTGCTGCGCCCGAACTGCGGG
CGCCGAGTCAGGCAGCGACGGGGCGCGCCCGGCGCGCGCTCTGGCTCCAGCTCGCTCCTC
CCAACTTCGCCAGCCCATGCGGGGGCAGAGGTGGCTCCGGAGGTGGGCAGGCCAGGCGGA
CCCGGCGAGGCCACGCGAGAGGGAGCCCGTGCTCACCGGCGACGGGACCTGCGCGCCCCG
GCCCGTGCGCGCCGCGCTGCTCCCAGCGCCCCGCTACCCAACGCCGAGGGGCGGACCCG
ACCCGGCCGCCAATCACCGCGCCCGCCCCGCCCGGACCGCGAGTCCCGGCCCCACCGCG
AGGGGCGGGGGGCTCAGATTTAAAGACACACTCAGCCCAGCCGCAGCCCCGGGCGGGAG
GAACGCGGGCGCCACGTTCCCCGGCTGCGCTTCCTCCCTCCGCCCGCCCACCCTCCGCGA
GGAGGAAAAGTTTGGGGCGGGGGAGACTGCCCGGGAAGCAGTTCCTCTTCCCTCGTCGC
TAGTGCGGCTCCTTCTGGAAGACACCCAAACCCGACATCCAGCCTCCTGGCTGCGAGAGG
CAGCAGCGCTCTGGGCGCCACACCCCGTCCCGGACGCCGGCTACCCGCGACACCCGCTGG
CCCGGCTTCCCTCGCCCCCCTCTGCTTTACAGCCAGGCCGAGCCTCGGCGGGACCGAGCC
CAGCATCCGGGCTCCGGGCCGGCCTCGCTGTGCAGTGCGGCCGGAGCTGGATGATGGTGC
GCTCTGCACTTTTGCCTCCCACGTGTCGAAGGGGAGCCCCTAAACAGCAGACGGTCCCCC
CAAGCAGGGGCTTCTCCCACGCCCGGGGT
[SEQ ID NO: 146] - PALD

CCGAAAGGACCCGTCCCAGCGAGCCAGGGCCTGGTTTTCCTTCCGCAGAAGGCGGAGGGA
CCGGAGCGGGCGCGGGCACCCCTGGGCTCTGAGGGGCGCGCTCTGAAGGGCGGCGGACTT
CAGGGCCATGCTGGCTGTCCCCAGAAAGCAGGAGCCCGAAACCGCGGGGCCAACGAACGC
CCACATTCTCTGCTACAACCTCGCCACTCCCTGCGCCTCTCCCCTTGCCCCCTGCCCCC
ACAGGTAACGCCCAGAACGAGTGCTTCTCCCGGTGGGGTACTGAGGAGCCTGGGCTGCAG
CTGCCGAGCCGCCACAGCCACGCTGAGCCCGGCCTGGCCTGCACACTGGCGCCACCGCCT
GGCGGGGAGCGGGACTGACGCGCTCCTCTCCCTCTCCTCCAGCCCAGATCACGGAGGCGC
GGAGCTCCATCTCCTGCCCTGGGCGAGGGGAGTGAGGGAGACAAAGACTTTGGGCACAAC
ACCCACCACATAGAACCTATTCTCTAGTTGGGAAACAAGTCAAGGCAAAGGCGCACAGAG
TGAAAGTCAG
[SEQ ID NO: 147] - LOC399783

CTGACTTTCACTCTGTGCGCCTTTGCCTTGACTTGTTTCCCAACTAGAGAATAGGTTCTA
TGTGGTGGGTGTTGTGCCCAAAGTCTTTGTCTCCCTCACTCCCCTCGCCCAGGGCAGGAG
ATGGAGCTCCGCGCCTCCGTGATCTGGGCTGGAGGAGAGGGAGAGGAGCGCGTCAGTCCC
GCTCCCCGCCAGGCGGTGGCGCCAGTGTGCAGGCCAGGCCGGGCTCAGCGTGGCTGTGGC
GGCTCGGCAGCTGCAGCCCAGGCTCCTCAGTACCCCACCGGGAGAAGCACTCGTTCTGGG
CGTTACCTGTGGGGCAGGGGCAAGGGAGAGGCGCAGGGAGTGGCGAGGTTGTAGCA
GAGAATGTGGGCGTTCGTTGGCCCCGCGGTTTCGGGCTCCTGCTTTCTGGGGACAGCCAG
CATGGCCCTGAAGTCCGCCGCCCTTCAGAGCGCGCCCCTCAGAGCCCAGGGGTGCCCGCG
CCCGCTCCGGTCCCTCCGCCTTCTGCGGAAGGAAAACCAGGCCCTGGCTCGCTGGGACGG
GTCCTTTCGG
[SEQ ID NO: 148] - LOC399783
```

FIG 2N

```
CCCTCCAGTTTGCTGGAGTTGCCGGATTACATTGTTCCTCCCCGGTGTGCGGCGTGAGCT
TCCCCCACCCGAGCGCCCAACAAGTCTCCTTTCTCCAGCCTGCGCGCTGCTGCGCTGAGG
CCGAATGAAGCGCAGCACGGTGCGGGCAGCCCGAGGCCCCGAGGCTGGGCTCTGTCTGTC
TGGGACTGCGCCGTGCCCAGCCTCGGTCCCCTCTCTGTGGGTAAGGATGGTTGAGTCCAG
CCTCCACGGCAGCGGCTCCTTGTGCCACTAGCAGCCCTTCTTCTGCGCTCTCCGCCTTTT
CTCTCTAGACTGGATCTCTCCTCCCCCCGCGCCCCCTCCCCGCATCTCCCACTCGCTG
GCTCTCTCTCCAGCTGCCTCCTCTCCAGGTCTCTCCTGGCTGCGCGCGCTCCTCTCCCCG
CTTCTCCCCCTCCCGCAGCCTCGCCGCCTTGGTGCCTTCCTGCCCGGCTCGGCCGGCGCT
CGTCCCCGGCCCCGGCCCCGCCAGCCCGGGTCTCCGCGCTCGGAGCAGCTCAGCCCTGCA
GTGGCTCGGGACCCGATGCTATGAGAGGGAAGCGAGCCGGGCGCCCAGACCTTCAGGAGG
CGTCGGATGCGCGGCGGGTCTTGGGACCGGGCTCTCTCCGGCTCGCCTTGCCCTCGGG
TGATTATTTGGCTCCGCTCATAGCCCTGCCTTCCTCGGAGGAGCCATCGGTGTCGCGTGC
GTGTGGAGTATCTGCAGACATGACTGCGTGGAGGAGATTCCAGTCGCTGCTCCTGCTTCT
CGGGCTGCTGGTGCTGTGCGCGAGGCTCCTCACTGCAGCGAAGGGTAAGACGGACTTGCT
CCTGGCCGGGGAGGCGGTAGAGCCCTCGGAGGCCCCGTGTGCGGACGCGAGTGTGCGTTT
TGGGGACCGCAGGGTACGGAGTGGCCGCCTCTGCCCGGCGCTGCTCCATCGCCGAAGCTC
GGGGAACGCGATGCACGGGAGGGAGCTTCCATCGCGCTCTCCCCAGCCCTCCTGGGCCCC
CGCCCCACCCCGCCATTCCTTCCCCCTCTCTTGGGCTCACAGGAGAGATCTCTTTTTCTC
GGCAGTACAGGGTGTCAAGGAGAAAGGAACCCAATACGAGTTGGGCTGGAACTGTGCTCC
GCCGGGGCGGTGTTGCCTCCTCCGAGACGTGGACTCCACGGGTCGGGGTGGCTGAGGGGC
AGTTCCCAGGACTTTCTCCCCGGACCCGACGCGCCTGGGAAAGCGTCCCGGGTGAAGCCG
GCCTGGAAAGTTCGGGCTCTCTACGGGGGTTTTGGTACCAATAGGCAAAGGTCTCCGCCG
GCCCGGCCTCCTCGCACCCATACACCCCATTCCTCCTCTCCTCCTTCCCTCTCCAACGTC
CTCAGCCGGCGAGGAGTAGCTGCCTCTAGAAGGTCGCCCCGCTTTCCTCTCCCCGGAC
TTCGCTCCTTGCAAGTTGTAAGGTGTTGGCAAGGTGCGTGAAACAGGCTAGGAGTTCTGG
ACCGGCTTCCAAGTCAGATACATTCACTGTGGGCGCACGGGTATCCTCCT
```
[SEQ ID NO: 149] – CSMD1

```
AGGAGGATACCCGTGCGCCCACAGTGAATGTATCTGACTTGGAAGCCGGTCCAGAACTCC
TAGCCTGTTTCACGCACCTTGCCAACACCTTACAACTTGCAAGGAGCGAAGTCCGGGGGA
GAGGAAAGCGGGGGCGACCTTCTAGAGGCAGCTACTCCTCGCCGGCTGAGGACGTTGGAG
AGGGAAGGAGGAGAGGAGGAATGGGGTGTATGGGTGCGAGGAGGCCGGGCCGGCGGAGAC
CTTTGCCTATTGGTACCAAAACCCCCGTAGAGAGCCCGAACTTTCCAGGCCGGCTTCACC
CGGGACGCTTTCCCAGGCGCGTCGGGTCCGGGGAGAAAGTCCTGGGAACTGCCCCTCAGC
CACCCCGACCCGTGGAGTCCACGTCTCGGAGGAGGCAACACCGCCCCGGCGGAGCACAGT
TCCAGCCCAACTCGTATTGGGTTCCTTTCTCCTTGACACCCTGTACTGCCGAGAAAAGA
GATCTCTCCTGTGAGCCCAAGAGAGGGGAAGGAATGGCGGGGTGGGGCGGGGCCCAGG
AGGGCTGGGGAGAGCGCGATGGAAGCTCCCTCCCGTGCATCGCGTTCCCCGAGCTTCGGC
GATGGAGCAGCGCCGGGCAGAGGCGGCCACTCCGTACCCTGCGGTCCCCAAAACGCACAC
TCGCGTCCGCACACGGGGCCTCCGAGGGCTCTACCGCCTCCCCGGCCAGGAGCAAGTCCG
TCTTACCCTTCGCTGCAGTGAGGAGCCTCGCGCACAGCACCAGCAGCCCGAGAAGCAGGA
GCAGCGACTGGAATCTCCTCCACGCAGTCATGTCTGCAGATACTCCACACGCACGCGACA
CCGATGGCTCCTCCGAGGAAGGCAGGGCTATGAGCGGAGCCAAATAATCACCCGAGGGCA
AGGCGAGCCGGAGAGAGAGCCCGGTCCCAAGACCCGCCGCGCATCCGACGCCTCCTGAAG
GTCTGGGCGCCCGGCTCGCTTCCCTCTCATAGCATCGGGTCCCGAGCCACTGCAGGGCTG
AGCTGCTCCGAGCGCGGAGACCCGGGCTGGCGGGCCGGGGCCGGGGACGAGCGCCGGCC
GAGCCGGGCAGGAAGGCACCAAGGCGGCGAGGCTGCGGGAGGGGGAGAAGCGGGGAGAGG
AGCGCGCGCAGCCAGGAGAGACCTGGAGAGGAGGCAGCTGGAGAGAGAGCCAGCGAGTGG
GAGATGCGGGGAGGGGGCGCGGGGGGAGGAGAGATCCAGTCTAGAGAGAAAAGGCGGA
GAGCGCAGAAGAAGGCTGCTAGTGGCACAAGGAGCCGCTGCCGTGGAGGCTGGACTCAA
CCATCCTTACCCACAGAGAGGGGACCGAGGCTGGGCACGGCGCAGTCCCAGACAGACAGA
GCCCAGCCTCGGGGCCTCGGGCTGCCCGCACCGTGCTGCGCTTCATTCGGCCTCAGCGCA
GCAGCGCGCAGGCTGGAGAAAGGAGACTTGTTGGGCGCTCGGGTGGGGAAGCTCACGCC
GCACACCGGGGAGGAACAATGTAATCCGGCAACTCCAGCAAACTGGAGGG
```
[SEQ ID NO: 150] – CSMD1

FIG 20

```
TCCTCCTTGAGCAGGGAGACCATCGGGGTGCAACCTGGCCGGGGCGGGGAGGAGGTGCAG
GGCATTGCCAGAGCGGGCCTGTCCATGGGCAAGGGACAGCGACCTCCTGGGCCAGGACAT
GTGAGAGCTGCGCAGGCCTGGGCCCGGCGTGGCGGAGGTGCGCGAGAGCGGCCAGAAGAG
GGCGCCAGAGAGCCAGGCGCGGCCCGCGGAGGAGCCCGCGCCGGCCCCTATACCCAGCTC
CGCGCCGCGCGGACCCACCGAGCCCGCGCTCAGACGCCCCAGCTCCACCGAGAGGCCGCT
CGGGCCGTGTCCTTCCTCTTCTCCAGGTGCAGGCAGAGCCCCCGAGCCATGGCCAGCCCT
TCCGGCAGCTCCGAAGCCACTGGCAAGCCCCGAGGCAGGGATGGCCGGCCCAGGAGGGAG
GAGGACGACGTCCCTCCCGAAGAGAAGAGGCTGGGGCTGTAGCTGGAGGGGGGAAGCGCA
CAGCCCGAGGACTGCGAGAACGGGGAGGACGCGCCGCGGCCAGGCAGGGAGGAGACCGGC
ACCCAGACAGGTGGCGACCGCAGAGGAGTAAGTGACGCGGGCGCTGGGGTCCGGGGGTGC
CGGGGGCGCCGGTAGGGGCGGCGGGAGGCTCCGTGGCCGGCCCCGGGTTGAAGTTGGTAT
TTTAGCGGCAACTCCGAAGGGCGCGGAGTGACAGCGCGTGACGGCCTCCGAGACGCCAGC
TGCCGCTTCTCGGCTGTGTGGCTTTGACTTCCTGATTCTCCCACGACGTCGCTGGCTGGG
AGACCCACTGGACTCTGCGGCTGGCCAAAAAGAGAGGGGCAGCCCCGCGTCCTGGGGGCC
CCTAGCAGGGGAAGTGGCGGGTGTTGCGCTGGGCATCCTGTCTGGGGCATCTGTCTGGGA
CCCTGTTGGTGCCTCTCACCTGGCGAGGGGCCAGTGGTGGGGGTAGGGGGGAAGTCCCTG
GCGCCAGGCTTGGCCAAGCCCTGCTTGGCTGGACTGCGGGCTGGCGGCGCTCACCCAGCT
CCTCACCTGTCCCGCATCTTCCTGTTTTTC
[SEQ ID NO: 151] - LOC441320

GAAAAACAGGAAGATGCGGGACAGGTGAGGAGCTGGGTGAGCGCCGCCAGCCCGCAGTCC
AGCCAAGCAGGGCTTGGCCAAGCCTGGCGCCAGGGACTTCCCCCCTACCCCCACCACTGG
CCCCTCGCCAGGTGAGAGGCACCAACAGGGTCCCAGACAGATGCCCCAGACAGGATGCCC
AGCGCAACACCCGCCACTTCCCCTGCTAGGGGCCCCAGGACGCGGGGCTGCCCCTCTCT
TTTTGGCCAGCCGCAGAGTCCAGTGGGTCTCCCAGCCAGCGACGTCGTGGGAGAATCAGG
AAGTCAAAGCCACACAGCCGAGAAGCGGCAGCTGGCGTCTCGGAGGCCGTCACGCGCTGT
CACTCCGCGCCCTTCGGAGTTGCCGCTAAAATACCAACTTCAACCCGGGGCCGGCCACGG
AGCCTCCCGCCGCCCCTACCGGCGCCCCCGGCACCCCCGGACCCCAGCGCCCGCGTCACT
TACTCCTCTGCGGTCGCCACCTGTCTGGGTGCCGGTCTCCTCCCTGCCTGGCCGCGGCGC
GTCCTCCCCGTTCTCGCAGTCCTCGGGCTGTGCGCTTCCCCCTCCAGCTACAGCCCCAG
CCTCTTCTCTTCGGGAGGGACGTCGTCCTCCTCCCTCCTGGGCCGGCCATCCCTGCCTCG
GGGCTTGCCAGTGGCTTCGGAGCTGCCGGAAGGGCTGGCCATGGCTCGGGGGCTCTGCCT
GCACCTGGAGAAGAGGAAGGACACGGCCCGAGCGGCCTCTCGGTGGAGCTGGGGCGTCTG
AGCGCGGGCTCGGTGGGTCCGCGCGGCGCGGAGCTGGGTATAGGGGCCGGCGCGGGCTCC
TCCGCGGGCCGCGCCTGGCTCTCTGGCGCCCTCTTCTGGCCGCTCTCGCGCACCTCCGCC
ACGCCGGGCCCAGGCCTGCGCAGCTCTCACATGTCCTGGCCCAGGAGGTCGCTGTCCCTT
GCCCATGGACAGGCCCGCTCTGGCAATGCCCTGCACCTCCTCCCCGCCCCGGCCAGGTTG
CACCCCGATGGTCTCCCTGCTCAAGGAGGA
[SEQ ID NO: 152] - LOC441320
```

FIG 2P

```
CCCAGTAAGTCACCAATTAAGTCTTTACTACTTAAAAGCAAAATCCACCTATGTCCTGAA
CAGTATCCACTTTACGAGCCTCATTATATGTACGAGATAAAATTCAGAAATAAATAAATA
TACATGTATACGTATACAAATATATTTCAAATTAAAAAATACTTTTAGATAGTGGTATGT
ATTACATTTAGAAATTAATAACGAAGTAAATTATGGGATGTCATCCACGCCTGTCCCAAA
GGTACCGAATTTATAAATCATCTCAGGTGCGGAGCAGGACAGGTTGAAAATAGGAATGAC
ATGAACCCGCGCGGAACAGCTGCCGGCGCGGTGTCCAGGGCGGCACCCCGCCCGGTCCCG
GCCCCTCCAGCCCTGGGCCCGACCCCTACTACGCCTCTGCCTCGACGCGAACGCGGAGCC
CGAGCGCGCGTCACGCCGTGTGGGGCCGAAGAGGCTGCTACCCAGAGGCGGAGTGCGGGC
TCGCGAGGGTCCCCACCCGACTCTCGCTCCCGCCAGCACCTACGGACTCGCGTCCCCGCC
GCGCGCCGACTCGGGAGCAGCACCGCCCCCGGCACAGGAGCCTCACGCGCCTCTTACCTA
ACAGGAAGTTGGGTGGAAGCAGCGCGGACCCACGGCACACCGAACGCACTCCAACAGAAC
CCGACGCAGACACGCGCTTTCAACCGGCGGAGACACTGGCAGGGCCAGAAACGCGCGCAG
CGGGGGCGGGAGGTCGGTAAGCTCCCCGCCCCTGCCCGAGACCCCGCCCCGGCCCGGCCC
CGCCTTTTTCTCTGCCTCCCCTCCCTGCACGTACGGGCCCCGCCCCTCGCGCGACGTTTT
TTGTTGACCCGGAAACGGATTCTCCGGAGCCGAGGTCCGCTCGGGTGAGTGCCCTCCGCT
TTTTGTGGCCAAACCCAGCCACGCAGTTCCCTTCCTGCGGCGTCCTCCACACCCGGGGTC
TGCTGGTCTCCGCGGATGTCACAGGCTCGGCAACCGCCCTCCTGTCGGCGGGGAGTCCCG
CGACGCCCGGAAATGCTCCGAAGCCTGTCGCCCAGCTGCCAGATCTGCGTCTGTGTCCGG
TTCCGTCACTGAGGTCGCCCCTGTCCGGCCCTTCCACCCTAGTTCTCTTCACCGTCCGCC
CATCCTATCGCGCGCGGCCTCAGGTCCCGATTCGGCATGTGGCTTGTCTTCCATCGTCCC
CACCCTCGCCCCTCTTGGCCCCTCAGGGCAGCCCTGGGATTCGGCAGACGCCAGTCCTCC
CTGAGATGCTTCCCCATCCTTCCCTCCGCCAGGCCCTACG
[SEQ ID NO: 153] - ZNF596
```

```
CGTAGGGCCTGGCGGAGGGAAGGATGGGGAAGCATCTCAGGGAGGACTGGCGTCTGCCGA
ATCCCAGGGCTGCCCTGAGGGGCCAAGAGGGGCGAGGGTGGGGACGATGGAAGACAAGCC
ACATGCCGAATCGGGACCTGAGGCCGCGCGCGATAGGATGGGCGGACGGTGAAGAGAACT
AGGGTGGAAGGGCCGGACAGGGCGACCTCAGTGACGGAACCGGACACAGACGCAGATCT
GGCAGCTGGGCGACAGGCTTCGGAGCATTTCCGGGCGTCGCGGGACTCCCCGCCGACAGG
AGGGCGGTTGCCGAGCCTGTGACATCCGCGGAGACCAGCAGACCCCGGGTGTGGAGGACG
CCGCAGGAAGGGAACTGCGTGGCTGGGTTTGGCCACAAAAAGCGGAGGGCACTCACCCGA
GCGGACCTCGGCTCCGGAGAATCCGTTTCGGGTCAACAAAAAACGTCGCGCGAGGGGCG
GGGCCCGTACGTGCAGGGAGGGGAGGCAGAGAAAAGGCGGGGCCGGGCCGGGCGGGGT
CTCGGGCAGGGCGGGGAGCTTACCGACCTCCCGCCCCCGCTGCGCGCGTTTCTGGCCCT
GCCAGTGTCTCCGCCGGTTGAAAGCGCGTGTCTGCGTCGGGTTCTGTTGGAGTGCGTTCG
GTGTGCCGTGGGTCCGCGCTGCTTCCACCCAACTTCCTGTTAGGTAAGAGGCGCGTGAGG
CTCCTGTGCCGGGGGCGGTGCTGCTCCCGAGTCGGCGCGCGGCGGGGACGCGAGTCCGTA
GGTGCTGGCGGGAGCGAGAGTCGGGTGGGGACCCTCGCGAGCCCGCACTCCGCCTCTGGG
TAGCAGCCTCTTCGGCCCCACACGGCGTGACGCGCGCTCGGGCTCCGCGTTCGCGTCGAG
GCAGAGGCGTAGTAGGGGTCGGGCCCAGGGCTGGAGGGGCCGGGACCGGCGGGGTGCCG
CCCTGGACACCGCGCCGGCAGCTGTTCCGCGCGGGTTCATGTCATTCCTATTTTCAACCT
GTCCTGCTCCGCACCTGAGATGATTTATAAATTCGGTACCTTTGGGACAGGCGTGGATGA
CATCCCATAATTTACTTCGTTATTAATTTCTAAATGTAATACATACCACTATCTAAAAGT
ATTTTTTAATTTGAAATATATTTGTATACGTATACATGTATATTTATTTATTTCTGAATT
TTATCTCGTACATATAATGAGGCTCGTAAAGTGGATACTGTTCAGGACATAGGTGGATTT
TGCTTTTAAGTAGTAAAGACTTAATTGGTGACTTACTGGG
[SEQ ID NO: 154] - ZNF596
```

FIG 2Q

```
ACCGGCGTCCCGCTGGGGGCGCGCGAGCCCCACCCCCAGAGATGCTGACTCAGCAAGTCG
GGAGGGGTTGGGGGTGGGACCTGCCAATCTGCATTTCCAACCGGCGCCCAGGTGACGCTG
ACTCTGCTGGTCTACCGTCTTGGGGGTCACCTAATTTTTCAGCGATGCCTCCCAGCTGGG
GAGGCCAAGAAGTGCCTCGCTCAAGGTCTTCCAACACCCGACCTCCAGACCCTCAATCCT
GGGCCAGCTACACCGCAAACCTTTCCAGCTGTCTCTCCTGCGCCCTGCGTTTCTTCCCCA
CGTCACTTGCCAGGGAGCCGCTAAACAGCAAGACCGCGCGCTCTGCGGCTCCAGAGTGCG
GATTTCGGTCGCGTGCGGCTCTGACCGCGTCGCCCCATCCCTGGCGGGGCCACGCACGGA
CGCCATGGCTGGCGCCGCGGAGCCGGGCGATGCGCGCGGACTCTCCGGGGCCCTGACTG
TCCCTGAGTCCTCCCTGCGGGGGCGTGCGCGGCCCGCCCCCGCGGCGCCACGCGGCCC
CTCCTCGGCCGGGGATTGGTGCGCCGGGCGGGCGGGCGGGCGGGATAAAGGCGCGGG
GTCTGGCTGCGCGGGGTCTGCGGGCAGCTCCAACTCTGGGTTCGTAGTTTGCGCTGGGTG
CGCAGGAAGGTCAGTGTGGGGTCGCCCGACATTTCCCCCCCGCGGAGGTGGGAGCCGAG
CCACATCTTGGAGTGGGGACTGGCCGCGGAGCGGGTTGCCCAGGGCCGGCCGAGGTCGGG
GCGAGCCCTGCGCGGCGCTGGAGACTCTGCATTCCCGGGCGCGCGCAGGGTCCCCGGCCG
TGGTCGCAGAGTCAGGAGGGGCGGCTCCGGAGCCCGGCGCGGGGAGGGCCCAGGCGCAGT
CGGGGTTGGCAGGGCGCGACACTCGCTCCCCTCCACTTTTGAAAGGGCTTCCCACGCCGA
GAAGAGGGGCGGGCATGGCCGGCCCGGCGAAACCGGTTTGTACAGACTTTGGGAAGCCAT
CGCCTGCGGAGGGTGGGACCCCACAGCTTGTCCACCTGCCCAGGCTGAGACCTCGTGTCC
TAGTCCTGGATGCCCCACGGGTTTCTCGTCCCGGGCAGCGGCGCACGGGAGGAGAAGACT
CCCGGTCTGCAGTCAGACCTCCCTCTGAGACCCTCCCTAGCTCAGGCTTAGAGCTTTGGG
ATTTTTCTCGATCCTTTCTAGCTTTCAGATCATCCCCACGTAAAGTTCAGACTTTACCAG
CCCAGAGAGTTTAAAAAAAAAAAAAGAGAGAGAGAAAG
```
[SEQ ID NO: 155] - TDH

```
CTTTCTCTCTCTCTCTTTTTTTTTTTTAAACTCTCTGGGCTGGTAAAGTCTGAACTTTA
CGTGGGGATGATCTGAAAGCTAGAAAGGATCGAGAAAAATCCCAAAGCTCTAAGCCTGAG
CTAGGGAGGGTCTCAGAGGGAGGTCTGACTGCAGACCGGGAGTCTTCTCCTCCCGTGCGC
CGCTGCCCGGGACGAGAAACCCGTGGGGCATCCAGGACTAGGACACGAGGTCTCAGCCTG
GGCAGGTGGACAAGCTGTGGGTCCCACCCTCCGCAGGCGATGGCTTCCCAAAGTCTGTA
CAAACCGGTTTCGCCGGGCCGGCCATGCCCGCCCCTCTTCTCGGCGTGGGAAGCCCTTTC
AAAAGTGGAGGGGAGCGAGTGTCGCGCCCTGCCAACCCCGACTGCGCCTGGGCCCTCCCC
GCGCCGGGCTCCGGAGCCGCCCCTCCTGACTCTGCGACCACGGCCGGGGACCCTGCGCGC
GCCCGGGAATGCAGAGTCTCCAGCGCCGCGCAGGGCTCGCCCCGACCTCGGCCGGCCCTG
GGCAACCCGCTCCGCGGCCAGTCCCCACTCCAAGATGTGGCTCGGCTCCCACCTCCGCGG
GGGGGAAATGTCGGGCGACCCCCACACTGACCTTCCTGCGCACCCAGCGCAAACTACGAA
CCCAGAGTTGGAGCTGCCCGCAGACCCCGCGCAGCCAGACCCCGCGCCTTTATCCCGCCC
CGCCCCGCCCCGCCCGGCGCACCAATCCCCGGCCGAGGAGGGGCCGCGTGGCGCCGCGGG
GGGCGGGCCGCGCACGCCCCCGCAGGGAGGACTCAGGGACAGTCAGGGCCCCGGGAGAG
TCCGCGCGCATCGCCCGGCTCCGCGGCGCCAGCCATGGCGTCCGTGCGTGGCCCCGCCAG
GGATGGGGCGACGCGGTCAGAGCCGCACGCGACCGAAATCCGCACTCTGGAGCCGCAGAG
CGCGCGGTCTTGCTGTTTAGCGGCTCCCTGGCAAGTGACGTGGGGAAGAAACGCAGGGCG
CAGGAGAGACAGCTGGAAAGGTTTGCGGTGTAGCTGGCCCAGGATTGAGGGTCTGGAGGT
CGGGTGTTGGAAGACCTTGAGCGAGGCACTTCTTGGCCTCCCCAGCTGGGAGGCATCGCT
GAAAAATTAGGTGACCCCAAGACGGTAGACCAGCAGAGTCAGCGTCACCTGGGCGCCGGG
TTGGAAATGCAGATTGGCAGGTCCCACCCCCAACCCCTCCCGACTTGCTGAGTCAGCATC
TCTGGGGGTGGGGCTCGCGCGCCCCAGCGGGACGCCGGT
```
[SEQ ID NO: 156] - TDH

FIG 2R

```
CTCATTTCGGGCCGCTTTTCTCAGAGGGCAAAGATGGGTCAGGGTGGGATGTTACATTAG
TGTTGAGACTCTTTGGATCCGTTTCGTGGGTACCGAGGACGCCTGGGTACGCGGGACAGG
CTGCACCCGCCTGCTAGAGGCGCCCCATCGAGGCGCCACGGGTGAAGCTCCCGGCCCCAC
CTACGGGGCGGGGCTCCGGCTCGGTCCGACTATTGCCCGCGGTGGGGGAGGGGGATGGAT
CACGCCACGCGCCAAAGGCGATCGCGACTCTCCTTCTGCAGGTAGCCTGGAAGGCTCTCT
CTCTTTCTCTACGCCACCCTTTTCGTGGCACTGAAAAGCCCCGTCCTCTCCTCCCAGTCC
CGCCTCCTCCGAGCGTTCCCCCTACTGCCTGGAATGGTGCGGTCCCAGGTCGCGGGTCAC
GCGGCGGAGGGGGCGTGGCCTGCCCCCGGCCCAGCCGGCTCTTCTTTGCCTCTGCTGGAG
TCCGGGGAGTGGCGTTGGCTGCTAGAGCGATGCCGGGCCGGAGTTGCGTCGCCTTAGTCC
TCCTGGCTGCCGCCGTCAGCTGTGCCGTCGCGCAGCACGCGCCGCCGGTGAGTGAGCTTG
AGCCGAGGCGCAGAGAGGGGCGTGCAGGTGCGGGCGCGGATGGAGGCGCAGGTGTGGCGG
CGCGAGCGGGTACAAGGAACACCTCGTGCTGGGCAGCTTCTTTACGGGGGTCTGTGGTTT
CGTGCACAGGGGTGTGGGTGCAGAGCGGGCTGGCGAACCCCGTCCTCGGTAGATTCGGTG
CTACCTGCAACTAGAACTCC
[SEQ ID NO: 157] - ASAH1

GGAGTTCTAGTTGCAGGTAGCACCGAATCTACCGAGGACGGGGTTCGCCAGCCCGCTCTG
CACCCACACCCCTGTGCACGAAACCACAGACCCCCGTAAAGAAGCTGCCCAGCACGAGGT
GTTCCTTGTACCCGCTCGCGCCGCCACACCTGCGCCTCCATCCGCGCCCGCACCTGCACG
CCCCTCTCTGCGCCTCGGCTCAAGCTCACTCACCGGCGGCGCGTGCTGCGCGACGGCACA
GCTGACGGCGGCAGCCAGGAGGACTAAGGCGACGCAACTCCGGCCCGGCATCGCTCTAGC
AGCCAACGCCACTCCCCGGACTCCAGCAGAGGCAAAGAAGAGCCGGCTGGGCCGGGGGCA
GGCCACGCCCCCTCCGCCGCGTGACCCGCGACCTGGGACCGCACCATTCCAGGCAGTAGG
GGGAACGCTCGGAGGAGGCGGGACTGGAGGAGAGGACGGGGCTTTTCAGTGCCACGAAA
AGGGTGGCGTAGAGAAAGAGAGAGAGCCTTCCAGGCTACCTGCAGAAGGAGAGTCGCGAT
CGCCTTTGGCGCGTGGCGTGATCCATCCCCCTCCCCCACCGCGGGCAATAGTCGGACCGA
GCCGGAGCCCCGCCCCGTAGGTGGGGCCGGGAGCTTCACCCGTGGCGCCTCGATGGGGCG
CCTCTAGCAGGCGGGTGCAGCCTGTCCCGCGTACCCAGGCGTCCTCGGTACCCACGAAAC
GGATCCAAAGAGTCTCAACACTAATGTAACATCCCACCCTGACCCATCTTTGCCCTCTGA
GAAAAGCGGCCCGAAATGAG
[SEQ ID NO: 158] - ASAH1

TTCTGCAGAGCCAGCAGCCGGCTCCCACCTACCCAAGGAGAGAAGATCGCTCCAAGACAG
TGAGAGCTTCCCTGCCATTTCAGTGCAAAGTCCCTCCGGAGCGACCTCAGAGGAGTAACC
GGGCCTTAACTTTTTGCGCTCGTTTTGCTATAATTTTTCTCTATCCACCTCCATCCCACC
CCCACAACACTCTTTACTGGGGGGTCTTTTGTGTTCCGGATCTCCCCCTCCATGGCTCC
CTTAGCCGAAGTCGGGGGCTTTCTGGGCGGCCTGGAGGGCTTGGGCCAGCAGGTGGGTTC
GCATTTCCTGTTGCCTCCTGCCGGGGAGCGGCCGCCGCTGCTGGGCGAGCGCAGGAGCGC
GGCGGAGCGGAGCGCGCGCGGCGGGCCGGGGCTGCGCAGCTGGCGCACCTGCACGGCAT
CCTGCGCCGCCGGCAGCTCTATTGCCGCACCGGCTTCCACCTGCAGATCCTGCCCGACGG
CAGCGTGCAGGGCACCCGGCAGGACCACAGCCTCTTCGGTACGTACTAGCATCCCGACCC
CACCCCCATCTGCGCCCCAGCTCGGCTCCTCGTTCCCTCCCCTTGCACCTCCCTCTTTGC
CTGCCAAGGGCGTCATCGCCGCGCGGAGCCCGGAGCTCCCCTGGACCCATCCGGTGCAAG
ACGCAGGCTGGGCTGAAGGGCTGGCCAGAGCAGCCGCGGGGAGAAATTTTCCTGCTGGT
TTGTCGCCGCAGCCTCTAGCAGGGCAGCAGCTCCAGATGCTGGGGCGGGAGGAGAAAGG
GTGGGCGCTTCGCAAGCTCC
[SEQ ID NO: 159] - FGF20
```

FIG 2S

```
GGAGCTTGCGAAGCGCCCACCCTTTCTCCTCCCGCCCCCAGCATCTGGAGCTGCTGCCCT
GCTAGAGGCTGCGGCGACAAACCAGCAGGAAAATTTCTCCCCGCGGCTGCTCTGGCCAGC
CCTTCAGCCCCAGCCTGCGTCTTGCACCGGATGGGTCCAGGGGAGCTCCGGGCTCCGCGC
GGCGATGACGCCCTTGGCAGGCAAAGAGGGAGGTGCAAGGGGAGGAACGAGGAGCCGAG
CTGGGGCGCAGATGGGGGTGGGGTCGGGATGCTAGTACGTACCGAAGAGGCTGTGGTCCT
GCCGGGTGCCCTGCACGCTGCCGTCGGGCAGGATCTGCAGGTGGAAGCCGGTGCGGCAAT
AGAGCTGCCGGCGGCGCAGGATGCCGTGCAGGTGCGCCAGCTGCGCAGCCCCGGCCCGC
CGCGCGCGCTCCGCTCCGCCGCGCTCCTGCGCTCGCCCAGCAGCGGCGGCCGCTCCCCGG
CAGGAGGCAACAGGAAATGCGAACCCACCTGCTGGCCCAAGCCCTCCAGGCCGCCCAGAA
AGCCCCCGACTTCGGCTAAGGGAGCCATGGAGGGGGAGATCCGGAACACAAAAGACCCCC
CCAGTAAAGAGTGTTGTGGGGGTGGGATGGAGGTGGATAGAGAAAAATTATAGCAAAACG
AGCGCAAAAAGTTAAGGCCCGGTTACTCCTCTGAGGTCGCTCCGGAGGGACTTTGCACTG
AAATGGCAGGGAAGCTCTCACTGTCTTGGAGCGATCTTCTCTCCTTGGGTAGGTGGGAGC
CGGCTGCTGGCTCTGCAGAA
[SEQ ID NO: 160] - FGF20

CTTAACCCCCCCATCTCCAGTTATCCCAATGAACCGACCCCGAGGGGGCATTTCCGCTGA
AGTCCGGGGCTGTAAAAAATTAAGTGAGAAGAGCCGCGCTAAAGCCAAGCGTCGTCGTCA
CCCAAGGTACTGCGCTGATGCGCTGCGGGCCGACCAGGTGCTCCCGCCGGGGCGTCTTCT
CCTACGCAGGAAGGGCCACGCCGAGAGAGGCAGGCAACAAGGGCACGGCTGGAGGCCGGA
AGGTCACCCCGTCCCCGGCGGGGCGGGCGCGGCCCAGCCTCACTTCCCGGGCACGTTCGG
GCGGGGCGATTGCAGGGAACGGGGCGGGGAGGCGACAGTCCCCGGCTCCGCCGCGCGCCA
GCCCGCCTTCGCTGCCCGGAGGCGCCGCAGGCCTGGGTTCCCGGACAGCTGAGCCCGAGC
GCCGCCTCCCGAAAGGTGAAGGCGGCCCGGGGAGGCGGGGACGGTGACGGGGCGGGGGC
CGCGGGCGGTCTCCCGACGGCTGTCGCGGGCCAGCCCAAAGCCCCCGATCCCCGGTAGC
TGCGCTTCCCGCGCGGGCGCCGGAGTAGGGCGGGCCAAGCTGGCCTGCGGCCGCGGCGG
GAAGAAGGGCTAGCGAAGCACCCCCGACCGGGCCCAGGCGCCGGACGCCGGGGGGCGCCT
CGCTGCAACTTCTCTTTGGAAGCCCCGACACGAGCCCCGGCCCGCGCGCGCGCTCCCCCA
CGGCCACGCGCGCACCCTGCCGCCCGCACCCCCGCGCGCCCTCCGTCTATTTTTTCCTCT
TCCTTTCATCCTCACACTCTAAAATAGGTCAAGGGGTGGAAGTTACACCTGGTGCAGCCC
TCGGCTCTGATGCAAAAGCAGCTTTTGCCCCTGGCTGCGGGACAGCGCTGTGACTACTCG
CAACGGGAGAGCTGCTGCCAGTCGCCACACCGTGCGGAAAGCGCCGGCGACCGGAGCACT
GACAATGGTCTGCATAGGGGAGCGGAGAGAAGCTTCTGTTGCGCCCTAGATCCGCTGCCT
CGGCGCCCGCCCGCAGGGAGGAGGGGCGCGACAGGTCGTCTAGCGCGTGCCCCGGAGCC
CGCGCCCGGGTCTGGCCGCCTGGGTGAGTTCCTGCTCGTCCCCTGCCTTTCCAGTAGCCC
GGGGTGGCTGTTTACCTTGCAAACAGCCTTGCAATACGATCAAAACAGGCGAGACAGCCA
TGCAGTAAGGGATTGCGGGATGTGCTTTGGGTGTGAGATTGGATAAATCAGAATTCAGAG
ATAAAGGACATGTCTAGTGCCTTAAGGGTTAAAGTGGATT
[SEQ ID NO: 161] - FLJ36980
```

FIG 2T

```
AATCCACTTTAACCCTTAAGGCACTAGACATGTCCTTTATCTCTGAATTCTGATTTATCC
AATCTCACACCCAAAGCACATCCCGCAATCCCTTACTGCATGGCTGTCTCGCCTGTTTTG
ATCGTATTGCAAGGCTGTTTGCAAGGTAAACAGCCACCCCGGGCTACTGGAAAGGCAGGG
GACGAGCAGGAACTCACCCAGGCGGCCAGACCCGGGCGCGGGCTCCGGGGCACGCGCTAG
ACGACCTGTCGCGCCCCTCCTCCCTGCGGGCGGGCGCCGAGGCAGCGGATCTAGGGCGC
AACAGAAGCTTCTCTCCGCTCCCTATGCAGACCATTGTCAGTGCTCCGGTCGCCGGCGC
TTTCCGCACGGTGTGGCGACTGGCAGCAGCTCTCCCGTTGCGAGTAGTCACAGCGCTGTC
CCGCAGCCAGGGGCAAAAGCTGCTTTTGCATCAGAGCCGAGGGCTGCACCAGGTGTAACT
TCCACCCCTTGACCTATTTTAGAGTGTGAGGATGAAAGGAAGAGGAAAAAATAGACGGAG
GGCGCGCGGGGGTGCGGCGGCAGGGTGCGCGCGTGGCCGTGGGGAGCGCGCGCGCGGG
CCGGGGCTCGTGTCGGGCTTCCAAAGAGAAGTTGCAGCGAGGCGCCCCCGGCGTCCGG
CGCCTGGGCCCGGTCGGGGGTGCTTCGCTAGCCCTTCTTCCCGCCGCGGCCGCAGGCCAG
CTTGGCCCGCCCTACTCCGGCGCCCCGCGCGGGAAGCGCAGCTACCGGGGATCGGGGCT
TTGGGCTGGCCCCGCGACAGCCGTCGGGAGACCGCCCGCGGCCCCCGCCCCGTCACCGT
CCCCGCCTCCCCGGGCCGCCTTCACCTTTCGGGAGGCGGCGCTCGGGCTCAGCTGTCCGG
GAACCCAGGCCTGCGGCGCCTCCGGGCAGCGAAGGCGGGCTGGCGCGCGGCGGAGCCGGG
GACTGTCGCCTCCCCGCCCCGTTCCCTGCAATCGCCCCGCCCGAACGTGCCCGGGAAGTG
AGGCTGGGCCGCGCCCGCCCCGCCGGGACGGGGTGACCTTCCGGCCTCCAGCCGTGCCC
TTGTTGCCTGCCTCTCTCGGCGTGGCCCTTCCTGCGTAGGAGAAGACGCCCCGGCGGGAG
CACCTGGTCGGCCCGCAGCGCATCAGCGCAGTACCTTGGGTGACGACGACGCTTGGCTTT
AGCGCGGCTCTTCTCACTTAATTTTTTACAGCCCCGGACTTCAGCGGAAATGCCCCCTCG
GGGTCGGTTCATTGGGATAACTGGAGATGGGGGGGTTAAG
[SEQ ID NO: 162] - FLJ36980

CTAGCATTTACTGGATTCCAGAGTCTTGTTATTTAAGAATGCATCTTAAACGGTACTATC
AAATTCATGTTACGTGCAGCCCAGATTGTTTTGGGCAGCACGAAAAGTTTCTGAGGCGCT
GCGTGTACCCCACCCCAGGACACCGTGTGTGCGCGCCGAGCTGAGTGCGAGGAACGTGGC
GCGAGGGCCGGGGGATGCCGGGCTGCGTGGGTGTGAGCCCTCGCGCGACCGCGACCCCGC
GCCTCTCCCGCTCTCGCCGGAACGTGACCGCAGCCGCACCTCTCCTCCAGCCCTTTCCCA
GCCAGACGCTTCCTTTTAGGTCCTTCTGGGCGTTTATTGTAAATTCTGCGACTAAAACAC
GCCGGTGAGCCCGGCCCACCGACAGATGGATCAATCGCCCCCTTCCCGGCTAGGGGAGGA
GGAACCCCCCAACCCCGGAGCCTAGGGAGCCGGGAGCTGCCTCGGGACGAGCTCCTCGGA
GCCCAGCCGGCTGCGGAGCCCCGGCCCGGGTCGGTCTCGGGGCCTCCTGCCGGGGTGGG
GTGCGAGCCCCTGCCCGATTCCTCTGGGCGGTTCAGGCAGGTTTGCCGGCCTCCAGGA
GGTGGTCAGGGCGCCCTGGCCCAGCAGGCTTCTTCCCGAGCCGGGGGGAGGGGAGACCGG
CTGGGGAAGGGGCATCTCGAAGGGGTGGAGGCCGGGGCGGGCGGGAGGCAAGCGCGCCGC
GGGCGTGAGGGCAAAGTTCCCGAGGTCCGCGCGGAGAGCACACGTGTATGTGCGCGCGGG
GCTAGGCCGGGGCCGGCAGGATGCGTTGGGTTCGGGGGCGCGCGGGGCCGGCGCCGAAGG
GGATAATTCCTTTCCCTGGCACCATCGGGGAGACGCTTTGTCGGCCTCGGCTCCTGGGCG
CAGGGACGCCTTAGCCCACGGAGGGTGGAGCCCCCTCAGACCCGGGCCACCGGCTGGGG
TTTTTCTAACGCCCTGCCCCCGAGCCCCGGATGGCTCGGGCCCCACGGACTCCGCGCC
CTCCAGCCTCAGCTCAGCTCCCCAGGCTTCCCAGACCCAGCGGCGCAGGGGCGGGGCA
GGGGCAGTGGGGGTTGGAGGGCGCAGCCGGTCCCCAGGGTGGGGAGAGCTGCGGGGGGAG
GAGGAGGAGGGTGCCGACGCTTGAGTGGGTTCGAGCCCGAGCCGTAGCCGGGGGAGCCAG
TCAGTTTCCGGCCAAGGCAGCAGGTCAGTCCCAGGAAGGGCGGGCGATTGAGCCGAGGGA
GCCGGCGGCTGGGCTCTCCTCTCGGCCCGCGATCCCCGGCGCCGCCGCCGCCGCCACCGC
CACCGCCACCGCCTTCGCCTTGTCGCCGCCGCCGCTGCAGAGCATCGTAGCTCCGCCGCG
CTCCCGCGCCCCGCGCCCCGCGCCGCCAGCCGCCTGGGAGCCCGAGCGCCGAGCCCGGGG
CGGAGGAGAGGGGCGCTGGCGCGAGAGCCCGGGCGAGGGAGCCGCGAAGGGAGAAGGGGG
CGGGCGGAGGGAGGAGCAGGGAGAGTGGGAGAAGGGGGAGGGAGAGAGGAGAGCGAGGGA
GAGCTGGAGAGAGCGAGAGCAAAGAGCGAGCGAGGGAGAGGAGAGAGAGAGAGGAGAG
AGAAAGACACACGCACGCAGAGACACACGGTCACTGGAATTCCATTAGAAAAAAGTGAGC
CGAGCAAGGGTTAGCGGGAGAAGATTTTTTTGAATCTTGTCTTCGTCTTGGTGCGAAAGA
AGCGACTCCAGTCTCTCGTCCTCGAAGCTCCGACTGGATTGTTCTTGGGCGCTGACACCC
[SEQ ID NO: 163] - GFRA2
```

FIG 2U

```
GGGTGTCAGCGCCCAAGAACAATCCAGTCGGAGCTTCGAGGACGAGAGACTGGAGTCGCT
TCTTTCGCACCAAGACGAAGACAAGATTCAAAAAAATCTTCTCCCGCTAACCCTTGCTCG
GCTCACTTTTTTCTAATGGAATTCCAGTGACCGTGTGTCTCTGCGTGCGTGTGTCTTTCT
CTCTCCTCTCTCTCTCTCCTCTCCCTCGCTCGCTCTTTGCTCTCGCTCTCTCCAGCTC
TCCCTCGCTCTCCTCTCTCCCTCCCCCTTCTCCCACTCTCCCTGCTCCTCCCTCCGCCCG
CCCCCTTCTCCCTTCGCGGCTCCCTCGCCCGGGCTCTCGCGCCAGCGCCCCTCTCCTCCG
CCCCGGGCTCGGCGCTCGGGCTCCCAGGCGGCTGGCGGCGCGGGCGCGGGGCGCGGGAG
CGCGGCGGAGCTACGATGCTCTGCAGCGGCGGCGGCGACAAGGCGAAGGCGGTGGCGGTG
GCGGTGGCGGCGGCGGCGGCGCCGGGGATCGCGGGCCGAGAGGAGAGCCCAGCCGCCGGC
TCCCTCGGCTCAATCGCCCGCCCTTCCTGGGACTGACCTGCTGCCTTGGCCGGAAACTGA
CTGGCTCCCCGGCTACGGCTCGGGCTCGAACCCACTCAAGCGTCGGCACCCTCCTCCTC
CTCCCCCCGCAGCTCTCCCCACCCTGGGGACCGGCTGCGCCCTCCAACCCCCACTGCCCC
TGCCCCCGCCCCCTGCGCCGCTGGGTCTGGGAAGCCTGGGGAGCTGAGCTGAGGCTGGAG
GGCGCGGAGTCCGTGGGGCCCGAGCCATCCGGGGGCTCGGGGGCAGGGCGTTAGAAAAA
CCCCAGCCGGTGGCCCGGGTCTGAGGGGGGCTCCACCCTCCGTGGGCTAAGGCGTCCCTG
CGCCCAGGAGCCGAGGCCGACAAAGCGTCTCCCCGATGGTGCCAGGGAAAGGAATTATCC
CCTTCGGCGCCGGCCCCGCGCGCCCCGAACCCAACGCATCCTGCCGGCCCCGGCCTAGC
CCCGCGCGCACATACACGTGTGCTCTCCGCGCGGACCTCGGGAACTTTGCCCTCACGCCC
GCGGCGCGCTTGCCTCCCGCCCGCCCCGGCCTCCACCCCTTCGAGATGCCCCTTCCCCAG
CCGGTCTCCCCTCCCCCGGCTCGGGAAGAAGCCTGCTGGGCCAGGGCGCCCTGACCACC
TCCTCGGAGGCCGGCAAACCTGCCTGAACCGCCCAGAGGAATCGGGCAGGGCTCGCAC
CCCACCCCGGCAGGAGGGCCCCGAGACCGACCCGGGCCGGGGCTCCGCAGCCGGCTGGGC
TCCGAGGAGCTCGTCCCGAGGCAGCTCCCGGCTCCCTAGGCTCCGGGGTTGGGGGGTTCC
TCCTCCCCTAGCCGGGAAGGGGGCGATTGATCCATCTGTCGGTGGGCCGGGCTCACCGGC
GTGTTTTAGTCGCAGAATTTACAATAAACGCCCAGAAGGACCTAAAAGGAAGCGTCTGGC
TGGGAAAGGGCTGGAGGAGAGGTGCGGCTGCGGTACGTTCCGGCGAGAGCGGGAGAGGC
GCGGGGTCGCGGTCGCGCGAGGGCTCACACCCACGCAGCCCGGCATCCCCCGGCCCTCGC
GCCACGTTCCTCGCACTCAGCTCGGCGCGCACACACGGTGTCCTGGGGTGGGGTACACGC
AGCGCCTCAGAAACTTTTCGTGCTGCCCAAAACAATCTGGGCTGCACGTAACATGAATTT
GATAGTACCGTTTAAGATGCATTCTTAAATAACAAGACTCTGGAATCCAGTAAATGCTAG
[SEQ ID NO: 164] - GFRA2

AAACAGCATTAGCCTTCTCCCATCAAAAGTCCGGAAGCTGCCCTTCAGTCGTCAAAGTGT
TTGCCTTAATTTGCAATCGTTATGACTTGAGCCAAATGCTTATACCTCATTTGTGTCGTA
TATGTGAAGATACAATTGCAAATCGTTCACGACCTTGAGTCAAGACCTTGAGTTTCCTGA
GGTCAGGAGACCGTTAGGGAATGTGAGTGTCCCAGACGGGCGCTGAGCCCAGCTCGGAGA
CCCACCCCGCCCGTAGCAGCGGCGCGGGCCCCAGAGAGCCCCGCACTCGGCCGCGCCTCA
GTTACGCTGACTCGGCTGTGCCCGCAGTGTCGCGCTGTCGCGTAGCCAGGTGTCGCCGGG
CTGGCGCGGTTATTTATGACTGCGTGGTTGGGCTGGGGGTTCGGGGCCGGGGAGCAGCCG
GGATCCGCCGCCTCTTCCATGATCTTCCCGGGCCGAACCACGGGACCGCTACGCTGAAGG
TGGCGTCGCGGGTCCCCGGGGCCGCGCGAGTGTAGGGGTCGCTCTCGGCCGGCCGCGAAG
CTCGCGGCACCGACTTCTCGCGAGATTTCGGCGACCCCCCCCCGCCCCGCCCCTCCG
TTCTCTGCCCCCTCCCAGCTCTGGTGTGGCGGCCTCCGCTATGGCTGCGCTGCGAAGGC
TCTTGTGGCCGCCACCCCGGGTGTCTCCTCCACTCTGCGCTCACCAGCCCCTCCTTGGGC
CGTGGGGGCGGCCTGCGGTGACCACCCTGGGCCTTCCTGGCCGGCCCTTCTCCTCCCGAG
AGGATGAGGAGAGGGCTGTGGCGGAGGCGGCATGGAGGCGGCGGCGGCGCTGGGGGAGC
TGAGCGTGGCGGCGGCGGCCGGCGGGGGCTGGTCGGCCTGGTATGCTACCAGCTGTACG
GGGACCCCAGGGCCGGCTCGCCGGCGACCGGGCGACCCTCAAAGAGCGCGGCCACGGAGC
CCGAGGACCCGCCCCGCGGCCGGGGATGCTGCCCATCCCAGTGGCGGCTGCCAAGGAGA
CGGTGAGTGCGCGAGCGCGCGTCACACCTGCGCGGGGATGTGACCTTCGTGCCGGGTAC
GCAGGACCCTGGAGGCTGTGGGGACGGTGCAAGCGCTGTGGCCGCGGGTGAGGAACTTCC
CGTGAGCGAGGCTGACACCTAGGCCGGACAGCCTAGGATCCGGTCACCCACGTATTGGGA
AGACCAGTGATGCTGTCCCTGATGCATCAGGACCTTAAAGGTGGCTGCAGCTACCAAGTA
TCAATCCAAACCCAAAACCAACACCCCTCCCCCTCTTACA
[SEQ ID NO: 165] - EFHA2
```

FIG 2V

```
TGTAAGAGGGGGAGGGGTGTTGGTTTTGGGTTTGGATTGATACTTGGTAGCTGCAGCCAC
CTTTAAGGTCCTGATGCATCAGGGACAGCATCACTGGTCTTCCCAATACGTGGGTGACCG
GATCCTAGGCTGTCCGGCCTAGGTGTCAGCCTCGCTCACGGGAAGTTCCTCACCCGCGGC
CACAGCGCTTGCACCGTCCCCACAGCCTCCAGGGTCCTGCGTACCCGGCACGAAGGTCAC
ATCCCCCGCGCAGGTGTGACGCGCGCTCGCGCACTCACCGTCTCCTTGGCAGCCGCCACT
GGGATGGGCAGCATCCCCCGGCCGCGGGGCGGGTCCTCGGGCTCCGTGGCCGCGCTCTTT
GAGGGTCGCCCGGTCGCCGGCGAGCCGGCCCTGGGGTCCCCGTACAGCTGGTAGCATACC
AGGCCGACCAGCCCCCGCCGGCCGCCGCCGCCACGCTCAGCTCCCCCAGCGCCGCCGC
CGCCTCCATGCCGCCTCCGCCACAGCCCTCTCCTCATCCTCTCGGGAGGAGAAGGGCCGG
CCAGGAAGGCCCAGGGTGGTCACCGCAGGCCGCCCCACGGCCCAAGGAGGGGCTGGTGA
GCGCAGAGTGGAGGAGACACCCGGGGTGGCGGCCACAAGAGCCTTCGCAGCGCAGCCATA
GCGGAGGCCGCCCACACCAGAGCTGGGAGGGGGCAGAGAACGGAGGGGCGGGGGCGGGGG
GGGGGGTCGCCGAAATCTCGCGAGAAGTCGGTGCCGCGAGCTTCGCGGCCGGCCGAGAGC
GACCCCTACACTCGCGCGGCCCCGGGGACCCGCGACGCCACCTTCAGCGTAGCGGTCCCG
TGGTTCGGCCCGGGAAGATCATGGAAGAGGCGGCGGATCCCGGCTGCTCCCCGGCCCCGA
ACCCCCAGCCCAACCACGCAGTCATAAATAACCGCGCCAGCCCGGCGACACCTGGCTACG
CGACAGCGCGACACTGCGGGCACAGCCGAGTCAGCGTAACTGAGGCGCGGCCGAGTGCGG
GGCTCTCTGGGGCCCGCGCCGCTGCTACGGGCGGGGTGGGTCTCCGAGCTGGGCTCAGCG
CCCGTCTGGGACACTCACATTCCCTAACGGTCTCCTGACCTCAGGAAACTCAAGGTCTTG
ACTCAAGGTCGTGAACGATTTGCAATTGTATCTTCACATATACGACACAAATGAGGTATA
AGCATTTGGCTCAAGTCATAACGATTGCAAATTAAGGCAAACACTTTGACGACTGAAGGG
CAGCTTCCGGACTTTTGATGGGAGAAGGCTAATGCTGTTT
[SEQ ID NO: 166] - EFHA2

CCTGGCGCGGACAGGACCCAGAAACAAACCACAGCCCGGGGCGCAGCCGCCAGGGCGAAG
GTTAGTTCCGGTCCCTTCCCCTCCCCTCCCCACTTGGACGCGCTTGCGGAGGATTGCGTT
GACGAGACTCTTATTTATTGTCACCAACCTGTGGTGGAATTTGCAGTTGCACATTGGATC
TGATTCGCCCCGCCCCGAATGACGCCTGCCCGGAGGCAGTGAAAGTACAGCCGCGCCGCC
CCAAGTCAGCCTGGACACATAAATCAGCACGCGGCCGGAGAACCCCGCAATCTCTGCGCC
CACAAAATACACCGACGATGCCCGATCTACTTTAAGGGCTGAAACCCACGGGCCTGAGAG
ACTATAAGAGCGTTCCCTACCGCCATGGAACAACGGGGACAGAACGCCCCGGCCGCTTCG
GGGGCCCGGAAAAGGCACGGCCCAGGACCCAGGGAGGCGCGGGGAGCCAGGCCTGGGCCC
CGGGTCCCCAAGACCCTTGTGCTCGTTGTCGCCGCGGTCCTGCTGTTGGTGAGTCCCCGC
CGCGGTCCCTGGCTGGGGAAGAGCGTGCCTGGCGCCTGGAGAGGGCAGGGAGAGAGGGGG
ACACGGCGGGGGTGCGTGGCCCGGGTCGCCTGCGGCCGGGCATGTCCGGGCAAGACGCAC
CAGTCGTCGGAGTCGGGGGAAGAGATGGGTCCCCGGGTTGGGCAGGAGCGACCTGGGCCG
CCAGGGAACAGAGCGCGCGCTCCACTTGGTGTAAATTCCCGAATCCAGTGGGGGAGGGCG
ACAAGGAGGGAATTCCCGAGTAAGCTGCGTGAAGCCACGGAGAGGTCGTCGGACTTTGAT
TTTGTTTTCTTTCCTTACTTTCTGTTTCTTTCTCTTTTTCTCTTTCTTCCTTTCTTTCCC
TCCCTTCCTTCCTCGCTCAGTTCCTGCCTTAATTTCTTTTTCTTTTGCGCCTTCGAATGA
ATTCCTAAAGGCGCTCATTGCAGATCGCTTTGAACCTGCGGCCGGCGAAGAACTCCCCTG
TGGTCGCTGCGGCCCAGTGGTTCCGTTCCGTGCGCGGGAGTCGTCGCGGGCGCAGCTGGA
GAGGCCCCTTCCCCTCCTTAGCGGCTGCGCCCCTACGCGTGCGGGGCCGCTCATCGCCAA
TGCCATTGTTTGGGGTTCCTTGGGAAAACGAGATTTAGGAGAAGGGAGTTGTGGCACTTG
GGGCCTGACCTGCTTGATAATAGCAGCTGCATTTTGGCCTGGGAAGAGCCTTTCTTGCCA
CCTCTTGGCAAGTATCCGTGATAATGGGGAAGGGACAAAG
[SEQ ID NO: 167] - TNFRSF10B
```

FIG 2W

```
CTTTGTCCCTTCCCCATTATCACGGATACTTGCCAAGAGGTGGCAAGAAAGGCTCTTCCC
AGGCCAAAATGCAGCTGCTATTATCAAGCAGGTCAGGCCCCAAGTGCCACAACTCCCTTC
TCCTAAATCTCGTTTTCCCAAGGAACCCCAAACAATGGCATTGGCGATGAGCGGCCCCGC
ACGCGTAGGGGCGCAGCCGCTAAGGAGGGGAAGGGGCCTCTCCAGCTGCGCCCGCGACGA
CTCCCGCGCACGGAACGGAACCACTGGGCCGCAGCGACCACAGGGGAGTTCTTCGCCGGC
CGCAGGTTCAAAGCGATCTGCAATGAGCGCCTTTAGGAATTCATTCGAAGGCGCAAAAGA
AAAAGAAATTAAGGCAGGAACTGAGCGAGGAAGGAAGGGAGGGAAAGAAAGGAAGAAAGA
GAAAAAGAGAAAGAAACAGAAAGTAAGGAAAGAAAACAAAATCAAAGTCCGACGACCTCT
CCGTGGCTTCACGCAGCTTACTCGGGAATTCCCTCCTTGTCGCCCTCCCCACTGGATTC
GGGAATTTACACCAAGTGGAGCGCGCGCTCTGTTCCCTGGCGGCCCAGGTCGCTCCTGCC
CAACCCGGGGACCCATCTCTTCCCCCGACTCCGACGACTGGTGCGTCTTGCCCGGACATG
CCCGGCCGCAGGCGACCCGGGCCACGCACCCCGCCGTGTCCCCTCTCTCCCTGCCCTC
TCCAGGCGCCAGGCACGCTCTTCCCCAGCCAGGGACCGCGGCGGGGACTCACCAACAGCA
GGACCGCGGCGACAACGAGCACAAGGGTCTTGGGGACCCGGGGCCCAGGCCTGGCTCCCC
GCGCCTCCCTGGGTCCTGGGCCGTGCCTTTTCCGGGCCCCGAAGCGGCCGGGGCGTTCT
GTCCCCGTTGTTCCATGGCGGTAGGGAACGCTCTTATAGTCTCTCAGGCCCGTGGGTTTC
AGCCCTTAAAGTAGATCGGGCATCGTCGGTGTATTTGTGGGCGCAGAGATTGCGGGGTT
CTCCGGCCGCGTGCTGATTTATGTGTCCAGGCTGACTTGGGGCGGCGCGGCTGTACTTTC
ACTGCCTCCGGGCAGGCGTCATTCGGGGCGGGGCGAATCAGATCCAATGTGCAACTGCAA
ATTCCACCACAGGTTGGTGACAATAAATAAGAGTCTCGTCAACGCAATCCTCCGCAAGCG
CGTCCAAGTGGGGAGGGGAGGGAAGGGACCGGAACTAACCTTCGCCCTGGCGGCTGCGC
CCCGGGCTGTGGTTTGTTTCTGGGTCCTGTCCGCGCCAGG
[SEQ ID NO: 168] - TNFRSF10B

TGCCCCTTTTCTGAGTGCTTGGAAGTGACTGCTGCAAGTGACAAGTGACCACGCCTTTTC
CCCCGCGGGTATAAATTCAGAGGCGCTGCGCTCCGATTCTGGCAGTGCAGCTGTGGGAAC
CTCTCCACGCGCACGAACTCAGCCAACGATTTCTGATAGATTTTTGGGAGTTTGACCAGA
GATGCAAGGGGTGAAGGAGCGCTTCCTACCGTTAGGGAACTCTGGGGACAGAGCGCCCCG
GCCGCCTGATGGCCGAGGCAGGGTGCGACCCAGGACCCAGGACGGCGTCGGGAACCATAC
CATGGCCCGGATCCCCAAGACCCTAAAGTTCGTCGTCGTCATCGTCGCGGTCCTGCTGCC
AGTGAGTCCCGGCCGCGGTCCCTGGCTGGGGAAGAGCGCACCTGGCGCCGGGAGGGGGCA
GGGAGACGGGGACACGGCAGGGATGCCTGGCCCTGGTCACCTGCGGCCGGGCATGTCCGG
GCAGGACGAACTCGCCGTCGGAGTCAGGGGAAGAACTGGGTCCCCGGGCTGGGCAGGAGG
GACCCGGCCGCGAGGGAGCAGAGAGGCGGTCCCCCTGGCTGCCCCGAGCCCGCGAAGGGA
GGGAAGTTCCAGAATCGAGAGAGGGAGGGAGTCAAGGTGGAACCCATAGAGTGAGCCTCC
TGAAGACACAGAGCGGTTGCCTCTCTCATTAATTAATTAATTAGTTAATAAAATTAACCC
CATGTTTACATTCTTAAACGTGTTCCTTGGAGATCGGTTTAACCAACAGCCAGTGAAAAA
ACTTTTCAGCGCTGTCTTTA
[SEQ ID NO: 169] - TNFRSF10C

TAAAGACAGCGCTGAAAAGTTTTTTCACTGGCTGTTGGTTAAACCGATCTCCAAGGAACA
CGTTTAAGAATGTAAACATGGGGTTAATTTTATTAACTAATTAATTAATTAATGAGAGAG
GCAACCGCTCTGTGTCTTCAGGAGGCTCACTCTATGGGTTCCACCTTGACTCCCTCCCTC
TCTCGATTCTGGAACTTCCCTCCCTTCGCGGGCTCGGGGCAGCCAGGGGGACCGCCTCTC
TGCTCCCTCGCGGCCGGGTCCCTCCTGCCCAGCCCGGGGACCCAGTTCTTCCCCTGACTC
CGACGGCGAGTTCGTCCTGCCCGGACATGCCCGGCCGCAGGTGACCAGGGCCAGGCATCC
CTGCCGTGTCCCCGTCTCCCTGCCCCCTCCCGGCGCCAGGTGCGCTCTTCCCCAGCCAGG
GACCGCGGCCGGGACTCACTGGCAGCAGGACCGCGACGATGACGACGACGAACTTTAGGG
TCTTGGGGATCCGGGCCATGGTATGGTTCCCGACGCCGTCCTGGGTCCTGGGTCGCACCC
TGCCTCGGCCATCAGGCGGCCGGGGCGCTCTGTCCCAGAGTTCCCTAACGGTAGGAAGC
GCTCCTTCACCCCTTGCATCTCTGGTCAAACTCCCAAAAATCTATCAGAAATCGTTGGCT
GAGTTCGTGCGCGTGGAGAGGTTCCCACAGCTGCACTGCCAGAATCGGAGCGCAGCGCCT
CTGAATTTATACCCGCGGGGGAAAAGGCGTGGTCACTTGTCACTTGCAGCAGTCACTTCC
AAGCACTCAGAAAAGGGGCA
[SEQ ID NO: 170] - TNFRSF10C
```

FIG 2X

```
GAAATAACTTGAGCCAGGGATCAAACACTAAGATTGGCAGGAAATGAGCAGGAAGAGGTA
GCGGGGTCCCTGACGCCATCTATTCAATTGTTTTTCAGAAGAGGTATCAGCTCTTGAAGG
CTTACTTCTCAATACTGGCTGCGAGAGCAAGAATGGTGTGTAATTTACAAAAGCCGTCAT
TGCTGTAGGTAAGTTGTAGCAAACGACTCGCGCCCGAGCATTCCCGCCCCCGCCTTCGCT
GCGGCCCCGCCCACGACGACCCTGGGGAACTACAAGTCCCGCCATACAGCGGGGAGCGCC
CGGAGCTCGCGCCGGCCCCGCCCCAGCCCGGTCCCCACCCCCGGCTCCGCCCCCGGCCC
CCTCCCGCCGGGTCAACCCCGAAGAGTCGCCGGTGGCCGCGGCAGACGGAAGCCGAACGA
GTTCCTCGGCGGCTGCAGGATGGGGGACTCCAAAGTGAAAGTGGCGGTGCGGATACGACC
CATGAACCGGCGAGGTGAGAGCCGAGCCCTCCTGGGCCGCCGGGGCGGAGGCGGCAGGTG
CCTGGCGCGCCCTTCCCTCGGCCGCCGTGGGGGGTCCGGCGGCCCCGCCCCTATAGTCAG
CGGCGGGGCGCGAGGAGGGGCCCGGGGACCCTGAAACCCGCTCCCGCGCTGAGACGCCCG
GCTCCCTCTTCTCCCCTCCCTTCCCCCCTGGCCAGCCCCGTCCCTGGCGCCGTCGGGCCC
CTCGTGCCGGCCCCGCTGCCCCTTCCGCCTGCGCCCGCCCCGCCCCTGCGCCCTTTTGCC
CTCTCGTCTCCCCCGGAGGTTCCCGAGGGCGCCCTCGGCCCTCGCGCCCAGCCTCGTCCT
GGCCCCTCAGCCTCGCTCCTTCCCCGCCAGCTGTCATCGTCGCCCCGCGCGCGGGTCGC
CAGCCCCTGCAGCCCGCCTCGGGACCGCCCGGGACCCCCGGGACCCCGCGTCTCGCCCG
GGTCGCCCAAGCCTGCACCGCCTTGGCCCGCGGCGGGAAGAAGGGCAGGGGGCCAGGCGG
GTGCCCCGCGGCGAGTTCCTTCCACCTGGGCGTCCTGAGATTGGGGTCAGGTGGAGGAGA
TGCCCTTTTCGTTGTTTTTGGACAGTTGAGAAAGTTTTGGTTTTGCCTGAAGTCTCATTC
ATCATCTCTCAATAAATAGCTAAAGTGCCAAGATTCTTGTGGAATTGTATCTTTCTGACA
TTCTCTTAACTCTGCAGGGAGTGTAGAGAAGGCAGATAAACCGAGTACATTTAAATAATC
TGTAGACCCGGGGAGTGGAGAGAACCCCAAAAGTCAGGGG
[SEQ ID NO: 171] - KIF13B

CCCCTGACTTTTGGGGTTCTCTCCACTCCCCGGGTCTACAGATTATTTAAATGTACTCGG
TTTATCTGCCTTCTCTACACTCCCTGCAGAGTTAAGAGAATGTCAGAAAGATACAATTCC
ACAAGAATCTTGGCACTTTAGCTATTTATTGAGAGATGATGAATGAGACTTCAGGCAAAA
CCAAAACTTTCTCAACTGTCCAAAAACAACGAAAAGGGCATCTCCTCCACCTGACCCCAA
TCTCAGGACGCCCAGGTGGAAGGAACTCGCCGCGGGGCACCCGCCTGGCCCCCTGCCCTT
CTTCCCGCCGCGGGCCAAGGCGGTGCAGGCTTGGGCGACCCGGGCGAGACGCGGGGTCCC
GGGGGGTCCCGGGCGGTCCCGAGGCGGGCTGCAGGGGCTGGCGACCCGCGCGCGGGGGCG
ACGATGACAGCTGGCGGGGAAGGAGCGAGGCTGAGGGGCCAGGACGAGGCTGGGCGCGAG
GGCCGAGGGCGCCCTCGGGAACCTCCGGGGGAGACGAGAGGGCAAAAGGGCGCAGGGGCG
GGGCGGGCGCAGGCGGAAGGGGCAGCGGGGCCGGCACGAGGGGCCCGACGGCGCCAGGGA
CGGGGCTGGCCAGGGGGAAGGGAGGGGAGAAGAGGGAGCCGGGCGTCTCAGCGCGGGAG
CGGGTTTCAGGGTCCCCGGGCCCCTCCTCGCGCCCCGCCGCTGACTATAGGGGCGGGGCC
GCCGGACCCCCACGGCGGCCGAGGGAAGGGCGCGCCAGGCACCTGCCGCCTCCGCCCCG
GCGGCCCAGGAGGGCTCGGCTCTCACCTCGCCGGTTCATGGGTCGTATCCGCACCGCCAC
TTTCACTTTGGAGTCCCCCATCCTGCAGCCGCCGAGGAACTCGTTCGGCTTCCGTCTGCC
GCGGCCACCGGCGACTCTTCGGGGTTGACCCGGCGGGAGGGGCCGGGGCGGAGCCGGG
GGTGGGGACCGGGCTGGGGCGGGGCCGGCGCGAGCTCCGGGCGCTCCCCGCTGTATGGC
GGGACTTGTAGTTCCCCAGGGTCGTCGTGGGCGGGGCCGCAGCGAAGGCGGGGGCGGGAA
TGCTCGGGCGCGAGTCGTTTGCTACAACTTACCTACAGCAATGACGGCTTTTGTAAATTA
CACACCATTCTTGCTCTCGCAGCCAGTATTGAGAAGTAAGCCTTCAAGAGCTGATACCTC
TTCTGAAAAACAATTGAATAGATGGCGTCAGGGACCCCGCTACCTCTTCCTGCTCATTTC
CTGCCAATCTTAGTGTTTGATCCCTGGCTCAAGTTATTTC
[SEQ ID NO: 172] - KIF13B
```

FIG 2Y

```
ACCCCCTCCTTCCTTCTTTCCCTACCGCCCCACGCGCGACCCGGGGATGGCTCCGTGGCC
TCACGAGAACAGCTCTCTTGCCCCATGGCCGGACCTCCCCACCCTGGCGCCCAATACCGC
CAACACCAGTGGGCTGCCAGGGGTTCCGTGGGAGGCGGCCCTAGCCGGGGCCCTGCTGGC
GCTGGCGGTGCTGGCCACCGTGGGAGGCAACCTGCTGGTCATCGTGGCCATCGCCTGGAC
TCCGAGACTCCAGACCATGACCAACGTGTTCGTGACTTCGCTGGCCGCAGCCGACCTGGT
GATGGGACTCCTGGTGGTGCCGCCGGCGGCCACCTTGGCGCTGACTGGCCACTGGCCGTT
GGGCGCCACTGGCTGCGAGCTGTGGACCTCGGTGGACGTGCTGTGTGTGACCGCCAGCAT
CGAAACCCTGTGCGCCCTGGCCGTGGACCGCTACCTGGCTGTGACCAACCCGCTGCGTTA
CGGCGCACTGGTCACCAAGCGCTGCGCCCGGACAGCTGTGGTCCTGGTGTGGGTCGTGTC
GGCCGCGGTGTCGTTTGCGCCCATCATGAGCCAGTGGTGGCGCGTAGGGGCCGACGCCGA
GGCGCAGCGCTGCCACTCCAACCCGCGCTGCTGTGCCTTCGCCTCCAACATGCCCTACGT
GCTGCTGTCCTCCTCCGTCTCCTTCTACCTTCCTCTTCTCGTGATGCTCTTCGTCTACGC
GCGGGTTTTCGTGGTGGCTACGCGCCAGCTGCGCTTGCTGCGCGGGGAGCTGGGCCGCTT
TCCGCCCGAGGAGTCTCCGCCGGCGCCGTCGCGCTCTCTGGCCCCGGCCCCGGTGGGGAC
GTGCGCTCCGCCCGAAGGGGTGCCCGCCTGCGGCCGGCGGCCCGCGCGCCTCCTGCCTCT
CCGGGAACACCGGGCCCTGTGCACCTTGGGTCTCATCATGGGCACCTTCACTCTCTGCTG
GTTGCCCTTCTTTCTGGCCAACGTGCTGCGCGCCCTGGGGGGCCCCTCTCTAGTCCCGGG
CCCGGCTTTCCTTGCCCTGAACTGGCTAGGTTATGCCAATTCTGCCTTCAACCCGCTCAT
CTACTGCCGCAGCCCGGACTTTCGCAGCGCCTTCCGCCGTCTTCTGTGCCGCTGCGGCCG
TCGCCTGCCTCCGGAGCCCTGCGCCGCCGCCCGCCCGGCCCTCTTCCCCTCGGGCGTTCC
TGCGGCCCGGAGCAGCCCAGCGCAGCCCAGGCTTTGCCAACGGCTCGACGGGTAGGTAAC
CGGGGCAGAGGGACCGGCGGCTCAGGGTCGGGAAGCATGCGATGTGTCCGTGGGTCAACT
TTTTGAGTGTGGAGTTTATTAAGAGAAGGTGGGATGGCTTTGCTTGGAGAGAAAAGGGAA
CGAGGAGTAGCGAACCAAAATGGGACCCAGGGTCCTTTTCTTTCCGGATCCAGTCACTAG
GGTAGAAGCAAAGGAGGGCGAGCGGGCCGTCGTTCCTCACCCAAGGACCCAAGGTGCGCC
ACCGGAAAGCGCTGCGGTGTCCCGAGGACTCTCGCCTCGCCTGGTCGGCT
[SEQ ID NO: 173] - ADRB3

AGCCGACCAGGCGAGGCGAGAGTCCTCGGGACACCGCAGCGCTTTCCGGTGGCGCACCTT
GGGTCCTTGGGTGAGGAACGACGGCCCGCTCGCCCTCCTTTGCTTCTACCCTAGTGACTG
GATCCGGAAAGAAAAGGACCCTGGGTCCCATTTTGGTTCGCTACTCCTCGTTCCCTTTTC
TCTCCAAGCAAAGCCATCCCACCTTCTCTTAATAAACTCCACACTCAAAAAGTTGACCCA
CGGACACATCGCATGCTTCCCGACCCTGAGCCGCCGGTCCCTCTGCCCCGGTTACCTACC
CGTCGAGCCGTTGGCAAAGCCTGGGCTGCGCTGGCTGCTCCGGGCCGCAGGAACGCCCG
AGGGGAAGAGGGCCGGGCGGGCGGCGGCGCAGGGCTCCGGAGGCAGGCGACGGCCGCAGC
GGCACAGAAGACGGCGGAAGGCGCTGCGAAAGTCCGGGCTGCGGCAGTAGATGAGCGGGT
TGAAGGCAGAATTGGCATAACCTAGCCAGTTCAGGGCAAGGAAAGCCGGGCCCGGGACTA
GAGAGGGGCCCCCCAGGGCGCGCAGCACGTTGGCCAGAAAGAAGGGCAACCAGCAGAGAG
TGAAGGTGCCCATGATGAGACCCAAGGTGCACAGGGCCCGGTGTTCCCGGAGAGGCAGGA
GGCGCGCGGGCCGCCGGCCGCAGGCGGGCACCCCTTCGGGCGGAGCGCACGTCCCCACCG
GGGCCGGGGCCAGAGAGCGCGACGGCGCCGGCGGAGACTCCTCGGGCGGAAAGCGGCCCA
GCTCCCCGCGCAGCAAGCGCAGCTGGCGCGTAGCCACCACGAAAACCCGCGCGTAGACGA
AGAGCATCACGAGAAGAGGAAGGTAGAAGGAGACGGAGGAGGACAGCAGCACGTAGGGCA
TGTTGGAGGCGAAGGCACAGCAGCGCGGGTTGGAGTGGCAGCGCTGCGCCTCGGCGTCGG
CCCCTACGCGCCACCACTGGCTCATGATGGGCGCAAACGACACCGCGGCCGACACGACCC
ACACCAGGACCACAGCTGTCCGGGCGCAGCGCTTGGTGACCAGTGCGCCGTAACGCAGCG
GGTTGGTCACAGCCAGGTAGCGGTCCACGGCCAGGGCGCACAGGGTTTCGATGCTGGCGG
TCACACACAGCACGTCCACCGAGGTCCACAGCTCGCAGCCAGTGGCGCCCAACGGCCAGT
GGCCAGTCAGCGCCAAGGTGGCCGCCGGCGGCACCACCAGGAGTCCCATCACCAGGTCGG
CTGCGGCCAGCGAAGTCACGAACACGTTGGTCATGGTCTGGAGTCTCGGAGTCCAGGCGA
TGGCCACGATGACCAGCAGGTTGCCTCCCACGGTGGCCAGCACCGCCAGCGCCAGCAGGG
CCCCGGCTAGGGCCGCCTCCCACGGAACCCCTGGCAGCCCACTGGTGTTGGCGGTATTGG
GCGCCAGGGTGGGGAGGTCCGGCCATGGGCAAGAGAGCTGTTCTCGTGAGGCCACGGAG
CCATCCCCGGGTCGCGCGTGGGCGGTAGGGAAGAAGGAAGGAGGGGGT
[SEQ ID NO: 174] - ADRB3
```

FIG 2Z

```
CGCAGACCCAGCAGGAGAGCGCAACCTAGCATCTTTAAGGTTCGCTTAGCCCTTCCTGTG
CACCTGGAAGGAAGCCTTATCTTAAACTCCCTTCCACCTAGAGTTTATTTTCGCCTGCGT
GCGACAGGGCTTTTGTACTTAAGTGAGTTAAGGAATGAACCCCGAACTCTTCTGGGAAAG
CCACCAACGTTCCCCCCGCACCCCTCCCAGGGTTCCTGACCACGGAGACTCTGCTTGGGG
CACAGGTGTGGGAGTCGCAAACTTTTCTCTGCGCCGTCCTTTTCCGCGTGGAATGGGACG
GAGCAGCCCTCCCAGGCGCTGCCTGGCTGCGGAGGGGAGCGGGCAGCGAGAGCCTCGGGT
CTCCGCCTGGGTTCCCGGGTCTCCGGGGCGCTGGCCTCGGTCTCCGCGCAGCGTCCAGCG
ACCCTGTCGGGGGTTCCCGGCAGCCGCGCCGCCACCCCCGCCCGGCCAGCGCGGGAGG
AAAAGGGGCTGCGCCCGGGAGCGCCGAGCCCAGGCTCCTCCCGGTGGCGTGTCCGCGCCT
CGGGGTGGGGGTGTGGTGGGGAAGAGGGAGGGGGCGAGGCCAGGGGAGGGTGCGAAGGAG
GCGCCTGCCTCCAACCTGCGGGCGGGAGGTGGGTGGCTGCGGGGCAATTGAAAAAGAGCC
GGCGAGGAGTTCCCCGAAACTTGTTGGAACTCCGGGCTCGCGCGGAGGCCAGGAGCTGAG
CGGCGGCGGCTGCCGGACGATGGGAGCGTGAGCAGGACGGTGATAACCTCTCCCCGATCG
GGTTGCGAGGGCGCCGGGCAGAGGCCAGGACGCGAGCCGCCAGCGGTGGGACCCATCGAC
GACTTCCCGGGGCGACAGGAGCAGCCCCGAGAGCCAGGGCGAGCGCCCGTTCCAGGTGGC
CGGACCGCCCGCCGCGTCCGCGCCGCGCTCCCTGCAGGCAACGGGAGACGCCCCCGCGCA
GCGCGAGCGCCTCAGCGCGGCCGCTCGCTCTCCCCCTCGAGGGACAAACTTTTCCCAAAC
CCGATCCGAGCCCTTGGACCAAACTCGCCTGCGCCGAGAGCCGTCCGCGTAGAGCGCTCC
GTCTCCGGCGAGATGTCCGAGCGCAAAGAAGGCAGAGGCAAAGGGAAGGGCAAGAAGAAG
GAGCGAGGCTCCGGCAAGAAGCCGGAGTCCGCGGCGGGCAGCCAGAGCCCAGGTGGGTGC
GCAGCGCGGCCCGGGCCCCACGATCCTCCTCCTGCTCCTCCTACTCCTCCTCCTCCTCGG
ATGCCGTGGCCTCTCCCTCCCCCTCTCCCTCGCCCGTCCTCTTCGCCCTGCGCTCTGAGC
GCCCGTTGAGTCGCGCGGTGCTTCCCCTCCTGGGGGCCGCCGCTCACCTGGGCGCCGAGT
CCTACCGGGCGCCTACGCCCAGAGCTCAGGGCAAGGGACAGCAGTCCCGGCCGCACCCTC
CCAGAGTCCCGGGAGCGCTTCGCTCCCTGGCACGGCCCCTCCCCAGCGCCTTAGCGGCTG
AGCCCAGCCCGGGAGTGGGACCTGGGCTATAGGAGTCGAGGCTGCGTGCGCGCGTGCCCC
GCGCCATAAGCGCTTTGCACGGGGCCGTGTGCCCTCTAGCGGGAAACGCTGGAATGGGC
CGCCTGGAGGGAGAGCCGGTCCCCTCGGTGTGCCTGGCAGCGCAGAAGTGGGTGGTCGAG
CAAGAGGCCGCGTGGGAAGTTAGCTTCGGCGTTTTGGGGCACAGGGCAAGCGATGTAGAG
TGCGCGCCGGTTCATCTTGATTCAGTCCTGTGCTACGAGACTCAAGAGCAGCGGCAGGG
[SEQ ID NO: 175] - NRG1
```

FIG 2AA

```
CCCTGCCGCTGCTCTTGAGTCTCCGTAGCACAGGACTGAATCAAGATGAACCGGCGCGCA
CTCTACATCGCTTGCCCTGTGCCCCAAAACGCCGAAGCTAACTTCCCACGCGGCCTCTTG
CTCGACCACCCACTTCTGCGCTGCCAGGCACACCGAGGGGACCGGCTCTCCCTCCAGGCG
GCCCATTCCAGCGTTTCCCGCTAGAGGGCACACGGCCCCCGTGCAAAGCGCTTATGGCGC
GGGGCACGCGCGCACGCAGCCTCGACTCCTATAGCCCAGGTCCCACTCCCGGGCTGGGCT
CAGCCGCTAAGGCGCTGGGGAGGGGCCGTGCCAGGGAGCGAAGCGCTCCCGGGACTCTGG
GAGGGTGCGGCCGGGACTGCTGTCCCTTGCCCTGAGCTCTGGGCGTAGGCGCCCGGTAGG
ACTCGGCGCCCAGGTGAGCGGCGGCCCCCAGGAGGGGAAGCACCGCGCGACTCAACGGGC
GCTCAGAGCGCAGGGCGAAGAGGACGGGCGAGGGAGAGGGGAGGGAGAGGCCACGGCAT
CCGAGGAGGAGGAGGAGTAGGAGGAGCAGGAGGAGGATCGTGGGGCCCGGGCCGCGCTGC
GCACCCACCTGGGCTCTGGCTGCCCGCCGCGGACTCCGGCTTCTTGCCGGAGCCTCGCTC
CTTCTTCTTGCCCTTCCCTTTGCCTCTGCCTTCTTTGCGCTCGGACATCTCGCCGGAGAC
GGAGCGCTCTACGCGGACGGCTCTCGGCGCAGGCGAGTTTGGTCCAAGGGCTCGGATCGG
GTTTGGGAAAAGTTTGTCCCTCGAGGGGAGAGCGAGCGGCCGCGCTGAGGCGCTCGCGC
TGCGCGGGGCGTCTCCCGTTGCCTGCAGGGAGCGCGGCGCGGACGCGGCGGGCGGTCCG
GCCACCTGGAACGGGCGCTCGCCCTGGCTCTCGGGGCTGCTCCTGTCGCCCCGGGAAGTC
GTCGATGGGTCCCACCGCTGGCGGCTCGCGTCCTGGCCTCTGCCCGGCGCCCTCGCAACC
CGATCGGGGAGAGGTTATCACCGTCCTGCTCACGCTCCCATCGTCCGGCAGCCGCCGCCG
CTCAGCTCCTGGCCTCCGCGCGAGCCCGGAGTTCCAACAAGTTTCGGGGAACTCCTCGCC
GGCTCTTTTTCAATTGCCCCGCAGCCACCCACCTCCCGCCCGCAGGTTGGAGGCAGGCGC
CTCCTTCGCACCCTCCCCTGGCCTCGCCCCTCCCTCTTCCCCACCACACCCCCACCCCG
AGGCGCGGACACGCCACCGGGAGGAGCCTGGGCTCGGCGCTCCCGGGCGCAGCCCCTTTT
CCTCCCGCGCTGGCCGGGCGGGGGTGGCGGCGCGGCTGCCGGGAACCCCCGACAGGGGT
CGCTGGACGCTGCGCGGAGACCGAGGCCAGCGCCCCGGAGACCCGGGAACCCAGGCGGAG
ACCCGAGGCTCTCGCTGCCCGCTCCCCTCCGCAGCCAGGCAGCGCCTGGGAGGGCTGCTC
CGTCCCATTCCACGCGGAAAAGGACGGCGCAGAGAAAAGTTTGCGACTCCCACACCTGTG
CCCCAAGCAGAGTCTCCGTGGTCAGGAACCCTGGGAGGGGTGCGGGGGGAACGTTGGTGG
CTTTCCCAGAAGAGTTCGGGGTTCATTCCTTAACTCACTTAAGTACAAAAGCCCTGTCGC
ACGCAGGCGAAAATAAACTCTAGGTGGAAGGGAGTTTAAGATAAGGCTTCCTTCCAGGTG
CACAGGAAGGGCTAAGCGAACCTTAAAGATGCTAGGTTGCGCTCTCCTGCTGGGTCTGCG
```
[SEQ ID NO: 176] - NRG1

FIG 2BB

```
GGGAGGGTGGCCTGCAAGGCGGGGCCGGTTGCGGTCAAGTTCAAGTAGGGTCAGAGCAGG
AGAACACTGGCATAAAAAATAGCCACATCCAAGGAAGCAGTGAGGTGTGGGGACCATCTA
TTTCGGTGGGCCTTCCCACCCCCAGGCCGGCCTTCCCATCACGCGTGGGTGTGGGGGCAC
TGCCCCCGCTGCGCGCAGGAACAGCGGGGAGAGCCAGGAGCGGAGCGGCTTCGGGATGCC
AGACTGAGCAGTGGGTTCGTCTGCGGCCACCTCTCAGGGAACAAGCTTCCCCCCGCGGAG
ACTCTGCTTCTTTTAAAAGCCTTCCTGGGTTTAGTCTAGGGCGACAGGACGACCTCCCTT
GGGAAGGGAGAGCCTGCCAGTCCCCCTCCCATTCGCCAGGCGGTGCAGCCCCTCCTCCCG
CCCGGGGCGCGCGCACCTCAGCGTCGCGGGCCTAGCGCCCAGCAGCCGCGCCCCAGGCCG
GGCCTCGGGTTCCGGGAGCCCGCAGGCGCGCGCCCGGCCGGGCGTGTCGGGAGCGCGCGG
CGGCCGGGGGCGGAGCGCAGCCAGGGCTGCGCGGCGCGCCCCGGCTCCCGCCCGCTCCCA
GCCGGGCCCCCAGCGGTCGGCGGGACGGCTCCCGGCTGCAGTCTGCCCGCCCGCCCCGC
GCGGGGGCCGAGTCGCGAAGCGCGCCTGCGACCCGGCGTCCGGGCGCGCTGGAGAGGACG
CGAGGAGCCATGAGGCGCCAGCCTGCGAAGGTGGCGGCGCTGCTGCTCGGGCTGCTCTTG
GAGGTAGGGGCCGGGGACCGGGTGCTGCCGGAGGCGCGGCGCCCACCATGCTGGCGGCTG
GGGGCGCGCAGTTCCGAGGCGCCCCAGAGGACCTTGCCTGGGAGCGCAGACGGTGGAGCG
ACGGGGAGCCACAGCCCTGCGCGCCTCCCGGAGCTGGGAGGTGCGGGACCCTGGTGACGG
GGAGGCTCCCGCCCCGGTCCGCGCCTTCCGTCGTTCCTTCGGTTTTCGCACCCCGCCCCC
ACCCTGCGGGTGAGCGCGTTTCCCGCGCCGACCGCCTCCGTTAGCTCGGGGTGACCTTTG
TGCACCGTCCGCCCCCTCTCCCCGCCGCAGAGGGCCGAGGATCGGATGGACCCGGGGTTG
GGCGGGGGTGGTCCTCGGGCGCGGCGCAGGCGCGGAGAGCCCGGGGCGCCGGGCAGTTTG
GGGTTAGGAAAGGATGGGTGCCGAGCCGGGGTGAGGGGAGCGGGCGGAGGGGACTGTGGG
GAAGTGTCGCGGGAGTGCCGGGAGTTGTGGAGGTGAGCAGCGGGAGGAGGCGTTCCCGCG
TGTGAAAATGAAGTGCAGCCTTTAGGTGCGGGAGGAAATTCTGCGGAGAGCCTGGCTGG
GTGGGGGTGCGGAGCCGAAGCCGGCGGGGAACTTGTTGAGCGGCTTCCGGGTGCGAGCGC
CCGTGACCGCATCCCTGGCGGGGACCGCGGCTGCTCCTGGCTGTGAAATTGCATCCTCGG
ATGGGGCCACATACTTCTCACTAAAGCAGGTTCCTTAAAATGCGAACTAG
[SEQ ID NO: 177] - ECOP

CTAGTTCGCATTTTAAGGAACCTGCTTTAGTGAGAAGTATGTGGCCCCATCCGAGGATGC
AATTTCACAGCCAGGAGCAGCCGCGGTCCCGCCAGGGATGCGGTCACGGGCGCTCGCAC
CCGGAAGCCGCTCAACAAGTTCCCCGCCGGCTTCGGCTCCGCACCCCCACCCAGCCAGGC
TCTCCGCAGAATTTCCTCCCCGCACCTAAAGGCTGCACTTCATTTTCACACGCGGGAACG
CCTCCTCCCGCTGCTCACCTCCACAACTCCCGGCACTCCCGCGACACTTCCCCACAGTCC
CCTCCGCCCGCTCCCCTCACCCCGGCTCGGCACCCATCCTTTCCTAACCCCAAACTGCCC
GGCGCCCCGGGCTCTCCGCGCCTGCGCCGCGCCCGAGGACCACCCCCGCCCAACCCCGGG
TCCATCCGATCCTCGGCCCTCTGCGGCGGGGAGAGGGGCGGACGGTGCACAAAGGTCAC
CCCGAGCTAACGGAGGCGGTCGGCGCGGGAAACGCGCTCACCCGCAGGGTGGGGGCGGGG
TGCGAAAACCGAAGGAACGACGGAAGGCGCGGACCGGGGCGGGAGCCTCCCCGTCACCAG
GGTCCCGCACCTCCCAGCTCCGGGAGGCGCGCAGGGCTGTGGCTCCCCGTCGCTCCACCG
TCTGCGCTCCCAGGCAAGGTCCTCTGGGGCGCCTCGGAACTGCGCGCCCCAGCCGCCAG
CATGGTGGGCGCCGCGCCTCCGGCAGCACCCGGTCCCCGGCCCCTACCTCCAAGAGCAGC
CCGAGCAGCAGCGCCGCCACCTTCGCAGGCTGGCGCCTCATGGCTCCTCGCGTCCTCTCC
AGCGCGCCCGGACGCCGGGTCGCAGGCGCGCTTCGCGACTCGGCCCCCGCGCGGGCGGG
CGGGCAGACTGCAGCCGGGAGCCGTCCGCCGACCGCTGGGGGCCCGGCTGGGAGCGGG
CGGGAGCCGGGGCGCGCCGCGCAGCCCTGGCTGCGCTCCGCCCCGGCCGCCGCGCGCTC
CCGACACGCCCGGCCGGGCGCGCGCCTGCGGGCTCCCGGAACCCGAGGCCCGGCCTGGGG
CGCGGCTGCTGGGCGCTAGGCCCGCGACGCTGAGGTGCGCGCGCCCCGGGCGGGAGGAGG
GGCTGCACCGCCTGGCGAATGGGAGGGGACTGGCAGGCTCTCCCTTCCCAAGGGAGGTC
GTCCTGTCGCCCTAGACTAAACCCAGGAAGGCTTTTAAAAGAAGCAGAGTCTCCGCGGGG
GGAAGCTTGTTCCCTGAGAGGTGGCCGCAGACGAACCCACTGCTCAGTCTGGCATCCCGA
AGCCGCTCCGCTCCTGGCTCTCCCCGCTGTTCCTGCGCGCAGCGGGGCAGTGCCCCCAC
ACCCACGCGTGATGGGAAGGCCGGCCTGGGGGTGGGAAGGCCCACCGAAATAGATGGTCC
CCACACCTCACTGCTTCCTTGGATGTGGCTATTTTTATGCCAGTGTTCTCCTGCTCTGA
CCCTACTTGAACTTGACCGCAACCGGCCCCGCCTTGCAGGCCACCCTCCC
[SEQ ID NO: 178] - ECOP
```

FIG 2CC

```
TGCTGGGCAATGCGTGCGTGGTGGCTGCCATCGCCTTGGAGCGCTCCCTGCAGAACGTGG
CCAATTATCTTATTGGCTCTTTGGCGGTCACCGACCTCATGGTGTCGGTGTTGGTGCTGC
CCATGGCCGCGCTGTATCAGGTGCTCAACAAGTGGACACTGGGCCAGGTAACCTGCGACC
TGTTCATCGCCCTCGACGTGCTGTGCTGCACCTCATCCATCTTGCACCTGTGCGCCATCG
CGCTGGACAGGTACTGGGCCATCACGGACCCCATCGACTACGTGAACAAGAGGACGCCCC
GGCGCGCCGCTGCGCTCATCTCGCTCACTTGGCTTATTGGCTTCCTCATCTCTATCCCGC
CCATGCTGGGCTGGCGCACCCCGGAAGACCGCTCGGACCCCGACGCATGCACCATTAGCA
AGGATCATGGCTACACTATCTATTCCACCTTTGGAGCTTTCTACATCCCGCTGCTGCTCA
TGCTGGTTCTCTATGGGCGCATATTCCGAGCTGCGCGCTTCCGCATCCGCAAGACGGTCA
AAAAGGTGGAGAAGACCGGAGCGGACACCCGCCATGGAGCATCTCCCGCCCCGCAGCCCA
AGAAGAGTGTGAATGGAGAGTCGGGGAGCAGGAACTGGAGGCTGGGCGTGGAGAGCAAGG
CTGGGGGTGCTCTGTGCGCCAATGGCGCGGTGAGGCAAGGTGACGATGGCGCCGCCCTGG
AGGTGATCGAGGTGCACCGAGTGGGCAACTCCAAAGAGCACTTGCCTCTGCCCAGCGAGG
CTGGTCCTACCCCTTGTGCC
[SEQ ID NO: 179] - HTR1A

GGCACAAGGGGTAGGACCAGCCTCGCTGGGCAGAGGCAAGTGCTCTTTGGAGTTGCCCAC
TCGGTGCACCTCGATCACCTCCAGGGCGGCGCCATCGTCACCTTGCCTCACCGCGCCATT
GGCGCACAGAGCACCCCCAGCCTTGCTCTCCACGCCCAGCCTCCAGTTCCTGCTCCCCGA
CTCTCCATTCACACTCTTCTTGGGCTGCGGGCGGGAGATGCTCCATGGCGGGTGTCCGC
TCCGGTCTTCTCCACCTTTTTGACCGTCTTGCGGATGCGGAAGCGCGCAGCTCGGAATAT
GCGCCCATAGAGAACCAGCATGAGCAGCAGCGGGATGTAGAAAGCTCCAAAGGTGGAATA
GATAGTGTAGCCATGATCCTTGCTAATGGTGCATGCGTCGGGGTCCGAGCGGTCTTCCGG
GGTGCGCCAGCCCAGCATGGGCGGGATAGAGATGAGGAAGCCAATAAGCCAAGTGAGCGA
GATGAGCGCAGCGGCGCGCCGGGGCGTCCTCTTGTTCACGTAGTCGATGGGGTCCGTGAT
GGCCCAGTACCTGTCCAGCGCGATGGCGCACAGGTGCAAGATGGATGAGGTGCAGCACAG
CACGTCGAGGGCGATGAACAGGTCGCAGGTTACCTGGCCCAGTGTCCACTTGTTGAGCAC
CTGATACAGCGCGGCCATGGGCAGCACCAACACCGACACCATGAGGTCGGTGACCGCCAA
AGAGCCAATAAGATAATTGGCCACGTTCTGCAGGGAGCGCTCCAAGGCGATGGCAGCCAC
CACGCACGCATTGCCCAGCA
[SEQ ID NO: 180] - HTR1A

TGACGCAAGGTCCAGTCCAGATTGCCAGGCCCGGGGCATGAGAGAGGATCCTTGTAGGTT
TCGGAGGTGGGGGGGCTGCACTCCATTGTTCACTCCGGGCCAATCAGGGTTGGCCCACTT
CCTCCCAGCCAATCTCCCTTCACCCCCAGCCTCCAACCCAACCCACCCCGCCCATCAGCC
CCTGGATCCCCATCACCTCCCCCGCATCCCCGGCAGTTCTGGGGAAGCTTCGTGACGCCA
CAGGTCCCGCCCCCAGCTCCGGCCCGGGGCTAGTGCGTGTTGACGTCATGCTGCGTGCGG
GCCGGTGCGGAATCGCTCCTTCAACTCCGCGGGGCAGTAGGAGTTAGTTAGCAAAGAGCC
GAGGCCGGGCGCGCGACCCTCGTCCTTCTGCCCCTGGCCGCACACTTTGCGCACATCTCT
TTTTCTGCATGGTGGATATTATTTTTCATTATCCTTTTCTGGGTGCTATGGGTGATCATT
CCAAGAGTAAGTATTTCTGTGTGTGTGTGGGGTGGGGTGTGTGTGTATGCTTAATATGCA
AAATTTCTAA
[SEQ ID NO: 181] - ISL2
```

FIG 2DD

```
TTAGAAATTTTGCATATTAAGCATACACACACACCCCACCCCACACACACACAGAAATAC
TTACTCTTGGAATGATCACCCATAGCACCCAGAAAAGGATAATGAAAAATAATATCCACC
ATGCAGAAAAAGAGATGTGCGCAAAGTGTGCGGCCAGGGGCAGAAGGACGAGGGTCGCGC
GCCCGGCCTCGGCTCTTTGCTAACTAACTCCTACTGCCCCGCGGAGTTGAAGGAGCGATT
CCGCACCGGCCCGCACGCAGCATGACGTCAACACGCACTAGCCCCGGGCCGGAGCTGGGG
GCGGGACCTGTGGCGTCACGAAGCTTCCCCAGAACTGCCGGGGATGCGGGGGAGGTGATG
GGGATCCAGGGGCTGATGGGCGGGGTGGGTTGGGTTGGAGGCTGGGGGTGAAGGGAGATT
GGCTGGGAGGAAGTGGGCCAACCCTGATTGGCCCGGAGTGAACAATGGAGTGCAGCCCCC
CCACCTCCGAAACCTACAAGGATCCTCTCTCATGCCCCGGGCCTGGCAATCTGGACTGGA
CCTTGCGTCA
[SEQ ID NO: 182] - ISL2

CAGGGAACAGACCCAGTAGTTGGCTTGGATCTCTTAACTCCAGAAAAGGCCGAGTGAGGA
CAAGGGAGACCACAGGGATAATTTCTGTGGCTCTGGTAAGGGGATGACAAGGGAGAAAAA
CTTTCCCACGGTTCCGTCTGGCCCGCGGCGCTTGTCTGCCTGCGCGGGGTCAAAGCCCGG
CGCCGCCCACGCGCGGCTCGGGTGGGAACCCGCAGACGTGGGGCGAGCAGGGCCGCTGGC
TGTGGCGGGCGAGCGCCGGGGCGCCACGTCCGAGGCCGCGGGGTCGGGGCTGCAGGCACA
GCTCGAGCGCTTTCCGCGGGGTTTGGCTCCTGTCGCTTCCCGTCTCGCCGAACCGGCATC
GCCGCCGCCGGAGCCGCAGCGAGTCCTCAGAGCCTGGCTGCTGGCGGCCGGGAGCGCCGG
GACGGGGCGCGAAGCCGGAGGCTCCGGGACGTGGATACAGGTAAAGGCCGGCGGGTCGGA
GTCGGGCGGGGCGCGGCGGCGGCGCCTCTCGGAGGGACCTGGCCTCGGCCGGGCCCTACC
CAGCCGCGGTGGCCCGGGCCCCCACGTTGGCCCAGGCGGGGACGTGCCAAGGGGCTGGGC
TAGGGTTGCCGCTGGCCTGGCCGCCTCTCGCCCGGCGGGCCTCAGGTGACGCGGCCGCGG
CTTAACTTTCGCACCTGAGGCTCTCGGAGCGGCCTCGGGGCGCGCCCACCTGGAGGTTGG
AATTACACAGGGTCGAAAAAGCTGAGTCCTGGAGGCGAGGCGCTGTAGGTGTGGCGGAGG
AGGCCGGGGAAGGTGGGGTGGGTGCCAGGGGTCCAGTACTGAACCCTCTCCAGGTCTGAG
GTGGGGAACTGCGTCTTGTTTAATTTCGGAGCTTGTGGGGACCACACAGCCCCTTCCACG
GCCGATTCCCTCTGCACGGTTCCACTTTCCTTTGTCTAGCCCATTTCAGTATCGGCGTCG
CAGTCGCTTTTGTTGCAGCCTTGGGTCCGGAGTGTACGACTTTCTGCTAGGCAGAGGTCA
TAAGCTCTGAAATCCATCGGCGGAGGTGG
[SEQ ID NO: 183] - LOC285671

CCACCTCCGCCCGATGGATTTCAGAGCTTATGACCTCTGCCTAGCAGAAAGTCGTACACT
CCGGACCCAAGGCTGCAACAAAAGCGACTGCGACGCCGATACTGAAATGGGCTAGACAAA
GGAAAGTGGAACCGTGCAGAGGGAATCGGCCGTGGAAGGGGCTGTGTGGTCCCCACAAGC
TCCGAAATTAAACAAGACGCAGTTCCCCACCTCAGACCTGGAGAGGGTTCAGTACTGGAC
CCCTGGCACCCACCCCACCTTCCCCGGCCTCCTCCGCCACACCTACAGCGCCTCGCCTCC
AGGACTCAGCTTTTTCGACCCTGTGTAATTCCAACCTCCAGGTGGGCGCGCCCCGAGGCC
GCTCCGAGAGCCTCAGGTGCGAAAGTTAAGCCGCGGCCGCGTCACCTGAGGCCCGCCGGG
CGAGAGGCGGCCAGGCCAGCGGCAACCCTAGCCCAGCCCCTTGGCACGTCCCGCCTGGG
CCAACGTGGGGGCCCGGGCCACCGCGGCTGGGTAGGGCCCGGCCGAGGCCAGGTCCCTCC
GAGAGGCGCCGCCGCCGCGCCCCGCCCGACTCCGACCCGCCGGCCTTTACCTGTATCCAC
GTCCCGGAGCCTCCGGCTTCGCGCCCCGTCCCGGCGCTCCCGGCCGCCAGCAGCCAGGCT
CTGAGGACTCGCTGCGGCTCCGGCGGCGGCGATGCCGGTTCGGCGAGACGGGAAGCGACA
GGAGCCAAACCCCGCGGAAAGCGCTCGAGCTGTGCCTGCAGCCCCGACCCCGCGGCCTCG
GACGTGGCGCCCGGCGCTCGCCCGCCACAGCCAGCGGCCCTGCTCGCCCCACGTCTGCG
GGTTCCCACCCGAGCCGCGCGTGGGCGGCGCCGGGCTTTGACCCCGCGCAGGCAGACAAG
CGCCGCGGGCCAGACGGAACCGTGGGAAAGTTTTTCTCCCTTGTCATCCCCTTACCAGAG
CCACAGAAATTATCCCTGTGGTCTCCCTTGTCCTCACTCGGCCTTTTCTGGAGTTAAGAG
ATCCAAGCCAACTACTGGGTCTGTTCCCTG
[SEQ ID NO: 184] - LOC285671
```

FIG 2EE

```
GGCAGCAGCCGCTGGCTTCTGCGCCCACTAGGAGCTTCGGATGCCCGAGTTAGGGCTGCG
CCAAGGCGGCCGGAGCAGAGAGGGAGACGGGGACGGGGACAGGCAGGGACAAAGTGCAAG
AGGCAAAACTGGCTGAAAAGCAGAAGTGTAGGAGCCGCCAAGGGGCGGGACGAACAGGTC
CGTGGGCCGGGCGGAGCCAAGGGTGGGGGCCGGGGTCCCTCCAGGTGGCACTCGCGGCGC
TAGTCCCCAGCCTCCTCCCTTCCCCCGGCCCTGATTGGCAGGCGGCCTGCGACCAGCCGC
GAACGCCACAGCGCCCCGGGCGCCCAGGAGAACGCGAACGGCCCCCCGCGGGAGCGGGCG
AGTAGGAGGGGCGCCGGGCTATATATATAGCGGCTCGGCCTCGGGCGGGCCTGGCGCTC
AGGGAGGCGCGCACTGCTCCTCAGAGTCCCAGCTCCAGCCGCGCGCTTTCCGCCCGGCTC
GCCGCTCCATGCAGCCGGGGTAGAGCCCGGCGCCCGGGGGCCCCGTCGCTTGCCTCCCGC
ACCTCCTCGGTTGCGCACTCCTGCCCGAGGTCGGCCGTGCGCTCCCGCGGGACGCCACAG
GCGCAGCTCTGCCCCCCAGCTTCCCGGGCGCACTGACCGCCTGACCGACGCACGGCCCTC
GGGCCGGGATGTCGGGGCCCGGGACGGCCGCGGTAGCGCTGCTCCCGGCGGTCCTGCTGG
CCTTGCTGGCGCCCTGGGCGGGCCGAGGGGGCGCCGCCGCACCCACTGCACCCAACGGCA
CGCTGGAGGCCGAGCTGGAGCGCCGCTGGGAGAGCCTGGTGGCGCTCTCGTTGGCGCGCC
TGCCGGTGGCAGCGCAGCCCAAGGAGGCGGCCGTCCAGAGCGGCGCCGGCGACTACCTGC
TGGGCATCAAGCGGCTGCGGCGGCTCTACTGCAACGTGGGCATCGGCTTCCACCTCCAGG
CGCTCCCCGACGGCCGCATCGGCGGCGCGCACGCGGACACCCGCGACAGTGAGTGGCGCG
GCCAGGCGCGAAGGGGCGGGGGCGGGGGCAACGGCCGCCGGGCCAACCCGCTCAGTCAC
ACTCTGAGACCCTCGGCGGGCACCTGCTCGGGGGCCCCGGGAACCGGGGCGGACTCGGGC
TCCGGTCCCTTCTGACGCGGGGCTGGGGACGCAGACACTCTTGGCTCCGGCAGCCCAGCG
CAACCCCTGAGGTCGGGCGCCGCCTCCCGCCTTCAGAAACTCGGGCTCCGAGCGCCGAAT
TCCAGCGCCTTCGCCCGTGGGCACAGGGCGCGCGGTGCAGCCACAGGGGGCCCGAGACAC
GCGCCCCGGCCTGGCCCAGGCTGGGGAACCGCTGGGGTCGGGCTCGCGTCTGAAGGTCCG
GGACTGGGTGCGGCCGCCGGGGGTCCCCTACACAGGCAAGCTAATCTGAGCTAGCGCAGG
CTTGGGCTCCGGAGGCCCTAGAGGGCAGCTTGGGCTCTGGAGGCCCTTGGGGCGGCTGC
GCCGGGAACCCTGGCCCTTTATCCCCAACCCCACCCCAGAAATAGGGTCCCCGGAGGCGA
ACAAGCCGAGGGGCGGAGTGGGCCAGGGATCACCTGCCCCGCAATGACCTGCGCCCCGCC
CCCAGGCCTGCTGGAGCTCTCGCCCGTGGAGCGGGGCGTGGTGAGCATCTTCGGCGTGGC
CAGCCGGTTCTTCGTGGCCATGAGCAGCAAGGGCAAGCTCTATGGCTCGGTGAGTACCGC
AGGGGTCTGGCTAGGCACCTAGTTGGGAACAGCGGACATGGCTAGCAGGCTCGTGGCTTC
```
[SEQ ID NO: 185] - FGF4

FIG 2FF

```
GAAGCCACGAGCCTGCTAGCCATGTCCGCTGTTCCCAACTAGGTGCCTAGCCAGACCCCT
GCGGTACTCACCGAGCCATAGAGCTTGCCCTTGCTGCTCATGGCCACGAAGAACCGGCTG
GCCACGCCGAAGATGCTCACCACGCCCCGCTCCACGGGCGAGAGCTCCAGCAGGCCTGGG
GGCGGGGCGCAGGTCATTGCGGGGCAGGTGATCCCTGGCCCACTCCGCCCCTCGGCTTGT
TCGCCTCCGGGGACCCTATTTCTGGGGTGGGGTTGGGGATAAAGGGCCAGGGTTCCCGGC
GCAGCCGCCCCCAAGGGCCTCCAGAGCCCAAGCTGCCCTCTAGGGCCTCCGGAGCCCAAG
CCTGCGCTAGCTCAGATTAGCTTGCCTGTGTAGGGGACCCCGGCGGCCGCACCCAGTCC
CGGACCTTCAGACGCGAGCCCGACCCCAGCGGTTCCCCAGCCTGGGCCAGGCCGGGGCGC
GTGTCTCGGGCCCCCTGTGGCTGCACCGCGCGCCCTGTGCCCACGGGCGAAGGCGCTGGA
ATTCGGCGCTCGGAGCCCGAGTTTCTGAAGGCGGGAGGCGGCGCCCGACCTCAGGGGTTG
CGCTGGGCTGCCGGAGCCAAGAGTGTCTGCGTCCCCAGCCCCGCGTCAGAAGGGACCGGA
GCCCGAGTCCGCCCCGGTTCCCGGGGCCCCCGAGCAGGTGCCCGCCGAGGGTCTCAGAGT
GTGACTGAGCGGGTTGGCCCGGCGGCCGTTGCCCCCGCCCCGCCCCTTCGCGCCTGGC
CGCGCCACTCACTGTCGCGGGTGTCCGCGTGCGCGCCGCCGATGCGGCCGTCGGGGAGCG
CCTGGAGGTGGAAGCCGATGCCCACGTTGCAGTAGAGCCGCCGCAGCCGCTTGATGCCCA
GCAGGTAGTCGCCGGCGCCGCTCTGGACGGCCGCCTCCTTGGGCTGCGCTGCCACCGGCA
GGCGCGCCAACGAGAGCGCCACCAGGCTCTCCCAGCGGCGCTCCAGCTCGGCCTCCAGCG
TGCCGTTGGGTGCAGTGGGTGCGGCGGCGCCCCTCGGCCCGCCCAGGGCGCCAGCAAGG
CCAGCAGGACCGCCGGGAGCAGCGCTACCGCGGCCGTCCCGGGCCCCGACATCCCGGCCC
GAGGGCCGTGCGTCGGTCAGGCGGTCAGTGCGCCCGGGAAGCTGGGGGGCAGAGCTGCGC
CTGTGGCGTCCCGCGGGAGCGCACGGCCGACCTCGGGCAGGAGTGCGCAACCGAGGAGGT
GCGGGAGGCAAGCGACGGGGCCCCCGGGCGCCGGGCTCTACCCCGGCTGCATGGAGCGGC
GAGCCGGGCGGAAAGCGCGCGGCTGGAGCTGGGACTCTGAGGAGCAGTGCGCGCCTCCCT
GAGCGCCAGGCCCGCCCGAGGCCGAGCCGCTATATATAGCCCGGCGCCCCCTCCTACT
CGCCCGCTCCCGCGGGGGCCGTTCGCGTTCTCCTGGGCGCCCGGGGCGCTGTGGCGTTC
GCGGCTGGTCGCAGGCCGCCTGCCAATCAGGGCCGGGGGAAGGGAGGAGGCTGGGGACTA
GCGCCGCGAGTGCCACCTGGAGGGACCCCGGCCCCCACCCTTGGCTCCGCCCGGCCCACG
GACCTGTTCGTCCCGCCCCTTGGCGGCTCCTACACTTCTGCTTTTCAGCCAGTTTTGCCT
CTTGCACTTTGTCCCTGCCTGTCCCCGTCCCCGTCTCCCTCTCTGCTCCGGCCGCCTTGG
CGCAGCCCTAACTCGGGCATCCGAAGCTCCTAGTGGGCGCAGAAGCCAGCGGCTGCTGCC
[SEQ ID NO: 186] - FGF4

TGAGGTGAGGGGCCGGAGGAGCAAGGGACAAGAGGAGCAGAGGACAGGTGATGGAAATCC
TGCAGCTTTAGGCTCCATTCTGCCATCTACATCCCAGCGCAGGGTGAAGCCTGAGAGCCC
AAATGGCCAACTCCACAGGGCTGAACGCCTCAGAAGTCGCAGGCTCGTTGGGGTTGATCC
TGGCAGCTGTCGTGGAGGTGGGGCACTGCTGGGCAACGGCGCGCTGCTGGTCGTGGTGC
TGCGCACGCCGGGACTGCGCGACGCGCTCTACCTGGCGCACCTGTGCGTCGTGGACCTGC
TGGCGGCCGCCTCCATCATGCCGCTGGGCCTGCTGGCCGCACCGCCGCCCGGGCTGGGCC
GCGTGCGCCTGGGCCCCGCGCCATGCCGCGCCGCTCGCTTCCTCTCCGCCGCTCTGCTGC
CGGCCTGCACGCTCGGGGTGGCCGCACTTGGCCTGGCACGCTACCGCCTCATCGTGCACC
CGCTGCGGCCAGGCTCGCGGCCGCCGCCTGTGCTCGTGCTCACCGCCGTGTGGGCCGCGG
CGGGACTGCTGGGCGCGCTCTCCCTGCTCGGCACGCCGCCCGCACCGCCCCTGCTCCTG
CTCGCTGCTCGGTCCTGGCTGGGGCCTCGGGCCCTTCCGGCCGCTCTGGGCCCTGCTGG
CCTTCGCGCTGCCCGCCCTCCTGCTGCTCGGCGCCTACGGCGGCATCTTCGTGGTGGCGC
GTCGCGCTGCCCTGAGGCCCCCACGGCCGGCGCGCGGGTCCCGACTCCACTCGGACTCTC
TGGATAGCCGCCTTTCCATCTTGCCGCCGCTCCGGCCTCGCCTGCCCGGGGCAAGGCGG
CCCTGGCCCCAGCGCTGGCCGTGGGCCAATTTGCAGCCTGCTGGCTGCCTTATGGCTGCG
CGTGCCTGGCGCCCGCAGCGCGGGCCGCGGAAGCCGAAGCGGCTGTCACCTGGGTCGCCT
ACTCGGCCTTCGCGGCTCACCCCTTCCTGTACGGGCTGCTGCAGCGCCCCGTGCGCTTGG
CACTGGGCCGCCTCTCTCGCCGTGCACTGCCTGGACCTGTGCGGGCCTGCACTCCGCAAG
CCTGGCACCCGCGGGCACTCTTGCAATGCCTCCAGAGACCCCAGAGGGCCCTGCCGTAG
GCCCTTCTGAGGCTCCAGAACAGACCCCGAGTTGGCAGGAGGGCGGAGCCCCGCATACC
AGGGGCCACCTGAGAGTTCTCTCTCCTGAGCAGGAGAAAGGAGGGTGGTTTCCGTGGGGG
CTCATCCAACCCCTGCACAGGTCACAGCAGGTGCCCTGCT
[SEQ ID NO: 187] - GPR62
```

FIG 2GG

```
AGCAGGGCACCTGCTGTGACCTGTGCAGGGGTTGGATGAGCCCCCACGGAAACCACCCTC
CTTTCTCCTGCTCAGGAGAGAGAACTCTCAGGTGGCCCCTGGTATGCGGGGCTCCGCCCT
CCTGCCAACTCGGGGGTCTGTTCTGGAGCCTCAGAAGGGCCTACGGCAGGGCCCTCTGGG
GGTCTCTGGAGGCATTGCAAGAGTGCCCGCGGGTGCCAGGCTTGCGGAGTGCAGGCCCGC
ACAGGTCCAGGCAGTGCACGGCGAGAGAGGCGGCCCAGTGCCAAGCGCACGGGGCGCTGC
AGCAGCCCGTACAGGAAGGGGTGAGCCGCGAAGGCCGAGTAGGCGACCCAGGTGACAGCC
GCTTCGGCTTCCGCGGCCCGCGCTGCGGGCGCCAGGCACGCGCAGCCATAAGGCAGCCAG
CAGGCTGCAAATTGGCCCACGGCCAGCGCTGGGGCCAGGGCCGCCTTGCCCCCGGGCAGG
CGAGGCCGGAGCGGCGGCAAGATGGAAAGGCGGCTATCCAGAGAGTCCGAGTGGAGTCGG
GACCCGCGCGCCGGCCGTGGGGGCCTCAGGGCAGCGCGACGCGCCACCACGAAGATGCCG
CCGTAGGCGCCGAGCAGCAGGAGGGCGGGCAGCGCGAAGGCCAGCAGGGCCCAGAGCGGC
CGGAAGGGCCCGAGGCCCCCAGCCAGGACCGAGCAGCGAGCAGGAGCAGGGGGCGGTGCG
GGCGGCGTGCCGAGCAGGGAGAGCGCGCCCAGCAGTCCCGCCGCGGCCCACACGGCGGTG
AGCACGAGCACAGGCGGCGGCCGCGAGCCTGGCCGCAGCGGGTGCACGATGAGGCGGTAG
CGTGCCAGGCCAAGTGCGGCCACCCCGAGCGTGCAGGCCGGCAGCAGAGCGGCGGAGAGG
AAGCGAGCGGCGCGGCATGGCGCGGGGCCCAGGCGCACGCGGCCCAGCCCGGGCGGCGGT
GCGGCCAGCAGGCCCAGCGGCATGATGGAGGCGGCCGCCAGCAGGTCCACGACGCACAGG
TGCGCCAGGTAGAGCGCGTCGCGCAGTCCCGGCGTGCGCAGCACCACGACCAGCAGCGCG
CCGTTGCCCAGCAGTGCCCCCACCTCCACGACAGCTGCCAGGATCAACCCCAACGAGCCT
GCGACTTCTGAGGCGTTCAGCCCTGTGGAGTTGGCCATTTGGGCTCTCAGGCTTCACCCT
GCGCTGGGATGTAGATGGCAGAATGGAGCCTAAAGCTGCAGGATTTCCATCACCTGTCCT
CTGCTCCTCTTGTCCCTTGCTCCTCCGGCCCCTCACCTCA
[SEQ ID NO: 188] - GPR62

CCGCGACCTTCGAGAACCCGCATGCTGTTCTCCACCAGGTCTCTCAGTCCTCCCTGCCCC
AATCCCCATGCCCGCCTCCGCGACCCTGTGATGCCTCCCTTCTTGCACAGGAGCAGTGAC
CTCAGCACTTACTTAATCCTCTCCCGGCGCCGAGCTCAGTTGGAGAGGCTAGGGGTGGTA
GTGACTGGCAGGAGGCCGGGGCGGGGGGAACCCCCAAGCCCGGCGTCTGGGGCTGCGGGT
CCGACCCGAGATCCGCCCTCCCTGCAAGCCCCGAGCCGCTGGCCAGGCCCGCTACTGCGC
ACCAGCCGCATCCGCGAGCGCTGGCTCTGCCGGCCTGAGCTAGGGTGGGTAGGGCCGGGA
CCCACGGCGGAGGTGGGGCCGGGCCGAGCAGCCTCGGGGGATCCCCGAAGCTACAGCGCC
TTGCCCTCCCTGCACGCTCCGCGCCCCGGCCTCCGATTGGCTGTCGGGCCTAGAGCCCGC
CCAGAATTGGACCGTTCGCTTGTCGCTCGGGTCTGGCTCCACCCCCAGAGGGAGCCTAGA
ACCTGGTCGCAGTTTTTAGAGACTACCCTCACCCCGTGGCCTGCGCCGAAGTTGGGCGGA
GGACAGTGGGTGGCCAGGCCCTTCCGGGCCAGAACTCGGGACCCCTGCCAGCTACCCGTG
CCAGGACAGACTCAAGCCCCCAAAACGCGGATGGATGTACAGAGGAGACTTGGGGAGAGC
ACTGGACTGGGAGTCCTTGGGCCTGCACTGAACTCTGGCTGACTTTGTGACCTTGAAGAA
ACTGCTTTTCCCTTCCTGAA
[SEQ ID NO: 189] - HEMK1

TTCAGGAAGGGAAAAGCAGTTTCTTCAAGGTCACAAAGTCAGCCAGAGTTCAGTGCAGGC
CCAAGGACTCCCAGTCCAGTGCTCTCCCCAAGTCTCCTCTGTACATCCATCCGCGTTTTG
GGGGCTTGAGTCTGTCCTGGCACGGGTAGCTGGCAGGGTCCCGAGTTCTGGCCCGGAAG
GGCCTGGCCACCCACTGTCCTCCGCCCAACTTCGGCGCAGGCCACGGGGTGAGGGTAGTC
TCTAAAAACTGCGACCAGGTTCTAGGCTCCCTCTGGGGGTGGAGCCAGACCCGAGCGACA
AGCGAACGGTCCAATTCTGGGCGGGCTCTAGGCCCGACAGCCAATCGGAGGCCGGGGGCG
CGGAGCGTGCAGGGAGGCAAGGCGCTGTAGCTTCGGGGATCCCCGAGGCTGCTCGGCCC
GGCCCCACCTCCGCCGTGGGTCCCGGCCCTACCCACCCTAGCTCAGGCCGGCAGAGCCAG
CGCTCGCGGATGCGGCTGGTGCGCAGTAGCGGGCCTGGCCAGCGGCTCGGGCTTGCAGG
GAGGGCGGATCTCGGGTCGGACCCGCAGCCCCAGACGCCGGGCTTGGGGTTCCCCCCGC
CCCGGCCTCCTGCCAGTCACTACCACCCCTAGCCTCTCCAACTGAGCTCGGCGCCGGGAG
AGGATTAAGTAAGTGCTGAGGTCACTGCTCCTGTGCAAGAAGGGAGGCATCACAGGGTCG
CGGAGGCGGGCATGGGGATTGGGGCAGGGAGGACTGAGAGACCTGGTGGAGAACAGCATG
CGGGTTCTCGAAGGTCGCGG
[SEQ ID NO: 190] - HEMK1
```

FIG 2HH

```
CTGCAGCAGGACGTAAGCACAGTCATCGCTGCAAACTGCAAACTCGTAAGCACAGTCATC
GCTGCAAACTGCAAACTCGTGCTCCGAGCGCTGCCCTCCCCTGTGGAGCGGAGGAGGGGA
GGCCTGGGGCCGCGGCGGTGTGCGCCCCGCTCTGACCGCAGAGCCCCCTTCCCGAGGAAA
GCGGCTGGCCCGGTCCCGGCTGGTGATCACGCGGGGCCCCTGTCTGCTTGGTGCGCAGGT
GAGGGTCTGCCCTTCCGCTGCGCCCCGGACAGCCTGGAGGTGAGCACGCGCTGGGCCCTG
GACCGCGAGCAGCGGGAGAAGTACGAGCTGGTGGCCGTGTGCACCGTGCACGCCGGCGCG
CGCGAGGAGGTGGTGATGGTGCCCTTCCCGGTGACCGTGTACGACGAGGACGACTCGGCG
CCCACCTTCCCCGCGGGCGTCGACACCGCCAGCGCCGTGGTGGAGTTCAAGCGGAAGGAG
GTGCTTGTCCGCGCGTGCTGTGGTCTACCCAGTGTCTGTCTCCGGCCACAGTTCGTTTCT
CGGTCGGTTTAGTGTCCGTGTAGCCACCCAACCGTGTGGCCGACCATTCGCGCTTTCATT
TGTCCTTCGCCTCCGTCTGCGCCGTCTGTCCTAGGGGAGGGGAAGGGGGAGTCCTGCCA
GCACCCAGCTGGGCCTTGCCTCGGGAGGCAAGGACCAGGACGAGGCCCGAGGGCTCGCGT
CTGGGGCATACTTGTGCCGCTGCAGGCGGGCGCGGCGCGCTGCCCGGGCGGGGAGCATCT
GCCGGGAGGGCACTCCCTCCCACCAGCAGTTAGCCCCCAACGGGAGGGCCCTTGAGTGAC
CACGAGCAGAGCCGGGGATTGGAGAAGGACGGGAAGGCGGATCACCTCCGGCGCCGCCCG
CCCCGCCCTTCTCCGGCTCGCGCTGGTGGAGCGCGACCGCCACCTGCTGGGCCTCGGCCT
TCCTGCAGCCGGCCCACCCAGCAGGGGCCGTGGGAGAGTGGGCGTGGGGACTGAGGTAGG
TAGTACGTTGCCTTGTTCCGCTTCTCTGGG
[SEQ ID NO: 191] - RET

CCCAGAGAAGCGGAACAAGGCAACGTACTACCTACCTCAGTCCCCACGCCCACTCTCCCA
CGGCCCCTGCTGGGTGGGCCGGCTGCAGGAAGGCCGAGGCCCAGCAGGTGGCGGTCGCGC
TCCACCAGCGCGAGCCGGAGAAGGGCGGGGCGGGCGGCGCCGGAGGTGATCCGCCTTCCC
GTCCTTCTCCAATCCCCGGCTCTGCTCGTGGTCACTCAAGGGCCCTCCCGTTGGGGGCTA
ACTGCTGGTGGGAGGGAGTGCCCTCCCGGCAGATGCTCCCCGCCCGGGCAGCGCGCCGCG
CCCGCCTGCAGCGGCACAAGTATGCCCCAGACGCGAGCCCTCGGGCCTCGTCCTGGTCCT
TGCCTCCCGAGGCAAGGCCCAGCTGGGTGCTGGCAGGACTCCCCCTTCCCCTCCCCTAG
GACAGACGGCGCAGACGGAGGCGAAGGACAAATGAAAGCGCGAATGGTCGGCCACACGGT
TGGGTGGCTACACGGACACTAAACCGACCGAGAAACGAACTGTGGCCGGAGACAGACACT
GGGTAGACCACAGCACGCGCGGACAAGCACCTCCTTCCGCTTGAACTCCACCACGGCGCT
GGCGGTGTCGACGCCCGCGGGAAGGTGGGCGCCGAGTCGTCCTCGTCGTACACGGTCAC
CGGGAAGGGCACCATCACCACCTCCTCGCGCGCGCCGGCGTGCACGGTGCACACGGCCAC
CAGCTCGTACTTCTCCCGCTGCTCGCGGTCCAGGGCCCAGCGCGTGCTCACCTCCAGGCT
GTCCGGGGCGCAGCGGAAGGGCAGACCCTCACCTGCGCACCAAGCAGACAGGGGCCCCGC
GTGATCACCAGCCGGGACCGGGCCAGCCGCTTTCCTCGGGAAGGGGGCTCTGCGGTCAGA
GCGGGGCGCACACCGCCGCGGCCCCAGGCCTCCCCTCCTCCGCTCCACAGGGGAGGGCAG
CGCTCGGAGCACGAGTTTGCAGTTTGCAGCGATGACTGTGCTTACGAGTTTGCAGTTTGC
AGCGATGACTGTGCTTACGTCCTGCTGCAG
[SEQ ID NO: 192] - RET

GCGCCGACGGGGCGGGTGGTAGGGGATGTACGGGTGTGTATATGCAGAGGTATGCCAGG
CTCTGCCCCTTAAAGTTTGGGGGCCGGCGGAGGCGGCGCCGTGGCCGGGAGAAAGTGTCT
CTCATTTAGGAGGGTTTGCAGGTCCAGAGTAAAGTCACTGAAGAGTGGAAGCGAGGAAGG
AACAGGATGATTAGACCTCAGCTGCGGACCGCGGGGCTGGACGATGCCTCCTGCCGGGG
CTGCTGCTGCTCCTGGTGCCCGTCCTCTGGGCCGGGCTGAAAAGCTACATACCCAGCCC
TCCTGCCCCGCGGTCTGCCAGCCCACGCGCTGCCCCGCGCTGCCCACCTGCGCGCTGGGG
ACCACGCCGGTGTTCGACCTGTGCCGCTGTTGCCGCGTCTGCCCCGCGGCCGAGCGTGAA
GTCTGCGGCGGGGCGCAGGGCCAACCGTGCGCCCCGGGGCTGCAGTGCCTCCAGCCGCTG
CGCCCCGGGTTCCCCAGCACCTGCGGTTGCCCGACGCTGGGAGGGCCGTGTGCGGCAGC
GACAGGCGCACCTACCCCAGCATGTGCGCGCTCCGGCCGAAAACCGCGCCGCGCGCCGC
CTGGGCAAGGTCCCGGCCGTGCCTGTGCAGTGGGGAACTGCGGGGATACAGGTGAGCCG
CGGGGGCGCGCGCCCTCGGAACACTTTCTAACTCTGGAGGAGCGTAAAGGAACAAGACCT
CACTGAGACCGCACAGTTCGCGCCTGGTCCTCCTGCGTCATTTGCCTCCTGGATTCGACA
CCTCTGTGTTCCTGATTTCC
[SEQ ID NO: 193] - HTRA4
```

FIG 2II

```
GGAAATCAGGAACACAGAGGTGTCGAATCCAGGAGGCAAATGACGCAGGAGGACCAGGCG
CGAACTGTGCGGTCTCAGTGAGGTCTTGTTCCTTTACGCTCCTCCAGAGTTAGAAAGTGT
TCCGAGGGCGCGCGCCCCGCGGCTCACCTGTATCCCCGCAGTTCCCCCACTGCACAGGC
ACGGCCGGGACCTTGCCCAGGCGGCGCGCGGCGCGGTTTTCGGCCCGGAGCGCGCACATG
CTGGGGTAGGTGCGCCTGTCGCTGCCGCACACGGCCCCTCCCAGCGTCGGGCAACCGCAG
GTGCTGGGGAACCCGGGGCGCAGCGGCTGGAGGCACTGCAGCCCCGGGGCGCACGGTTGG
CCCTGCGCCCCGCCGCAGACTTCACGCTCGGCCGCGGGGCAGACGCGGCAACAGCGGCAC
AGGTCGAACACCGGCGTGGTCCCCAGCGCGCAGGTGGGCAGCGCGGGGCAGCGCGTGGGC
TGGCAGACCGCGGGGCAGGAGGGCTGGGTATGTAGCTTTTCAGCCCCGGCCCAGAGGACG
GGCACCAGGAGCAGCAGCAGCCCCGGCAGGAGGCATCGTCCCAGCCCCGCGGTCCGCAGC
TGAGGTCTAATCATCCTGTTCCTTCCTCGCTTCCACTCTTCAGTGACTTTACTCTGGACC
TGCAAACCCTCCTAAATGAGAGACACTTTCTCCCGGCCACGGCGCCGCCTCCGCCGGCCC
CCAAACTTTAAGGGGCAGAGCCTGGCATACCTCTGCATATACACACCCGTACATCCCCTA
CCACCCGCCCCCGTCGGCGC
[SEQ ID NO: 194] - HTRA4

TTGTCTTCTCCCTTCCGACCTCCCGTGGCCCCAGCGCGGCCAGCTCACAGTAGGTGCTCG
GGCAGCGTTTCTTCAGGGACCTAGACGGCCTGGAGAGGAAGGGCCCCAGCCCAGCCGCCC
GGGCCTCTCACCTGGCTCTCGGGGCGCCCGGCTCGCACTTCCTCCCGCCGCCCCGCCCCT
TCCACATTCCTGCCCCGCCGGGCCTGCCCCGCGCAGTCTGGGTCTCTGCCGCAGCCGC
CCGCCCGCCCGCTCAGCGCCCGGCCCCGGGATGACGGCGGCCCAGGCCGCGGGTGAGGAG
GCGCCACCAGGCGTGCGGTCCGTCAAGGTGGTCCTGGTGGGCGACGGCGGCTGCGGGAAG
ACGTCGCTGCTGATGGTCTTCGCCGATGGGCCTTCCCCGAGGTGAGTGCCCCGCGCCTC
CGCCTCGCCCGGTTCCGCTCGCGCGCCCGGGTGTACAGGTCCGTGCCGGAGCGGCCCAGG
CTGTGCGCCTAACCCGGCCTCCGAGGGGTGTCCCAGCGGGGCCTGGGGTCCAGGGCAGAG
TTCTTCCGCCCCAGCCATTGGGAATGAAGGCCTCAGTGATGTTATCTGTAAAGCCGGAGG
AATGGCATCCACCGGGGAGAGGTGTCACAAGGACTGAGTGAGGCGACCTGGGTGCACACA
AGATCCTAAGACAGCACTTGGCCACACAATTCCGCTGAGGGCCTGAGAGCTTGGAAGCCA
GACTGCCGAGGTTCAAATTATGGCTTTGCCTCTTATAGCTGTGTGCCCTTGGGTAAGTCC
CCTAACCCTGCTGTGCCTGTG
[SEQ ID NO: 195] - RHOD

ATTGAGAGAGAGGGAGGGCGAAAGGAAGGAAGGGGAGCCAGAGGTGGGAGTGGAAGAGGC
AGCCTCGCCTGGGGCTGATTGGCTCCCGAGGCCAGGGCTCTCCAAGCGGTTTATAAGAGT
TGGGGCTGCCGGGCGCCCTGCCCGCTCGCCCGCGCGCCCCAGGACCCAAAGCCGGGCTCC
AAGTCGGCGCCCCACGTCGAGGCTCCGCCGCAGCCTCCGGAGTTGGCCGCAGACAAGAAG
GGGAGGGAGCGGGAGAGGGAGGAGAGCTCCGAAGCGAGAGGGCCGAGCGCCATGCGCCGC
GCCAGCAGAGACTACACCAAGTACCTGCGTGGCTCGGAGGAGATGGGCGGCGGCCCCGGA
GCCCCGCACGAGGGCCCCCTGCACGCCCCGCCGCCGCCTGCGCCGCACCAGCCCCCTGCC
GCCTCCCGCTCCATGTTCGTGGCCCTCCTGGGGCTGGGGCTGGGCCAGGTTGTCTGCAGC
GTCGCCCTGTTCTTCTATTTCAGAGCGCAGGTGAGTGGCCACCTTCCCAGGGGATCGCGG
CTGAGAGCGCCCATCTCCTTCCCCCGCACTTGGAAACTGAGTCTGGCGGCAGGGCTGGGC
CACCCAGAGCTTGCATATTCCGGAAGGGAAAGTGACTCCAGAAGGGAGAGAGGAAGTGTT
GAGTTTGGGGACAACCTGGCGCAGGGCTGTCGGGCGCACCCTGCTCTCTCTCCGCCCACG
CACCCCAGCTTCTCGGTGCTCTGGGGCGGACTCCCCTGGCCGGACGATGGGTTTGAATC
TCACCCCGTCCCTTCGCTGGGAAACAACACTGGCCTCTCACCTTTTCTGGTAGTGATTGC
ATACTTTTTCTCCCTGTCATTTCTCACTTGAAGTTAAGAATCAACTTCTGTTCACGTAGG
AAAAAAGATGAGCGCCTTCACTTGGGCATCTACCTTTCCCTTCCCGCCCACCACCCGGCG
GGTTTCGGTTCCTGCGCCTGGCTGCTCTGCAGGTGTGCTGGGGCCACGGTGCTGGAGGGC
TGCGCGGAGCGGGAGGTCGCGGTGCTCGTGCCCAGGTCGCCCAATGGGTGGGCAGAATGA
CACGGCGCGACCAGAGAGGCGCGGGCTCGGGATGGGGCTCTGCGGCTGTGGCGCTGTCC
TGTGGGGGTGAAGGAAGAGGGACAGCCCCACGTGCCTGCTAGGGATGTGGGCGGAGGAAG
GAAGCGAGGTGAGTGTGATGGCACAGTGTTACTACAGTCTAGCAAATAACCAACCTTCGG
AAAGATGAAGAGGTTTTTTGCACGACGGCTAGGAACTGCAG
[SEQ ID NO: 196] - TNFSF11
```

FIG 2JJ

```
GCAATTTATAGATGAGAGCGTGGACGGCAGAGAGCATTGTGTATGTTGAAGTCTCTGCGATATGGGGT
GTCCCTGCTGCCCCGCTCCAGCCTTTCACTTCTGACCTCCTTCCTCTGGCTCTTACGCTACAGGATCC
AAAACTACTCGGAAGACTTGCCGCGGGCGGTGATTGACGACGCCTTTGCCCGCGCCTTCGCACTGTGG
AGCGCGGTGACGCCGCTCACCTTCACTCGCGTGTACAGCCGGGACGCAGACATCGTCATCCAGTTTGG
TGTCGCGGGTGAGAACGTGAGGAGGGAAAATCCAAGAGACCTGGGCGGGGTCAGGGAAGGGAGGACCA
CGGAGAGCGTGGAGGCAGCAGTGGCCCCGGCTTCCTCTTGCCTGCCCGCGCTGCCCTGGCTTATACGG
CCCCTCCTGCCAGACAGTGCACAGGGCCAGGGCGCCAGGCTGGGAGAGCTTCGCGCAGGCGGGATTTC
AGCCCGCACTTATTTCGGAGCCCTTGCCTTGGGCAGCGCACAATCTGCGCAGCAGTACTCGGCTAACC
CTCTTCCTCTCGACCTGTTTCTTCAGAGCACGGAGACGGGTATCCCTTCGACGGGAAGGACGGGCTCC
TGGCACACGCCTTTCCTCCTGGCCCCGGCATTCAGGGAGACGCCCATTTCGACGATGACGAGTTGTGG
TCCCTGGGCAAGGGCGTCGGTGAGATTCTGAGTCCTCCTGGCCCCTGATTCCCTTCATTCTCTCCCAC
TCATCACCCGCCGCCCTAACTCCGGTCCCCCCTCCTCCTGCAGTGGTTCCAACTCGGTTTGGAAACGC
AGATGGCGCGGCCTGCCACTTCCCCTTCATCTTCGAGGGCCGCTCCTACTCTGCCTGCACCACCGACG
GTCGCTCCGACGGCTTGCCCTGGTGCAGTACCACGGCCAACTACGACACCGACGACCGGTTTGGCTTC
TGCCCCAGCGAGAGTGAGTGAGGGGGCTCGCCGAGGGCTGGGGGCGCCCACCACCCTTGATGGTCCTG
GGTTCTAATTCCAGCTCTGCCACTAGTGCTGTGTGGCCTGCAATTCACCCTCCCGCACTCTGGGCCCA
ATTTTCTCATCTGAGAAATGATGAGAGATGGGATGAACTGCAGACCATCCATGGGTCAAAGAACAGGA
CACACTTGGGGGTTATAATGTGCTGTCTCCGCCTTCTCCCCCTTTCCCACATCCTCCTCGCCCCAGGA
CTCTACACCCAGGACGGCAATGCTGATGGGAAACCCTGCCAGTTTCCATTCATCTTCCAAGGCCAATC
CTACTCCGCCTGCACCACGGACGGTCGCTCCGACGGCTACCGCTGGTGCGCCACCACCGCCAACTACG
ACCGGGACAAGCTCTTCGGCTTCTGCCCGACCCGAGGTACCTCCACCCTGTCTACCAGGTTCAGCCCC
GCCCTCTCATCATGTATTGGCCCCCAAAACGCGGCTCTTCCCTCCCATCAGTTTGTCTTTCCACTCTC
ATTGGTCCTCAGGACGACCGTGACTCCGCCCACCTACACCACATTTCCACCACTATCCCTGACTTCCA
ATGGCCCCGCCCCAGCCACTAAGGTTCGGCCTTTTCTGCCCAGCTGGCCGCCTCTTCCTTGGTCTGGT
GTCCCAGGCACCGCCCACGGGTCTAGCCTCTTCTCAGGAGTGCTCTACAGCGCCCCCTAGGCCACCAA
GATTGTTTAGCTCCCTGTCGGGTCGGCCCCTGACTCCTTATTGGACTCATCCATCTGGCTCATCCAAG
GCCTTGGGTCTCTCCAGCTGACTCGACGGTGATGGGGGGCAACTCGGCGGGGGAGCTGTGCGTCTTCC
CCTTCACTTTCCTGGGTAAGGAGTACTCGACCTGTACCAGCGAGGGCCGCGGAGATGGGCGCCTCTGG
TGCGCTACCACCTCGAACTTTGACAGCGACAAGAAGTGGGGCTTCTGCCCGGACCAAGGTAGGCGTGG
TCCCGCGGCTCCGGGGCTGGGGTTCCCGGCAGTGGTGGTGGTGGGGTGGCCAGGGCTGGGGCTCGGC
CCGGCGCTCACGTCTCAGGCTCCCTCTCCCTCCAGGATACAGTTTGTTCCTCGTGGCGGCGCATGAGT
TCGGCCACGCGCTGGGCTTAGATCATTCCTCAGTGCCGGAGGCGCTCATGTACCCTATGTACCGCTTC
ACTGAGGGGCCCCCCTTGCATAAGGACGACGTGAATGGCATCCGGCACCTCTATGGTGAGGCAGGGGC
AGGGATGGGAGGAGGAGGGGAAAGGGCGTGGCTGTGCCACAGTACCAAAGAATTGGGGGTTGGGGATC
GGGGGAGGAACGGGGCGTGCAGGAGAGGTGGGACCTCAACGTCTGTCTGGAAGCAGAGCCTGGGCCCA
GTCGCTGCCATGTCAGTGCTTAGAGGTGGTGATAAAGAGACTCTAGAGAGAGATAGGTGTGACTTCAA
AAGCCAGTCTACTCTGGGCATGGTGGCTCACGCCTCTAATCCCAGGCTTTGGGAGACCCAAGGCGGG
AGGATTGCTTAAGCCCAGGAGTTCCAGACCAGCCTCGGCAACATAGCCAGACTCCCATCTCTACAAAA
AATAAATGAGCAAGGCGTGAAGGCACATGTCTGTAGTCCTAGCTACTCTGGAGGCTGAGGTGGGAGGA
TCTCTTGAGCCCAGGAGTTCGAGGCTGTAGTGAGCTATGATTGCACCACTGCATTCCATCCTGGGCCA
TAGAGGATGTCGCTTAAAACGAAAAGAAGAAGAAGAAAGTCCTGTGGTTTGGGAAGGGAGGCTGAGT
GAGGAGGGGCCTGTGTGCCAGAGGAGGCTTCACTGAGAAGCTTAGGGGAGCAGATGTTCTAGGGGTAC
AGAGGTATGCAGGAATAGGAAGAGTCTCACCCCGTGTCTCTTTTTAGGTCCTCGCCCTGAACCTGAGC
CACGGCCTCCAACCACCACCACACCGCAGCCCACGGCTCCCCGACGGTCTGCCCCACCGGACCCCCC
ACTGTCCACCCCTCAGAGCGCCCCACAGCTGGCCCCACAGGTCCCCCCTCAGCTGGCCCCACAGGTCC
CCCCACTGCTGGCCCTTCTACGGCCACTACTGTGCCTTTGAGTCCGGTGGACGATGCCTGCAACGTGA
ACATCTTCGACGCCCATCGCGGAGATTGGGAACCAGCTGTATTTGTTCAAGGATGGGTGAGGAGGCGGG
GTTGTGTGGATGCGGGAGGGGGCTTTGCGGAGGGGCTGCCCGTCCCTTCCCGCCCACTGGCCCTGTGT
CCAAGGCTTAGAGCCCGTCCTTTCCCTCCTCGCTTTCTCAGGAAGTACTGGCGATTCTCTGAGGGCAG
GGGGAGCCGGCCGCAGGGCCCCTTCCTTATCGCCGACAAGTGGCCCGCGCTGCCCCGCAAGCTGGACT
CGGTCTTTGAGGAGCGGCTCTCCAAGAAGCTTTTCTTCTTCTCTGGTTAGTTACCTACTTTCCCTCCC
CCGCCCGGTCAATCCCCATCAGTCAAGGAGGCTCAAGAGACCATCGATAACCCACGAAACGTCTTGTG
CGTTTTAGAAAAATACGCCCCTGGCGGACGCAGTTTAGCAAACGTAGGGCGGCTGAGTTTCTGCCC
CCTCCTCTCCACGCCCTCGCGTCGCTCTACCCAGCGCCTCTGCCCCTGGGTTGCAGGGACTGCGGGCA
CGCGGGCTAGGAAAGGCCTCGCCGGAATCTCCCTCCTCGCGTTCTAGGGATACGTGCTCCCTCTGCGC
CCCCAAACCGACGTGACCCTCCTCCCCTGCAGGGCGCCAGGTGTGGGTGTACACAGGCGCGTCGGTGC
TGGGCCCGAGGCGTCTGGACAAGCTGGGCCTGGGAGCCGACGTGGCCCAGGTGACCGGGGCCCTCCGG
AGTGGCAGGGGGAAGATGCTGCTGTTCAGCGGGCGGCGCCTCTGGAGGTGAGCGCCGCCGCGGCCGCC
GGCAGGGGGAGCCGGGCGCCGTCGGTCCGTCCGCTAGCCGGCTCAGCACCTGTCTCCTCCGCGCCTG
CCCGCAGGTTCGACGTGAAGGCGCAGATGGTGGATCCCCGGAGCGCCAGCGAGGTGGACCGGATGTTC
CCCGGGGTGCCTTTGGACACGCACGACGTCTTCCAGTACCGAGGTGAGGGCTGAGGAGGATCCCTTCG
TGAGACACCACACTAAGCTCCTCTTAGTGAGTGGTCAAATTCTGAGCGAGGAAGAAAAAGCCCTTGGA
AATGGAAACAAATGCCCCAGCACAGACAAGATCCCAGCAGAGGCAGAGGCCTTCTCCAGGTCATTTAG
GAAGTCAGGGATGCAAC
[SEQ ID NO: 197] - MMP9
```

FIG 2KK

```
CAGGAACTTTCGAGATGAGGTGCCTTTCCCAAGGTGACACTAAGTGGAGGAGCCCAGCCA
GAGTCCAGGGGTCCTTACACAACCTTCGGTGGTCTCTCTTTACCTGTGAAGCTGCAGCCT
GCTTCCCAGCTCGGGGGCGTGTACAGGAGACTGGACCTGGGGCAGCCTCAGAATGCCTGG
CTGCCTGGAGCTCTCCTCGCGTGTCCAGGCGGCCTGCTTGGTCTCCCTCCTCTCCCCTCT
TAGGTGCCGGGGCGGGCACCCGGTGCAGGGTGGGCACGGCGCCTGCCACCAGCCTCAGGC
GCTGGGAGAAGCGCAGGTTCTTCTGGATAACCGAAGAGACGTCAAAACAGGCTGGGGCAA
AGTGGTCAGAGCAGATGACCGAGCGGTCATTGCCTCCGTACCAGTCGGCGCGGCAACCCC
GCACGAAGCGGTCCCAGAGCAGCCGCACGGCCCGGTCCTTGGGAAAGCGGAACAGCGACT
TCCCAGACTTGGTGGTGTTGCCGCAGTGGGCGGCCACACAACGGGCCGGCATGGCGGCCG
TCTTCGGTGCGCGGGAGCCGGGTTCCCTGGACCTTCGCCCTTGGGCACGCTCCTCGCAGC
GGCCTCGGCGAGGCAAGTCCTCCCCTCCTCACCTGTCCACTCCGGGTCGGGATTGTTTCC
TTCCCTACCTCTGGTCACCGGAAGTGGCGATCTGGGGCCCCCAATGGGAGGGCTCTTTGA
TATCTTCCTCCTCCTCCCTGCGCTGCTCCCCAGGAGCCAGTGGACACAAGCAGAGGG
ATACAAATTTCGCGCGGGCAG
```
[SEQ ID NO: 198] - LRRC49

MATERIALS AND METHOD FOR ASSAYING FOR METHYLATION OF CPG ISLANDS ASSOCIATED WITH GENES IN THE EVALUATION OF CANCER

CROSS-REFERENCE TO RELATED APPLICATIONS

This patent application is a divisional of U.S. patent application Ser. No. 12/115,674, filed on May 6, 2008, now abandoned, which is a continuation of International Patent Application No. PCT/US2006/060685, filed Nov. 8, 2006, designating the United States, which claims the benefit of U.S. Provisional Patent Application No. 60/734,577, filed Nov. 8, 2005, which are incorporated by reference herein in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 214,875 Byte ASCII (Text) file named "702375_ST25.TXT," created on May 2, 2008.

BACKGROUND OF THE INVENTION

Phosphate linked cytosine-guanine (CpG) dinucleotides are statistically underrepresented in the genomes of higher eukaryotes, including mammals. The dinucleotide is reportedly found at only 5-10% of its predicted frequency. The majority of CpG dinucleotides that do remain in the human genome are normally located within repetitive sequences that are characterized by low gene expression levels and exhibit methylation at the cytosine residues.

CpG islands, on the other hand, represent genomic sequences that contain clusters of CpG dinucleotide. CpG islands may be associated with the promoter region or 5' end of coding sequences or may be present within introns or in genomic regions that are not known to be associated with coding sequences. They may be unmethylated or methylated in normal tissues and the methylation pattern may be used to control tissue specific expression and the expression of imprinted genes. Methylation of CpG islands within promoter regions can result in the downregulation or silencing of the associated gene. An increase in methylation of normally unmethylated islands is observed in aging tissues even as the overall methylcytosine content of the DNA is reduced. The aberrant methylation pattern is more pronounced in cancer cells with increased methylation or hypermethylation detected in various cancer tissues. CpG islands may be methylated to varying densities within the same tissue. Thus, aberrant methylation of cytosines within CpG islands can be a primary epigenetic event that acts to suppress the expression of genes involved in critical cellular processes, such as DNA damage repair, hormone response, cell-cycle control, and tumor-cell adhesion/metastasis, leading to tumor initiation, progression and metastasis (Li et al., *Biochim. Biophys. Acta,* 1704: 87-102 (2004)). It has been proposed that a unique profile of promoter hypermethylation exists for each human cancer in which some gene changes are shared and other gene changes are cancer-type specific (Esteller et al., *Cancer Res.,* 61: 3225-3229 (2001)). Given that aberrant methylation represents new information not normally present in genomic DNA and that aberrant methylation is a common DNA modification and affects a large number of genomic targets, it is feasible to develop diagnostic and prognostic tests based on information obtained from multiple target CpGs. Such tests may be based on CpGs that are aberrantly hypermethylated or hypomethylated in the diseased tissues. They may also be based on changes in methylation density in CpG islands as long as the changes corrolate with the presence of cancer.

Prostate cancer, for example, which is the most common malignancy and the second leading cause of death among men in the U.S. (Li et al. (2004), supra), has been found to be associated with the methylation of CpG islands in the promoters of over 30 genes, in particular the CpG island of the glutathione S-transferase P1 (GSTP1) gene. GSTP1 methylation has been detected in over 50% of DNA recovered from urine and plasma of prostate cancer patients (Goessl et al., *Ann. N.Y. Acad. Sci.,* 945: 51-58 (2001); Cairns et al., *Clin. Cancer Res.,* 7: 2727-2730 (2001); Jeronimo et al., *Urology,* 60: 1131-1135 (2002); and Gonzalgo et al., *Clin. Cancer Res.,* 9: 2673-2677 (2003)). However, if diagnosis of prostate cancer relied solely on the detection of the methylation of the CpG island in the GSTP1 gene, the theoretical limit of the sensitivity of such a test would only be approximately 90%. GSTP1 is also methylated in prostatic intraepithelial lesions (PIN) which may lead to a false positive diagnosis. Some CpG islands are methylated in prostate cancer and other diseases of the prostate, such as benign prostatic hyperplasia (BPH). They may even exhibit some degree of methylation in normal aging prostates. Such markers may not be suitable individually for prostate cancer diagnosis. Therefore, a panel of markers is required to achieve the sensitivity and specificity needed for a clinical test.

The prostate-specific antigen or PSA test continues to be widely used in the early detection of prostate cancer. While the PSA test has resulted in the majority of prostate cancer cases being diagnosed in asymptomatic men (Mettlin et al., *Cancer,* 83(8): 1679-1684 (1998a); Mettlin et al., *Cancer,* 82(2): 249-251 (1998b); Humphrey et al., *J. Urol.,* 155: 816-820 (1996); and Grossfeld et al., *Epidemiol. Rev.,* 23(1): 173-180 (2001)), the PSA test suffers from poor specificity, which can be as low as 33% when a PSA cut-off level of 2.6 ng/ml is used (Thompson et al., *N. Engl. J. Med.,* 350: 2239-2246 (2004)), even though the sensitivity can be as high as 83%. The poor specificity of the PSA test is a direct result of increased secretion of PSA in other diseases of the prostate, such as BPH and prostatitis. Thus, an elevated PSA level indicates the need for additional screening in the form of needle biopsy. Ultimately, the results of needle biopsies lead to the diagnoses of prostate cancer.

Over 1 million needle biopsies of prostates are performed each year at a cost of about $1,500 each and much discomfort to the patient. However, less than 200,000 of these result in a diagnosis of prostate cancer. Therefore, the majority of needle biopsies are being performed needlessly.

In view of the above, there is a need for non-invasive methods of diagnosing and prognosticating cancer, such as prostate cancer, that reduce the cost and suffering associated with currently available cancer screening methods. It is an object of the invention to provide materials and methods for non-invasive diagnosis and prognosis of cancer, such as prostate cancer. This and other objects and advantages, as well as additional inventive features, will become apparent from the detailed description provided herein.

BRIEF SUMMARY OF THE INVENTION

The invention provides materials and methods for evaluating cancer. Methods of evaluating can include methods of diagnosing and prognosticating cancer as well as methods of assessing the efficacy of cancer treatment. Generally, the methods provided involve assaying for methylation of CpG islands associated with specific genes. The invention also provides pairs of isolated or purified primers that can be used in the methods of the invention, for example, to amplify and/or detect the methylation state of the CpG islands associated with specific genes. The invention also provides kits comprising one or more pairs of primers useful in the disclosed methods.

The invention provides methods of diagnosing cancer by assaying for one or more methylated CpG islands that are indicative of cancer. Generally, the method comprises providing a biological sample from a subject in need of cancer diagnosis and assaying the sample for methylation of one or more CpG islands associated with at least one gene selected from the group consisting of: neuregulin cell-surface ligand (NRG1), adrenergic B3 receptor (ADRB3), glycosylphosphatidyl-inositol cell-surface receptor (GFRA2), kinesin family member 13B (KIF13B), RET proto-oncogene (RET), G-protein-coupled protein receptor 147 (GPR147), neurogenin 3 transcription factor (NEUROG3), paladin (predicted protein tyrosine phosphatase) (PALD), methyltransferase family member 1 (HEMK1), fibroblast growth factor 4 oncogene (FGF4), 5-hydroxytryptamine (serotonin) receptor 1A (HTR1A), ring finger protein 180 (LOG 285671 or RNF180), EGFR-co-amplified and overexpressed (DKFZP564K0822 or ECOP), zinc finger protein 596 (ZNF596), similar to 7 transmembrane helix receptor (LOC441320), L-threonine dehydrogenase (TDH), hypothetical protein FLJ36980 (FLJ36980), fibroblast growth factor receptor 20 (FGF20), EF-hand domain family member 2A (LOC286097 or EFHA2), N-acylsphingosine amidohydrolase (acid ceraminase) 1 (ASAH1), nodal homolog (TGF-β signaling pathway) (NODAL), hypothetical protein similar to zinc finger protein 532 (LOC399783), transcription factor LIM homeodomain (ISL2) Kinesin family member C2 (KIFC2), chromosome 20 open reading frame 23 (Kinesin-like motor protein) (C20orf23), GDNF family receptor alpha 1 (GFRA1), Glutathione peroxidase 7 (GPX7), Dickkopf homolog 2 (DKK2), netrin 1 (NTN1), matrix metallopeptidase 9 (MMP9), tumor necrosis factor superfamily member 11 (TNFSF11), ras homolog gene family member D (RHOD), and leucine rich repeat containing 49 (LRRC49).

The invention also provides a method of diagnosing prostate cancer in a male mammal by assaying for one or more methylated CpG islands that are indicative of prostate cancer. The method can include providing a biological sample from a subject in need of cancer diagnosis and assaying the sample for methylation of a CpG island associated with at least one gene selected from the group consisting of: NRG1, ADRB3, GFRA2, KIF13B, RET, GPR147, NEUROG3, PALD, HEMK1, FGF4, HTR1A, RNF180, ECOP, ZNF596, LOC441320, TDH, FLJ36980, EFHA2, ASAH1, NODAL, LOC399783, ISL2, MMP9, TNFSF11, RHOD, LRRC49, Kinesin family member C2 (KIFC2), chromosome 20 open reading frame 23 (Kinesin-like motor protein) (C20orf23), GDNF family receptor alpha 1 (GFRA1), Glutathione peroxidase 7 (GPX7), Dickkopf homolog 2 (DKK2), netrin 1 (NTN1), Ras association (Ra1GDS/AF-6) domain family 5 (RASSF5), and HtrA serine peptidase 4 (HTRA4). Optionally, the method of diagnosing prostate cancer can also include assaying for methylation of one or more CpG island associated with at least one gene that is known to be methylated in prostate cancer but is known not to be detectably methylated or is methylated at a lower level (e.g., about 50% or less, about 40% or less, 30% or less, about 20% or less, or about 10% or less) in BPH.

The invention also provides methods of prognosticating cancer by assaying for the methylation of one or more genes that are indicative of the grade or stage of the cancer, and/or the length of disease-free survival following treatment for cancer. Generally, the method comprises providing a biological sample from a subject in need of cancer prognosis and assaying the sample for methylation of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, FLJ36980, FGF20, EFHA2, ASAH1, NODAL, LOC399783, ISL2, KIFC2, C20orf23, GFRA1, GPX7, DKK2, NTN1, MMP9, TNFSF11, RHOD and LRRC49.

Further provided by the invention is a method of prognosticating prostate cancer in a male mammal by assaying for one or more methylated CpG islands that are indicative of the grade or stage of prostate cancer, and/or the length of disease-free survival following treatment of prostate cancer. The method comprises providing a biological sample from the male mammal and assaying the sample for methylation of a CpG island associated with at least one of the following genes: NRG1, ADRB3, GFRA2, KIF13B, RET, GPR147, NEUROG3, PALD, HEMK1, FGF4, GPR62, HTR1A, RNF180, DKFZP5640822, ZNF596, LOC441320, TDH, FLJ36980, FGF20, EFHA2, ASAH1, NODAL, LOC399783, ISL2, KIFC2, C20orf23, GFRA1, GPX7, DKK2, NTN1, RASSF5, HTRA4, MMP9, TNFSF11, RHOD or LRRC49. Optionally, the method of prognosticating prostate cancer can also include assaying the biological sample for methylation of a CpG island associated with at least one gene that is known to be methylated in prostate cancer but is known not to be detectably methylated or is methylated at a lower level (e.g., about 50% or less, about 40% or less, 30% or less, about 20% or less, or about 10% or less) in BPH. Methylation of the CpG islands associated with the genes is indicative of the grade or stage of the cancer, and/or the length of disease-free survival following treatment.

Furthermore, the invention provides methods of assessing the efficacy of treatment of cancer by assaying for the reduced methylation of CpG islands that indicates efficacy of treatment. Generally, the method comprises providing a first and a second biological sample from a subject in need of assessing the efficacy of treatment of cancer and assaying the samples for a change in methylation level of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, FLJ36980, FGF20, EFHA2, ASAH1, NODAL, LOC399783, ISL2, KIFC2, C20orf23, GFRA1, GPX7, DKK2, NTN1, MMP9, TNFSF11, RHOD and LRRC49. The first biological sample is taken before the second biological sample, and the second biological sample is taken during or after a course of treatment. A decrease or absence of methylation of the assayed one or more CpG islands in the second sample (i.e., following the course of treatment) indicates that the treatment is effective. Alternatively, the maintenance or increase of methylation in the assayed CpG islands in the second sample can indicate a reduction or absence of treatment efficacy.

Also provided is a method of assessing the efficacy of treatment of prostate cancer in a male mammal by assaying biological samples, which are taken from the male mammal periodically during the course of treatment, for methylation of a CpG island and wherein a decrease or absence of methylation of the CpG islands following the course of treatment indicates that the treatment is effective. The method comprises (a) providing a first and a second biological sample from a subject undergoing a course of cancer treatment, wherein the first sample is taken at an earlier time than the second sample, and the second sample is taken during or following a course of treatment and (b) assaying the samples for methylation of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, FLJ36980, FGF20, EFHA2, ASAH1, NODAL, LOC399783, ISL2, KIFC2, C20orf23, GFRA1, GPX7, DKK2, NTN1, RASSF5, HTRA4, MMP9, TNFSF11, RHOD and LRRC49. Optionally, this method can also include assaying the biological sample for methylation of a CpG island associated with at least one gene that is known to be methylated in prostate cancer but is known not to be detectably methylated or is methylated at a lower level (e.g. about 50% or less, about 40% or less, 30% or less, about 20% or less, or about 10% or less in BPH.

In preferred embodiments, the aforementioned methods of diagnosing, prognosticating and assessing the efficacy of treatment of cancer can further include assaying the biological sample for methylation of multiple CpG islands, for example, CpG islands associated with two, three, four, five, six, seven, eight, nine, ten, eleven, or more genes.

Additionally, the invention provides a terminator-coupled linear amplification method of determining the methylation status of a CpG island. Generally, the method includes providing a DNA sample for terminator-coupled linear amplification and then incubating the DNA sample under deaminating conditions to thereby produce a deaminated DNA sample. Optionally, the deaminated DNA sample can be purified. The deaminated sample is used as template to amplify a target sequence or target sequences that include one or more CpG islands or portions of one or more CpG islands thereby producing one or more amplified target sequences. Optionally, the one or more amplified target sequences are purified. One or more sequences in the amplified target sequences are linearly amplified in the presence of a primer and a dideoxynucleotide to generate one or more fragments of different lengths, wherein each length corresponds to the distance in bases from the 5' end of the primer to the position where the dideoxynucleotide is incorporated. Optionally, the one or more fragments is purified. The one or more fragments are analyzed to determine their lengths. The lengths of the fragments can be used to determine the methylation status of methylated cytosines within the one or more amplified target sequences.

The invention also provides pairs of primers suitable for amplifying a CpG-island associated with genes described herein. Primers can include isolated or purified nucleic acid molecules suitable for amplifying a CpG island containing target sequence. Target sequences can include genomic sequence that has been fully methylated and fully deaminated such as those in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 33, SEQ ID NO: 34, SEQ ID NO: 35, SEQ ID NO: 36, SEQ ID NO: SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 49, SEQ ID NO: 50, SEQ ID NO: 51, SEQ ID NO: 52, SEQ ID NO: 53, and SEQ ID NO: 54.

Exemplary primer pairs include SEQ ID NOs: 55 and 56, SEQ ID NOs: 57 and 58, SEQ ID NOs: 59 and 60, SEQ ID NOs: 61 AND 62, SEQ ID NOs: 63 and 64, SEQ ID NOs: 65 and 66, SEQ ID NOs: 67 and 68, SEQ ID NOs: 69 and 70, SEQ ID NOs: 71 and 72, SEQ ID NOs: 73 and 74, SEQ ID NOs: 77 and 78, SEQ ID NOs: 79 and 80, SEQ ID NOs: 81 and 82, SEQ ID NOs: 83 and 84, SEQ ID NOs: 87 and 88, SEQ ID NOs: 89 and 90, SEQ ID NOs: 91 and 92, SEQ ID NOs: 93 and 94, SEQ ID NOs: 95 and 96, SEQ ID NOs: 97 and 98, SEQ ID NOs: 103 and 104, SEQ ID NOs: 105 and 106, SEQ ID NOs: 107 and 108, SEQ ID NOs: 109 and 110, SEQ ID NOs: 111 and 112, SEQ ID NOs: 113 and 114, SEQ ID NOs: 115 and 116, SEQ ID NOs: 117 and 118, SEQ ID NOs: 199 and 200, SEQ ID NOs: 201 and 202, SEQ ID NOs: 203 and 204, SEQ ID NOs: 205 and 206, SEQ ID NOs: 207 and 208, SEQ ID NOs: 209 and 210, SEQ ID NOs: 211 and 212, SEQ ID NOs: 213 and 214, SEQ ID NOs: 215 and 216, SEQ ID NOs: 217 and 218, SEQ ID NOs: 219 and 220, SEQ ID NOs: 221 and 222, SEQ ID NOs: 224 and 225, SEQ ID NOs: 227 and 228, SEQ ID NOs: 227 and 228, SEQ ID NOs: 230 and 231.

Also provided are kits that include one or more of the aforementioned pairs of primers.

BRIEF DESCRIPTION OF THE FIGURES

FIGS. 1A-1DD set forth the nucleotide sequences for SEQ ID NOs: 1-54. Sequences are presented in accordance with convention from left to right and top to bottom.

FIGS. 2A-2KK set forth the nucleotide sequences for SEQ ID NOs: 119-198. Sequences are presented in accordance with convention from left to right and top to bottom.

DETAILED DESCRIPTION OF THE INVENTION

The invention provides a method of diagnosing cancer by assaying for the methylation of one or more CpG islands that are indicative of cancer. Cancer can include, for example, lung, liver, pancreas, head and neck, throat, thyroid, esophagus, brain, ovarian, kidney, skin, colorectal, and hematopoeietic (e.g., lymphomas and leukemic) cancer. Generally, the method comprises providing a biological sample from a subject in need of cancer diagnosis and assaying the sample for methylation of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, FLJ36980, FGF20, EFHA2, ASAH1, NODAL, LOC399783, ISL2, KIFC2, C20orf23, GFRA1, GPX7, DKK2, NTN1, MMP9, TNFSF11, RHOD or LRRC49. In preferred embodiments, the method can include assaying for methylation of CpG islands associated with two, three, four, five, six, seven, eight, nine, ten, eleven, or more of the foregoing genes. Methylation of the CpG islands associated with these genes is indicative of cancer.

The invention further provides a method of diagnosing prostate cancer by assaying for the methylation of one or more CpG islands that are indicative of prostate cancer in a male mammal. In one embodiment, the method comprises providing a biological sample from a male mammal in need of cancer diagnosis and assaying the sample for methylation of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, FLJ36980, FGF20, EFHA2, ASAH1, NODAL, LOC399783, KIFC2, C20orf23, GFRA1, GPX7, DKK2, NTN1, HTRA4, MMP9, TNFSF11, RHOD and LRRC49. For example, the method of diagnosing prostate cancer includes assaying the biological sample for methylation of a CpG island associated with NRG1, KIF13B, or both. In another example, the method includes assaying for methylation of a CpG island associated with at least one gene selected from the group consisting of: TDH, ASAH1, FGF20, HEMK1, PALD NEUROG, EFHA2, KIFC2, GFRA1, DKK2, TNFSF11, NTN1, and RHOD. In preferred embodiments, the method of diagnosing prostate cancer can include assaying for methylation of CpG islands associated with two, three, four, five, six, seven, eight, nine, ten, eleven, or more of the foregoing genes. Methylation of the CpG islands associated with these genes is indicative of cancer.

The foregoing method of diagnosing prostate cancer can optionally include, in combination with assaying for methylation of CpG islands associated with the foregoing genes, further assaying the biological sample for methylation of a CpG island associated with at least one gene that is known to be (i) methylated in prostate cancer and (ii) not detectably methylated or methylated at a lower level (e.g., about 50% or less, about 40% or less, about 30% or less, about 20% or less, or less than about 10%) in BPH. In this regard, when the method includes assaying for at least one CpG island that is known to be methylated in prostate cancer but is known not to be detectably methylated or methylated at a lower level in BPH, the method preferably includes assaying the biological sample for methylation of CpG islands associated with at least three different genes. Examples of CpG islands known to be methylated in prostate cancer but not detectably methylated or methylated at a lower level in BPH include CpG islands associated with glutathione S-transferase P1 (GSTP1), glutathione peroxidase 3 (GPX3), glutathione S-transferase M1 (GSTM1), glutathione S-transferase M4 (GSTM4), Cub and Sushi multiple domains1 (CSMD1), tumor necrosis factor receptor superfamily member 10A (TNFRSF10A) tumor necrosis factor receptor superfamily member 10B (TNFRSF10B), tumor necrosis factor receptor superfamily member 10C (TNFRSF10C), tumor necrosis factor receptor superfamily 10D (TNFRSF10D), secreted frizzled-related protein 1 (SFRP1), secreted frizzled-related protein 2 (SFRP2), dickkopf homolog 3 (DKK3), prostaglandin-endoperoxide synthase 2 (PTGS2), cyclin-dependent kinase inhibitor 1C (CDKN1C/p57), Ras association (Ra1GDS/AF-6) domain family 1 (RASSF1), and G-protein coupled receptor 62 (GPR62).

The invention also provides a method of prognosticating cancer by assaying for the methylation of one or more genes that are indicative of the grade or stage of the cancer, and/or the length of disease-free survival following treatment for cancer. Generally, the method comprises providing a biological sample from a subject in need of cancer prognosis and assaying the sample for methylation of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, F1136980, FGF20, EFHA2, ASAH1, NODAL, LOC399783, ISL2, KIFC2, C20orf23, GFRA1, GPX7, DKK2, NTN1, MMP9, TNFSF11, RHOD and LRRC49. In preferred embodiments, the method can include assaying for methylation of CpG islands associated with two, three, four, five, six, seven, eight, nine, ten, eleven, or more of the foregoing genes. Methylation of the CpG islands associated with these genes is indicative of the grade or stage of the cancer, and/or the length of disease-free survival following treatment for cancer.

The invention also provides a method of prognosticating prostate cancer in a male mammal by assaying for the methylation of one or more CpG islands that are indicative of the grade or stage of the prostate cancer, and/or the length of disease-free survival following treatment for prostate cancer. In one embodiment, the method comprises assaying a biological sample from the male mammal for methylation of a CpG island associated with at least one of the following genes: NRG1, ADRB3, GFRA2, KIF13B, RET, GPR147, NEUROG3, PALD, HEMK1, FGF4, HTRIA, RNF180, DKFZP5640822, ZNF596, LOC441320, TDH, F1136980, FGF20, EFHA2, ASAH1, NODAL, LOC399783, or ISL2. In addition to or instead of the foregoing, the method can include assaying the biological sample for methylation of a CpG island associated with at least one of the following genes: KIFC2, C20orf23, GFRA1, GPX7, DKK2, NTN1, RASSF5, HTRA4, MMP9, TNFSF11, RHOD or LRRC49. For example, the method of diagnosing prostate cancer includes assaying the biological sample for methylation of a CpG island associated with NRG1, KIF13B, or both. In another example, the method includes assaying for at least one of the following genes: TDH, ASAH1, FGF20, HEMK1, PALD NEUROG, EFHA2, KIFC2, GFRA1, DKK2, TNFSF11, NTN1, or RHOD. In preferred embodiments, the method of diagnosing prostate can include assaying for methylation of CpG islands associated with two, three, four, five, six, seven, eight, nine, ten, eleven, or more of the foregoing genes. Methylation of the CpG islands associated with these genes is indicative of the grade or stage of prostate cancer, and/or the length of disease-free survival following treatment for prostate cancer.

The foregoing method of prognosticating prostate cancer can optionally include, in combination with assaying for methylation of CpG islands associated with the foregoing genes, further assaying the biological sample for methylation of a CpG island associated with at least one gene that is known to be (i) methylated in prostate cancer and (ii) not detectably methylated or methylated at a lower level (e.g., about 50% or less, about 40% or less, about 30% or less, about 20% or less, or less than about 10%) in BPH. Percent methylation level in BPH refers to the percent of patients that exhibit some detectable level of methylation at that locus. In this regard, when the method includes assaying for methylation of at least one CpG island that is known to be methylated in prostate cancer but is known not to be detectably methylated or is methylated at a lower level in BPH, the method preferably includes assaying the biological sample for methylation of CpG islands associated with at least three different genes. Examples of CpG islands known to be methylated in prostate cancer but not detectably methylated or methylated at a lower level in BPH include CpG islands associated with GSTP1, GPX3, GSTM1, GSTM4, CSMD1, TNFRSF10A, TNFRSF10B, TNFRSF10C, TNFRSF10D, SFRP1, SFRP2, DKK3, PTGS2, CDKN1C/p57, RASSF1, and GPR62. Methylation of CpG islands associated with the genes is indicative of the grade or stage of the prostate cancer, and/or the length of disease-free survival following treatment for prostate cancer.

Obtaining information about the aggressiveness of the cancer, its grade, and its stage is helpful when choosing a course of treatment. The patterns of CpG methylation may be correlated to the pathological stage and grade of the tumor. For example, in prostate cancer, patterns of CpG methylation may be correlated to the Gleason score of the primary tumor. The molecular information derived from CpG methylation may also be correlated to the likelihood of survival and the length of disease-free survival following treatment. The above prognostic methods can enable the prediction of the course of the cancer, as well as the prediction of the best approach to treatment.

Also provided are methods of assessing the efficacy of treatment of cancer by assaying for the reduced methylation of CpG islands that indicates efficacy of treatment. Generally, the method comprises providing a first and a second biological sample from a subject in need of assessing the efficacy of treatment of cancer and assaying the samples for a change in methylation level of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, F1136980, FGF20, EFHA2, ASAH1, NODAL, LOC399783, ISL2, KIFC2, C20orf23, GFRA1, GPX7, DKK2, NTN1, MMP9, TNFSF11, RHOD and LRRC49. Generally, the first biological sample is taken (e.g, prior to commencing treatment or during treatment) before the second biological sample, and the second biological sample is taken after a course of treatment. In preferred embodiments, the method includes assaying for a change in methylation of CpG islands associated with two, three, four, five, six, seven, eight, nine, ten, eleven, or more of the foregoing genes. A decrease or absence of methylation of the assayed one or more CpG islands in the second sample (i.e., following the course of treatment) indicates that the treatment is effective. Alternatively, the maintenance or increase of methylation in the assayed CpG islands in the second sample can indicate a reduction or absence of treatment efficacy.

The invention provides a method of assessing the efficacy of treatment of prostate cancer in a male mammal by assaying for the reduced methylation of CpG islands that indicate efficacy of treatment of prostate cancer. In one embodiment, the method comprises assaying biological samples, which are taken from the male mammal periodically during the course of treatment, for methylation of a CpG island associated with at least one gene selected from the group consisting of: NRG1, ADRB3, GFRA2, KIF13B, RET, GPR147, NEUROG3, PALD, HEMK1, FGF4, HTR1A, RNF180, DKFZP5640822, ZNF596, LOC441320, TDH, F1136980, FGF20, EFHA2, ASAH1, NODAL, LOC399783, and ISL2. In addition to or instead of the foregoing, the method can include assaying the biological samples for methylation of a CpG island associated with at least one gene selected from the group consisting of: KIFC2, C20orf23, GFRA1, GPX7, DKK2, NTN1, RASSF5, HTRA4, MMP9, TNFSF11, RHOD and LRRC49. For example, the method of assessing the efficacy of treatment of prostate cancer includes assaying the biological sample for methylation of a CpG island associated with NRG1, KIF13B, or both. In another example, the method includes assaying for a CpG island associated with at least one gene selected from the group consisting of: TDH, ASAH1, FGF20, HEMK1, PALD NEUROG, EFHA2, KIFC2, GFRA1, DKK2, TNFSF11, NTN1, and RHOD. In preferred embodiments, the method can include assaying for methylation of CpG islands associated with two, three, four, five, six, seven, eight, nine, ten, eleven, or more of the foregoing genes. Generally, the assayed biological samples in the method include a first and a second biological sample. The first biological sample can be taken, for example, prior to commencing treatment or during treatment, though in any event prior to taking the second biological sample. The second biological sample is taken during or after a course of treatment. A decrease or absence of methylation of the assayed one or more CpG islands in the second sample (i.e., following the course of treatment) as compared to the first sample indicates that the treatment is effective. Alternatively, the maintenance or increase of methylation in the assayed CpG islands in the second sample as compared to the first sample can indicate a reduction in or absence of treatment efficacy.

The foregoing method of assessing the efficacy of prostate cancer treatment can optionally include, in combination with assaying for methylation of CpG islands associated with the foregoing genes, further assaying the biological sample for reduced methylation of a CpG island associated with at least one gene that is known to be (i) methylated in prostate cancer and (ii) not detectably methylated or methylated at a lower level (e.g., about 50% or less, about 40% or less, about 30% or less, about 20% or less, or less than about 10%) in BPH. In this regard, when the method includes assaying the biological samples for methylation of at least one CpG island that is known to be methylated in prostate cancer but known not to be detectably methylated or methylated at a lower level in BPH, the method preferably includes assaying for methylation of CpG islands associated with at least three different genes. Examples of CpG islands known not to be methylated in prostate cancer but not detectably methylated or methylated at a lower level in BPH include GSTP1, GPX3, GSTM1, GSTM4, CSMD1, TNFRSF10A, TNFRSF10B, TNFRSF10C, TNFRSF10D, SFRP1, SFRP2, DKK3, PTGS2, CDKN1C/p57, RASSF1, and GPR62. A decrease or absence of methylation of the CpG islands associated with the assayed genes in the second sample as compared to the first sample following some or all of the course of treatment indicates that the treatment is effective. Alternatively, the maintenance or increase of methylation in the assayed CpG islands in the second sample as compared to the first sample can indicate a reduction or absence of treatment efficacy.

CpG islands (Bird, Nature 321: 209-213 (1986); and Gardiner-Garden et al., J. Molec. Biol. 196: 261-282 (1987)) comprise about 1% of vertebrate genomes and account for about 15% of the total number of CpG dinucleotides. CpG islands typically are between about 0.2 and about 2.0 kb in length. They can be located upstream of (e.g., in a promoter or enhancer region) of the coding sequence of the associated genes or they may also extend into or be found within gene-coding regions of their associated genes. A gene-coding region can include exons and introns. Use of the phrase "associated with" to describe a CpG island's relation to a gene, is intended to encompass CpG islands that are upstream of gene coding sequences as well as internal CpG islands. For example, the CpG island associated with the RET gene is internal and not expected to affect the expression of the RET gene when methylated. Some CpG islands are associated with the promoter of two genes and it can affect the expression of both genes. CpGs were labeled based on their location with respect to the nearest gene. In some cases, a CpG island may be located near the promoter of two different genes and may in this case influence the expression of both genes. In such case, the CpG island was named after one of the genes. For example, the LRRC49 CpG island is also associated with the THAP domain containing 10 (THAP10) gene. A CpG island can also be associated with a pseudogene or be located in a genomic region that includes no known genes or pseudogenes. The CpG island can still be of interest so long as its methylation status correlates with a disease status.

A CpG island can be separated by up to 25 kilobases (kb) (e.g., up to 20 kb, up to 19 kb, up to 18, kb, up to 17 kb, up to 16 kb, up to 15 kb, up to 10 kb, up to 9 kb, up to 8 kb, up to 7 kb, up to 6 kb, up to 5 kb, up to 4 kb, up to 3 kb, up to 2 kb, or up to 1 kb) from the transcription start site for the nearest gene and still be considered "associated with" the gene. Preferably, CpG islands associated with at least three genes are assayed. However, CpG islands associated with 4, 5, 6, 7, 8, 9, 10, 11, 12, 13, 14, 15, 16, 17, 18, 19, 20, 21, 22, 23, 24, 25, 26, 27, or even more genes can be assayed.

Methods of identifying CpG islands have been described (e.g., Takai et al., *Proc. Nat'l. Assoc. Sci. USA,* 99:3740-3745 (2002)). For example, genomic sequences can be analyzed to identify segments containing CpG islands that are at least 200 bp in length, have at least a 60% GC content, and contain at least 7% CpG dinucleotides. Preferred sequences are at least 250 bp in length, are at least 60% GC rich, and contain at least 7% CpG dinucleotides. Moreover, undesirable highly repetitive sequences can be screened out using a repeat masker that filters out sequences. Desirable sequences contain less than 50% repeats (i.e., a sequence of reduced complexity or a sequence that is present at multiple genomic locations) within the length of the identified CpG island. Preferably, the CpG island is no more than 45%, 40%, 35%, 30%, 25%, 20%, 19%, 18%, 17%, 16%, 15%, 14%, 13%, 12%, or 11% repetitive. Most desirable sequences are no more than 10% repetitive. Examples of repetitive sequences are available, for example, at the web site for National Center for Biotechnology Information (NCBI).

"Biological sample" is intended to encompass any suitable sample that enables accurate assay of CpG island methylation. Examples of suitable biological samples include, but are not limited to, whole blood, blood plasma, blood serum, urine, saliva, cells (e.g., cells obtained from blood, such as epithelial cells), and tissue. Such samples are obtained in accordance with methods known in the art. When the biological sample is whole blood, blood plasma, or urine, preferably, CpG islands associated with more than three genes are assayed.

A CpG island is "not detectably methylated" when it is not methylated or it is methylated at a level below the level of sensitivity of the assay method employed.

"Noncancerous" tissue can be benign or normal. Alternatively, but not preferably, the tissue can be diseased, as long as it is not cancerous.

Methods of assaying methylation of CpG islands are known in the art and include, for example, restriction enzyme-based technology, such as one that employs digestion with a methylation-sensitive restriction endonuclease coupled with Southern blot analysis, methylation-sensitive enzymes and polymerase chain reaction (PCR), such as methylation-sensitive arbitrarily primed PCR (AP-PCR; see, e.g., Gonzalgo et al., *Cancer Res.,* 57: 594-599 (1997)), restriction landmark genomic scanning (RLGS; see, e.g., Plass et al., *Genomic* 58: 254-262 (1999)), methylated CpG island amplification (MCA; see, e.g., Toyota et al., *Cancer Res.,* 59: 2307-2312 (1999)), differential methylation hybridization (DMH; see, e.g., Huang et al., *Human Mol. Genet.,* 8: 459-470 (1999)), and Not I-based differential methylation hybridization (see, e.g., International Patent Publication No. WO 02/086163). Other methods are described in U.S. Pat. App. Pub. No. 2003/0170684 and International Patent Publication No. WO 04/05122.

Alternatively, cytosine conversion-based technology can be used. Such technology relies on methylation status-dependent chemical modification of CpG islands (i.e., deamination of unmethylated cytosines in CpG islands) within isolated genomic DNA or fragments thereof followed by DNA sequence analysis. Such methods employ reagents like hydrazine and bisulfite. Bisulfite treatment followed by alkaline hydrolysis is described by Olek et al., *Nucl. Acids Res.,* 24: 5064-5066 (1996); and Frommer et al., *PNAS USA,* 89: 1827-1831 (1992). The use of methylation-sensitive primers to assay methylation of CpG islands in isolated genomic DNA is described by Herman et al., *PNAS USA,* 93: 9821-9826 (1996), and in U.S. Pat. Nos. 5,786,146 and 6,265,171. Bisulfite-treated DNA can be subsequently analyzed by conventional molecular techniques, such as PCR amplification, fluorescence-based, real-time PCR (see, e.g., Eads et al., *Cancer Res.,* 59: 2302-2306 (1999); Heid et al., *Genome Res.,* 6: 986-994 (1996); and U.S. Pat. No. 6,331,393), sequencing, oligonucleotide hybridization detection, and methylation-sensitive single nucleotide primer extension (Ms-SNuPE; see, e.g., Gonzalgo et al., *Nucl. Acids Res.,* 25: 2529-2531 (1997); and U.S. Pat. No. 6,251,594).

A preferred method of assaying for methylation of a CpG island includes isolating genomic DNA (and/or fragments thereof) from a biological sample, treating the DNA under deaminating conditions that convert unmethylated cytosines to uracil, using the treated DNA as a template in a PCR reaction to amplify a target sequence that includes the CpG-island of interest, thereby producing an amplified sequence. Unmethylated cytosines in the target sequence, which are converted to uracils by the deaminating treatment, are amplified as thymines in the corresponding position of the amplified sequence. Since the sequence of the forward and the reverse strand of the CpG island lose their complimentarity after the deamination reaction, the methylation status of the CpG island can be determined by assaying one or both of the original strands by utilizing primers capable of annealing to the strand of interest.

The deamination reaction may not proceed to completion, which results in false positives. For example, deamination of DNA sequences using bisulfite salt is sensitive to the purity of the DNA, length of incubation, and the secondary structure of the denatured templates. Quantitative PCR methods can be used to assay for the efficiency of deamination. However, quantitative PCR methods are limited to assaying the conversion status within the sites where the primers and probes anneal to the template.

Quantitative PCR methods are also limited to assaying for the methylation of cytosines within the sites where the primers and probes anneal to the template. The primers and the probe only anneal efficiently to the templates that are fully converted and contain methylation at the appropriate cytosine nucleotides. Thus, they fail to provide methylation information for CpG dinucleotides that are not assayed for. The CpG islands may also be analyzed using direct sequencing following the deamination treatment. However, due to the heterogeneity of the methylation pattern within a CpG island and the presence of homopolymeric stretches within the sequence, direct sequencing of CpG islands can yield a sequencing pattern that is too noisy and complex for the available sequencing software.

To overcome these disadvantages and to minimize the overall cost of analysis for a clinical test, we developed a method to analyze the amplified sequences by termination-coupled linear amplification. The DNA is linearly amplified using a forward or a reverse primer in the presence of dNTPs and one or two dideoxynucleotides such as dideoxycytidine or dideoxyguanine. The amplified sequence can, optionally, be analyzed using only thymine and/or cytosine terminators when assaying for a methylated CpG dinucleotide (or adenine and/or guanine terminators when analyzing the amplified strand opposite to the CpG dinucleotide of interest) to make extension reaction products that terminate at thymines and/or cytosines nucleotides (or at guanine and/or adenine when assaying the opposite strand). The amplification reaction results in the generation of fragments with multiple lengths, each length of which corresponds to the distance in bases between the primer used for amplification and the position within the target sequence of a nucleotide that is complementary to the dideoxynucleotide added to the amplification reaction. Such amplification can result in the generation of 10 to 20 fragments from an average CpG island-containing amplicon of 100 to 150 bp. The extension products can be separated by size on an acrylamide gel and compared to (a) a size standard and/or (b) by comparing the fragments to those generated when fully unmethylated (PCR generated template or clones in *E. coli*) or fully methylated (enzymatically methylated in vitro) template to thereby determine the presence of cytosine (or guanine on the opposite strand) or the presence of thymine (or adenine on the opposite strand) in the amplified CpG island-containing sequence. When bisulfite is used as the deaminating agent, the amplified sequence may contain large stretches of thymine or adenine which may result in additional fragments due to the DNA polymerase slippage during amplification. Such "stutter" patterns may be minimized by selectively analyzing segments of the CpG islands that have shorter homopolymeric sequences. Stutter fragments can also be identified by analyzing the control templates.

When a fluoresent label is used to tag the primers or the dideoxynucleotides used in the terminator-coupled linear amplification, the resulting fragments may be analyzed using automated sequencing machines and software designed for determining the size of DNA fragments. In this regard, commercially available software such as GENESCAN (Applied Biosystems, Foster City, Calif.) and GENEMAPPER (Applied Biosystems) are trained to recognize and account for stutter patterns due to DNA polymerase slippage during the amplification of microsatellite repeats. Such software may also be used to account for the stutter pattern that is observed when amplifying homopolymeric stretches of DNA, as might be seen after bisulfite conversion of CpG islands. There are a number of fluorescent dyes available for the automated analysis of DNA such as but not limited to 6-carboxyfluorescein (6-FAM), Hexachlorofluorescein (HEX), VIC dye, 5-carboxytetramethylrhodamine (TAMRA), 5-carboxy-X-rhodamine, succinimidyl ester (5-ROX), 6-carboxy-2',4,7,7'-tetrachlorofluorescein (TET). The methods and equipment to determine amplicon size have been available for over a decade and in use for genetic linkage mapping, DNA identity, and forensic. For example, Applied Biosystems has a set of 5 dyes that can be used to multiplex fragments from 4 separate amplification reaction and one standard for use in linkage mapping on the ABI sequencers. Four different CpG islands from a single individual can be linearly amplified using fluorescently tagged primers, and the products pooled before analysis. Alternatively, different CpG islands from different individuals can be linearly amplified using fluorescently tagged primers, and the products pooled before analysis.

Since methylation of a particular CpG dinucleotide is not always complete in a sample, i.e., the CpG sequence is heterogenous, the methods provided herein can be advantageously used to analyze the extent of or percent methylation of a particular CpG dinucleotide site within a sample. In a preferred method, two different fluorescent-dye terminators are used for thymine and cytosine, respectively (or adenine and guanine, respectively, when analyzing the opposite strand) in a fluorescent dideoxy sequencing reaction. The relative abundance of the two dyes in same-size extension products are indicative of the relative abundance of the two nucleotides at a particular sequence position, and can thereby indicate the percent methylation of a particular CpG dinucleotide site within a CpG island. To determine the expected relative abundance of the two dyes, control reactions with a range of known ratios of fully methylated to fully unmethylated templates can be used. The data obtained from the control reactions can be used as a reference to estimate relative abundance of methylated and unmethylated cytosines in a sample.

The levels of methylation or patterns of methylation at given CpG islands can be assayed as appropriate. The assay can employ the use of a reference standard when appropriate to enable the determination of abnormal methylation. A reference standard can be determined based on reference samples obtained from age-matched noncancerous classes of adjacent tissues, and with normal peripheral blood lymphocytes. When, for example, efficacy of treatment is being assessed, the assay results of biological samples taken over the course of treatment can be compared without the use of a reference standard.

When the DNA obtained from a biological sample is in limited quantities and is not sufficient for the analysis of multiple markers, the methods described herein can include amplifying the DNA from the sample. Amplification can be done using PCR amplification or isothermal amplification methods, for example, those described in U.S. Pat. Nos. 5,854,033; 6,124,120; 6,143,495; 6,210,884; 6,642,034; 6,280,949; 6,632,609; and 6,642,034; and U.S. Pat. App. Pub. Nos. 2003/0032024; 2003/0143536; 2003/0235849; 2004/0063144; and 2004/0265897, which are incorporated herein by reference in their entirety. Isothermal amplification can include rolling circle or strand displacement amplification. Methods that combine PCR and isothermal amplification have also been described (U.S. Pat. Nos. 6,777,187; and 6,828,098; and U.S. Pat. App. Pub. Nos. 2004/0209298; 2005/0032104; and 2006/0068394, each of which is incorporated herein by reference in its entirety). U.S. Pat. App. Pub. No. 2005/0202490, which is incorporated herein by reference in its entirety, describes the use of such methods in combination with methylation-sensitive restriction enzymes to study the methylation pattern of DNA. DNA amplification can also include methylation-coupled whole genomic amplification to generate the DNA needed, such as described in U.S. Pat. App. Pub. No. 2006/0257905, which is incorporated by reference herein in its entirety. The methylation-coupled whole genomic amplification can be especially advantageous when DNA is recovered from minute biological samples or from bodily fluids such as urine or plasma.

Skilled artisans will appreciate that the various amplification methods described herein, e.g., the PCR amplification, isothermal amplification, and termination-coupled linear amplification method, can employ nucleotides, nucleotide analogues, nucleotide or nucleotide analogue derivatives, and/or combinations thereof.

If desired, mRNA and protein levels can be assayed, and alterations in their expression levels can be indicative of a change in the level of methylation or the patterns of methylation at given CpG islands. Such methods of assaying mRNA and protein levels are also within the skill in the art. For example, the mRNA assay methods described in U.S. Provisional Patent Application No. 60/705,964 filed on Aug. 5, 2005 and International Patent Publication No. WO 2007/019444, which are hereby incorporated by reference, can be used. Such methods are particularly useful if a degraded tissue sample is used as the biological sample. Alternatively, reverse transcription with gene-specific primers can be used to assay mRNA levels. Proteins levels can be assayed, for example, using antibody and staining techniques.

It is important to note that even though aberrant methylation of a CpG island can affect expression of the associated gene, the methods described herein are not dependent on a biological role for the hypermethylation. That is a hypermethylated CpG island can be useful in the methods of the invention regardless of its effect on gene expression. Accordingly, the only requirement is that there be a correlation between the methylated state of a CpG island and the presence of cancer.

The invention further provides target sequences and corresponding primers or probes that are useful in the above methods. The target sequences provide the context for the selection of CpG islands to assay for methylation. If a given target sequence contains more than one CpG island, all or less than all of the CpG islands, even one CpG dinucleotide, can be assayed for methylation with respect to that particular target sequence. In this regard, a target sequence can include a genomic sequence that is fully methylated and fully deaminated such as SEQ ID NO: 1 or 2 [NRG1], SEQ ID NO: 3 or 4 [ADRB3], SEQ ID NO: 5 or 6 [GFRA2], SEQ ID NO: 7 or 8 [KIF13B], SEQ ID NO: 9 or 10 [RET], SEQ ID NO: 11 or 12 [GPR147], SEQ ID NO: 13 or 14 [NEUROG3], SEQ ID NO: 15 or 16 [PALD], SEQ ID NO: 17 or 18 [HEMK1], SEQ ID NO: 19 or 20 [FGF4], SEQ ID NO: 23 or 24 [HTR1A], SEQ ID NO: 25 or 26 [RNF180], SEQ ID NO: 27 or 28 [ECOP], SEQ ID NO: 29 or 30 [ZNF596], ID NO: 33 or 34 [LOC441320], SEQ ID NO: 35 or 36 [TDH], SEQ ID NO: 37 or 38 [FLJ36980], SEQ ID NO: 39 or 40 [FGF20], SEQ ID NO: 41 or 42 [EFHA2], SEQ ID NO: 43 or 44 [ASAH1], SEQ ID NO: 45 or 46 SEQ ID NO: 49 or 50 [NODAL], SEQ ID NO: 51 or 52 [LOC399783], SEQ ID NO: 53 or 54 [ISL2]. These fully methylated and deaminated sequences are used for illustrative purposed and do not exclude the use of partially methylated and deaminated sequences in the methods of the invention. A target sequence can include a genomic sequence that is partially methylated, such as in DNA obtained from a tumor, and then deaminated such that the target differs from the sequence listed above. Persons of skill in the art will appreciate that a target sequence that includes a partially methylated and deaminated CpG island will result in a population of DNA molecules that differ at one or more positions that correspond to the cytosine residues in one or more CpG dinucleotides. Thus, a target sequence can include a variety of partially methylated and deaminated sequences based on the following genomic sequences SEQ ID NOs: 119 or 220 [KIFC2], SEQ ID NOs: 121 or 122 [C200RF23], SEQ ID NOs: 123 or 124 [GFRA1], SEQ ID NOs: 129 or 130 [DKK2], SEQ ID NOs: 133 or 134 [RASSF5], SEQ ID NOs: 135 or 136 [NTN1], SEQ ID NOs: 139 or 140 [GPR147], SEQ ID NOs: 141 or 142 [NEUROG3], SEQ ID NOs: 143 or 144 [NODAL], SEQ ID NOs: 145 or 146 [PALD], SEQ ID NOs: 147 or 148 [LOC399783], SEQ ID NOs: 151 or 152 [LOC441320], SEQ ID NOs: 153 or 154 [ZNF596], SEQ ID NOs: 155 or 156 [TDH], SEQ ID NOs: 157 or 158 [ASAH1], SEQ ID NOs: 159 or 160 [FGF20], SEQ ID NOs: 161 or 162 [FLJ36980], SEQ ID NOs: 163 or 164 [GFRA2], SEQ ID NOs: 165 or 166 [EFHA2], SEQ ID NOs: 171 or 172 [KIF13B], SEQ ID NOs: 173 or 174 [ADRB3], SEQ ID NOs: 175 or 176 [NRG1], SEQ ID NOs: 177 or 178 [ECOP], SEQ ID NOs: 179 or 180 [HTR1A], SEQ ID NOs: 181 or 182 [ISL2], SEQ ID NOs: 183 or 184 [LOC285671], SEQ ID NOs: 185 or 186 [FGF4], SEQ ID NOs: 189 or 190, [HEMK1], SEQ ID NOs: 191 or 192 [RET] SEQ ID NOs: 193 or 194 [HTRA4], SEQ ID NO: 195 [RHOD], SEQ ID NO: 196[ TNFSF11], SEQ ID NO: 197 [MMP9], and SEQ ID NO: 198 [LRRC49].

These targets can be used in combination with known targets (for example known CpG islands associated with GSTP1, GPX3, GSTM1, GSTM4, CSMD1, TNFRSF10A, TNFRSF10B, TNFRSF10C, TNFRSF10D, SFRP1, SFRP2, DKK3, PTGS2, CDKN1C/p57, RASSF1, and GPR62. For example, fully methylated and deaminated sequences for some of these genes are provided in SEQ ID NO: 31 or 32 [CSMD1], SEQ ID NO: 45 or 46 [TNFRSF10C], SEQ ID NO: 47 or 48 [TNFRSF10B] SEQ ID NO: 21 and 22 [GPR62]. Also for example, a target sequence can include fully or partially methylated and (subsequently) deaminated sequences based on the following genomic sequences SEQ ID NOs: 131 or 132 [GPX3], SEQ ID NOs: 125 or 126 [GPX7], SEQ ID NOs: 127 or 128 [GSTM4], SEQ ID NOs: 137 or 138 [SFRP2], SEQ ID NOs: 149 or 150 [CSMD1], SEQ ID NOs: 167 or 168 [TNFRSF10B], SEQ ID NOs: 169 or 170 [TNFRSF10C], and SEQ ID NOs: 187 or 188 [GPR62]. Such target sequences can be isolated or purified in accordance with methods known in the art.

Also provided are isolated or purified primers derived from and suitable for amplifying sequences internal to the above isolated or purified nucleic acid molecules. The isolated or purified primers can be DNA, RNA, PNA, and the like. It will be understood by one of ordinary skill in the art, however, that one type of nucleic acid can be preferred over another, depending on the particular biological sample, the methodology employed in assaying CpG islands for methylation, and the ability of the particular type of nucleic acid to detect methylation. One or more (e.g., two, three four, four, five, six, seven, eight, nine ten or more) isolated pairs of primers can be provided. Optionally, primers are provided as part of a kit useful in the methods disclosed herein. The pair of primers can consist essentially of SEQ ID NOs: 55 and 56, SEQ ID NOs: 57 and 58, SEQ ID NOs: 59 and 60, SEQ ID NOs: 61 AND 62, SEQ ID NOs: 63 and 64, SEQ ID NOs: 65 and 66, SEQ ID NOs: 67 and 68, SEQ ID NOs: 69 and 70, SEQ ID NOs: 71 and 72, SEQ ID NOs: 73 and 74, SEQ ID NOs: 75 and 76, SEQ ID NOs: 77 and 78, SEQ ID NOs: 79 and 80, SEQ ID NOs: 81 and 82, SEQ ID NOs: 83 and 84, SEQ ID NOs: 85 and 86, SEQ ID NOs: 87 and 88, SEQ ID NOs: 89 and 90, SEQ ID NOs: 91 and 92, SEQ ID NOs: 93 and 94, SEQ ID NOs: 95 and 96, SEQ ID NOs: 97 and 98, SEQ ID NOs: 99 and 100, SEQ ID NOs: 101 and 102, SEQ ID NOs: 103 and 104, SEQ ID NOs: 105 and 106, or SEQ ID NOs: 107 and 108. It is understood that these primer pairs are examples of suitable primers for use in the context of the invention. For example, each primer can be between 10 and 40 nucleotides and together the pair of primers can flank a region of at least 10, 20, 30, 40, 50, 60, 70, 80, 90, 100, 120, 130, 140, 150, 200, 250, 300 by in length that includes one or more CpG dinucloetides in a CpG island of interest. Primer pairs can be modified in various ways, such as by chemical modification of a base, and still be useful in the context of the invention. Other primers derived from the target sequences, namely SEQ ID NOs: 1-54 and 119-198, and variants thereof, also can be used in the context of the invention. The only requirement is that such primers function to assay for methylation of a given CpG island. Thus, for example, alternate primers can be selected or the provided primers can be modified or provided in degenerate form to account for target sequence polymorphisms within a given population, so long as the primers are still suitable for assaying modification of CpG islands associated with the genes disclosed herein.

Like the target sequences, the primer pairs can be isolated or purified in accordance with methods known in the art. Alternatively, they can be synthesized using routine methods.

The primers can be part of a kit. Preferably, the kit comprises at least three pairs of primers, wherein each primer pair is specific for a CpG island associated with a different gene. However, the kit can comprise additional primer pairs, such as primer pairs for other CpG islands associated with the same gene or primer pairs for amplifying CpG islands associated with four, five, six, seven, eight, nine, 10, 11, 12, 13, 14, 15, 16, 17, 18, 19, 20, 21, 22, 23, 24, 25, 26, 27 or even more genes. The kit can further comprise one or more reagents for assaying for methylation of CpG islands, instructions for use, and/or other components as are typically found in kits. For example, the kit can comprise a buffer suitable for (a) isolating genomic DNA comprising a target sequence from a biological sample, (b) amplifying a portion of the target sequence, and/or (c) deaminating a target sequence. In embodiments directed to the evaluation of prostate cancer, a kit can comprise one or more buffers suitable for preparing genomic DNA from serum and/or urine samples.

EXAMPLES

The following examples serve to illustrate the invention. The examples are not intended to limit the scope of the invention.

Example 1

This example demonstrates the determination of the methylation status of markers based on methylation-specific PCR amplification. Paraffin-embedded prostate tissues were obtained following radical prostatectomies. The tissue samples were sectioned into 23 10-micron sections and slide 1, 12, and 23 were stained using hematoxylin and eosin (H&E). Using the H&E slides as guide, the areas corresponding to the tumor tissues were microdissected from the unstained slides. The remaining tissues were recovered to use as a normal paired sample. Following deparaffinization using two xylene extractions and two ethanol washes, the DNA was isolated from the tumor tissue and surrounding normal tissues using standard proteinase K digest for 5 days at 50° C., extraction with phenol/chloroform and ethanol precipitation (*Current Protocols in Molecular Biology*, edited by Ausubel, et al., Wiley-Interscience (New York 1988, revised 1988-2006)). The DNA was resuspended in TE8 and the quality and quantity of the DNA was assessed by agarose gel electrophoresis using concentration and size standards as reference. Following denaturation in the presence of 0.3 M NaOH, the DNA was treated with 2.5 M sodium metabisulfite, pH 5.5, in the presence of 1 mM hydroquinone at a concentration of 1 µg of DNA/500 µl. The reaction was incubated in a thermocycler for a total of 8 cycles (95° C. for 5 minutes; 55° C. for 115 minutes).

Following bisulfite treatment, the DNA was purified using the QIAEX II purification kit (Qiagen, Valencia, Calif.) according to the manufacturer's recommendations and eluted in 50 µl of TE8. Sodium hydroxide (5.5 µl of 2 N) was added, and the DNA was incubated at RT for 15 min. The DNA was then precipitated with 3 volumes of ethanol and 0.3 volumes of 5 M NH$_4$OAC. The DNA was resuspended in 50 µl of TE8 and stored at −20° C.

In order to determine if a specific CpG position is methylated in genomic DNA isolated from tumor tissue, methylation-specific polymerase chain reaction (PCR) was performed, using primers designed to overlap the position of the CpG island of interest. All PCR reactions were performed in a MASTERCYCLER thermocycler (Eppendorf, Westbury, N.Y.) for 42 cycles of 95° C. for 15 seconds, 63° C. for 30 seconds, and 72° C. for 10 seconds. Each reaction was carried out in 30 µl of 1× PLATINUM Taq PCR buffer containing 1.5 mM magnesium chloride, 0.25 mM dNTPS, 12.5 pmoles of each primer, and 0.5 units of PLATINUM Taq enzyme (Invitrogen, Carlsbad Calif.). The primers used for each CpG island and the size of the product are shown in Table 1, wherein "F" indicates forward primer, "R" indicates reverse primer, "m" indicates methylated, and "u" indicates unmethylated.

TABLE 1

| Gene associated with CpG island | Primer sequences | Annealing temperature (° C.) | Product size (bp) |
| --- | --- | --- | --- |
| NRG1 | mF: GAGCGGGTAGCGAGAGTTTCGG [SEQ ID NO: 55]<br>mR: TAACGACGCGACTACCGAAAACC [SEQ ID NO: 56] | 63 | 119 |
| ADRB3 | mF: GATTAACGTGTTCGTGATTTCGTT [SEQ ID NO: 57]<br>mR: CAACGACCAATAACCAATCAACGCC [SEQ ID NO: 58] | 63 | 102 |
| GFRA2 | mF: ATACGTCGGTGAGTTCGGTTTATC [SEQ ID NO: 59]<br>mR: ACTCCCGACTCCCTAAACTCCGAA [SEQ ID NO: 60] | 63 | 101 |
| KIF13b | mF: TGAATCGGCGAGGTGAGAGTCG [SEQ ID NO: 61]<br>mR: ACCGAACGTCTCAACGCGAAAACG [SEQ ID NO: 62] | 65 | 179 |
| RET | mF: TATCGTTAGCGTCGTGGTGGAGTT [SEQ ID NO: 63]<br>mR: CTACACGAACACTAAACCGACCGA [SEQ ID NO: 64] | 63 | 120 |
| GPR147 | mF: TCGGTCGTTACGTTGATCGTTATTC [SEQ ID NO: 65]<br>mR: ACCCTACGCATACCCTTCTCGAAC [SEQ ID NO: 66] | 63 | 119 |
| NEUROG3 | mF: GTTTCGAGGAAGTTTCGGGTACGG [SEQ ID NO: 67] | 63 | 103 |

TABLE 1-continued

| Gene associated with CpG island | Primer sequences | Annealing temperature (° C.) | Product size (bp) |
|---|---|---|---|
| | mR: GATCGTTAACCTTCTTTCGCCGAC [SEQ ID NO: 68] | | |
| PALD | mF: CGAAGTTGGGAGGAGCGAGTT [SEQ ID NO: 69] <br> mR: AAACATCCGTACTCCTACGACCGA [SEQ ID NO: 70] | 63 | 115 |
| HEMK | [tiF: CGTATTAGTCGTATTCGCGAGCGT [SEQ ID NO: 71] <br> mR: CGAAACTACTCGACCCGACCC [SEQ ID NO: 72] | 63 | 99 |
| FGF4 | mF: TAACGGTACGTTGGAGGTCGAGTT [SEQ ID NO: 73] <br> mR: ACGACCGCCTCCTTAAACTACGCT [SEQ ID NO: 74] | 63 | 102 |
| GPR62 | mF: TATCGTGTATTCGTTGCGGTTAGG [SEQ ID NO: 75] <br> mR: AACGATACGAACGACGTACCGAA [SEQ ID NO: 76] | 63 | 120 |
| HTR1A | mF: TACGTGAATAAGAGGACGTTTCGG [SEQ ID NO: 77] <br> mR: AACGATCTTCCGAAATACGCCAA [SEQ ID NO: 78] | 63 | 115 |
| RNF180 | mF: TCGTCGAATCGGTATCGTCGTC [SEQ ID NO: 79] <br> mR: ACCTATATCCACGTCCCGAAACCT [SEQ ID NO: 80] | 63 | 118 |
| ECOP | mF: CGGTTGTAGTTTGTTCGTTCGTTTC [SEQ ID NO: 81] <br> mR: CTAACGCCTCATAACTCCTCGCGT [SEQ ID NO: 82] | 63 | 108 |
| ZNF596 | mF: GCGTCGATTCGGGAGTAGTATCGT [SEQ ID NO: 83] <br> mR: ATACCGTAAATCCGCGCTACTTCC [SEQ ID NO: 84] | 63 | 96 |
| CSMD1 | mF: CGTTGAGGTCGAATGAAGCGTAGT [SEQ ID NO: 85] <br> mR: AACCGAAACTAAACACGACGCAA [SEQ ID NO: 86] | 63 | 96 |
| LOC441320 | mF: AAGCGTATAGTTCGAGGATTGCGA [SEQ ID NO: 87] <br> mR: CCGCGTCACTTACTCCTCTACGA [SEQ ID NO: 88] | 63 | 107 |
| TDH | mF: CGTTGGGTGCGTAGGAAGGTTAGT [SEQ ID NO: 89] <br> mR: GACCGACCCTAAACAACCCGCT [SEQ ID NO: 90] | 63 | 120 |
| FLJ36980 | mF: GTTGCGGGATAGCGTTGTGATT [SEQ ID NO: 91] <br> mR: ACCATTATCAATACTCCGATCGCC [SEQ ID NO: 92] | 63 | 96 |
| FGF20 | mF: TTTGTTTGTTAAGGGCGTTATCGT [SEQ ID NO: 93] <br> mR: CCGCGACTACTCTAACCAACCC [SEQ ID NO: 94] | 63 | 105 |
| EFHA2 | mF: GGGCGTTGAGTTTAGTTCGGAGA [SEQ ID NO: 95] <br> mR: ACGAACACAACCGAATCAACGTAA [SEQ ID NO: 96] | 63 | 108 |

TABLE 1-continued

| Gene associated with CpG island | Primer sequences | Annealing temperature (° C.) | Product size (bp) |
|---|---|---|---|
| ASHA1 | mF: GGCGTTGGTTGTTAGAGCGATG [SEQ ID NO: 97]<br>mR: GACTCAAACTCACTCACCGACGAC [SEQ ID NO: 98] | 63 | 114 |
| TNFRSF10C | mF: GGTGCGATTTAGGATTTAGGACGG [SEQ ID NO: 99]<br>mR: GCGACCGAAACTCACTAACAACAA [SEQ ID NO: 100] | 63 | 115 |
| TNFRSF10B | mF: GCGATTTGGGTCGTTAGGGAATAG [SEQ ID NO: 101]<br>mR: ACCTCTCCGTAACTTCACGCAACTT [SEQ ID NO: 102] | 63 | 119 |
| NODAL | mF: GGTAGTCGCGGTCGTTTACGTT [SEQ ID NO: 103]<br>mR: ACGAACAAACGACAAATCGAATCA [SEQ ID NO: 104] | 63 | 111 |
| LOC399783 | mF: TACGTTGAGTTCGGTTTGGTTTGT [SEQ ID NO: 105]<br>mR: CGCGCCTCCGTAATCTAAACTAA [SEQ ID NO: 106] | 63 | 103 |
| ISL2 | mF: GTGCGTGTTGACGTTATGTTGCGT [SEQ ID NO: 107]<br>mR: CGCCCGACCTCGACTCTTTACT [SEQ ID NO: 108] | 63 | 99 |
| GSTP1 | mF: CGGCGATTTCGGGGATTTTAGGGC [SEQ ID NO: 109]<br>mR: GACCGCTCTTCTAAAAAATCCCGCG [SEQ ID NO: 110] | 63 | 109 |
| GSTP1 | mF: ACGTTCGGGGTGTAGCGGTCGTC [SEQ ID NO: 111]<br>mR: CCCCAATACTAAATCACGACGCCG [SEQ ID NO: 112] | 63 | 93 |
| GSTP1 | mF: GGTCGGCGTCGTGATTTAGTATTGG [SEQ ID NO: 113]<br>mR: ACTACGACGACGAAACTCCAACGA [SEQ ID NO: 114] | 63 | 99 |
| GSTP1 | uF: TGTGGTGATTTTGGGGATTTTAGGGT [SEQ ID NO: 115]<br>uR: CCAACCACTCTTCTAAAAAATCCCACA [SEQ ID NO: 116] | 63 | 113 |
| GSTP1 | uF: GATGTTTGGGGTGTAGTGGTTGTTG [SEQ ID NO: 117]<br>uR: CTCCACCCCAATACTAAATCACAACA [SEQ ID NO: 118] | 63 | 99 |
| KIFC2 | mF: TGATGGTCGTATTGCGGGTTTATC [SEQ ID NO: 199]<br>mR: ATACCTAAACCCAACGCCGACTAC [SEQ ID NO: 200] | 62 | 91 |
| C20orf23 | mF: CGCGATTTGAGTAGTTAGCGTCGT [SEQ ID NO: 201]<br>mR: AACCAACGCGACGACCTAACTAAC [SEQ ID NO: 202] | 62 | 90 |
| GFRA1 | mF: TAGATTTCGGTGTTTCGGGCGTT [SEQ ID NO: 203]<br>mR: CCGCTAATTCCCAATCGTACTACTCA [SEQ ID NO: 204] | 62 | 98 |
| GPX7 | mF: TTCGTTTCGTTCGGTCGTGATT [SEQ ID NO: 205]<br>mR: GACTACGAACGCTTCGAATTCCTC [SEQ ID NO: 206] | 62 | 116 |

TABLE 1-continued

| Gene associated with CpG island | Primer sequences | Annealing temperature (° C.) | Product size (bp) |
|---|---|---|---|
| DKK2 | mF: GTTGCGTTGGTAGCGATTCGTTGT [SEQ ID NO: 207]<br>mR: CCCGAACCGAATCCTCGAAATCT [SEQ ID NO: 208] | 62 | 117 |
| NTN1 | mF: GACGTAGTATGATGCGCGTAGTGTG [SEQ ID NO: 209]<br>mR: GCGAACATACTAAACCCGAACCC [SEQ ID NO: 210] | 62 | 103 |
| HTRA4 | mF: GGATTACGTCGGTGTTCGATTTGT [SEQ ID NO: 211]<br>mR: AACGCACGATTAACCCTACGCC [SEQ ID NO: 212] | 62 | 95 |
| MMP9 | mF: TCGGATTAAGGTAGGCGTGGTTTC [SEQ ID NO: 213]<br>mR: AACGTAAACGCCGAACCGAAC [SEQ ID NO: 214] | 62 | 102 |
| RHOD | mF: GGAAGACGTCGTTGTTGATGGTTT [SEQ ID NO: 215]<br>mR: ACCGCTCCGACACGAACCTATAC [SEQ ID NO: 216] | 62 | 120 |
| TNSF11 | mF: AGCGTTATGCGTCGCGTTAGTAG [SEQ ID NO: 217]<br>mR: GCAAACGACGACGAAACGTACA [SEQ ID NO: 218] | 62 | 116 |
| SFRP2 | mF: GAAGAGAGCGGGTTCGGGATAAG [SEQ ID NO: 219]<br>mR: CTACAACATCGTAAACGCGCGAC [SEQ ID NO: 220] | 62 | 101 |

The products of the PCR reactions were separated on 8% acrylamide gel. Only templates that exhibited methylation at all of the CpG islands that were present within the primers could serve as efficient templates for the amplification reactions. Control reactions were performed using fully methylated templates that were methylated in vitro using SS1 (CpG) methylase (NEB, Beverly, Mass.) according to the manufacturer's protocol. All primer pairs listed in Table 1 yielded a product of the correct size from fully methylated control template. Two negative controls (water and DNA isolated from white blood cells) were included for each target PCR amplification, which did not yield a PCR product. When a CpG island is methylated in a DNA sample, an amplification product of the expected size is obtained. This example demonstrates that the above primers can be used to assay for methylation of CpG islands in prostate cancer and that the CpG islands exhibit methylation in prostate cancer.

Example 2

This example demonstrates the determination of the methylation status of CpG islands at the ADRB3 locus by DNA sequencing. DNA is obtained from tumor samples and treated with sodium bisulfite as described in example 1. Two microliters of the bisulfite treated DNA are amplified with the following primers: ADRB3-F1: GAGAAGAGGAAGGTA-GAAGGAG [SEQ ID NO: 221] and ADRB3-R1: CTAC-CTAACTATAACCAACCC [SEQ ID NO: 222] for 40 cycles as described in example 1 except for the annealing temperature, which is lowered to 55° C. The amplified 250 bp product is purified using QIAquick PCR purification kit (Qiagen, Valencia Calif.) and recovered in TE8. Fifty nanograms of the ADRB3 amplified product is sequenced using 1.25 pmole of ADRB3-F2: ACGGAGGAGGATAGTAGTACG [SEQ ID NO: 223] using BigDye Terminator v3.1 cycle sequencing kit (Applied Biosystems) and the sequencing reaction is purified using Centri-Sep columns (Applied Biosystems) according to the manufacturer's protocols. The products of the sequencing reaction are analyzed using an ABI 3700 sequencer according to manufacturer's specification. The resulting DNA sequence shows one or more sequence peaks corresponding to cytosine base or a mixed cytosine/thymidine base at the cytosine residue position of CpG dinucleotides that are fully or partially methylated in the original tumor DNA.

Alternatively, a more detailed sequence analysis is obtained by cloning the product of the amplification reaction using a TOPO TA cloning kit (Invitrogen, Carlsbad Calif.) according to supplier's protocol. Approximately 20 colonies are chosen for further analysis. Each colony is grown in 3 ml of LB media for 16 hours. DNA is isolated from 1.5 ml aliquot using plasmid preparation kit from Qiagen. The plasmid DNA is quantitated using spectrophotometer and 1 microgram aliquot is sequenced as described above. The sequence of the 20 individual clones is compared to determine which cytosines are methylated and to provide an estimate of their rate of methylation in the tumor sample. This example shows that the methylation status of cytosines within CpG islands can be determined using a sequencing approach.

Example 3

This example demonstrates the determination of the methylation pattern of multiple CpG islands associated with KIFC2, GFRA1 and GPX7 using terminator-coupled linear amplification. From DNA from tumor samples prepared as described in example 1, fragments of the CpG islands associated with KIFC2, GFRA1, GPX7 are amplified individually using the mF1 and mR1 primers shown below for each CpG island. The amplification reactions are performed for 42 cycles as described in example 1 except for the annealing temperature, which was lowered to 58° C. An aliquot of the amplification reaction is separated on an 8% acrylamide gel to verify that fragments of the appropriate length are obtained (264 bp for KIFC2, 326 bp for GFRA1, 367 bp for GPX7). The product of the PCR reaction were purified using QIAQUICK PCR purification kit (Qiagen).

Each amplification product (25 nanograms) is subjected to linear terminator-coupled amplification using 1.5 pmoles of the fluorescently labeled F2 primer shown below for the corresponding amplicon. The amplification reaction includes 1× VentR (exo-) DNA polymerase (New England Biolabs, Beverly Mass.), 30 µM dATP, 37 µM dCTP, 100 µM dGTP, 100 µM dTTP, 480 µM ddCTP and 2 units of VentR (exo-) DNA polymerase. Reactions are performed in an MASTERCYCLER thermocycler (Eppendorf) for 30 cycles of 95° C. for 15 seconds, 58° C. for 30 seconds, and 72° C. for 30 seconds. Following amplification, the reaction products are pooled into a single tube and purified using Centri-Sep columns (Applied Biosystems) according to the manufacturer's protocols. One microliter of GENESCAN 500 LIZ standard (Applied Biosystems) is added to one tenth of the purified fragment and the DNA separated using the ABI Prism 3100 Genetic Analyzer (Applied Biosystems) according to manufacture's instructions. The data is analyzed using the GENESCAN and the GENEMAPPER software (Applied Biosystems).

The following primers are used for the amplifications:

```
KIFC2-F1:
AGGTA(C/T)GTTGTATTTGGTGGATTTGG      [SEQ ID NO: 224]

KIFC2-R1:
CCCACCTACAACAACAACACC               [SEQ ID NO: 225]

KIFC2-F2:
6FAM-GAACGCGTACGGAAGGTAGG           [SEQ ID NO: 226]

GFRA1-F1:
GTGATAGGTTTGTAGATTTGATAGTTG         [SEQ ID NO: 227]

GFRA1-R1:
AACTAACCTCCATTTTAACTATTTC           [SEQ ID NO: 228]

GFRA1-F2:
NED-GAGAGATGAATTTGGATATTAGT         [SEQ ID NO: 229]

GPX7-F1:
GGTAAATTGGTGT(C/T)GTTGGAGAAG        [SEQ ID NO: 230]

GPX7-R1:
ACTAAACAATAATACCC(A/G)ACCTC         [SEQ ID NO: 231]

GPX7-F2:
VIC-GTCGTTGGGTTCGGTTTCGTTTTG        [SEQ ID NO: 232]
```

The F1 and R1 primers are used for the amplification of a fragment of a CpG island from the tumor DNA. The F2 primers are used for termination-coupled linear amplification.

This example shows that termination-coupled linear amplification fragment lengths can be analyzed to (i) determine the presence and/or the positions of methylated cytosines in CpG islands in a sequence of interest as well as (ii) provide information about the efficiency of the deamination reaction, since incomplete deamination results in fragments with length that differ than what is expected from the positions of the CpG dinucleotides within the sequence.

Example 4

This example demonstrates the use of methylation-coupled whole genome amplification on DNA recovered from urine samples to increase the amount of DNA available for CpG island marker assays. Urine samples were obtained from 4 patients that were recently diagnosed with prostate cancer. 50 ml samples were spun down at 4000 rpm for 15 min, transferred to 1.5 ml tubes and washed twice with PBS. The DNA was extracted using proteinase K digest (100 µl of 25 mM Tris pH8.0, 100 mM NaCL, 1% SDS, 5 mM EDTA and 10 µg of Proteinase K followed by phenol/chloroform extraction and ethanol precipitation. The DNA was resuspended in 10 µl TE8 buffer (10 mM Tris, pH 8.0, 1 mM EDTA).

A partially random primer with the sequence $GGGN_6$ (50 ng) was added to 5 µl of DNA. 12 µl of a denaturing solution (50 mM KOH, 0.1 mM EDTA) was added to the DNA/random primer mix. After a five-minute incubation at room temperature, 12 µl of a neutralization solution (60 mM Tris (pH 7.5), 50 mM HCl) was added to neutralize the reaction. The DNA/primer mix was denatured at 94° C. for 5 minutes, incubated at room temperature for 10 minutes, and then placed on ice.

The amplification reaction was set up in a final volume of 30 µl. The following reagents were added to give the indicated final concentrations: (a) 1×NEB buffer 2 (1× NEB buffer 2: 50 mM NaCl, 10 mM Tris-HCl, pH 7.9, 10 mM $MgCl_2$, 1 mM dithiothreitol), 333 µM dATP, dCTP, dGTP, dTTP, 160 µM S-adenosylmethionine, and 10 ng/µl of bovine serum albumin (BSA) were combined and to which was added (b) DNA methyltransferase enzyme 1 (0.15 units/µl) (New England Biolabs) and incubated at 37° C. for 10 minutes, and followed by (c) adding Klenow polymerase to a final concentration of 0.167 units/µl, and Klenow exo- to a final concentration of 0.167 units/µl (New England Biolabs).

The reaction was incubated at 37° C. for 16 hours, and the reaction was stopped by the addition of EDTA to a final concentration of 5 mM, phenol/chloroform extracted, and ethanol precipitated. The DNA was resuspended in 40 µl of TE8 and 41 were separated on agarose gel to verify the presence of DNA.

The DNA was treated with sodium bisulfite and analyzed by methylation specific PCR as described in Example 1 using the GPR147 and RET assays. The presence of a band of the expected size for either marker indicated the methylation of the associated marker in the input DNA.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

The invention claimed is:

1. A method of determining the methylation status of one or more CpG islands indicative of prostate cancer in a human male undergoing prostate cancer evaluation, which method comprises:
   isolating or amplifying genomic DNA from a biological sample from a human male undergoing prostate cancer evaluation; and
   assaying the genomic DNA for methylation of one or more CpG islands including a CpG island in SEQ ID NO: 49 or SEQ ID NO: 50 associated with NODAL,
   wherein the presence of the methylation of the one or more CpG islands, including the CpG island associated with NODAL, is indicative of prostate cancer.

2. The method of claim 1, wherein the method further comprises assaying the isolated or amplified genomic DNA for methylation of one or more CpG islands associated with HEMK1, GPX7, PALD, or FGF20, and wherein the presence of the methylation of the one or more CpG islands associated with HEMK1, GPX7, PALD, or FGF20 is indicative of prostate cancer.

3. The method of claim 1, wherein the method further comprises assaying the isolated or amplified genomic DNA for methylation of CpG islands associated with HEMK1, GPX7, PALD, and FGF20, and wherein the presence of the methylation of the CpG islands is indicative of prostate cancer.

4. The method of claim 1, wherein the method further comprises assaying the isolated or amplified genomic DNA for methylation of a CpG island associated with at least one gene that is known to be methylated in prostate cancer and that is known not to be detectably methylated or methylated at a lower level in benign prostate hyperplasia (BPH), and wherein the presence or increased methylation of the assayed CpG islands is indicative of prostate cancer.

5. The method of claim 2, wherein the method further comprises assaying the isolated or amplified genomic DNA for methylation of a CpG island associated with at least one gene that is known to be methylated in prostate cancer and that is known not to be detectably methylated or methylated at a lower level in benign prostate hyperplasia (BPH), wherein the presence or increased methylation of the assayed CpG islands is indicative of prostate cancer.

6. The method of claim 4, wherein the CpG island associated with at least one gene that is known to be methylated in prostate cancer and that is known to be unmethylated or methylated at a lower level in BPH is or includes one or more CpG islands associated with glutathione S-transferase P1 (GSTP1), glutathione peroxidase 3 (GPX3), cyclin-dependent kinase inhibitor 1C (CDKN1C/p57), or G-protein coupled receptor 62 (GPR62).

7. The method of claim 4, wherein the CpG island associated with at least one gene that is known to be methylated in prostate cancer and that is known to be unmethylated or methylated at a lower level in BPH includes a CpG island associated with glutathione S-transferase P1 (GSTP1).

8. The method of claim 1, wherein the method further comprises assaying the isolated or amplified genomic DNA for methylation of at least one CpG island associated with a gene selected from the group consisting of kinesin family member 13B (KIF13B), neurogenin 3 transcription factor (NEUROG3), L-threonine dehydrogenase (TDH), N-acyl-sphingosine amidohydrolase (acid ceraminase) 1 (ASAH1), Kinesin family member C2 (KIFC2), GDNF family receptor alpha 1 (GFRA1), Dickkopf homolog 2 (DKK2), Ras association (Ra1GDS/AF-6) domain family 5 (RASSF5), tumor necrosis factor superfamily member 11 (TNFSF11), and leucine rich repeat containing 49 (LRRC49), and wherein the presence of the methylation of the CpG islands is indicative of prostate cancer.

9. The method of claim 4, wherein the method further comprises assaying the isolated or amplified genomic DNA for methylation of at least one CpG island associated with a gene selected from the group consisting of kinesin family member 13B (KIF13B), neurogenin 3 transcription factor (NEUROG3), L-threonine dehydrogenase (TDH), N-acyl-sphingosine amidohydrolase (acid ceraminase) 1 (ASAH1), Kinesin family member C2 (KIFC2), GDNF family receptor alpha 1 (GFRA1), Dickkopf homolog 2 (DKK2), Ras association (Ra1GDS/AF-6) domain family 5 (RASSF5), tumor necrosis factor superfamily member 11 (TNFSF11), and leucine rich repeat containing 49 (LRRC49), and wherein the presence of the methylation of the CpG islands is indicative of prostate cancer.

10. The method of claim 8, wherein the method comprises assaying for methylation of CpG islands associated with at least 7 genes.

11. The method of claim 8, wherein the method comprises assaying for methylation of CpG islands associated with at least 8 genes.

12. The method of claim 8, wherein the method comprises assaying for methylation of CpG islands associated with at least 9 genes.

13. The method of claim 1, wherein the assaying for methylation of a CpG island comprises amplifying a target sequence that includes a CpG island in SEQ ID NO: 49 or SEQ ID NO: 50.

14. The method of claim 8, wherein the assaying for methylation of the at least one CpG island associated with a gene comprises amplifying a target sequence that includes at least one CpG island in sequence selected from the group consisting of (a) SEQ ID NOs: 7 or 8 [KIF13B], SEQ ID NOs: 13 or 14 [NEUROG3], SEQ ID NOs: 35 or 36 [TDH], SEQ ID NOs: 43 or 44 [ASAH1], SEQ ID NOs: 119 or 220 [KIFC2], SEQ ID NOs: 123 or 124 [GFRA1], SEQ ID NOs: 129 or 130 [DKK2], SEQ ID NOs: 133 or 134 [RASSF5], SEQ ID NO: 196 [TNFSF11], and SEQ ID NO: 198 [LRRC49], and (b) fully or partially methylated sequences of (a).

15. The method of claim 1, wherein assaying the genomic DNA for methylation comprises terminator-coupled linear amplification.

16. The method of claim 1, wherein assaying the genomic DNA for methylation comprises using methylation-sensitive restriction endonuclease.

17. The method of claim 1, wherein assaying the genomic DNA for methylation comprises differential methylation hybridization.

18. The method of claim 1, wherein the amplification of genomic DNA comprises methylation coupled genomic amplification.

19. The method of claim 1, wherein assaying the genomic DNA for methylation comprises quantitative PCR.

20. The method of claim 1, wherein assaying the genomic DNA for methylation comprises sequencing.

21. The method of claim 1, wherein the biological sample is whole blood, blood plasma, or blood serum.

22. The method of claim 1, wherein the biological sample is urine.

23. The method of claim 1, wherein the biological sample is prostate tissue.

24. The method of claim 2, wherein the method comprises assaying the isolated or amplified genomic DNA for methylation of one or more CpG islands in SEQ ID NO: 17 or 18 [HEMK1], SEQ ID NOs: 125 or 126 [GPX7], SEQ ID NO: 15 or 16 [PALD], or SEQ ID NO: 39 or 40 [FGF20], and wherein the presence of the methylation of the one or more CpG islands associated with HEMK1, GPX7, PALD, or FGF20 is indicative of prostate cancer.

* * * * *

SEQUENCE LISTING

```
<160> NUMBER OF SEQ ID NOS: 232

<210> SEQ ID NO 1
<211> LENGTH: 1600
<212> TYPE: DNA
<213> ORGANISM: Homo sapiens

<400> SEQUENCE: 1
gagtttattt tcgtttgcgt gcgatagggt ttttgtattt aagtgagtta aggaatgaat      60
ttcgaatttt tttgggaaag ttattaacgt tttttcgta tttttttag ggtttttgat      120 tacggagatt ttgtttgggg tataggtgtg ggagtcgtaa attttttttt gcgtcgtttt      180
ttttcgcgtg gaatgggacg gagtagtttt tttaggcgtt gtttggttgc ggaggggagc      240
gggtagcgag agtttcgggt tttcgtttgg gttttcgggt tttcggggcg ttggtttcgg      300
ttttcgcgta gcgtttagcg attttttgtcg ggggttttcg gtagtcgcgt cgttatttt      360 cgttcggtta gcgcgggagg aaaaggggtt gcgttcggga gcgtcgagtt taggttttt      420 tcggtggcgt gttcgcgttt cggggtgggg gtgtggtggg gaagagggag ggggcgaggt      480
tagggagggg tgcgaaggag gcgtttgttt ttaatttgcg ggcgggaggt gggtggttgc      540
ggggtaattg aaaaagagtc ggcgaggagt ttttcgaaat ttgttggaat ttcgggttcg      600
cgcggaggtt aggagttgag cggcggcggt tgtcggacga tgggagcgtg agtaggacgg      660
tgataatttt ttttcgatcg ggttgcgagg gcgtcgggta gaggttagga cgcgagtcgt      720
tagcggtggg atttatcgac gattttttcgg ggcgatagga gtagtttcga gagttagggc      780
gagcgttcgt tttaggtggt cggatcgttc gtcgcgttcg cgtcgcgttt tttgtaggta      840
acgggagacg ttttcgcgta gcgcgagcgt tttagcgcgg tcgttcgttt ttttttcga      900 gggataaatt ttttttaaat tcgattcgag ttttttggatt aaattcgttt gcgtcgagag      960
tcgttcgcgt agagcgtttc gttttcggcg agatgttcga gcgtaaagaa ggtagaggta     1020
aagggaaggg taagaagaag gagcgaggtt tcggtaagaa gtcggagttc gcggcgggta     1080
gttagagttt aggtgggtgc gtagcgcggt tcgggtttta cgattttttt tttgtttttt     1140
ttattttttt tttttttcgg atgtcgtggt tttttttttt tttttttttt cgttcgtttt     1200
tttcgttttg cgttttgagc gttcgttgag tcgcgcggtg tttttttttt tgggggtcgt     1260
cgtttatttg ggcgtcgagt tttatcgggc gtttacgttt agagtttagg gtaagggata     1320
gtagtttcgg tcgtattttt ttagagtttc gggagcgttt cgttttttgg tacggttttt     1380
ttttagcgtt ttagcggttg agtttagttc gggagtggga tttgggttat aggagtcgag     1440
gttgcgtgcg cgcgtgtttc gcgttataag cgttttgtac gggggtcgtg tgttttttag     1500
cgggaaacgt tggaatgggt cgtttggagg gagagtcggt ttttcggtg tgtttggtag     1560 cgtagaagtg ggtggtcgag taagaggtcg cgtgggaagt                           1600

<210> SEQ ID NO 2
<211> LENGTH: 1600
<212> TYPE: DNA
<213> ORGANISM: Homo sapiens
```

-continued

<400> SEQUENCE: 2

```
attttttacg cggttttttg ttcgattatt tattttttgcg ttgttaggta tatcgagggg      60
atcggttttt tttttaggcg gtttatttta gcgttttttcg ttagagggta tacggttttc     120
gtgtaaagcg tttatggcgc ggggtacgcg cgtacgtagt ttcgattttt atagtttagg     180
ttttatttttc gggttgggtt tagtcgttaa ggcgttgggg aggggtcgtg ttagggagcg     240
aagcgttttc gggattttgg gagggtgcgg tcgggattgt tgtttttttgt tttgagtttt     300
gggcgtaggc gttcggtagg attcggcgtt taggtgagcg gcggtttttta ggaggggaag     360
tatcgcgcga tttaacgggc gtttagagcg tagggcgaag aggacgggcg agggagaggg     420
ggagggagag gttacggtat tcgaggagga ggaggagtag gaggagtagg aggaggatcg     480
tggggttcgg gtcgcgttgc gtatttattt gggttttggt tgttcgtcgc ggatttcggt     540
tttttgtcgg agtttcgttt tttttttttg ttttttttttt tgttttttgtt tttttttgcgt     600
tcggatattt cgtcggagac ggagcgtttt acgcggacgg ttttcggcgt aggcgagttt     660
ggtttaaggg ttcggatcgg gtttgggaaa agtttgtttt tcgagggggga gagcgagcgg     720
tcgcgttgag gcgttcgcgt tgcgcggggg cgttttttcgt tgtttgtagg gagcgcggcg     780
cggacgcggc gggcggttcg gttatttgga acggcgttc gttttggtttt tcggggttgt     840
ttttgtcgtt tcgggaagtc gtcgatgggt tttatcgttg gcggttcgcg ttttggttttt     900
tgttcggcgt tttcgtaatt cgatcgggga gaggttatta tcgttttgtt tacgttttta     960
tcgttcggta gtcgtcgtcg tttagttttt ggttttcgcg cgagttcgga gttttaataa    1020
gtttcgggga attttttcgtc ggttttttttt taattgtttc gtagttattt attttttcgtt    1080
cgtaggttgg aggtaggcgt tttttttcgta tttttttttg gtttcgtttt ttttttttttt    1140
tttattatat ttttatttcg aggcgcggat acgttatcgg gaggagtttg ggttcggcgt    1200
tttcgggcgt agtttttttt ttttttcgcgt tggtcgggcg ggggtggcg gcgcggttgt    1260
cgggaattttt cgatagggt cgttggacgt tgcgcggaga tcgaggttag cgtttcggag    1320
attcgggaat ttaggcggag attcgaggtt tcgttgttc gttttttttc gtagttaggt    1380
agcgtttggg aggggttgttt cgttttattt tacgcgaaaa aggacggcgt agagaaaagt    1440
ttgcgatttt tatatttgtg tttttaagtag agttttcgtg gttaggaatt ttgggagggg    1500
tgcgggggga acgttggtgg ttttttaga agagttcggg gtttattttt taatttattt    1560
aagtataaaa gttttgtcgt acgtaggcga aaataaattt                           1600
```

<210> SEQ ID NO 3
<211> LENGTH: 1350
<212> TYPE: DNA
<213> ORGANISM: Homo sapiens

<400> SEQUENCE: 3

```
attttggcgt ttaatatcgt taatattagt gggttgttag gggtttcgtg ggaggcggtt      60
ttagtcgggg ttttgttggc gttggcggtg ttggttatcg tgggaggtaa tttgttggtt     120
atcgtggtta tcgtttggat ttcgagattt tagattatga ttaacgtgtt cgtgatttcg     180
ttggtcgtag tcgatttggt gatgggattt ttggtggtgt cgtcggcggt tattttggcg     240
ttgattggtt attggtcgtt gggcgttatt ggttgcgagt tgtggatttc ggtggacgtg     300
ttgtgtgtga tcgttagtat cgaaattttg tgcgttttgg tcgtggatcg ttatttggtt     360
gtgattaatt cgttgcgtta cggcgtattg gttattaagc gttgcgttcg gatagttgtg     420
gttttggtgt gggtcgtgtc ggtcgcggtg tcgttttgcgt ttattatgag ttagtggtgg     480
```

-continued

| | |
|---|---|
| cgcgtagggg tcgacgtcga ggcgtagcgt tgttatttta attcgcgttg ttgtgttttc | 540 |
| gttttaata tgttttacgt gttgttgttt ttttcgttt ttttttatt ttttttttc | 600 |
| gtgatgtttt tcgtttacgc gcgggttttc gtggtggtta cgcgttagtt gcgtttgttg | 660 |
| cgcgggagt tgggtcgttt ttcgttcgag gagttttcgt cggcgtcgtc gcgttttttg | 720 |
| gtttcggttt cggtggggac gtgcgtttcg ttcgaagggg tgttcgtttg cggtcggcgg | 780 |
| ttcgcgcgtt ttttgttttt tcgggaatat cgggttttgt gtattttggg ttttattatg | 840 |
| ggtatttta ttttttgttg gttgttttt ttttggtta acgtgttgcg cgttttgggg | 900 |
| ggtttttttt tagtttcggg ttcggttttt tttgttttga attggttagg ttatgttaat | 960 |
| tttgttttta attcgtttat ttattgtcgt agttcggatt ttcgtagcgt ttttcgtcgt | 1020 |
| tttttgtgtc gttgcggtcg tcgtttgttt tcggagtttt gcgtcgtcgt tcgttcggtt | 1080 |
| tttttttttt cggcgttttt tgcggttcgg agtagtttag cgtagtttag gttttgttaa | 1140 |
| cggttcgacg ggtaggtaat cggggtagag ggatcggcgg tttagggtcg ggaagtatgc | 1200 |
| gatgtgttcg tgggttaatt ttttgagtgt ggagtttatt aagagaaggt gggatggttt | 1260 |
| tgtttggaga gaaaagggaa cgaggagtag cgaattaaaa tgggatttag ggttttttt | 1320 |
| ttttcggatt tagttattag ggtagaagta | 1350 |

<210> SEQ ID NO 4
<211> LENGTH: 1350
<212> TYPE: DNA
<213> ORGANISM: Homo sapiens

<400> SEQUENCE: 4

| | |
|---|---|
| tgtttttatt ttagtgattg gattcggaaa gaaaaggatt ttgggttttta ttttggttcg | 60 |
| ttattttcg tttttttttt ttttaagta aagttatttt atttttttt aataaatttt | 120 |
| atatttaaaa agttgattta cggatatatc gtatgttttt cgattttgag tcgtcggttt | 180 |
| ttttgtttcg gttatttatt cgtcgagtcg ttggtaaagt ttgggttgcg ttgggttgtt | 240 |
| tcgggtcgta ggaacgttcg aggggaagag ggtcgggcgg gcggcggcgt agggtttcgg | 300 |
| aggtaggcga cggtcgtagc ggtatagaag acggcggaag gcgttgcgaa agttcgggtt | 360 |
| gcggtagtag atgagcgggt tgaaggtaga attggtataa tttagttagt ttagggtaag | 420 |
| gaaagtcggg ttcgggatta gagaggggtt ttttagggcg cgtagtacgt tggttagaaa | 480 |
| gaagggtaat tagtagagag tgaaggtgtt tatgatgaga tttaaggtgt atagggttcg | 540 |
| gtgttttcgg agaggtagga ggcgcgcggg tcgtcggtcg taggcgggta ttttttcggg | 600 |
| cggagcgtac gttttttatcg gggtcggggt tagagagcgc gacggcgtcg gcggagattt | 660 |
| ttcgggcgga aagcggttta gttttttgcg tagtaagcgt agttggcgcg tagttattac | 720 |
| gaaaattcgc gcgtagacga agagtattac gagaagagga aggtagaagg agacggagga | 780 |
| ggatagtagt acgtagggta tgttggaggc gaaggtatag tagcgcgggt tggagtggta | 840 |
| gcgttgcgtt tcggcgtcgg ttttttacgcg ttattattgg tttatgatgg gcgtaaacga | 900 |
| tatcgcggtc gatacgattt atattaggat tatagttgtt cgggcgtagc gtttggtgat | 960 |
| tagtgcgtcg taacgtagcg ggttggttat agttaggtag cggtttacgg ttagggcgta | 1020 |
| tagggtttcg atgttggcgg ttatatatag tacgtttatc gaggtttata gttcgtagtt | 1080 |
| agtggcgttt aacggttagt ggttagttag cgttaaggtg gtcgtcggcg gtattattag | 1140 |
| gagtttatt attaggtcgg ttgcggttag cgaagttacg aatacgttgg ttatggttg | 1200 |
| gagtttcgga gtttaggcga tggttacgat gattagtagg ttgttttta cggtggttag | 1260 |

-continued

| | |
|---|---|
| tatcgttagc gttagtaggg tttcggttag ggtcgttttt tacggaattt ttggtagttt | 1320 |
| attggtgttg gcggtattgg gcgttagggt | 1350 |

<210> SEQ ID NO 5
<211> LENGTH: 1600
<212> TYPE: DNA
<213> ORGANISM: Homo sapiens

<400> SEQUENCE: 5

| | |
|---|---|
| cgaaaagttt ttgaggcgtt gcgtgtattt tattttagga tatcgtgtgt gcgcgtcgag | 60 |
| ttgagtgcga ggaacgtggc gcgagggtcg ggggatgtcg ggttgcgtgg gtgtgagttt | 120 |
| tcgcgcgatc gcgatttcgc gttttttttcg ttttcgtcgg aacgtgatcg tagtcgtatt | 180 |
| tttttttag ttttttttta gttagacgtt ttttttagg tttttttggg cgtttattgt | 240 |
| aaattttgcg attaaaatac gtcggtgagt tcggtttatc gatagatgga ttaatcgttt | 300 |
| tttttcggt taggggagga ggaattttt aatttcggag tttagggagt cgggagttgt | 360 |
| ttcgggacga gttttttcgga gtttagtcgg ttgcggagtt tcggttcggg tcggtttcgg | 420 |
| ggttttttttg tcggggtggg gtgcgagttt ttgttcgatt tttttgggc ggtttaggta | 480 |
| ggtttgtcgg ttttcgagga ggtggttagg gcgttttggt ttagtaggtt ttttttcgag | 540 |
| tcgggggag gggagatcgg ttggggaagg ggtatttcga aggggtggag gtcggggcgg | 600 |
| gcgggaggta agcgcgtcgc gggcgtgagg gtaaagtttt cgaggttcgc gcggagagta | 660 |
| tacgtgtatg tgcgcgcggg gttaggtcgg ggtcggtagg atgcgttggg ttcggggggcg | 720 |
| cgcggggtcg gcgtcgaagg ggataatttt ttttttggt attatcgggg agacgttttg | 780 |
| tcggtttcgg tttttgggcg tagggacgtt ttagttacg gagggtggag ttttttttag | 840 |
| attcgggtta tcggttgggg ttttttaac gttttgtttt tcgagttttc ggatggttcg | 900 |
| ggttttacgg atttcgcgtt tttagtttt agtttagttt tttaggtttt ttagatttag | 960 |
| cggcgtaggg ggcgggggta ggggtagtgg gggttggagg gcgtagtcgg tttttagggt | 1020 |
| gggagagtt gcgggggag gaggaggagg gtgtcgacgt ttgagtgggt tcgagttcga | 1080 |
| gtcgtagtcg ggggagttag ttagttttcg gttaaggtag taggttagtt ttaggaaggg | 1140 |
| cgggcgattg agtcgaggga gtcggcggtt gggtttttt ttcggttcgc gatttcggc | 1200 |
| gtcgtcgtcg tcgttatcgt tatcgttatc gttttcgttt tgtcgtcgtc gtcgttgtag | 1260 |
| agtatcgtag tttcgtcgcg tttttcgcgtt tcgcgtttcg cgtcgttagt cgtttgggag | 1320 |
| ttcgagcgtc gagttcgggg cggaggagag gggcgttggc gcgagagttc gggcgaggga | 1380 |
| gtcgcgaagg gagaaggggg cgggcggagg gaggagtagg gagagtggga gaaggggag | 1440 |
| ggagagagga gagcgaggga gagttggaga gagcgagagt aaagagcgag cgagggagag | 1500 |
| gagagagaga gagaggagag agaaagatat acgtacgtag agatatacgg ttattggaat | 1560 |
| tttattagaa aaagtgagt cgagtaaggg ttagcgggag | 1600 |

<210> SEQ ID NO 6
<211> LENGTH: 1545
<212> TYPE: DNA
<213> ORGANISM: Homo sapiens

<400> SEQUENCE: 6

| | |
|---|---|
| ttttcgttaa ttttttgttcg gtttattttt tttaatgga atttagtga tcgtgtgttt | 60 |
| ttgcgtgcgt gtgtttttt ttttttttt tttttttttt tttttttcg ttcgtttttt | 120 |
| gttttcgttt ttttagtttt ttttcgtttt ttttttttt gcggtttttt cgttcgggtt | 180 |

| | |
|---|---|
| ttcgcgttag cgttttttttt tttcgtttcg ggttcggcgt tcgggttttt aggcggttgg | 240 |
| cggcgcgggg cgcggggcgc gggagcgcgg cggagttacg atgttttgta gcggcggcgg | 300 |
| cgataaggcg aaggcggtgg cggtggcggt ggcggcggcg gcggcgtcgg ggatcgcggg | 360 |
| tcgagaggag agtttagtcg tcggtttttt cggtttaatc gttcgttttt tttgggattg | 420 |
| atttgttgtt ttggtcggaa attgattggt ttttcggtt acggtcggg ttcgaattta | 480 |
| tttaagcgtc ggtattttt tttttttttt ttcgtagttt tttttatttt ggggatcggt | 540 |
| tgcgtttttt aattttatt gtttttgttt tcgtttttg cgtcgttggg tttgggaagt | 600 |
| ttggggagtt gagttgaggt tggagggcgc ggagttcgtg gggttcgagt tattcggggg | 660 |
| ttcgggggt agggcgttag aaaaatttta gtcggtggtt cgggtttgag ggggttttta | 720 |
| tttttcgtgg gttaaggcgt ttttgcgttt aggagtcgag gtcgataaag cgttttttcg | 780 |
| atggtgttag ggaaaggaat tatttttttc ggcgtcggtt tcgcgcgttt tcgaattaa | 840 |
| cgtattttgt cggtttcggt ttagtttcgc gcgtatatat acgtgtgttt tcgcgcgga | 900 |
| tttcgggaat tttgttttta cgttcgcggc gcgtttgttt ttcgttcgtt tcggttttta | 960 |
| tttttcgag atgtttttt tttagtcggt tttttttttt ttcggttcgg gaagaagttt | 1020 |
| gttgggttag ggcgttttga ttattttttc ggaggtcggt aaatttgttt gaatcgtttt | 1080 |
| agaggaatcg ggtaggggtt cgtatttat ttcggtagga gggtttcgag atcgattcgg | 1140 |
| gtcggggttt cgtagtcggt tgggtttcga ggagttcgtt tcgaggtagt tttcggtttt | 1200 |
| ttaggtttcg gggttggggg gttttttttt ttttagtcgg gaaggggcg attgatttat | 1260 |
| ttgtcggtgg gtcgggttta tcggcgtgtt ttagtcgtag aatttataat aaacgtttag | 1320 |
| aaggatttaa aaggaagcgt ttggttggga aagggttgga ggagaggtgc ggttgcggtt | 1380 |
| acgtttcggc gagagcggga gaggcgcggg gtcgcgtcg cgcgagggtt tatatttacg | 1440 |
| tagttcggta ttttcggtt ttcgcgttac gttttcgta tttagttcgg cgcgtatata | 1500 |
| cggtgttttg gggtgggta tacgtagcgt tttagaaatt tttcg | 1545 |

<210> SEQ ID NO 7
<211> LENGTH: 1100
<212> TYPE: DNA
<213> ORGANISM: Homo sapiens

<400> SEQUENCE: 7

| | |
|---|---|
| gaggtattag tttttgaagg tttatttttt aatattggtt gcgagagtaa gaatggtgtg | 60 |
| taatttataa aagtcgttat tgttgtaggt aagttgtagt aaacgattcg cgttcgagta | 120 |
| ttttcgtttt cgttttcgtt gcggtttcgt ttacgacgat tttggggaat tataagtttc | 180 |
| gttatatagc ggggagcgtt cggagttcgc gtcggtttcg ttttagttc ggttttatt | 240 |
| ttcggtttcg ttttcggttt ttttcgtcg ggttaatttc gaagagtcgt cggtggtcgc | 300 |
| ggtagacgga agtcgaacga gttttcggc ggttgtagga tggggattt taaagtgaaa | 360 |
| gtggcggtgc ggatacgatt tatgaatcgg cgaggtgaga gtcgagtttt tttgggtcgt | 420 |
| cggggcggag gcgtaggtg tttggcgcgt ttttttttcg gtcgtcgtgg ggggttcggc | 480 |
| ggtttcgttt ttatagttag cggcggggcg cgaggagggg ttcgggggatt ttgaaattcg | 540 |
| ttttcgcgtt gagacgttcg gttttttttt tttttttttt tttttttttg gttagtttcg | 600 |
| ttttggcgt cgtcgggttt tcgtgtcgg tttcgttgtt tttcgtttt gcgttcgttt | 660 |
| cgttttgcg ttttttgtt tttcgttttt ttcggaggt tttcgagggc gttttcggtt | 720 |
| ttcgcgttta gtttcgtttt ggtttttag tttcgttttt tttcgttag ttgttatcgt | 780 |

| | |
|---|---:|
| cgttttcgcg cgcgggtcgt tagtttttgt agttcgtttc gggatcgttc gggatttttc | 840 |
| gggatttcgc gtttcgttcg ggtcgtttaa gtttgtatcg ttttggttcg cggcgggaag | 900 |
| aagggtaggg ggttaggcgg gtgtttcgcg gcgagttttt tttatttggg cgttttgaga | 960 |
| ttggggttag gtggaggaga tgttttttc gttgtttttg gatagttgag aaagttttgg | 1020 |
| ttttgtttga agttttattt attattttttt aataaatagt taaagtgtta agattttttgt | 1080 |
| ggaattgtat ttttttgata | 1100 |

<210> SEQ ID NO 8
<211> LENGTH: 1100
<212> TYPE: DNA
<213> ORGANISM: Homo sapiens

<400> SEQUENCE: 8

| | |
|---|---:|
| tgttagaaag atataatttt ataagaattt tggtatttta gttatttatt gagagatgat | 60 |
| gaatgagatt ttaggtaaaa ttaaaatttt tttaattgtt taaaaataac gaaaagggta | 120 |
| tttttttat ttgattttaa ttttaggacg tttaggtgga aggaattcgt cgcggggtat | 180 |
| tcgtttggtt ttttgttttt tttttcgtcg cgggttaagg cggtgtaggt ttgggcgatt | 240 |
| cgggcgagac gcgggttttc gggggtttc gggcggtttc gaggcgggtt gtaggggttg | 300 |
| gcgattcgcg cgcggggggcg acgatgatag ttggcgggga aggagcgagg ttgaggggtt | 360 |
| aggacgaggt tgggcgcgag ggtcgagggc gttttcggga atttcgggg gagacgagag | 420 |
| ggtaaaaggg cgtaggggcg gggcgggcgt aggcggaagg ggtagcgggg tcggtacgag | 480 |
| gggttcgacg gcgttaggga cggggttggt taggggggaa gggaggggag aagagggagt | 540 |
| cgggcgtttt agcgcgggag cgggttttag gttttcggg tttttttcg cgtttcgtcg | 600 |
| ttgattatag gggcggggtc gtcggatttt ttacggcggt cgaggaaagg gcgcgttagg | 660 |
| tatttgtcgt tttcgtttcg gcggtttagg agggttcggt ttttatttcg tcggtttatg | 720 |
| ggtcgtattc gtatcgttat ttttattttg gagtttttta ttttgtagtc gtcgaggaat | 780 |
| tcgttcggtt tcgttttgtc gcggttatcg gcgatttttc ggggttgatt cggcgggagg | 840 |
| gggtcggggg cggagtcggg ggtggggatc gggttggggg cggggtcggc gcgagtttcg | 900 |
| ggcgttttc gttgtatggc gggatttgta gtttttagg gtcgtcgtgg gcggggtcgt | 960 |
| agcgaaggcg ggggcgggaa tgttcgggcg cgagtcgttt gttataattt atttatagta | 1020 |
| atgacggttt ttgtaaatta tatattattt ttgttttcgt agttagtatt gagaagtaag | 1080 |
| tttttaagag ttgatattt | 1100 |

<210> SEQ ID NO 9
<211> LENGTH: 850
<212> TYPE: DNA
<213> ORGANISM: Homo sapiens

<400> SEQUENCE: 9

| | |
|---|---:|
| ttgtggagcg gaggagggga ggtttggggt cgcggcggtg tgcgtttcgt tttgatcgta | 60 |
| gagttttttt ttcgaggaaa gcggttggtt cggtttcggt tggtgattac gcggggtttt | 120 |
| tgtttgtttg gtgcgtaggt gagggtttgt ttttcgttg cgtttcggat agtttggagg | 180 |
| tgagtacgcg ttgggttttg gatcgcgagt agcgggagaa gtacgagttg gtggtcgtgt | 240 |
| gtatcgtgta cgtcggcgcg cgcgaggagg tggtgatggt gttttttttcg gtgatcgtgt | 300 |
| acgacgagga cgattcggcg tttatttttt tcgcgggcgt cgatatcgtt agcgtcgtgg | 360 |
| tggagtttaa gcggaaggag gtgtttgttc gcgcgtgttg tggtttattt agtgtttgtt | 420 |

-continued

| | |
|---|---|
| ttcggttata gttcgttttt cggtcggttt agtgttcgtg tagttattta atcgtgtggt | 480 |
| cgattattcg cgttttttatt tgttttttcgt tttcgtttgc gtcgtttgtt ttaggggggag | 540 |
| gggaaggggg agttttgtta gtatttagtt gggttttgtt tcggaggta aggattagga | 600 |
| cgaggttcga gggttcgcgt ttggggtata tttgtgtcgt tgtaggcggg cgcggcgcgt | 660 |
| tgttcgggcg gggagtattt gtcgggaggg tatttttttt tattagtagt tagtttttaa | 720 |
| cgggagggtt tttgagtgat tacgagtaga gtcgggggatt ggagaaggac gggaaggcgg | 780 |
| attattttcg gcgtcgttcg tttcgttttt tttcggttcg cgttggtgga gcgcgatcgt | 840 |
| tatttgttgg | 850 |

<210> SEQ ID NO 10
<211> LENGTH: 798
<212> TYPE: DNA
<213> ORGANISM: Homo sapiens

<400> SEQUENCE: 10

| | |
|---|---|
| ttagtaggtg gcggtcgcgt tttattagcg cgagtcggag aagggcgggg cgggcggcgt | 60 |
| cggaggtgat tcgttttttc gtttttttttt aatttcggt tttgttcgtg gttatttaag | 120 |
| ggttttttcg ttgggggtta attgttggtg ggagggagtg ttttttcggt agatgttttt | 180 |
| cgttcgggta gcgcgtcgcg ttcgtttgta gcggtataag tatgttttag acgcgagttt | 240 |
| tcgggtttcg ttttgttttt tttttagga tagacggcgt agacggaggc gaaggataaa | 300 |
| tgaaagcgcg aatggtcggt tatacggttg ggtggttata cggatattaa atcgatcgag | 360 |
| aaacgaattg tggtcggaga tagatattgg gtagattata gtacgcgcgg ataagtattt | 420 |
| tttttcgttt gaattttatt acggcgttgg cggtgtcgac gttcgcgggg aaggtgggcg | 480 |
| tcgagtcgtt ttcgtcgtat acggttatcg ggaagggtat tattattatt ttttcgcgcg | 540 |
| cgtcggcgtg tacggtgtat acggttatta gttcgtattt ttttcgttgt tcgcggttta | 600 |
| gggtttagcg cgtgtttatt tttaggttgt tcggggcgta gcggaagggt agattttttat | 660 |
| ttgcgtatta agtagatagg ggtttcgcgt gattattagt cgggatcggg ttagtcgttt | 720 |
| ttttcgggaa ggggttttttg cggttagagc ggggcgtata tcgtcgcggt tttaggtttt | 780 |
| ttttttttcg tttttatag | 798 |

<210> SEQ ID NO 11
<211> LENGTH: 850
<212> TYPE: DNA
<213> ORGANISM: Homo sapiens

<400> SEQUENCE: 11

| | |
|---|---|
| atcgtttttt cgtagggggtt ttaggattta tttagatttc gttgtttttt ttttttcgcgg | 60 |
| taggtttcgt tgtatcgtgt attttttttcg cgagaagttg attttgcgga aggcgttcgt | 120 |
| tattatcgtc gttatttggg ttttggcgtt gtttattatg tgttttttcgg tcgttacgtt | 180 |
| gatcgttatt cgtgaggagt attattttat ggtggacgtt cgtaatcgtt tttattcgtt | 240 |
| ttattttttgt tgggaggttt ggttcgagaa gggtatgcgt agggtttata ttattgtgtt | 300 |
| tttttcgtat atttatttgg cgtcgttggc gtttatcgtg gttatgtacg ttcgtatcgc | 360 |
| gcgtaagttt tgttaggttt cgggttcggt tttcggggggc gaggaggttg cggattcgcg | 420 |
| agtatcgcgg cgtagagcgc gcgtggtgta tatgttggtt atggtggcgt tgttttttac | 480 |
| gttgttttgg ttgtcgtttt gggcgttgtt ttgtttatc gattacgggt agtttagcgc | 540 |
| gtcgtagttg tatttggtta tcgtttacgt ttttttttttc gcgtattggt tggttttttt | 600 |

```
taatagtagc gttaatttta ttatttacgg ttattttaac gagaattttc gtcgcggttt    660
ttaggtcgtt tttcgcgttc gttttgttc gcgttcgtcg gggagttata aggaggttta    720
tttcgagcgg ttcggcgggt ttttgtatag gcgggttttc gtggtggtgc ggtttagcga    780
tttcgggttg ttttttgagt cgggttttag tagtggggtt tttaggttcg gtcgtttttc    840
gttgcggaat                                                         850

<210> SEQ ID NO 12
<211> LENGTH: 850
<212> TYPE: DNA
<213> ORGANISM: Homo sapiens

<400> SEQUENCE: 12
atttcgtagc gggaggcggt cgggtttggg ggttttattg ttaggttcg atttagaggg     60 tagttcggag tcgttgggtc gtattattac gaagattcgt ttgtgtagaa gttcgtcggg    120
tcgttcggag taggtttttt tgtggttttt cgacgggcgc gggtagaggc gggcgcggaa    180
ggcggtttgg aagtcgcggc ggaagttttc gttgaagtag tcgtagatga tggggttggc    240
gttgttgttg aagaaggtta gttagtgcgc gaagggaag gcgtagacgg tgattaggtg    300
tagttgcggc gcgttgagtt gttcgtagtc gatgagtagt agtagcgttt agagcggtag    360
ttaggatagc gtgaagaata gcgttattat gattagtatg tgtattacgc gcgttttgcg    420
tcgcgatgtt cgcgggttcg tagttttttc gttttcgggg gtcgggttcg gggtttggta    480
gagtttgcgc gcgatgcggg cgtatatgat tacgatgagc gttagcggcg ttaggtagat    540
gtgcgagaag agtatagtgg tgtagatttt gcgtatgttt ttttcgggtt aggttttta    600 gtaggagtag agcgggtagg agcggttgcg ggcgtttatt atgaagtggt gttttttacg    660
ggtgacggtt agcgtgacgg tcgagggata tatgatgagt agcgttaggg tttagatgac    720
ggcgatggtg acgagcgttt ttcgtagggt tagttttcg cggaaagggt gtacgatgta    780
gcggaatttg tcgcggggag agagataggc gggatttggg tgggttttag ggttttgcg    840 aggggacggt                                                         850

<210> SEQ ID NO 13
<211> LENGTH: 600
<212> TYPE: DNA
<213> ORGANISM: Homo sapiens

<400> SEQUENCE: 13
tttagtttcg gaatcgcgga ttgcgtttag tgacggattt aaatttattt tttttttga     60 tttcgtcgta ggatgacgtt ttaattttcg ggtgcgttta ttgtttaagt gattcgtgag    120
acggagcggt tttttttag agtttcggaa gacgaagtga tttgttttac gttcgtttcg    180
tttagtttta ttcgtatacg ggggaattgc gtagaggcgg aagagggagg ttgtcgaggg    240
gtttcgagga agtttcgggt acggcgcggg ggacgtagtc ggtttaagag cgagttggta    300
ttgagtaagt agcgacggag tcggcgaaag aaggttaacg atcgcgagcg taatcgaatg    360
tataatttta attcggtatt ggacgttttg cgcggtgttt tgtttatttt tttagacgac    420
gcgaagttta ttaagatcga gacgttgcgt ttcgtttata attatatttg ggcgttgatt    480
taaacgttgc gtatagcgga ttatagtttg tacgcgttgg agtcgtcggc gtcgtattgc    540
ggggagttgg gtagtttagg cggttttttc ggggattggg ggtttttta ttttttagtt    600

<210> SEQ ID NO 14
<211> LENGTH: 600
<212> TYPE: DNA
```

<213> ORGANISM: Homo sapiens

<400> SEQUENCE: 14

| | | | | | |
|---|---|---|---|---|---|
| gattggggag | tagagggatt | tttagttttc | ggggaatcg | tttgggttgt | ttagttttc | 60 |
| gtagtgcggc | gtcggcggtt | ttagcgcgta | taagttgtgg | ttcgttatgc | gtagcgtttg | 120 |
| agttagcgtt | tagatgtagt | tgtgggcgaa | gcgtagcgtt | tcgattttgg | tgagtttcgc | 180 |
| gtcgtttggg | aagtgggta | ggatatcgcg | tagggcgttt | agtgtcgagt | tgaggttgtg | 240 |
| tattcgattg | cgttcgcggt | cgttggtttt | ttttcgtcga | tttcgtcgtt | gtttgtttag | 300 |
| tgttaattcg | ttttaggtc | ggttgcgttt | ttcgcgtcgt | gttcggagtt | ttttcgggt | 360 |
| ttttcggtag | tttttttttt | tcgttttgc | gtagtttttt | cgtgtgcgag | tggggttggg | 420 |
| cggggcggac | gtggggtagg | ttatttcgtt | tttcgaggtt | ttggggaagg | atcgtttcgt | 480 |
| tttacgggtt | atttggatag | tgggcgtatt | cgagggttga | ggcgttattt | tacggcgggg | 540 |
| ttagagggaa | gggtaagttt | gagttcgtta | ttgggcgtag | ttcgcgattt | cgaggttagg | 600 |

<210> SEQ ID NO 15
<211> LENGTH: 850
<212> TYPE: DNA
<213> ORGANISM: Homo sapiens

<400> SEQUENCE: 15

| | | | | | |
|---|---|---|---|---|---|
| ttagtttcgg | tcgtattgta | tagcgaggtc | ggttcggagt | tcggatgttg | ggttcggttt | 60 |
| cgtcgaggtt | cggtttggtt | gtaaagtaga | gggggcgag | ggaagtcggg | ttagcgggtg | 120 |
| tcgcgggtag | tcgcgttcg | ggacggggtg | tggcgtttag | agcgttgttg | ttttcgtag | 180 |
| ttaggaggtt | ggatgtcggg | tttggtgtt | ttttagaagg | agtcgtatta | gcgacgaggg | 240 |
| aagaggaatt | ggtttttcgg | gtagtttttt | tcgttttaaa | ttttttttt | tcgcggaggg | 300 |
| tgggcgggcg | gagggaggaa | gcgtagtcgg | ggaacgtggc | gttcgcgttt | ttttcgttcg | 360 |
| ggggttgcgg | ttgggttgag | tgtgttttta | aatttgagtt | tttcgttttt | cgcggtgggg | 420 |
| tcgggattcg | cggttcgggc | ggggcgggc | gcggtgattg | gcggtcgggt | cgggttcgtt | 480 |
| tttcggcgtt | gggtagcggg | gcgttgggga | gtagcgcggc | gcgtacgggt | cggggcgcgt | 540 |
| aggtttcgtc | gtcggtgagt | acgggttttt | tttcgcgtgg | tttcgtcggg | ttcgtttggt | 600 |
| ttgtttattt | tcggagttat | ttttgttttc | gtatgggttg | gcgaagttgg | gaggagcgag | 660 |
| ttggagttag | agcgcgcgtc | gggcgcgttt | cgtcgttgtt | tgattcggcg | ttcgtagttc | 720 |
| gggcgtagta | cgtcggtcgt | aggagtacgg | atgttttcg | gagtcgcggg | ttggtaggta | 780 |
| tcgaagtgtt | ttgttttggg | gttggcgagg | ggagggtaaa | tttggaattt | tcgggtatt | 840 |
| ttttagttcg | | | | | | 850 |

<210> SEQ ID NO 16
<211> LENGTH: 850
<212> TYPE: DNA
<213> ORGANISM: Homo sapiens

<400> SEQUENCE: 16

| | | | | | |
|---|---|---|---|---|---|
| cgggttgggg | ggtgttcggg | ggattttaga | tttgtttttt | tttcgttagt | tttagggtag | 60 |
| gatatttcgg | tatttgttag | ttcgcggttt | cgggggtat | tcgtgttttt | gcggtcggcg | 120 |
| tgttgcgttc | gaattgcggg | cgtcgagtta | ggtagcgacg | gggcgcgttc | ggcgcgcgtt | 180 |
| ttggttttag | ttcgtttttt | ttaatttcgt | tagtttatgc | gggggtagag | gtggtttcgg | 240 |
| aggtgggtag | gttaggcgga | ttcggcgagg | ttacgcgaga | gggagttcgt | gtttatcggc | 300 |

```
gacgggattt gcgcgtttcg gttcgtgcgc gtcgcgttgt tttttagcgt ttcgttattt    360
aacgtcgagg ggcggattcg attcggtcgt taattatcgc gttcgttttc gttcggatcg    420
cgagtttcgg ttttatcgcg aggggcgggg ggtttagatt taaagatata tttagtttag    480
tcgtagtttt cgggcgggag gaacgcgggc gttacgtttt tcggttgcgt ttttttttttt   540
cgttcgttta ttttcgcga ggaggaaaag tttgggcgg gggagattgt tcgggaagtt     600
agttttttt ttttcgtcgt tagtgcggtt tttttggaa gatatttaaa ttcgatattt      660
agtttttgg ttgcgagagg tagtagcgtt tgggcgtta tatttcgttt cggacgtcgg     720
ttattcgcga tattcgttgg ttcggttttt tcgttttttt tttgttttat agttaggtcg    780
agtttcggcg ggatcgagtt tagtattcgg gtttcgggtc ggtttcgttg tgtagtgcgg    840
tcggagttgg                                                            850

<210> SEQ ID NO 17
<211> LENGTH: 600
<212> TYPE: DNA
<213> ORGANISM: Homo sapiens

<400> SEQUENCE: 17
ttttgtatag gagtagtgat tttagtattt atttaatttt ttttcggcgt cgagtttagt     60
tggagaggtt aggggtggta gtgattggta ggaggtcggg gcgggggggaa ttttttaagtt  120
cggcgtttgg ggttgcgggt tcgattcgag attcgttttt tttgtaagtt tcgagtcgtt   180
ggttaggttc gttattgcgt attagtcgta ttcgcgagcg ttggttttgt cggtttgagt    240
tagggtgggt aggtcggga tttacggcgg aggtggggtc gggtcgagta gtttcggggg    300
attttcgaag ttatagcgtt ttgttttttt gtacgtttcg cgttttcggt tttcgattgg    360
ttgtcgggtt tagagttcgt ttagaattgg atcgttcgtt tgtcgttcgg gtttggtttt   420
atttttagag ggagtttaga atttggtcgt agttttaga gattattttt atttcgtggt   480
ttgcgtcgaa gttgggcgga ggatagtggg tggttaggtt ttttcgggtt agaattcggg   540
atttttgtta gttattcgtg ttaggataga tttaagtttt taaaacgcgg atggatgtat   600

<210> SEQ ID NO 18
<211> LENGTH: 600
<212> TYPE: DNA
<213> ORGANISM: Homo sapiens

<400> SEQUENCE: 18
gtatatttat tcgcgttttg ggggtttgag tttgttttgg tacgggtagt tggtaggggt    60
ttcgagttttt ggttcggaag ggtttggtta tttattgttt ttcgtttaat ttcggcgtag   120
gttacggggt gagggtagtt tttaaaaatt gcgattaggt tttaggtttt ttttgggggt   180
ggagttagat tcgagcgata agcgaacggt ttaattttgg gcgggtttta ggttcgatag   240
ttaatcggag gtcgggggcg cggagcgtgt agggaggtaa ggcgttgtag tttcggggat    300
ttttcgaggt tgttcggttc ggttttatttt tcgtcgtggg tttcggtttt atttatttta   360
gtttaggtcg gtagagttag cgttcgcgga tgcggttggt gcgtagtagc gggtttggtt    420
agcggttcgg ggtttgtagg gagggcggat ttcgggtcgg attcgtagtt ttagacgtcg    480
ggtttgggggg tttttttcgt ttcggttttt tgttagttat tattatttttt agttttttta   540
attgagttcg gcgtcgggag aggattaagt aagtgttgag gttattgttt ttgtgtaaga   600

<210> SEQ ID NO 19
<211> LENGTH: 1548
<212> TYPE: DNA
```

<213> ORGANISM: Homo sapiens

<400> SEQUENCE: 19

```
aggtagggat aaagtgtaag aggtaaaatt ggttgaaaag tagaagtgta ggagtcgtta      60
aggggcggga cgataggtt cgtgggtcgg gcggagttaa gggtgggggt cggggttttt     120
ttaggtggta ttcgcggcgt tagttttta acgttatagc gtttcgggcg tttaggagaa     180
cgcgaacggt ttttcgcggg agcggcgag taggagggg cgtcgggtta tatatatagc     240
ggttcggttt cggcgggtt tggcgtttag ggaggcgcgt attgttttt agagttttag     300
ttttagtcgc gcgttttcg ttcggttcgt cgttttatgt agtcggggta gagttcggcg    360
ttcgggggtt tcgtcgtttg ttttcgtat tttttcggtt gcgtattttt gttcgaggtc    420
ggtcgtgcgt tttcgcggga cgttataggc gtagttttgt tttttagttt ttcgggcgta   480
ttgatcgttt gatcgacgta cggttttcgg gtcgggatgt cggggttcgg gacggtcgcg  540
gtagcgttgt tttcggcggt tttgttggtt ttgttggcgt tttgggcggg tcgaggggc    600
gtcgtcgtat ttattgtatt taacggtacg ttggaggtcg agttggagcg tcgttgggag   660
agttggtgg cgttttcgtt ggcgcgtttg tcggtggtag cgtagtttaa ggaggcggtc   720
gtttagagcg gcgtcggcga ttatttgttg ggtattaagc ggttgcggcg ttttattgt   780
aacgtgggta tcggttttta tttttaggcg ttttttcgacg tcgtatcgg cggcgcgtac  840
gcggatattc gcgatagtga gtggcgcggt taggcgcgaa ggggcggggg cgggggtaa   900
cggtcgtcgg gttaattcgt ttagttatat tttgagattt tcgcgggta tttgttcggg   960
ggtttcggga atcgggcgg attcgggttt cggttttttt tgacgcgggg ttggggacgt  1020
agatatttt ggtttcggta gtttagcgta attttgagg tcgggcgtcg ttttttcgttt  1080
ttagaaattc gggtttcgag cgtcgaattt tagcgttttc gttcgtgggt ataggcgcg   1140
cggtgtagtt ataggggtt cgagatacgc gtttcggttt ggtttaggtt ggggaatcgt  1200
tggggtcggg ttcgcgtttg aaggttcggg attgggtgcg gtcgtcgggg gttttttata   1260
taggtaagtt aatttgagtt agcgtaggtt tgggtttcgg aggttttaga gggtagtttg   1320
ggttttggag gtttttgggg gcggttgcgt cgggaattt ggttttttat ttttaatttt  1380
attttagaaa tagggtttc ggaggcgaat aagtcgaggg gcggagtggg ttagggatta   1440
tttgtttcgt aatgatttgc gtttcgtttt taggtttgtt ggagttttcg ttcgtggagc  1500
ggggcgtggt gagtattttc ggcgtggtta gtcggttttt cgtggtta              1548
```

<210> SEQ ID NO 20
<211> LENGTH: 1600
<212> TYPE: DNA
<213> ORGANISM: Homo sapiens

<400> SEQUENCE: 20

```
tggttacgaa gaatcggttg gttacgtcga agatgtttat tacgtttcgt tttacgggcg      60
agagttttag taggtttggg ggcggggcgt aggttattgc ggggtaggtg attttttggtt    120
tatttcgttt ttcggtttgt tcgttttcgg ggatttatt tttggggtgg ggttgggat      180
aaagggttag ggttttcggc gtagtcgttt ttaagggttt ttagagttta agttgttttt    240
tagggttttc ggagtttaag tttgcgttag tttagattag tttgtttgtg taggggattt    300
tcggcggtcg tatttagttt cggatttta gacgcgagtt cgattttagc ggtttttag    360
tttgggttag gtcggggcgc gtgtttcggg ttttttgtgg ttgtatcgcg cgttttgtgt   420
ttacgggcga aggcgttgga attcggcgtt cggagttcga gttttgaag gcgggaggcg   480
```

```
gcgttcgatt ttaggggttg cgttgggttg tcggagttaa gagtgtttgc gttttagtt        540
tcgcgttaga agggatcgga gttcgagttc gtttcggttt tcggggtttt cgagtaggtg       600
ttcgtcgagg gttttagagt gtgattgagc gggttggttc ggcggtcgtt gtttttcgtt       660
ttcgtttttt cgcgtttggt tcgcgttattt attgtcgcgg gtgttcgcgt gcgcgtcgtc      720
gatgcggtcg tcggggagcg tttggaggtg gaagtcgatg tttacgttgt agtagagtcg       780
tcgtagtcgt ttgatgttta gtaggtagtc gtcggcgtcg ttttggacgg tcgttttttt       840
gggttgcgtt gttatcggta ggcgcgttaa cgagagcgtt attaggtttt tttagcggcg       900
ttttagttcg gttttagcg tgtcgttggg tgtagtgggt gcggcggcgt tttttcggtt        960
cgtttagggc gttagtaagg ttagtaggat cgtcgggagt agcgttatcg cggtcgtttc      1020
gggtttcgat atttcggttc gagggtcgtg cgtcggttag gcggttagtg cgttcgggaa      1080
gttgggggt agagttgcgt ttgtggcgtt tcgcgggagc gtacggtcga tttcgggtag       1140
gagtgcgtaa tcgaggaggt gcggaggta agcgacgggg ttttcgggcg tcgggttttta      1200
tttcggttgt atggagcggc gagtcgggcg gaaagcgcgc ggttggagtt gggattttga      1260
ggagtagtgc gcgttttttt gagcgttagg ttcgttcgag gtcgagtcgt tatatatata      1320
gttcggcgtt ttttttatt cgttcgtttt cgcgggggt cgttcgcgtt tttttgggcg       1380
ttcggggcgt tgtggcgttc gcggttggtc gtaggtcgtt tgttaattag gtcgggga       1440
agggaggagg ttggggatta gcgtcgcgag tgttatttgg agggatttcg gttttatt        1500
ttggtttcgt tcggtttacg gatttgttcg tttcgttttt tggcggtttt tatattttg       1560
tttttagtt agttttgttt tttgtatttt gttttttgttt                             1600

<210> SEQ ID NO 21
<211> LENGTH: 1100
<212> TYPE: DNA
<213> ORGANISM: Homo sapiens

<400> SEQUENCE: 21
agggtgaagt ttgagagttt aaatggttaa ttttataggg ttgaacgttt tagaagtcgt        60
aggttcgttg gggttgattt tggtagttgt cgtggaggtg ggggtattgt tgggtaacgg       120
cgcgttgttg gtcgtggtgt tgcgtacgtc gggattgcgc gacgcgtttt atttggcgta      180
tttgtgcgtc gtggatttgt tggcggtcgt ttttattatg tcgttgggtt tgttggtcgt      240
atcgtcgttc gggttgggtc gcgtgcgttt gggtttcgcg ttatgtcgcg tcgttcgttt      300
tttttcgtc gttttgttgt cggtttgtac gttcggggtg tcgtatttg gtttggtacg         360
ttatcgtttt atcgtgtatt cgttgcggtt aggttcgcgg tcgtcgtttg tgttcgtgtt      420
tatcgtcgtg tgggtcgcgg cgggattgtt gggcgcgttt ttttgttcg gtacgtcgtt       480
cgtatcgttt tttgtttttg ttcgttgttc ggttttggtt ggggttttcg ggttttttcg      540
gtcgttttgg gttttgttgg tttcgcgtt gttcgttttt tgttgttcg gcgtttacgg        600
cggtatttc gtggtggcgc gtcgcgttgt tttgaggttt ttacggtcgg cgcgcgggtt      660
tcgattttat tcggattttt tggatagtcg ttttttttatt ttgtcgtcgt ttcggtttcg      720
tttgttcggg ggtaaggcgg ttttggtttt agcgttggtc gtgggttaat ttgtagtttg      780
ttggttgttt tatggttgcg cgtgtttggc gttcgtagcg cgggtcgcgg aagtcgaagc      840
ggttgttatt tgggtcgttt attcggtttt cgcggtttat ttttttttgt acgggttgtt      900
gtagcgtttc gtgcgtttgg tattgggtcg tttttttcgt cgtgtattgt ttggatttgt      960
gcgggtttgt atttcgtaag tttggtattc gcgggtattt ttgtaatgtt tttagagatt     1020
```

```
tttagagggt tttgtcgtag gttttttttga ggttttagaa tagattttcg agttggtagg    1080
agggcggagt tcgtatatt                                                 1100

<210> SEQ ID NO 22
<211> LENGTH: 1100
<212> TYPE: DNA
<213> ORGANISM: Homo sapiens

<400> SEQUENCE: 22
ggtatgcggg gtttcgtttt tttgttaatt cgggggtttg ttttggagtt ttagaagggt      60
ttacggtagg gttttttggg ggttttttgga ggtattgtaa gagtgttcgc gggtgttagg    120
tttgcggagt gtaggttcgt ataggtttag gtagtgtacg gcgagagagg cggtttagtg    180
ttaagcgtac ggggcgttgt agtagttcgt ataggaaggg gtgagtcgcg aaggtcgagt    240
aggcgattta ggtgatagtc gtttcggttt tcgcggttcg cgttgcgggc gttaggtacg    300
cgtagttata aggtagttag taggttgtaa attggtttac ggttagcgtt ggggttaggg    360
tcgttttgtt ttcgggtagg cgaggtcgga gcggcggtaa gatggaaagg cggttatttta    420 gagagttcga gtgagtcgg gattcgcgcg tcggtcgtgg gggttttagg gtagcgcgac     480
gcgttattac gaaagatgtcg tcgtaggcgt cgagtagtag gagggcgggt agcgcgaagg    540
ttagtagggt ttagagcggt cggaagggtt cgaggttttt agttaggatc gagtagcgag    600
taggagtagg gggcggtgcg ggcggcgtgt cgagtaggga gagcgcgttt agtagtttcg    660
tcgcggttta tacggcggtg agtacgagta taggcggcgg tcgcgagttt ggtcgtagcg    720
ggtgtacgat gaggcggtag cgtgttaggt taagtgcggt tatttcgagc gtgtaggtcg    780
gtagtagagc ggcggagagg aagcgagcgg cgcggtatgg cgcggggttt aggcgtacgc    840
ggtttagttc gggcggcggt gcggttagta ggttagcgg tatgatggag gcggtcgtta    900
gtaggtttac gacgtatagg tgcgttaggt agagcgcgtc gcgtagtttc ggcgtgcgta    960
gtattacgat tagtagcgcg tcgttgttta gtagtgtttt tattttttacg atagttgtta   1020 ggattaattt taacgagttt gcgatttttg aggcgtttag ttttgtggag ttggttattt   1080 gggttttttag gtttttatttt                                              1100

<210> SEQ ID NO 23
<211> LENGTH: 600
<212> TYPE: DNA
<213> ORGANISM: Homo sapiens

<400> SEQUENCE: 23
ggtgtcggtg ttggtgttgt ttatggtcgc gttgtattag gtgtttaata agtggatatt      60
gggttaggta atttgcgatt tgtttatcgt tttcgacgtg ttgtgttgta ttttatttat    120
tttgtatttg tgcgttatcg cgttggatag gtattgggtt attacggatt ttatcgatta    180
cgtgaataag aggacgtttc ggcgcgtcgt tgcgtttatt tcgtttattt ggtttattgg    240 ttttttttatt tttatttcgt ttatgttggg ttggcgtatt tcggaagatc gttcggattt    300
cgacgtatgt attattagta aggattatgg ttatattatt tatttatttt ttggagtttt    360
ttatatttcg ttgttgttta tgttggtttt ttatgggcgt atatttcgag ttgcgcgttt    420
tcgtattcgt aagacggtta aaaaggtgga gaagatcgga gcggatattc gttatggagt    480
atttttcgtt tcgtagttta agaagagtgt gaatggagag tcggggagta ggaattggag    540
gttgggcgtg gagagtaagg ttgggggtgt tttgtgcgtt aatggcgcgg tgaggtaagg    600

<210> SEQ ID NO 24
```

```
<211> LENGTH: 600
<212> TYPE: DNA
<213> ORGANISM: Homo sapiens

<400> SEQUENCE: 24
ttttgtttta tcgcgttatt ggcgtataga gtatttttag ttttgttttt tacgtttagt      60
ttttagtttt tgtttttcga tttttttattt atatttttt tgggttgcgg ggcgggagat     120
gttttatggc gggtgttcgt ttcggttttt tttattttt tgatcgtttt gcggatgcgg     180
aagcgcgtag ttcggaatat gcgtttatag agaattagta tgagtagtag cgggatgtag     240
aaagttttaa aggtggaata gatagtgtag ttatgatttt tgttaatggt gtatgcgtcg     300
gggttcgagc ggttttttcgg ggtgcgttag tttagtatgg gcgggataga gatgaggaag     360
ttaataagtt aagtgagcga gatgagcgta gcggcgcgtc ggggcgtttt tttgtttacg     420
tagtcgatgg ggttcgtgat ggtttagtat ttgtttagcg cgatggcgta taggtgtaag     480
atggatgagg tgtagtatag tacgtcgagg gcgatgaata ggtcgtaggt tatttggttt     540
agtgtttatt tgttgagtat ttgatatagc gcggttatgg gtagtattaa tatcgatatt     600

<210> SEQ ID NO 25
<211> LENGTH: 850
<212> TYPE: DNA
<213> ORGANISM: Homo sapiens

<400> SEQUENCE: 25
gggatgataa gggagaaaaa ttttttttacg gtttcgtttg gttcgcggcg tttgtttgtt      60
tgcgcggggt taaagttcgg cgtcgtttac gcgcggttcg ggtgggaatt cgtagacgtg     120
gggcgagtag ggtcgttggt tgtggcgggc gagcgtcggg gcgttacgtt cgaggtcgcg     180
gggtcggggt tgtaggtata gttcgagcgt ttttcgcggg gtttggtttt tgtcgttttt     240
cgtttcgtcg aatcggtatc gtcgtcgtcg gagtcgtagc gagttttag agtttggttg     300 ttggcggtcg ggagcgtcgg gacggggcgc gaagtcggag gtttcgggac gtggatatag     360
gtaaaggtcg gcgggtcgga gtcgggcggg gcgcggcggc ggcgtttttc ggagggattt     420
ggtttcggtc gggttttatt tagtcgcggt ggttcgggtt tttacgttgg tttaggcggg     480
gacgtgttaa ggggttgggt tagggttgtc gttggtttgg tcgttttttcg ttcggcgggt     540 tttaggtgac gcggtcgcgg tttaatttc gtatttgagg ttttcggagc ggtttcgggg     600
cgcgtttatt tggaggttgg aattatatag ggtcgaaaaa gttgagtttt ggaggcgagg     660
cgttgtaggt gtggcggagg aggtcgggga aggtggggtg ggtgttaggg gtttagtatt     720 gaatttttt taggtttgag gtggggaatt gcgttttgtt taatttcgga gtttgtgggg     780
attatatagt tttttttacg gtcgattttt tttgtacggt tttatttttt tttgtttagt     840 ttatttttagt                                                           850

<210> SEQ ID NO 26
<211> LENGTH: 850
<212> TYPE: DNA
<213> ORGANISM: Homo sapiens

<400> SEQUENCE: 26
attgaaatgg gttagataaa ggaaagtgga atcgtgtaga gggaatcggt cgtggaaggg      60
gttgtgtggt ttttataagt ttcgaaatta aataagacgt agtttttttat tttagatttg     120 gagagggttt agtattggat ttttggtatt tattttattt ttttcggttt ttttcgttat     180
atttatagcg tttcgttttt aggatttagt tttttcgatt ttgtgtaatt ttaattttta     240
```

-continued

```
ggtgggcgcg tttcgaggtc gtttcgagag ttttaggtgc gaaagttaag tcgcggtcgc    300
gttatttgag gttcgtcggg cgagaggcgg ttaggttagc ggtaattttta gtttagtttt    360 ttggtacgtt ttcgtttggg ttaacgtggg ggttcgggtt atcgcggttg ggtagggttc    420
ggtcgaggtt aggttttttc gagaggcgtc gtcgtcgcgt ttcgttcgat ttcgattcgt    480
cggtttttat ttgtatttac gtttcggagt tttcggtttc gcgtttcgtt tcggcgtttt    540
cggtcgttag tagttaggtt ttgaggattc gttgcggttt cggcggcggc gatgtcggtt    600
cggcgagacg ggaagcgata ggagttaaat ttcgcggaaa gcgttcgagt tgtgtttgta    660
gtttcgattt cgcggtttcg gacgtggcgt ttcggcgttc gttcgttata gttagcggtt    720
ttgttcgttt tacgtttgcg ggttttttatt cgagtcgcgc gtgggcggcg tcgggttttg    780
atttcgcgta ggtagataag cgtcgcgggt tagacggaat cgtgggaaag tttttttttt    840
ttgttatttt                                                            850
```

<210> SEQ ID NO 27
<211> LENGTH: 1350
<212> TYPE: DNA
<213> ORGANISM: Homo sapiens

<400> SEQUENCE: 27

```
tgaggtgtgg ggattattta tttcggtggg ttttttttatt tttaggtcgg tttttttatt      60
acgcgtgggt gtgggggtat tgttttcgtt gcgcgtagga atagcgggga gagttaggag    120
cggagcggtt tcgggatgtt agattgagta gtgggttcgt ttgcggttat ttttttaggga    180 ataagttttt tttcgcggag attttgtttt ttttaaaagt ttttttgggt ttagtttagg    240
gcgataggac gatttttttt gggaagggag agtttgttag ttttttttttt attcgttagg    300 cggtgtagtt ttttttttcg ttcggggcgc gcgtatttta gcgtcgcggg tttagcgttt    360
agtagtcgcg ttttaggtcg ggtttcgggt ttcgggagtt cgtaggcgcg cgttcggtcg    420
ggcgtgtcgg gagcgcgcgg cggtcggggg cggagcgtag ttagggttgc gcggcgcgtt    480
tcggttttcg ttcgtttttta gtcgggtttt ttagcggtcg gcgggacggt ttcggttgt    540 agtttgttcg ttcgtttcgc gcggggggtcg agtcgcgaag cgcgttttgcg attcggcgtt    600 cgggcgcgtt ggagaggacg cgaggagtta tgaggcgtta gtttgcgaag gtggcggcgt    660
tgttgttcgg gttgttttg gaggtagggg tcggggatcg ggtgttgtcg gaggcgcggc    720
gtttattatg ttggcggttg ggggcgcgta gtttcgaggc gttttagagg attttgtttg    780
ggagcgtaga cggtggagcg acgggagtt atagttttgc gcgttttttcg gagttgggag    840 gtgcgggatt ttggtgacgg ggaggttttc gtttcggttc gcgttttttcg tcgttttttc    900 ggttttcgta tttcgttttt attttgcggg tgagcgcgtt tttcgcgtcg atcgttttcg    960
ttagttcggg gtgattttttg tgtatcgttc gtttttttttt ttcgtcgtag agggtcgagg   1020
atcggatgga ttcggggttg ggcgggggtg gttttcgggc gcggcgtagg cgcggagagt   1080
tcggggcgtc gggtagtttg gggttaggaa aggatgggtg tcgagtcggg gtgaggggag   1140
cgggcggagg ggattgtggg gaagtgtcgc gggagtgtcg ggagtgtgg aggtgagtag   1200 cgggaggagg cgttttcgcg tgtgaaaatg aagtgtagtt tttaggtgcg gggaggaaat   1260
tttgcggaga gtttggttgg gtgggggtgc ggagtcgaag tcggcgggga atttgttgag   1320
cggttttcgg gtgcgagcgt tcgtgatcgt                                     1350
```

<210> SEQ ID NO 28
<211> LENGTH: 1350
<212> TYPE: DNA

<213> ORGANISM: Homo sapiens

<400> SEQUENCE: 28

```
gcggttacgg gcgttcgtat tcggaagtcg tttaataagt ttttcgtcgg tttcggtttc      60
gtattttat  ttagttaggt ttttcgtaga attttttttt cgtatttaaa ggttgtattt     120
tatttttata cgcgggaacg ttttttttcg ttgtttattt ttataatttt cggtattttc     180
gcgatatttt tttatagttt ttttcgttcg ttttttttat ttcggttcgg tatttatttt     240
tttttaattt taaattgttc ggcgtttcgg ttttttcgcg tttgcgtcgc gttcgaggat     300
tattttcgtt taatttcggg tttattcgat tttcggtttt ttgcggcggg gagagggggc     360
ggacggtgta taaaggttat ttcgagttaa cggaggcggt cggcgcggga aacgcgttta     420
ttcgtagggt gggggcgggg tgcgaaaatc gaaggaacga cggaaggcgc ggatcggggc     480
gggagttttt tcgttattag ggtttcgtat tttttagttt cgggaggcgc gtagggttgt     540
ggttttcgt cgttttatcg tttgcgtttt taggtaaggt tttttggggc gtttcggaat      600
tgcgcgtttt tagtcgttag tatggtgggc gtcgcgtttt cggtagtatt cggttttcgg     660
ttttatttt taagagtagt tcgagtagta gcgtcgttat tttcgtaggt tggcgtttta     720
tggttttcg cgtttttttt agcgcgttcg gacgtcgggt cgtaggcgcg tttcgcgatt      780
cggttttcgc gcggggcggg cgggtagatt gtagtcggga gtcgtttcgt cgatcgttgg     840
ggggttcggt tgggagcggg cgggagtcgg ggcgcgtcgc gtagttttgg ttgcgtttcg     900
ttttcggtcg tcgcgcgttt tcgatacgtt cggtcgggcg cgcgtttgcg ggttttcgga     960
attcgaggtt cggtttgggg cgcggttgtt gggcgttagg ttcgcgacgt tgaggtgcgc    1020
gcgtttcggg cgggaggagg ggttgtatcg tttggcgaat gggagggga ttggtaggtt    1080
ttttttttt aagggaggtc gttttgtcgt tttagattaa atttaggaag gttttttaaaa    1140
gaagtagagt tttcgcgggg ggaagttttgt ttttgagag gtggtcgtag acgaatttat    1200
tgtttagttt ggtatttcga agtcgtttcg ttttgggttt ttttcgttgt tttgcgcgt    1260
agcggggta gtgttttat  atttacgcgt gatgggaagg tcggtttggg ggtgggaagg    1320
tttatcgaaa tagatggttt ttatattta                                      1350
```

<210> SEQ ID NO 29
<211> LENGTH: 1100
<212> TYPE: DNA
<213> ORGANISM: Homo sapiens

<400> SEQUENCE: 29

```
aatttagaaa taaataaata tatatgtata cgtatataaa tatattttaa attaaaaaat      60
atttttagat agtggtatgt attatattta gaaattaata acgaagtaaa ttatgggatg     120
ttatttacgt ttgttttaaa ggtatcgaat ttataaatta ttttaggtgc ggagtaggat     180
aggttgaaaa taggaatgat atgaattcgc gcggaatagt tgtcggcgcg gtgtttaggg     240
cggtatttcg ttcggtttcg gttttttag ttttgggttc gattttttatt acgttttttgt    300
ttcgacgcga acgcggagtt cgagcgcgcg ttacgtcgtg tgggtcgaa gaggttgtta     360
tttagaggcg gagtgcgggt tcgcgagggt ttttattcga ttttcgtttt cgttagtatt     420
tacggattcg cgttttcgtc gcgcgtcgat tcggagtag tatcgttttc ggtataggag     480
ttttacgcgt ttttttattta ataggaagtt gggtggaagt agcgcggatt tacggtatat     540
cgaacgtatt ttaatagaat tcgacgtaga tacgcgtttt taatcggcgg agatattggt     600
agggttagaa acgcgcgtag cggggggcggg aggtcggtaa gttttttcgtt tttgttcgag    660
```

```
atttcgtttc ggttcggttt cgttttttttt tttgttttttt ttttttgtac gtacgggttt      720 cgttttttcgc gcgacgtttt tgttgattc ggaaacggat ttttcggagt cgaggttcgt        780
tcgggtgagt gttttcgtt tttttgtggtt aaatttagtt acgtagtttt tttttttgcgg       840 cgttttttat attcggggtt tgttggtttt cgcggatgtt ataggttcgg taatcgtttt        900
tttgtcggcg gggagtttcg cgacgttcgg aaatgtttcg aagtttgtcg tttagttgtt        960
agatttgcgt ttgtgttcgg tttcgttatt gaggtcgttt ttgttcggtt tttttatttt       1020
agtttttttt atcgttcgtt tattttatcg cgcgcggttt taggtttcga ttcggtatgt       1080 ggtttgttt  ttatcgtttt                                                   1100

<210> SEQ ID NO 30
<211> LENGTH: 1100
<212> TYPE: DNA
<213> ORGANISM: Homo sapiens

<400> SEQUENCE: 30
gggacgatgg aagataagtt atatgtcgaa tcgggatttg aggtcgcgcg cgataggatg         60
ggcggacggt gaagagaatt agggtggaag ggtcggatag gggcgatttt agtgacggaa        120
tcggatatag acgtagattt ggtagttggg cgataggttt cggagtatt tcgggcgtcg        180 cgggattttt cgtcgatagg agggcggttg tcgagtttgt gatattcgcg gagattagta       240
gatttcgggt gtggaggacg tcgtaggaag ggaattgcgt ggttgggttt ggttataaaa       300
agcggagggt atttattcga gcggatttcg gtttcggaga attcgttttc gggttaataa       360
aaaacgtcgc gcgaggggcg gggttcgtac gtgtaggag gggaggtaga gaaaaaggcg        420
gggtcgggtc ggggcgggt ttcgggtagg ggcgggagt ttatcgatt ttcgttttcg         480 ttgcgcgcgt ttttggtttt gttagtgttt tcgtcggttg aaagcgcgtg tttgcgtcgg       540
gttttgttgg agtgcgttcg gtgtgtcgtg ggttcgcgtt gttttttattt aattttttgt      600 taggtaagag gcgcgtgagg tttttgtgtc ggggcggtg ttgttttcga gtcggcgcgc        660
ggcggggacg cgagttcgta ggtgttggcg ggagcgagag tcgggtgggg attttcgcga       720 gttcgtatt  cgttttttggg tagtagtttt ttcggtttta tacggcgtga cgcgcgttcg      780
ggtttcgcgt tcgcgtcgag gtagaggcgt agtagggtc gggtttaggg ttggaggggt       840
cgggatcggg cggggtgtcg ttttggatat cgcgtcggta gttgtttcgc gcgggtttat      900 gttatttta tttttaatt gttttgtttc gtatttgaga tgatttataa attcggtatt         960
tttgggatag gcgtggatga tattttataa tttatttcgt tattaattt taaatgtaat      1020 atatattatt atttaaaagt atttttttaat ttgaaatata tttgtatacg tatatatgta   1080
tatttattta ttttttgaatt                                                 1100

<210> SEQ ID NO 31
<211> LENGTH: 1350
<212> TYPE: DNA
<213> ORGANISM: Homo sapiens

<400> SEQUENCE: 31
tgcgcgttgt tgcgttgagg tcgaatgaag cgtagtacgg tgcgggtagt tcgaggtttc         60
gaggttgggt tttgtttgtt tgggattgcg tcgtgtttag tttcggtttt tttttttgtgg      120 gtaaggatgg ttgagtttag ttttttacggt agcggttttt tgtgttatta gtagtttttt      180
ttttgcgttt ttcgtttttt tttttagat tggattttt tttttttttcg cgttttttttt      240 ttcgtatttt ttattcgttg gtttttttttt tagttgtttt tttttagt ttttttgt         300
```

```
tgcgcgcgtt ttttttttcg tttttttttt tttcgtagtt tcgtcgtttt ggtgtttttt      360
tgttcggttc ggtcggcgtt cgttttcggt ttcggtttcg ttagttcggg ttttcgcgtt      420
cggagtagtt tagttttgta gtggttcggg attcgatgtt atgagaggga agcgagtcgg      480
gcgtttagat ttttaggagg cgtcggatgc gcggcgggtt ttgggatcgg gttttttttt     540
cggttcgttt tgttttcggg tgattatttg gtttcgttta tagttttgtt ttttcggag      600 gagttatcgg tgtcgcgtgc gtgtggagta tttgtagata tgattgcgtg gaggagattt      660
tagtcgttgt ttttgttttt cgggttgttg gtgttgtgcg cgaggttttt tattgtagcg      720
aagggtaaga cggatttgtt tttggtcggg gaggcggtag agttttcgga ggtttcgtgt      780
gcggacgcga gtgtgcgttt tggggatcgt agggtacgga gtggtcgttt ttgttcggcg      840
ttgttttatc gtcgaagttc ggggaacgcg atgtacggga gggagttttt atcgcgtttt      900 ttttagttttt tttgggtttt cgttttattt cgttattttt tttttttttt ttgggtttat      960
aggagagatt ttttttttc ggtagtatag ggtgttaagg agaaaggaat ttaatacgag     1020
ttgggttgga attgtgtttc gtcggggcgg tgttgttttt ttcgagacgt ggattttacg     1080
ggtcggggtg gttgagggt agttttttagg atttttttttt cggattcgac gcgtttggga     1140
aagcgtttcg ggtgaagtcg gtttggaaag ttcgggtttt ttacgggggt tttggtatta     1200
ataggtaaag gttttcgtcg gttcggtttt ttcgtattta tatattttat tttttttttt     1260
tttttttttt tttaacgtt tttagtcggc gaggagtagt tgttttaga aggtcgtttt     1320 cgtttttttt tttttcggat ttcgtttttt                                      1350

<210> SEQ ID NO 32
<211> LENGTH: 1350
<212> TYPE: DNA
<213> ORGANISM: Homo sapiens

<400> SEQUENCE: 32
aaggagcgaa gttcggggga gaggaaagcg ggggcgattt tttagaggta gttattttttc        60 gtcggttgag gacgttggag agggaaggag gagaggagga atgggtgta tgggtgcgag     120 gaggtcgggt cggcggagat ttttgtttat tggtattaaa attttcgtag agagttcgaa     180
ttttttaggt cggttttatt cgggacgttt tttaggcgc gtcgggttcg gggagaaagt     240
tttgggaatt gttttttagt tatttcgatt cgtggagttt acgttcgga ggaggtaata     300 tcgtttcggc ggagtatagt tttagtttaa ttcgtattgg gtttttttttt ttttgatatt     360 ttgtattgtc gagaaaaaga gatttttttt gtgagtttaa gagaggggga aggaatggcg     420
gggtggggcg ggggtttagg agggttgggg agagcgcgat ggaagttttt tttcgtgtat     480
cgcgtttttc gagtttcggc gatggagtag cgtcgggtag aggcggttat ttcgtatttt     540
gcggttttta aaacgtatat tcgcgttcgt atacgggg tt ttcgagggtt ttatcgtttt     600
ttcggttagg agtaagttcg ttttattttt cgttgtagtg aggagtttcg cgtatagtat     660
tagtagttcg agaagtagga gtagcgattg gaattttttt tacgtagtta tgtttgtaga     720
tattttatac gtacgcgata tcgatggttt tttcgaggaa ggtagggtta tgagcggagt     780
taaataatta ttcgagggta aggcgagtcg gagagagagt tcggttttaa gattcgtcgc     840
gtattcgacg tttttttgaag gtttgggcgt tcggttcgtt ttttttttat agtatcgggt     900
ttcgagttat tgtagggttg agttgtttcg agcgcggaga ttcgggttgg cggggtcggg     960
gtcggggacg agcgtcggtc gagtcgggta ggaaggtatt aaggcggcga ggttgcggga     1020
gggggagaag cggggagagg agcgcgcgta gttaggagag atttggagag gaggtagttg     1080
```

```
gagagagagt tagcgagtgg gagatgcggg gagggggggcg cggggggggag gagagattta    1140 gtttagagag aaaaggcgga gagcgtagaa gaagggttgt tagtggtata aggagtcgtt    1200
gtcgtggagg ttggatttaa ttattttttat ttatagagag gggatcgagg ttgggtacgg    1260
cgtagtttta gatagataga gtttagtttc ggggtttcgg gttgttcgta tcgtgttgcg    1320
ttttattcgg ttttagcgta gtagcgcgta                                      1350
```

<210> SEQ ID NO 33  
<211> LENGTH: 850  
<212> TYPE: DNA  
<213> ORGANISM: Homo sapiens

<400> SEQUENCE: 33

```
gatttttgg gttaggatat gtgagagttg cgtaggtttg ggttcggcgt ggcggaggtg      60
cgcgagagcg gttagaagag ggcgttagag agttaggcgc ggttcgcgga ggagttcgcg     120
tcggttttta tatttagttt cgcgtcgcgc ggatttatcg agttcgcgtt tagacgtttt    180
agttttatcg agaggtcgtt cgggtcgtgt tttttttttt tttaggtgt aggtagagtt     240 ttcgagttat ggttagtttt ttcggtagtt tcgaagttat tggtaagttt cgaggtaggg    300
atggtcggtt taggagggag gaggacgacg ttttttttcga agagaagagg ttggggttgt   360
agttggaggg gggaagcgta tagttcgagg attgcgagaa cggggaggac gcgtcgcggt    420
taggtaggga ggagatcggt atttagatag gtggcgatcg tagaggagta agtgacgcgg    480 gcgttgggggt tcggggtgt cggggcgtc ggtaggggcg gcgggaggtt tcgtggtcgg     540 tttcggggttg aagttggtat tttagcgta atttcgaagg gcgcggagtg atagcgcgtg    600
acggttttcg agacgttagt tgtcgttttt cggttgtgtg gttttgattt tttgattttt    660
ttacgacgtc gttggttggg agatttattg gattttgcgg ttggttaaaa agagagggt    720 agtttcgcgt tttgggggtt tttagtaggg gaagtggcgg gtgttgcgtt gggtatttg     780 tttgggtgtat ttgtttggga ttttgttggt gtttttatt tggcgagggg ttagtggtgg    840
gggtaggggg                                                            850
```

<210> SEQ ID NO 34  
<211> LENGTH: 850  
<212> TYPE: DNA  
<213> ORGANISM: Homo sapiens

<400> SEQUENCE: 34

```
tttttattt ttattattgg ttttttcgtta ggtgagaggt attaatagg tttagatag      60 atgtttaga taggatgttt agcgtaatat tcgttatttt ttttgttagg ggttttagg      120 acgcggggtt gttttttttt ttttggttag tcgtagagtt tagtgggttt tttagttagc    180
gacgtcgtgg gagaattagg aagttaaagt tatatagtcg agaagcggta gttggcgttt    240
cggaggtcgt tacgcgttgt tatttcgcgt ttttcggagt tgtcgttaaa atattaattt   300
taattcgggg tcggttacgg agttttttcgt cgtttttatc ggcgttttcg gtattttcgg   360 atttagcgt tcgcgttatt tattttttg cggtcgttat ttgtttggt gtcggtttt       420 ttttgtttg gtcgcggcgc gtttttttcg ttttcgtagt tttcggggttg tgcgttttttt  480 tttttagtt atagttttag tttttttttt tcgggagga cgtcgttttt tttttttttg     540
ggtcggttat ttttgtttcg gggtttgtta gtggtttcgg agttgtcgga agggttggtt   600
atggttcggg ggttttgttt gtatttggag aagaggaagg atacggttcg agcggttttt    660
cggtggagtt gggggcgttttg agcgcgggtt cggtgggttc gcgcggcgcg gagttgggta   720
```

-continued

| | |
|---|---|
| tagggggtcgg cgcgggtttt ttcgcgggtc gcgtttggtt ttttggcgtt ttttttttggt | 780 |
| cgttttcgcg tattttcgtt acgtcgggtt taggtttgcg tagttttat atgttttggt | 840 |
| ttaggaggtt | 850 |

<210> SEQ ID NO 35
<211> LENGTH: 1100
<212> TYPE: DNA
<213> ORGANISM: Homo sapiens

<400> SEQUENCE: 35

| | |
|---|---|
| tcggcgttta ggtgacgttg attttgttgg tttatcgttt tggggggttat ttaattttttt | 60 |
| agcgatgttt tttagttggg gaggttaaga agtgtttcgt ttaaggtttt ttaatatttcg | 120 |
| attttttagat ttttaatttt gggttagtta tatcgtaaat tttttttagtt gtttttttttg | 180 |
| cgttttgcgt ttttttttttta cgttatttgt tagggagtcg ttaaatagta agatcgcgcg | 240 |
| ttttgcggtt ttagagtgcg gatttcggtc gcgtgcggtt ttgatcgcgt cgttttattt | 300 |
| ttggcggggt tacgtacgga cgttatggtt ggcgtcgcgg agtcgggcga tgcgcgcgga | 360 |
| tttttttcggg gttttgattg tttttgagtt tttttttgcgg ggggcgtgcg cggttcgttt | 420 |
| ttcgcggcgt tacgcggttt tttttcggtc ggggattggt gcgtcgggcg gggcggggcg | 480 |
| gggcgggata aaggcgcggg gtttggttgc gcggggtttg cgggtagttt taattttggg | 540 |
| ttcgtagttt gcgttgggtg cgtaggaagg ttagtgtggg ggtcgttcga tatttttttt | 600 |
| tcgcggaggt gggagtcgag ttatatttttg gagtggggat tggtcgcgga gcggttgtt | 660 |
| tagggtcggt cgaggtcggg gcgagttttg cgcggcgttg gagattttgt attttcgggc | 720 |
| gcgcgtaggg ttttcggtcg tggtcgtaga gttaggaggg gcggtttcgg agttcggcgc | 780 |
| ggggagggtt taggcgtagt cggggttggt agggcgcgat attcgttttt ttttattttt | 840 |
| gaaagggttt tttacgtcga gaagaggggc gggtatggtc ggttcggcga aatcggtttg | 900 |
| tatagatttt gggaagttat cgtttgcgga gggtgggatt ttatagtttg tttatttgtt | 960 |
| taggttgaga tttcgtgttt tagtttttgga tgttttacgg gtttttcgtt tcgggtagcg | 1020 |
| gcgtacggga ggagaagatt ttcggtttgt agttagattt ttttttgaga ttttttttag | 1080 |
| tttaggttta gagttttggg | 1100 |

<210> SEQ ID NO 36
<211> LENGTH: 1100
<212> TYPE: DNA
<213> ORGANISM: Homo sapiens

<400> SEQUENCE: 36

| | |
|---|---|
| tttaaagttt taagtttgag ttagggaggg tttttagaggg aggtttgatt gtagatcggg | 60 |
| agttttttttt tttcgtgcgt cgttgttcgg gacgagaaat tcgtggggta tttaggatta | 120 |
| ggatacgagg tttagtttg ggtaggtgga taagttgtgg ggttttattt ttcgtaggcg | 180 |
| atggttttttt aaagtttgta taaatcggtt tcgtcgggtc ggttatgttc gtttttttttt | 240 |
| tcggcgtggg aagttttttt aaaagtggag gggagcgagt gtcgcgtttt gttaatttcg | 300 |
| attgcgtttg ggttttttttc gcgtcgggtt tcggagtcgt tttttttgat tttgcgatta | 360 |
| cggtcggggga ttttgcgcgc gttcgggaat gtagagtttt tagcgtcgcg tagggttcgt | 420 |
| ttcgatttcg gtcggttttg ggtaattcgt ttcgcggtta gttttttattt taagatgtgg | 480 |
| ttcggttttt attttcgcgg gggggaaatg tcggcgatt tttatattga ttttttttgcg | 540 |
| tatttagcgt aaattacgaa tttagagttg gagttgttcg tagatttcgc gtagttagat | 600 |

-continued

```
ttcgcgtttt tatttcgttt cgtttcgttt cgttcggcgt attaattttc ggtcgaggag    660
gggtcgcgtg gcgtcgcggg gggcgggtcg cgtacgtttt tcgtagggag gatttaggga    720
tagttagggt tcgggagag ttcgcgcgta tcgttcggtt tcgcggcgtt agttatggcg     780
ttcgtgcgtg gtttcgttag ggatgggcg acgcggttag agtcgtacgc gatcgaaatt    840
cgtattttgg agtcgtagag cgcgcggttt tgttgtttag cggttttttg gtaagtgacg    900
tggggaagaa acgtagggcg taggagagat agttggaaag gtttgcggtg tagttggttt    960
aggattgagg gtttggaggt cgggtgttgg aagatttga gcgaggtatt ttttggtttt    1020
tttagttggg aggtatcgtt gaaaaattag gtgattttta agacggtaga ttagtagagt   1080
tagcgttatt tgggcgtcgg                                               1100
```

<210> SEQ ID NO 37
<211> LENGTH: 1100
<212> TYPE: DNA
<213> ORGANISM: Homo sapiens

<400> SEQUENCE: 37

```
aaagttaagc gtcgtcgtta tttaaggtat tgcgttgatg cgttgcgggt cgattaggtg     60
ttttcgtcgg ggcgtttttt tttacgtagg aagggttacg tcgagagagg taggtaataa    120
gggtacggtt ggaggtcgga aggttatttc gttttcggcg gggcgggcgc ggtttagttt    180 tattttttcgg gtacgttcgg gcggggcgat tgtagggaac ggggcgggga ggcgatagtt    240
ttcggtttcg tcgcgcgtta gttcgttttc gttgttcgga ggcgtcgtag gtttgggttt    300
tcggatagtt gagttcgagc gtcgtttttc gaaaggtgaa ggcggttcgg ggaggcgggg    360
acggtgacgg gggcggggt cgcggcggt ttttcgacgg ttgtcgcggg gttagtttaa     420
agttttcgat tttcggtagt tgcgttttc gcgcggggcg tcggagtagg gcgggttaag    480
ttggtttgcg gtcgcggcgg gaagaaggg tagcgaagta ttttcgatcg ggtttaggcg    540
tcggacgtcg gggggcgttt cgttgtaatt tttttttgga agtttcgata cgagtttcgg    600
ttcgcgcgcg cgttttttta cggttacgcg cgtattttgt cgttcgtatt ttcgcgcgtt    660
tttcgtttat tttttttttt tttttttatt tttatatttt aaaataggtt aaggggtgga    720
agttatattt ggtgtagttt tcggttttga tgtaaaagta gttttttgttt ttggttgcgg    780 gatagcgttg tgattattcg taacgggaga gttgttgtta gtcgttatat cgtgcgaaa     840 gcgtcggcga tcggagtatt gataatggtt tgtatagggg agcggagaga agttttttgtt   900 gcgttttaga ttcgttgttt cggcgttcgt tcgtagggag gagggggcgc gataggtcgt    960
ttagcgcgtg tttcggagtt cgcgttcggg tttggtcgtt tgggtgagtt tttgttcgtt   1020
ttttgttttt ttagtagttc ggggtggttg tttattttgt aaatagtttt gtaatacgat   1080
taaaataggc gagatagtta                                              1100
```

<210> SEQ ID NO 38
<211> LENGTH: 1100
<212> TYPE: DNA
<213> ORGANISM: Homo sapiens

<400> SEQUENCE: 38

```
tggttgtttc gtttgttttg atcgtattgt aaggttgttt gtaaggtaaa tagttatttc     60
gggttattgg aaaggtaggg gacgagtagg aatttattta ggcggttaga ttcgggcgcg    120
ggtttcgggg tacgcgttag acgatttgtc gcgtttttt ttttttgcgg gcgggcgtcg     180
aggtagcgga tttagggcgt aatagaagtt ttttttcgtt tttttatgta gattattgtt    240
```

```
agtgtttcgg tcgtcggcgt ttttcgtacg gtgtggcgat tggtagtagt ttttcgttg        300 cgagtagtta tagcgttgtt tcgtagtag gggtaaaagt tgttttgta ttagagtcga         360 gggttgtatt aggtgtaatt tttattttt gatttatttt agagtgtgag gatgaaagga        420
agaggaaaaa atagacggag ggcgcgcggg ggtgcgggcg gtaggtgcg cgcgtggtcg        480 tgggggagcg cgcgcgcggg tcggggttcg tgtcggggtt tttaaagaga agttgtagcg       540
aggcgttttt cggcgttcgg cgtttgggtt cggtcggggg tgtttcgtta gttttttttt       600
tcgtcgcggt cgtaggttag tttggttcgt tttatttcgg cgtttcgcgc gggaagcgta       660
gttatcgggg atcggggtt tgggttggt ttcgcgatag tcgtcgggag atcgttcgcg         720
gttttcgttt tcgttatcgt tttcgttttt tcgggtcgtt tttatttttc gggaggcggc       780
gttcgggttt agtgttcgg gaatttaggt ttgcggcgtt ttcgggtagc gaaggcgggt         840
tggcgcgcgg cggagtcggg gattgtcgtt ttttcgtttc gttttttgta atcgtttcgt       900
tcgaacgtgt tcgggaagtg aggttgggtc gcgttcgttt cgtcgggggac ggggtgattt      960 ttcggttttt agtcgtgttt tgttgtttg ttttttttcgg cgtggttttt tttgcgtagg      1020
agaagacgtt tcggcgggag tatttggtcg gttcgtagcg tattagcgta gtattttggg      1080
tgacgacgac gtttggtttt                                                  1100

<210> SEQ ID NO 39
<211> LENGTH: 600
<212> TYPE: DNA
<213> ORGANISM: Homo sapiens

<400> SEQUENCE: 39
gcgattttag aggagtaatc gggttttaat ttttgcgtt cgttttgtta taatttttt         60 ttatttattt ttattttatt tttataatat ttttattggg ggggttttt tgtgtttcgg       120 atttttttt ttatggtttt tttagtcgaa gtcgggggtt ttttgggcgg tttggagggt       180
ttgggttagt aggtgggttc gtattttttg ttgtttttg tcggggagcg gtcgtcgttg       240
ttgggcgagc gtaggagcgc ggcggagcgg agcgcgcgcg gcgggtcggg ggttgcgtag      300
ttggcgtatt tgtacggtat tttgcgtcgt cggtagtttt attgtcgtat cggttttat       360 ttgtagattt tgttcgacgg tagcgtgtag ggtattcggt aggattatag ttttttcggt      420
acgtattagt atttcgattt tattttatt tgcgttttag ttcggttttt cgtttttttt       480
ttttgtattt ttttttttgt ttgttaaggg cgttatcgtc gcgcggagtt cggagttttt      540
ttggatttat tcggtgtaag acgtaggttg gggttgaagg gttggttaga gtagtcgcgg      600

<210> SEQ ID NO 40
<211> LENGTH: 600
<212> TYPE: DNA
<213> ORGANISM: Homo sapiens

<400> SEQUENCE: 40
tcgcggttgt tttggttagt tttttagttt tagtttgcgt tttgtatcgg atgggtttag        60
gggagtttcg ggtttcgcgc ggcgatgacg ttttggtag gtaaagaggg aggtgtaagg       120
ggagggaacg aggagtcgag ttgggcgta gatggggtg gggtcgggat gttagtacgt        180
atcgaagagg ttgtggtttt gtcggttgtt ttgtacgttg tcgtcgggta ggatttgtag      240
gtggaagtcg gtgcggtaat agagttgtcg gcggcgtagg atgtcgtgta ggtgcgttag      300
ttgcgtagtt ttcggttcgt cgcgcgcgtt tcgtttcgtc gcgttttgc gttcgtttag       360 tagcggcggt cgttttcgg taggaggtaa taggaaatgc gaatttattt gttggtttaa       420
```

| | |
|---|---|
| gtttttagg tcgtttagaa agttttcgat ttcggttaag ggagttatgg aggggagat | 480 |
| tcggaatata aaagattttt ttagtaaaga gtgttgtggg ggtgggatgg aggtggatag | 540 |
| agaaaaatta tagtaaaacg agcgtaaaaa gttaaggttc ggttattttt ttgaggtcgt | 600 |

<210> SEQ ID NO 41
<211> LENGTH: 1100
<212> TYPE: DNA
<213> ORGANISM: Homo sapiens

<400> SEQUENCE: 41

| | |
|---|---|
| tatatttat ttgtgtcgta tatgtgaaga tataattgta aatcgtttac gattttgagt | 60 |
| taagattttg agtttttga ggttaggaga tcgttaggga atgtgagtgt tttagacggg | 120 |
| cgttgagttt agttcggaga tttatttcgt tcgtagtagc ggcgcgggtt ttagagagtt | 180 |
| tcgtattcgg tcgcgtttta gttacgttga ttcggttgtg ttcgtagtgt cgcgttgtcg | 240 |
| cgtagttagg tgtcgtcggg ttggcgcggt tatttatgat tgcgtggttg ggttgggggt | 300 |
| tcggggtcgg ggagtagtcg ggattcgtcg ttttttttat gattttttcg ggtcgaatta | 360 |
| cgggatcgtt acgttgaagg tggcgtcgcg ggttttcggg gtcgcgcgag tgtaggggtc | 420 |
| gttttcggtc ggtcgcgaag ttcgcggtat cgattttcg cgagatttcg gcgattttt | 480 |
| ttttcgtttt cgttttttcg tttttgtttt tttttagtt ttggtgtggg cggttttcgt | 540 |
| tatggttgcg ttgcgaaggt ttttgtggtc gttatttcgg gtgttttttt tattttgcgt | 600 |
| ttattagttt tttttgggt cgtggggcg gtttgcggtg attattttgg gttttttgg | 660 |
| tcggttttt tttttcgag aggatgagga gagggttgtg gcggaggcgg tatggaggcg | 720 |
| gcggcggcgt tgggggagt tgagcgtggc ggcggcggtc ggcggggggt tggtcggttt | 780 |
| ggtatgttat tagttgtacg gggattttag ggtcggttcg tcggcgatcg ggcgattttt | 840 |
| aaagagcgcg gttacggagt tcgaggattc gtttcgcggt cggggatgt tgtttatttt | 900 |
| agtggcggtt gttaaggaga cggtgagtgc gcgagcgcgc gttatatttg cgcgggggat | 960 |
| gtgatttcg tgtcgggtac gtaggatttt ggaggttgtg gggacggtgt aagcgttgtg | 1020 |
| gtcgcgggtg aggaatttt cgtgagcgag gttgatattt aggtcggata gtttaggatt | 1080 |
| cggttattta cgtattggga | 1100 |

<210> SEQ ID NO 42
<211> LENGTH: 1100
<212> TYPE: DNA
<213> ORGANISM: Homo sapiens

<400> SEQUENCE: 42

| | |
|---|---|
| ttttaatacg tgggtgatcg gattttaggt tgttcggttt aggtgttagt ttcgtttacg | 60 |
| ggaagtttt tattcgcggt tatagcgttt gtatcgtttt tatagttttt agggttttgc | 120 |
| gtattcggta cgaaggttat attttttcgcg taggtgtgac gcgcgttcgc gtatttatcg | 180 |
| ttttttggt agtcgttatt gggatgggta gtattttcg gtcgcggggc gggttttcgg | 240 |
| gtttcgtggt cgcgtttttt gagggtcgtt cggtcgtcgg cgagtcggtt ttggggtttt | 300 |
| cgtatagttg gtagtatatt aggtcgatta gttttcgtc ggtcgtcgtc gttacgttta | 360 |
| gtttttttta gcgtcgtcgt cgttttttatg tcgttttcgt tatagttttt tttttatttt | 420 |
| ttcgggagga gaagggtcgg ttaggaaggt ttagggtggt tatcgtaggt cgtttttacg | 480 |
| gtttaaggag gggttggtga gcgtagagtg gaggagatat tcggggtggc ggttataaga | 540 |
| gttttcgtag cgtagttata gcggaggtcg tttatattag agttgggagg gggtagagaa | 600 |

```
cggaggggcg ggggcggggg gggggtcgt cgaaatttcg cgagaagtcg gtgtcgcgag       660
tttcgcggtc ggtcgagagc gattttata ttcgcgcgt ttcggggatt cgcgacgtta        720
tttttagcgt agcggtttcg tggttcggtt cgggaagatt atggaagagg cggcggattt      780
cggttgtttt tcggtttcga atttttagtt taattacgta gttataaata atcgcgttag      840
ttcggcgata tttggttacg cgatagcgcg atattgcggg tatagtcgag ttagcgtaat      900
tgaggcgcgg tcgagtgcgg ggttttttgg ggttcgcgtc gttgttacgg gcggggtggg     960
ttttcgagtt gggtttagcg ttcgtttggg atatttatat ttttaacgg ttttttgatt      1020 ttaggaaatt taaggttttg atttaaggtc gtgaacgatt tgtaattgta tttttatata     1080
tacgatataa atgaggtata                                                 1100

<210> SEQ ID NO 43
<211> LENGTH: 600
<212> TYPE: DNA
<213> ORGANISM: Homo sapiens

<400> SEQUENCE: 43
gtttgggtac gcgggatagg ttgtattcgt ttgttagagg cgttttatcg aggcgttacg       60
ggtgaagttt cggttttat ttacggggcg gggtttcggt tcggttcgat tattgttcgc       120
ggtgggggag gggatggat tacgttacgc gttaaaggcg atcgcgattt ttttttgta        180 ggtagtttgg aaggttttt tttttttttt acgttatttt tttcgtggta ttgaaaagtt      240
tcgttttttt tttttagttt cgttttttc gagcgttttt tttattgttt ggaatggtgc       300
ggttttaggt cgcgggttac gcggcggagg gggcgtggtt tgttttcggt ttagtcggtt      360
tttttttgtt tttgttggag ttcggggagt ggcgttggtt gttagagcga tgtcgggtcg      420
gagttgcgtc gttttagttt ttttggttgt cgtcgttagt tgtgtcgtcg cgtagtacgc      480
gtcgtcggtg agtgagtttg agtcgaggcg tagagagggg cgtgtaggtg cgggcgcgga      540
tggaggcgta ggtgtggcgg cgcgagcggg tataaggaat atttcgtgtt gggtagtttt      600

<210> SEQ ID NO 44
<211> LENGTH: 600
<212> TYPE: DNA
<213> ORGANISM: Homo sapiens

<400> SEQUENCE: 44
gaagttgttt agtacgaggt gttttttgta ttcgttcgcg tcgttatatt tgcgtttta       60 ttcgcgttcg tatttgtacg ttttttttg cgtttcggtt taagtttatt tatcggcggc       120
gcgtgttgcg cgacggtata gttgacggcg gtagttagga ggattaaggc gacgtaattt      180
cggttcggta tcgttttagt agttaacgtt attttttcgga ttttagtaga ggtaaagaag    240
agtcggttgg gtcgggggta ggttacgttt ttttcgtcgc gtgattcgcg atttgggatc      300
gtattatttt aggtagtagg gggaacgttc ggaggaggcg ggattgggag gagaggacgg      360
ggttttttag tgttacgaaa agggtggcgt agagaaagag agagagtttt ttaggttatt     420
tgtagaagga gagtcgcgat cgttttggc gcgtggcgtg atttatttt tttttttatc       480 gcgggtaata gtcggatcga gtcggagttt cgtttcgtag gtggggtcgg gagttttatt     540
cgtggcgttt cgatggggcg tttttagtag gcgggtgtag tttgtttcgc gtatttaggt    600

<210> SEQ ID NO 45
<211> LENGTH: 600
<212> TYPE: DNA
<213> ORGANISM: Homo sapiens
```

<400> SEQUENCE: 45

```
ggtagtgtag ttgtgggaat ttttttacgc gtacgaattt agttaacgat ttttgataga    60
tttttgggag tttgattaga gatgtaaggg gtgaaggagc gttttttatc gttagggaat   120
tttgggata gagcgtttcg gtcgtttgat ggtcgaggta gggtgcgatt taggatttag   180
gacggcgtcg ggaattatat tatggttcgg atttttaaga ttttaaagtt cgtcgtcgtt   240
atcgtcgcgg ttttgttgtt agtgagtttc ggtcgcggtt tttggttggg gaagagcgta   300
tttggcgtcg ggagggggta gggagacggg gatacggtag ggatgtttgg ttttggttat   360
ttgcggtcgg gtatgttcgg gtaggacgaa ttcgtcgtcg gagttagggg aagaattggg   420
ttttcgggtt gggtaggagg gattcggtcg cgagggagta gagaggcggt tttttttggtt   480
gtttcgagtt cgcgaaggga gggaagtttt agaatcgaga gagggaggga gttaaggtgg   540
aatttataga gtgagttttt tgaagatata gagcggttgt ttttttttatt aattaattaa   600
```

<210> SEQ ID NO 46
<211> LENGTH: 600
<212> TYPE: DNA
<213> ORGANISM: Homo sapiens

<400> SEQUENCE: 46

```
ttaattaatt aatgagagag gtaatcgttt tgtgttttta ggaggtttat tttatgggtt    60
ttattttgat tttttttttt tttcgatttt ggaattttt ttttttcgcg ggttcggggt   120
agttaggggg atcgtttttt tgttttttcg cggtcgggtt ttttttgttt agttcgggga   180
tttagttttt tttttgattt cgacggcgag ttcgttttgt tcggatatgt tcggtcgtag   240
gtgattaggg ttaggtattt ttgtcgtgtt ttcgtttttt tgtttttttt cggcgttagg   300
tgcgttttt tttagttagg gatcgcggtc gggatttatt ggtagtagga tcgcgacgat   360
gacgacgacg aattttaggg ttttggggat tcgggttatg gtatggtttt cgacgtcgtt   420
ttgggttttg ggtcgtattt tgtttcggtt attaggcggt cggggcgttt tgttttttaga   480
gttttttaac ggtaggaagc gttttttttat tttttgtatt tttggttaaa tttttaaaaa   540
tttattagaa atcgttggtt gagttcgtgc gcgtggagag gttttttatag ttgtattgtt   600
```

<210> SEQ ID NO 47
<211> LENGTH: 1100
<212> TYPE: DNA
<213> ORGANISM: Homo sapiens

<400> SEQUENCE: 47

```
cgtttgcgga ggattgcgtt gacgagattt ttatttattg ttattaattt gtggtggaat    60
ttgtagttgt atattggatt tgattcgttt cgtttcgaat gacgtttgtt cggaggtagt   120
gaaagtatag tcgcgtcgtt ttaagttagt ttggatatat aaattagtac gcggtcggag   180
aatttcgtaa ttttttgcgtt tataaaatat atcgacgatg ttcgatttat tttaagggtt   240
gaaatttacg ggtttgagag attataagag cgttttttat cgttatggaa taacggggat   300
agaacgtttc ggtcgtttcg ggggttcgga aaaggtacgg tttaggattt agggaggcgc   360
ggggagttag gtttgggttt cgggtttttta agattttgt gttcgttgtc gtcgcggttt   420
tgttgttggt gagttttcgt cgcggttttt ggttggggaa gagcgtgttt ggcgtttgga   480
gagggtaggg agagagggg atacggcggg ggtgcgtggt tcgggtcgtt tgcggtcggg   540
tatgttcggg taagacgtat tagtcgtcgg agtcggggga agagatgggt tttcggttg   600
ggtaggagcg atttgggtcg ttagggaata gagcgcgcgt tttatttggt gtaaattttc   660
```

-continued

```
gaatttagtg ggggagggcg ataaggaggg aattttcgag taagttgcgt gaagttacgg    720
agaggtcgtc ggattttgat tttgtttttt tttttttattt tttgttttttt ttttttttttt    780 tttttttttt tttttttttt tttttttttt tttcgtttag ttttttgtttt aattttttttt    840 ttttttgcgt tttcgaatga attttttaaag gcgtttattg tagatcgttt tgaatttgcg    900
gtcggcgaag aatttttttg tggtcgttgc ggtttagtgg tttcgtttcg tgcgcgggag    960
tcgtcgcggg cgtagttgga gaggtttttt ttttttttta gcggttgcgt ttttacgcgt    1020
gcggggtcgt ttatcgttaa tgttattgtt tggggttttt tgggaaaacg agatttagga    1080
gaagggagtt gtggtatttg                                                1100
```

<210> SEQ ID NO 48
<211> LENGTH: 1048
<212> TYPE: DNA
<213> ORGANISM: Homo sapiens

<400> SEQUENCE: 48

```
taagtgttat aatttttttt ttttaaattt cgttttttta aggaattttta ataatggta     60 ttggcgatga gcggtttcgt acgcgtaggg gcgtagtcgt taaggagggg aagggggtttt    120 tttagttgcg ttcgcgacga ttttcgcgta cggaacggaa ttattgggtc gtagcgatta    180
taggggagtt tttcgtcggt cgtaggttta aagcgatttg taatgagcgt ttttaggaat    240
ttattcgaag gcgtaaaaga aaagaaatt aaggtaggaa ttgagcgagg aaggaaggga    300 gggaagaaa ggaagaaaga gaaaagaga agaaataga aagtaaggaa agaaaataaa    360
attaaagttc gacgattttt tcgtggtttt acgtagttta ttcgggaatt tttttttttgt    420 cgttttttt tattggattc gggaatttat attaagtgga gcgcgcgttt tgtttttggg    480
cggtttaggt cgttttttgtt taattcgggg atttattttt tttttcgatt tcgacgattg    540
gtgcgttttg ttcggatatg ttcggtcgta ggcgattcgg gttacgtatt ttcgtcgtgt    600
ttttttttgc ggggatttat taatagtagg atcgcggcga taacgagtat aagggttttg    660
gggattcggg gtttaggttt ggttttttcgc gttttttttgg gttttgggtc gtgttttttt    720
cgggttttcg aagcggtcgg ggcgttttgt tttcgttgtt ttatggcggt agggaacgtt    780
tttatagttt tttaggttcg tgggtttttag ttttttaaagt agatcgggta tcgtcggtgt    840
attttgtggg cgtagagatt gcggggtttt tcggtcgcgt gttgatttat tgtttaggt    900 tgatttgggg cggcgcggtt gtattttttat tgttttcggg taggcgttat tcggggcggg    960
gcgaattaga tttaatgtgt aattgtaaat tttattatag gttggtgata ataaataaga    1020
gtttcgttaa cgtaatttttt cgtaagcg                                      1048
```

<210> SEQ ID NO 49
<211> LENGTH: 1299
<212> TYPE: DNA
<213> ORGANISM: Homo sapiens

<400> SEQUENCE: 49

```
tgtacgttta ttgtttgttt ttttttttgt acgtttggtg ggttttatttt taggcgggtg     60 ttgcgacggt ggttattgcg ttttttgcgta cgcggggggta gttttcgtcg ttattttttt    120
tggcgtatat gttgagtttt tatcgcgatt cgttgtcgag ggtagatatt attcgtagtt    180
tataggtaga aggtaggtag tgtcgcgtgt cgcgttttgt tgggtatttt cggggcgttt    240
tcgtcgcgtt tagttagcgg attcgggaag tgttgtgggt tggggggttgc ggtttcgagt    300 cgggtttgta gtcgttcggg cgtttcgagt ttagggttta gttttgcggg tgttttcgcg    360
```

```
ttagtaggtt cggggtgtag cgttggtggt tgggggcgta tttacggtcg agtcgggaag    420 ggatttttagc gtttagggtg tgttttcgac ggggattatt gttttttgggt tttggtttgg   480 gattgcgcgg agcgtagcgc ggaagggtgg gagttttttaa ttttttagttt tgtgaagttg   540 tttatttcgg agtttgggtt tgcgtatttg taggataggt gtaataaata atatttcgtt   600
tattagattg tggaaagcgc gagatgataa tgcgcgcgaa acgtttagcg tagtattcgg   660
tatagttata gttaacggtc gttggtatta ttgtaatggt ttggttttgg cgcgggagta   720
tcggtagttg agttggtaat atcggggatt cgggtttacg gttcggagat tagggatggg   780
ttgtttcgaa gtcgcgaatt gtggtagttt tgggtttttt agtcgcgtcg gggaagtgtt   840
aagtgtttcg tttaatttcg ggttcggggt tatgatttgt aggggagtgg gtgttaagga   900
cggtagggat ttgagggtat cgttttcgag gatttggtag cgcgttttgg gtatttagcg   960
cggcgagtag gtgggtgttg cggagaggga gttttttttcg cgttttaatt tatattttgt  1020
cgtttgggta gtcgcggtcg tttacgtttt ttttcgtttg cggggggttag acggtttttt  1080 ttggggtcgg ggcgtaattt ataaacgtta atttgattcg atttgtcgtt tgttcgtttt  1140
ttgtgatttg gtgtcggggg tttttcgttt tcgcgtttgg ggttagatag tcggtgattt  1200
ttttcggaag ggttatttgg ggattagtta gattagggga tattttcggg ggcggggtaa  1260
tgagaaattt gttggagtgt tcggtttttt aatcgaaaa                          1299

<210> SEQ ID NO 50
<211> LENGTH: 1350
<212> TYPE: DNA
<213> ORGANISM: Homo sapiens

<400> SEQUENCE: 50
ttttcggttg aggggtcgag tattttagta aatttttttat tgtttcgttt tcgagggtgt    60
tttttggttt ggttggtttt tagatgattt tttcggagag ggttatcggt tgtttgatttt   120 taggcgcggg agcgaagggt tttcggtatt aggttataag gggcgggtag gcggtaggtc   180
ggattagatt agcgtttgtg gattgcgttt cggttttagg gagggtcgtt tggttttcgt   240
aggcggaggg aggcgtgggc ggtcgcggtt gtttaggcgg tagaatgtgg attgaggcgc   300
ggaaggggtt ttttttttcgt agtatttatt tgttcgtcgc gttgggtgtt tagaacgcgt   360
tgttaggttt tcgagggcga tattttttaga ttttttgtcgt ttttgatatt tatttttttg   420
taaattatgg tttcgaattc ggggttaagc gagatatttg atatttttttc ggcgcggttg   480 gaggatttaa ggttgttata gttcgcgatt tcggatagt ttatttttga ttttcgggtc     540
gtgagttcga atttcgatg ttattagttt agttgtcgat attttcgacg ttatatttcg    600
ggatttattt attttttattc gtagaaagaa aaaaaaatcg ttaagattaa attattatag   660
taatattaac gatcgttgat tgtggttgtg tcgggtattg cgttgagcgt tcgcgcgta    720 ttgttatttc gcgttttttta tagtttgata ggcgaggtgt tatttattat atttatttta   780
tagatgcgta gatttaggtt tcgggataag taatttttata agattggaga ttagaagttt   840 ttatttttttc gcgttgcgtt tcgcgtaatt ttaaattaaa atttagagat aatggttttc   900
gtcgaggata tattttgaac gttagaattt ttttttcgatt cggtcgtgga tacgtttta    960 gttattaacg ttgtatttcg agtttgttga cgcggagata ttcgtagagt taggttttgg  1020
gttcgggacg ttcgggcggt tgtaaattcg gttcggagtc gtagttttta atttatagta  1080 ttttttcgagt tcgttggttg gacgcggcgg aggcgtttcg ggggtgttta gtagggcgcg  1140
gtacgcggta ttgtttattt tttgtttgta ggttgcggat gatgtttgtt ttcggtagcg  1200
```

-continued

```
ggtcgcggta gaggtttagt atgtacgtta gaggggatgg cgacgagggt tgttttcgcg    1260
tacgtaggag cgtagtggtt atcgtcgtag tattcgtttg gagtagggtt tattaggcgt    1320
gtagaaggaa gggtaggtag tgggcgtgta                                     1350
```

<210> SEQ ID NO 51
<211> LENGTH: 350
<212> TYPE: DNA
<213> ORGANISM: Homo sapiens

<400> SEQUENCE: 51

```
ttttgaaggg cggcggattt tagggttatg ttggttgttt ttagaaagta ggagttcgaa      60 atcgcgggt taacgaacgt ttatatttt tgttataatt tcgttatttt tttgcgtttt      120
tttttttgtt tttgtttt ataggtaacg tttagaacga gtgtttttt cggtggggta      180 ttgaggagtt tgggttgtag ttgtcgagtc gttatagtta cgttgagttc ggtttggttt      240
gtatattggc gttatcgttt ggcggggagc gggattgacg cgtttttttt tttttttttt      300
agtttagatt acggaggcgc ggagttttat ttttgtttt gggcgagggg              350
```

<210> SEQ ID NO 52
<211> LENGTH: 350
<212> TYPE: DNA
<213> ORGANISM: Homo sapiens

<400> SEQUENCE: 52

```
ttttcgttt agggtaggag atggagtttc gcgttttcgt gatttgggtt ggaggagagg      60
gagaggagcg cgttagtttc gttttcgtt aggcggtggc gttagtgtgt aggttaggtc      120
gggtttagcg tggttgtggc ggttcggtag ttgtagttta ggttttttag tattttatcg      180
ggagaagtat tcgttttggg cgttatttgt ggggtaggg ggtaagggga gaggcgtagg      240
ggagtggcga ggttgtagta gagaatgtgg gcgttcgttg gtttcgcggt tcgggtttt      300 tgttttttgg ggatagttag tatggttttg aagttcgtcg ttttttagag              350
```

<210> SEQ ID NO 53
<211> LENGTH: 350
<212> TYPE: DNA
<213> ORGANISM: Homo sapiens

<400> SEQUENCE: 53

```
taattagggt tggtttattt tttttagtt aatttttttt tatttttagt ttttaattta      60
atttatttcg tttattagtt tttggatttt tattattttt ttcgtatttt cggtagtttt      120
ggggaagttt cgtgacgtta taggtttcgt tttagtttc ggttcggggt tagtgcgtgt      180
tgacgttatg ttgcgtgcgg gtcggtgcgg aatcgttttt ttaatttcgc ggggtagtag      240
gagttagtta gtaaagagtc gaggtcgggc gcgcgatttt cgttttttg tttttggtcg      300 tatatttgc gtatatttt tttttgtat ggtggatatt attttttatt                  350
```

<210> SEQ ID NO 54
<211> LENGTH: 350
<212> TYPE: DNA
<213> ORGANISM: Homo sapiens

<400> SEQUENCE: 54

```
aatgaaaaat aatatttatt atgtagaaaa agagatgtgc gtaaagtgtg cggttagggg      60
tagaaggacg agggtcgcgc gttcggtttc ggttttttgt taattaattt ttattgtttc      120
gcggagttga aggagcgatt tcgtatcggt tcgtacgtag tatgacgtta atacgtatta      180
```

```
gtttcgggtc ggagttgggg gcgggatttg tggcgttacg aagttttttt agaattgtcg    240
gggatgcggg ggaggtgatg gggatttagg ggttgatggg cggggtgggt tgggttggag    300 gttggggggtg aagggagatt ggttgggagg aagtgggtta attttgattg              350
```

```
<210> SEQ ID NO 55
<211> LENGTH: 22
<212> TYPE: DNA
<213> ORGANISM: Artificial
<220> FEATURE:
<223> OTHER INFORMATION: Primer

<400> SEQUENCE: 55
gagcgggtag cgagagtttc gg                                              22

<210> SEQ ID NO 56
<211> LENGTH: 23
<212> TYPE: DNA
<213> ORGANISM: Artificial
<220> FEATURE:
<223> OTHER INFORMATION: Primer

<400> SEQUENCE: 56
taacgacgcg actaccgaaa acc                                             23

<210> SEQ ID NO 57
<211> LENGTH: 24
<212> TYPE: DNA
<213> ORGANISM: Artificial
<220> FEATURE:
<223> OTHER INFORMATION: Primer

<400> SEQUENCE: 57
gattaacgtg ttcgtgattt cgtt                                            24

<210> SEQ ID NO 58
<211> LENGTH: 25
<212> TYPE: DNA
<213> ORGANISM: Artificial
<220> FEATURE:
<223> OTHER INFORMATION: Primer

<400> SEQUENCE: 58
caacgaccaa taaccaatca acgcc                                           25

<210> SEQ ID NO 59
<211> LENGTH: 24
<212> TYPE: DNA
<213> ORGANISM: Artificial
<220> FEATURE:
<223> OTHER INFORMATION: Primer

<400> SEQUENCE: 59
atacgtcggt gagttcggtt tatc                                            24

<210> SEQ ID NO 60
<211> LENGTH: 24
<212> TYPE: DNA
<213> ORGANISM: Artificial
<220> FEATURE:
<223> OTHER INFORMATION: Primer

<400> SEQUENCE: 60
actcccgact ccctaaactc cgaa                                            24

<210> SEQ ID NO 61
```

<211> LENGTH: 22
<212> TYPE: DNA
<213> ORGANISM: Artificial
<220> FEATURE:
<223> OTHER INFORMATION: Primer

<400> SEQUENCE: 61
tgaatcggcg aggtgagagt cg                                          22

<210> SEQ ID NO 62
<211> LENGTH: 24
<212> TYPE: DNA
<213> ORGANISM: Artificial
<220> FEATURE:
<223> OTHER INFORMATION: Primer

<400> SEQUENCE: 62
accgaacgtc tcaacgcgaa aacg                                        24

<210> SEQ ID NO 63
<211> LENGTH: 24
<212> TYPE: DNA
<213> ORGANISM: Artificial
<220> FEATURE:
<223> OTHER INFORMATION: Primer

<400> SEQUENCE: 63
tatcgttagc gtcgtggtgg agtt                                        24

<210> SEQ ID NO 64
<211> LENGTH: 24
<212> TYPE: DNA
<213> ORGANISM: Artificial
<220> FEATURE:
<223> OTHER INFORMATION: Primer

<400> SEQUENCE: 64
ctacacgaac actaaaccga ccga                                        24

<210> SEQ ID NO 65
<211> LENGTH: 25
<212> TYPE: DNA
<213> ORGANISM: Artificial
<220> FEATURE:
<223> OTHER INFORMATION: Primer

<400> SEQUENCE: 65
tcggtcgtta cgttgatcgt tattc                                       25

<210> SEQ ID NO 66
<211> LENGTH: 24
<212> TYPE: DNA
<213> ORGANISM: Artificial
<220> FEATURE:
<223> OTHER INFORMATION: Primer

<400> SEQUENCE: 66
accctacgca taccttctc gaac                                         24

<210> SEQ ID NO 67
<211> LENGTH: 24
<212> TYPE: DNA
<213> ORGANISM: Artificial
<220> FEATURE:
<223> OTHER INFORMATION: Primer

<400> SEQUENCE: 67

```
gtttcgagga agtttcgggt acgg                                          24

<210> SEQ ID NO 68
<211> LENGTH: 24
<212> TYPE: DNA
<213> ORGANISM: Artificial
<220> FEATURE:
<223> OTHER INFORMATION: Primer

<400> SEQUENCE: 68
gatcgttaac cttctttcgc cgac                                          24

<210> SEQ ID NO 69
<211> LENGTH: 21
<212> TYPE: DNA
<213> ORGANISM: Artificial
<220> FEATURE:
<223> OTHER INFORMATION: Primer

<400> SEQUENCE: 69
cgaagttggg aggagcgagt t                                             21

<210> SEQ ID NO 70
<211> LENGTH: 24
<212> TYPE: DNA
<213> ORGANISM: Artificial
<220> FEATURE:
<223> OTHER INFORMATION: Primer

<400> SEQUENCE: 70
aaacatccgt actcctacga ccga                                          24

<210> SEQ ID NO 71
<211> LENGTH: 24
<212> TYPE: DNA
<213> ORGANISM: Artificial
<220> FEATURE:
<223> OTHER INFORMATION: Primer

<400> SEQUENCE: 71
cgtattagtc gtattcgcga gcgt                                          24

<210> SEQ ID NO 72
<211> LENGTH: 21
<212> TYPE: DNA
<213> ORGANISM: Artificial
<220> FEATURE:
<223> OTHER INFORMATION: Primer

<400> SEQUENCE: 72
cgaaactact cgacccgacc c                                             21

<210> SEQ ID NO 73
<211> LENGTH: 24
<212> TYPE: DNA
<213> ORGANISM: Artificial
<220> FEATURE:
<223> OTHER INFORMATION: Primer

<400> SEQUENCE: 73
taacggtacg ttggaggtcg agtt                                          24

<210> SEQ ID NO 74
<211> LENGTH: 24
<212> TYPE: DNA
<213> ORGANISM: Artificial
<220> FEATURE:
```

<223> OTHER INFORMATION: Primer

<400> SEQUENCE: 74
acgaccgcct ccttaaacta cgct                                          24

<210> SEQ ID NO 75
<211> LENGTH: 24
<212> TYPE: DNA
<213> ORGANISM: Artificial
<220> FEATURE:
<223> OTHER INFORMATION: Primer

<400> SEQUENCE: 75
tatcgtgtat tcgttgcggt tagg                                          24

<210> SEQ ID NO 76
<211> LENGTH: 23
<212> TYPE: DNA
<213> ORGANISM: Artificial
<220> FEATURE:
<223> OTHER INFORMATION: Primer

<400> SEQUENCE: 76
aacgatacga acgacgtacc gaa                                           23

<210> SEQ ID NO 77
<211> LENGTH: 24
<212> TYPE: DNA
<213> ORGANISM: Artificial
<220> FEATURE:
<223> OTHER INFORMATION: Primer

<400> SEQUENCE: 77
tacgtgaata agaggacgtt tcgg                                          24

<210> SEQ ID NO 78
<211> LENGTH: 23
<212> TYPE: DNA
<213> ORGANISM: Artificial
<220> FEATURE:
<223> OTHER INFORMATION: Primer

<400> SEQUENCE: 78
aacgatcttc cgaaatacgc caa                                           23

<210> SEQ ID NO 79
<211> LENGTH: 22
<212> TYPE: DNA
<213> ORGANISM: Artificial
<220> FEATURE:
<223> OTHER INFORMATION: Primer

<400> SEQUENCE: 79
tcgtcgaatc ggtatcgtcg tc                                            22

<210> SEQ ID NO 80
<211> LENGTH: 24
<212> TYPE: DNA
<213> ORGANISM: Artificial
<220> FEATURE:
<223> OTHER INFORMATION: Primer

<400> SEQUENCE: 80
acctatatcc acgtcccgaa acct                                          24

<210> SEQ ID NO 81

```
<211> LENGTH: 25
<212> TYPE: DNA
<213> ORGANISM: Artificial
<220> FEATURE:
<223> OTHER INFORMATION: Primer

<400> SEQUENCE: 81
cggttgtagt ttgttcgttc gtttc                                          25

<210> SEQ ID NO 82
<211> LENGTH: 24
<212> TYPE: DNA
<213> ORGANISM: Artificial
<220> FEATURE:
<223> OTHER INFORMATION: Primer

<400> SEQUENCE: 82
ctaacgcctc ataactcctc gcgt                                           24

<210> SEQ ID NO 83
<211> LENGTH: 24
<212> TYPE: DNA
<213> ORGANISM: Artificial
<220> FEATURE:
<223> OTHER INFORMATION: Primer

<400> SEQUENCE: 83
gcgtcgattc gggagtagta tcgt                                           24

<210> SEQ ID NO 84
<211> LENGTH: 24
<212> TYPE: DNA
<213> ORGANISM: Artificial
<220> FEATURE:
<223> OTHER INFORMATION: Primer

<400> SEQUENCE: 84
ataccgtaaa tccgcgctac ttcc                                           24

<210> SEQ ID NO 85
<211> LENGTH: 24
<212> TYPE: DNA
<213> ORGANISM: Artificial
<220> FEATURE:
<223> OTHER INFORMATION: Primer

<400> SEQUENCE: 85
cgttgaggtc gaatgaagcg tagt                                           24

<210> SEQ ID NO 86
<211> LENGTH: 23
<212> TYPE: DNA
<213> ORGANISM: Artificial
<220> FEATURE:
<223> OTHER INFORMATION: Primer

<400> SEQUENCE: 86
aaccgaaact aaacacgacg caa                                            23

<210> SEQ ID NO 87
<211> LENGTH: 24
<212> TYPE: DNA
<213> ORGANISM: Artificial
<220> FEATURE:
<223> OTHER INFORMATION: Primer

<400> SEQUENCE: 87
```
aagcgtatag ttcgaggatt gcga                                        24

<210> SEQ ID NO 88
<211> LENGTH: 23
<212> TYPE: DNA
<213> ORGANISM: Artificial
<220> FEATURE:
<223> OTHER INFORMATION: Primer

<400> SEQUENCE: 88
ccgcgtcact tactcctcta cga                                         23

<210> SEQ ID NO 89
<211> LENGTH: 24
<212> TYPE: DNA
<213> ORGANISM: Artificial
<220> FEATURE:
<223> OTHER INFORMATION: Primer

<400> SEQUENCE: 89
cgttgggtgc gtaggaaggt tagt                                        24

<210> SEQ ID NO 90
<211> LENGTH: 22
<212> TYPE: DNA
<213> ORGANISM: Artificial
<220> FEATURE:
<223> OTHER INFORMATION: Primer

<400> SEQUENCE: 90
gaccgaccct aaacaacccg ct                                          22

<210> SEQ ID NO 91
<211> LENGTH: 22
<212> TYPE: DNA
<213> ORGANISM: Artificial
<220> FEATURE:
<223> OTHER INFORMATION: Primer

<400> SEQUENCE: 91
gttgcgggat agcgttgtga tt                                          22

<210> SEQ ID NO 92
<211> LENGTH: 24
<212> TYPE: DNA
<213> ORGANISM: Artificial
<220> FEATURE:
<223> OTHER INFORMATION: Primer

<400> SEQUENCE: 92
accattatca atactccgat cgcc                                        24

<210> SEQ ID NO 93
<211> LENGTH: 24
<212> TYPE: DNA
<213> ORGANISM: Artificial
<220> FEATURE:
<223> OTHER INFORMATION: Primer

<400> SEQUENCE: 93
tttgtttgtt aagggcgtta tcgt                                        24

<210> SEQ ID NO 94
<211> LENGTH: 22
<212> TYPE: DNA
<213> ORGANISM: Artificial
<220> FEATURE:

<223> OTHER INFORMATION: Primer

<400> SEQUENCE: 94
ccgcgactac tctaaccaac cc                                    22

<210> SEQ ID NO 95
<211> LENGTH: 23
<212> TYPE: DNA
<213> ORGANISM: Artificial
<220> FEATURE:
<223> OTHER INFORMATION: Primer

<400> SEQUENCE: 95
gggcgttgag tttagttcgg aga                                   23

<210> SEQ ID NO 96
<211> LENGTH: 24
<212> TYPE: DNA
<213> ORGANISM: Artificial
<220> FEATURE:
<223> OTHER INFORMATION: Primer

<400> SEQUENCE: 96
acgaacacaa ccgaatcaac gtaa                                  24

<210> SEQ ID NO 97
<211> LENGTH: 22
<212> TYPE: DNA
<213> ORGANISM: Artificial
<220> FEATURE:
<223> OTHER INFORMATION: Primer

<400> SEQUENCE: 97
ggcgttggtt gttagagcga tg                                    22

<210> SEQ ID NO 98
<211> LENGTH: 24
<212> TYPE: DNA
<213> ORGANISM: Artificial
<220> FEATURE:
<223> OTHER INFORMATION: Primer

<400> SEQUENCE: 98
gactcaaact cactcaccga cgac                                  24

<210> SEQ ID NO 99
<211> LENGTH: 24
<212> TYPE: DNA
<213> ORGANISM: Artificial
<220> FEATURE:
<223> OTHER INFORMATION: Primer

<400> SEQUENCE: 99
ggtgcgattt aggatttagg acgg                                  24

<210> SEQ ID NO 100
<211> LENGTH: 24
<212> TYPE: DNA
<213> ORGANISM: Artificial
<220> FEATURE:
<223> OTHER INFORMATION: Primer

<400> SEQUENCE: 100
gcgaccgaaa ctcactaaca acaa                                  24

<210> SEQ ID NO 101

```
<211> LENGTH: 24
<212> TYPE: DNA
<213> ORGANISM: Artificial
<220> FEATURE:
<223> OTHER INFORMATION: Primer

<400> SEQUENCE: 101
gcgatttggg tcgttaggga atag                                          24

<210> SEQ ID NO 102
<211> LENGTH: 25
<212> TYPE: DNA
<213> ORGANISM: Artificial
<220> FEATURE:
<223> OTHER INFORMATION: Primer

<400> SEQUENCE: 102
acctctccgt aacttcacgc aactt                                         25

<210> SEQ ID NO 103
<211> LENGTH: 22
<212> TYPE: DNA
<213> ORGANISM: Artificial
<220> FEATURE:
<223> OTHER INFORMATION: Primer

<400> SEQUENCE: 103
ggtagtcgcg gtcgtttacg tt                                            22

<210> SEQ ID NO 104
<211> LENGTH: 24
<212> TYPE: DNA
<213> ORGANISM: Artificial
<220> FEATURE:
<223> OTHER INFORMATION: Primer

<400> SEQUENCE: 104
acgaacaaac gacaaatcga atca                                          24

<210> SEQ ID NO 105
<211> LENGTH: 24
<212> TYPE: DNA
<213> ORGANISM: Artificial
<220> FEATURE:
<223> OTHER INFORMATION: Primer

<400> SEQUENCE: 105
tacgttgagt tcggtttggt ttgt                                          24

<210> SEQ ID NO 106
<211> LENGTH: 23
<212> TYPE: DNA
<213> ORGANISM: Artificial
<220> FEATURE:
<223> OTHER INFORMATION: Primer

<400> SEQUENCE: 106
cgcgcctccg taatctaaac taa                                           23

<210> SEQ ID NO 107
<211> LENGTH: 24
<212> TYPE: DNA
<213> ORGANISM: Artificial
<220> FEATURE:
<223> OTHER INFORMATION: Primer

<400> SEQUENCE: 107
```
gtgcgtgttg acgttatgtt gcgt                      24

<210> SEQ ID NO 108
<211> LENGTH: 22
<212> TYPE: DNA
<213> ORGANISM: Artificial
<220> FEATURE:
<223> OTHER INFORMATION: Primer

<400> SEQUENCE: 108
cgcccgacct cgactcttta ct                        22

<210> SEQ ID NO 109
<211> LENGTH: 24
<212> TYPE: DNA
<213> ORGANISM: Artificial
<220> FEATURE:
<223> OTHER INFORMATION: Primer

<400> SEQUENCE: 109
cggcgatttc ggggatttta gggc                      24

<210> SEQ ID NO 110
<211> LENGTH: 25
<212> TYPE: DNA
<213> ORGANISM: Artificial
<220> FEATURE:
<223> OTHER INFORMATION: Primer

<400> SEQUENCE: 110
gaccgctctt ctaaaaaatc ccgcg                     25

<210> SEQ ID NO 111
<211> LENGTH: 23
<212> TYPE: DNA
<213> ORGANISM: Artificial
<220> FEATURE:
<223> OTHER INFORMATION: Primer

<400> SEQUENCE: 111
acgttcgggg tgtagcggtc gtc                       23

<210> SEQ ID NO 112
<211> LENGTH: 24
<212> TYPE: DNA
<213> ORGANISM: Artificial
<220> FEATURE:
<223> OTHER INFORMATION: Primer

<400> SEQUENCE: 112
ccccaatact aaatcacgac gccg                      24

<210> SEQ ID NO 113
<211> LENGTH: 25
<212> TYPE: DNA
<213> ORGANISM: Artificial
<220> FEATURE:
<223> OTHER INFORMATION: Primer

<400> SEQUENCE: 113
ggtcggcgtc gtgatttagt attgg                     25

<210> SEQ ID NO 114
<211> LENGTH: 24
<212> TYPE: DNA
<213> ORGANISM: Artificial
<220> FEATURE:

```
<223> OTHER INFORMATION: Primer

<400> SEQUENCE: 114
actacgacga cgaaactcca acga                                          24

<210> SEQ ID NO 115
<211> LENGTH: 26
<212> TYPE: DNA
<213> ORGANISM: Artificial
<220> FEATURE:
<223> OTHER INFORMATION: Primer

<400> SEQUENCE: 115
tgtggtgatt ttggggattt tagggt                                        26

<210> SEQ ID NO 116
<211> LENGTH: 27
<212> TYPE: DNA
<213> ORGANISM: Artificial
<220> FEATURE:
<223> OTHER INFORMATION: Primer

<400> SEQUENCE: 116
ccaaccactc ttctaaaaaa tcccaca                                       27

<210> SEQ ID NO 117
<211> LENGTH: 25
<212> TYPE: DNA
<213> ORGANISM: Artificial
<220> FEATURE:
<223> OTHER INFORMATION: Primer

<400> SEQUENCE: 117
gatgtttggg gtgtagtggt tgttg                                         25

<210> SEQ ID NO 118
<211> LENGTH: 26
<212> TYPE: DNA
<213> ORGANISM: Artificial
<220> FEATURE:
<223> OTHER INFORMATION: Primer

<400> SEQUENCE: 118
ctccacccca atactaaatc acaaca                                        26

<210> SEQ ID NO 119
<211> LENGTH: 1300
<212> TYPE: DNA
<213> ORGANISM: Homo sapiens

<400> SEQUENCE: 119
gtcaggtggg ctactccacc agggaggcct tctccccacc cctggcccag ggcccttccg    60
gatttccaga gaattctgga accaagacct tccccttcct caccagggac ctccttgctc   120
cagggcctcc cgagcgcctg ccgtgaggc agggcccaga aggccagggc gggatccagg    180
tggctggcct cacccactgg gacgtgccca acctggagac attgcaccag gtagggctgc   240
accgctctcc gagacccgc cccgtgcttc cacttggggg cggggaccct gcacctgacc    300
agcccttcgc cccgccttcc agatgctgaa actggggagg agcaaccggg ccaccgccgc   360
caccgccatg aaccagcgca gctcccgctc gcatgccctg gtcacgctga cgctgcgcgc   420
ggcgtctcca ccgcgcgctc caggcaccgc aggtaccacg gccggtgcct gagccctgcg   480
gagtctccag agcacccgag gcccggcctt cccccatgtc gggctcgctc gcccctctag   540
```

```
gcacgctgca cctggtggac ctggcgggat ccgaacgcgc acggaaggca ggggcggccg    600 gccccgccgcg gggagaccca gacggcgccc ggcgcctgcg ggaggcccag accataaacc    660
gctcgctgct ggcgctagga ggcgtgatgg ccgcactgcg ggcccaccgg ccgcacgtgc    720
ccttccgcga ctcgcagctc acgcgactgc tgcagccggc gctgggccca ggcaccaccg    780
cggtgctgct gctgcaggtg ggcgccgggg cggggcaggt gtgtgcgtgc cggtcgccgc    840
ccacccgggc ccgcccaccc gcgcctcttg cccgcagatc tccacgcggc cggaggatct    900
cggggagaca gtctgctccc tcaagttcgc cgaccgagtg ggtcaagtgg agctggggcc    960
agcccggcgc gcagggtcc cgcgctcctc cgggacgccc tcttccctca gcaccgacac   1020
tccgctcacc gggacccct gcaccccta ccgtccct ggcagtcctc catgcccag   1080 tcccgacaac ggctcgggct cggctctcgc gcccgcagag ggcctgcccc tctagtcctg   1140
ggtcgcggcc ctgcccatgg ggtctcaggc caggtctctg ctggcagagg cggtagtaaa   1200
gtccctgtac cccgtctccc agggcacaag ctccctagcc tctttggatc cattgcccct   1260
gagctcccag agtcacccct ccacctccgc agccagtgaa                         1300

<210> SEQ ID NO 120
<211> LENGTH: 1300
<212> TYPE: DNA
<213> ORGANISM: Homo sapiens

<400> SEQUENCE: 120
ttcactggct gcggaggtgg aggggtgact ctgggagctc aggggcaatg gatccaaaga     60
ggctagggag cttgtgccct gggagacggg gtacagggac tttactaccg cctctgccag    120
cagagacctg gcctgagacc ccatgggcag ggccgcgacc caggactaga ggggcaggcc    180
ctctgcgggc gcgagagccg agcccgagcc gttgtcggga ctggggcatg gaggactgcc    240
aggggacggc gtaggggtgc aggggtccc ggtgagcgga gtgtcggtgc tgagggaaga    300
aggcgtcccg gaggagcgcg ggaccctgcg gcgccgggct ggcccagct ccacttgacc    360 cactcggtcg gcgaacttga gggagcagac tgtctccccg agatcctccg gccgcgtgga    420
gatctgcggg caagaggcgc gggtgggcgg gcccgggtgg gcggcgaccg gcacgcacac    480
acctgccccg ccccggcgcc cacctgcagc agcagcaccg cggtggtgcc tgggcccagc    540
gccggctgca gcagtcgcgt gagctgcgag tcgcggaagg gcacgtgcgg ccggtgggcc    600
cgcagtgcgg ccatcacgcc tcctagcgcc agcagcgagc ggtttatggt ctgggcctcc    660
cgcaggcgcc gggcgccgtc tgggtctccc cgcggcgggc cggccgcccc tgccttccgt    720
gcgcgttcgg atcccgccag gtccaccagg tgcagcgtgc ctagaggggc gagcgagccc    780
gacatggggg aaggccgggc ctcgggtgct ctggagactc cgcagggctc aggcaccggc    840
cgtggtacct gcggtgcctg gagcgcgcgg tggagacgcc gcgcgcagcg tcagcgtgac    900
cagggcatgc gagcgggagc tgcgctggtt catggcggtg gcggcggtgg cccggttgct    960
cctccccagt ttcagcatct ggaaggcggg gcgaagggct ggtcaggtgc agggtccccg   1020 ccccaagtg gaagcacggg gcgggtctc ggagagcggt gcagccctac ctggtgcaat   1080
gtctccaggt tgggcacgtc ccagtgggtg aggccagcca cctggatccc gccctggcct   1140
tctgggccct gcctcacggc caggcgctcg ggaggccctg gagcaaggag gtccctggtg   1200
agaaagggga aggtcttggt tccagaattc tctggaaatc cggaagggcc ctgggccagg   1260 ggtgggaga aggcctccct ggtggagtag cccacctgac                         1300

<210> SEQ ID NO 121
```

```
<211> LENGTH: 550
<212> TYPE: DNA
<213> ORGANISM: Homo sapiens

<400> SEQUENCE: 121
aacacgtgta ggttgttgga attacattaa cgaatgaatg agcaaaacct tctaaaccac    60
cgaccaatga aacccgata cagaaaatcg ctgtcatgag taagttagca ctcctgaaga   120
gtttgaatac tgaactggcc agagtctgcg cgccgacgcc cccaggtgg ccggagtgac   180
ccggagcagg cgtggctgtc tctcagaccc gcgcgttggg cccgaacagt tgtccccac   240
gcagctccca tataaggcgg gcccctcccc tgcccagcc agctaggtcg ccgcgctggc   300
tccctggcgg cttctcaaac caacccgccg ctactgcgca tgcttggcaa gctcgcccgc   360
tccttaatat cctgctccgg ctgttcctgc cacccgttgg tcaaattcgc acccagctct   420
gctccagaca gagggaaaac ccagtgattt ccgggctcta gaaacaaagg gaggctatga   480
ttccctgctg gccctagggg tccagggaag gttatggaaa gataattctt tgtgtaagcg   540
ggttgcgtac                                                          550

<210> SEQ ID NO 122
<211> LENGTH: 550
<212> TYPE: DNA
<213> ORGANISM: Homo sapiens

<400> SEQUENCE: 122
gtacgcaacc cgcttacaca aagaattatc tttccataac cttccctgga cccctagggc    60
cagcagggaa tcatagcctc cctttgtttc tagagcccgg aaatcactgg gttttccctc   120
tgtctggagc agagctgggt gcgaatttga ccaacgggtg gcaggaacag ccggagcagg   180
atattaagga gcgggcgagc ttgccaagca tgcgcagtag cggcgggttg gtttgagaag   240
ccgccaggga ccagcgcgg cgacctagct ggctggggca ggggaggggc ccgccttata   300
tgggagctgc gtgggacaa actgttcggg cccaacgcgc gggtctgaga cagccacg   360
cctgctccgg gtcactccgg ccacctgggg ggcgtcggcg cgcagactct ggccagttca   420
gtattcaaac tcttcaggag tgctaactta ctcatgacag cgattttctg tatcggggtt   480
tcattggtcg gtggtttaga aggttttgct cattcattcg ttaatgtaat ccaacaacc   540
tacacgtgtt                                                          550

<210> SEQ ID NO 123
<211> LENGTH: 550
<212> TYPE: DNA
<213> ORGANISM: Homo sapiens

<400> SEQUENCE: 123
cagccgaggg gcgcgcctgg ctgatgtgtg gttgaatgga gagcggccca accctcctcc    60
ttcctcctct tcttctcccc gccctgacac ccgggcctca aacttcaacc aaagcccgtg   120
ccctttttcaa tttacccccc tcgatcaaaa tgagccattc ttgtctgtcc tccgcggcgg   180
cccattgtct ggcgtgatag gtttgcagat ttgacagctg gcgcacgca gatttgattc   240
aaactcggtc tccccgagag atgaacttgg acatcagcaa agatcccgag cactgccggc   300
tggctcctag accggtctcc cgacccagtg tagacttcgg tgccccggc gcccccggc   360
gtgcgggaag gggagcgtgt gtcaggcgtg ggggcgggg ggtgagcagc acgactggga   420
accagcggtc ccaggggttg gggcgaaggg ctgtgtacat gttaggcttt ttttgttgtt   480
gttaatttac tctcgaaaca gccaaaatgg aggtcagctt ataaattttc taaagccagg   540
```

```
tctggccggg                                                                550
```

<210> SEQ ID NO 124
<211> LENGTH: 550
<212> TYPE: DNA
<213> ORGANISM: Homo sapiens

<400> SEQUENCE: 124

```
cccggccaga cctggcttta gaaaatttat aagctgacct ccattttggc tgtttcgaga    60
gtaaattaac aacaacaaaa aaagcctaac atgtacacag cccttcgccc caacccctgg   120
gaccgctggt tcccagtcgt gctgctcacc ccccgccccc cacgcctgac acacgctccc   180
cttcccgcac gccggggggc gcccggggca ccgaagtcta cactgggtcg ggagaccggt   240
ctaggagcca gccggcagtg ctcgggatct ttgctgatgt ccaagttcat ctctcgggga   300
gaccgagttt gaatcaaatc tgcgtgcgcc cagctgtcaa atctgcaaac ctatcacgcc   360
agacaatggg ccgccgcgga ggacagacaa gaatggctca ttttgatcga gggggggtaaa  420
ttgaaaaggg cacgggcttt ggttgaagtt tgaggcccgg gtgtcagggc ggggagaaga   480
agaggaggaa ggaggagggt tgggccgctc tccattcaac cacacatcag ccaggcgcgc   540
ccctcggctg                                                          550
```

<210> SEQ ID NO 125
<211> LENGTH: 1050
<212> TYPE: DNA
<213> ORGANISM: Homo sapiens

<400> SEQUENCE: 125

```
agaaactgag gtcggagtgg gggcgtgacc aggccagcct aaggccgctg cactaatgag    60
aagctgagct ctcagatttt tgcctccctg tccctgccaa gtcgctgttt cctgggacaa   120
gagggagcct cactgaaacg aactccggtc tcagggaca gaatcctgaa accctggctc    180
tggggtccgg ggcaggggtg cgctgcctca ggacagacgg tgaaactgag gtccagagcc   240
ggacatccac cgcctgcgga gggaacgaga acgcggcgcg tcctgccttg cgggccgagc   300
ggcgccagag ccgcctcctc ccgcccccg cgctagatcc ccccgccccg tctttgccct    360
cgcgacgccg ccacctccgg aacaagccat ggtggcggcg acggtggcag cggcgtggct   420
gctcctgtgg gctgcggcct gcgcgcagca ggagcaggac ttctacgact caaggcggt   480
caacatccgg ggcaaactgg tgtcgctgga gaagtaccgc ggatcggtga gtgcgcgggg   540
tctgcggcg ccgctgggcc cggcctcgcc ctggcggggc ctgctgggga cgcccgcag    600
cccggtcccc cgcgcggtgt ggctccgagg acgctccagc cgcgcggccg ccaaaccccg   660
gccccgccc cgctcggccg tgacctctgg cgcggcgccc catcccgcg cccggccgg     720
cccggcccgc ggctacgtgg cacggccttg gcgcggagga acccgaagcg ctcgcagtcg   780
gcgcccactt cgctaccggc accttttgggc agcggggtcc agaccttcgc cgggaggccg   840
ggcaccactg cccagccttt gccattcacg ggtgaaaaaa gtaaccgtag catcgtgcgg   900
cctttccctc tcccgtcctc attttctgca tctggaacgg ggagtggctg attcggagtc   960
cagtgaagaa cactgtggag atcaatgtgc agggcagaga gagagttatt tcagatgcac  1020
ggagacctca cacggatcat ccctgggaga                                   1050
```

<210> SEQ ID NO 126
<211> LENGTH: 1050
<212> TYPE: DNA
<213> ORGANISM: Homo sapiens

<400> SEQUENCE: 126

```
tctcccaggg atgatccgtg tgaggtctcc gtgcatctga ataactctc tctctgccct      60
gcacattgat ctccacagtg ttcttcactg gactccgaat cagccactcc ccgttccaga    120
tgcagaaaat gaggacggga gagggaaagg ccgcacgatg ctacggttac ttttttcacc    180
cgtgaatggc aaaggctggg cagtggtgcc cggcctcccg gcgaaggtct ggacccccgct  240
gcccaaaggt gccggtagcg aagtgggcgc cgactgcgag cgcttcgggt tcctccgcgc    300
caaggccgtg ccacgtagcc gcgggccggg ccgggccggg cgcgggatgg gggcgccgcg    360
ccagaggtca cggccgagcg gggcggggc cggggtttgg cggccgcgcg gctggagcgt     420
cctcggagcc acaccgcgcg ggggaccggg ctgcggggcg tccccagcag gccccgccag    480
ggcgaggccg ggcccagcgg cgccgccaga ccccgcgcac tcaccgatcc gcggtacttc    540
tccagcgaca ccagtttgcc ccggatgttg accgccttga agtcgtagaa gtcctgctcc    600
tgctgcgcgc aggccgcagc ccacaggagc agccacgccg ctgccaccgt cgccgccacc    660
atggcttgtt ccggaggtgg cggcgtcgcg agggcaaaga cggggcgggg ggatctagcg    720
cggggggcgg gaggaggcgg ctctggcgcc gctcggcccg caaggcagga cgcgccgcgt    780
tctcgttccc tccgcaggcg gtggatgtcc ggctctggac ctcagtttca ccgtctgtcc    840
tgaggcagcg caccccctgcc ccggaccca gagccagggt ttcaggattc tgtcccctga    900
gaccggagtt cgtttcagtg aggctccctc ttgtcccagg aaacagcgac ttggcaggga    960
cagggaggca aaaatctgag agctcagctt ctcattagtg cagcggcctt aggctggcct   1020
ggtcacgccc ccactccgac ctcagtttct                                    1050
```

<210> SEQ ID NO 127
<211> LENGTH: 550
<212> TYPE: DNA
<213> ORGANISM: Homo sapiens

<400> SEQUENCE: 127

```
ttctcttacg atctggcttt actctcacgc gcacagccga gtccctgggg acccagcaga     60
ggtccgaagc ggagcggggc ggggcggggc tacggaagct ggcgaggccg agcccctcct    120
agtgcttccg gaccttgctc cctgaacact cggaggtggc ggtggatctt actccttcca    180
gccagtgagg atccagcaac ctgctccgtg cctcccgcgc ctgttggttg aagtgacga    240
ccttgaagat cggccggttg gaagtgacga ccttgaagat cggcgggcgc agcggggccg    300
aggggggcggg tctggcgcta ggtccagccc ctgcgtgccg gaacccag aggaggtcgc     360
agttcagccc agctgaggcc tgtctgcaga atcgacacca accagcatca tgtccatgac    420
actggggtac tgggacatcc gcggggtgag tgagggtccg ctgcactgtg gaccgggcg    480
cgtgggcggg aagtgccgag cggctgggga ccggctctag ggacggttcc ctccttaggg    540
ctatctctca                                                           550
```

<210> SEQ ID NO 128
<211> LENGTH: 550
<212> TYPE: DNA
<213> ORGANISM: Homo sapiens

<400> SEQUENCE: 128

```
tgagagatag ccctaaggag ggaaccgtcc ctagagccgg tccccagccg ctcggcactt     60
cccgcccacg cgcccggtcc cacagtgcag cggaccctca ctcacccgc ggatgtccca    120
gtaccccagt gtcatggaca tgatgctggt tggtgtcgat tctgcagaca ggcctcagct    180
```

```
gggctgaact gcgacctcct ctggggttcc cggcacgcag gggctggacc tagcgccaga    240
cccgccccct cggccccgct gcgcccgccg atcttcaagg tcgtcacttc caaccggccg    300
atcttcaagg tcgtcacttc caaccaacag gcgcgggagg cacggagcag gttgctggat    360
cctcactggc tggaaggagt aagatccacc gccacctccg agtgttcagg agcaaggtc    420 cggaagcact aggaggggct cggcctcgcc agcttccgta gccccgcccc gccccgctcc    480
gcttcggacc tctgctgggt ccccagggac tcggctgtgc gcgtgagagt aaagccagat    540
cgtaagagaa                                                          550

<210> SEQ ID NO 129
<211> LENGTH: 550
<212> TYPE: DNA
<213> ORGANISM: Homo sapiens

<400> SEQUENCE: 129
tcttgaattg ggggcggagg taaaaaaaaa aaaaaagtcc tcactgtggg aagctataaa    60
aagcaaagag gactggggag agagcagaga gagagaaagc gggagcccgc ggcgagcgta    120
gcgcaagtcc gctccctagg catcgctgcg ctggcagcga ttcgctgtct cttgtgagtc    180
aggggacaac gcttcggggc aactgtgagt gcgcgtgtgg gggacctcga ttctcttcag    240
atctcgagga ttcggtccgg ggacgtctcc tgatccccta ctaaagcgcc tgctaacttt    300
gaaaaggagc actgtgtcct gcaaagtttg acacataaag gataggaaaa gagaggagag    360
aaaagcaact gagttgaagg agaaggagct gatgcgggcc tcctgatcaa ttaagaggag    420
agttaaaccg ccgagatccc ggcgggacca aggaggtgcg gggcaagaag gaacggaagc    480
ggtgcgatcc acagggctgg gttttcttgc accttgggtc acgcctcctt ggcgagaaag    540
cgcctcgcat                                                          550

<210> SEQ ID NO 130
<211> LENGTH: 550
<212> TYPE: DNA
<213> ORGANISM: Homo sapiens

<400> SEQUENCE: 130
atgcgaggcg ctttctcgcc aaggaggcgt gacccaaggt gcaagaaaac ccagccctgt    60
ggatcgcacc gcttccgttc cttcttgccc cgcacctcct tggtcccgcc gggatctcgg    120
cggtttaact ctcctcttaa ttgatcagga ggcccgcatc agctccttct ccttcaactc    180
agttgctttt ctctcctctc ttttcctatc ctttatgtgt caaactttgc aggacacagt    240
gctccttttc aaagttagca ggcgctttag tagggggatca ggagacgtcc ccggaccgaa    300
tcctcgagat ctgaagagaa tcgaggtccc ccacacgcgc actcacagtt gcccgaagc    360 gttgtcccct gactcacaag agacagcgaa tcgctgccag cgcagcgatg cctagggagc    420
ggacttgcgc tacgctcgcc gcgggctccc gctttctctc tctctgctct ctccccagtc    480
ctctttgctt tttatagctt cccacagtga ggactttttt tttttttta cctccgcccc    540 caattcaaga                                                          550

<210> SEQ ID NO 131
<211> LENGTH: 550
<212> TYPE: DNA
<213> ORGANISM: Homo sapiens

<400> SEQUENCE: 131
cgattggctg caagggtctc ggcttggccg cggattggtc acacccgagg gcttgaaagg    60
```

-continued

```
tggctgggag cgccggacac ctcagacgga cggtggccag ggatcaggca gcggctcagg    120
cgaccctgag tgtgccccca ccccgccatg gcccggctgc tgcaggcgtc ctgcctgctt    180
tccctgctcc tggccggctt cgtctcgcag agccggggac aagagaagtc gaaggtgagt    240
gagcctccgg gccgggggcc gggagaaaaa acctagcccc tcggtgtcca cgcgctcagtg   300 caatgcaccc cttttcccag gctccccgcc agatgggcaa tccccaggtg cgagagacct    360
cctgaacccc ttttgccgcc ccctccgccg ccgggacccc gccccgaccc gtcgtcgtct    420
cgtagttcca tctgttggag agccgagacc tggtgcttca ggcgggcaga atgactaagg    480
gaggaaggtc tctctccccg agctcgcact ttctccccac tgccacctcg agggtcgcct    540
tgctacatct                                                           550

<210> SEQ ID NO 132
<211> LENGTH: 550
<212> TYPE: DNA
<213> ORGANISM: Homo sapiens

<400> SEQUENCE: 132
agatgtagca aggcgaccct cgaggtggca gtggggagaa agtgcgagct cggggagaga     60
gaccttcctc ccttagtcat tctgcccgcc tgaagcacca ggtctcggct ctccaacaga    120
tggaactacg agacgacgac ggtcgggggc ggggtcccgg cggcgagggg ggcggcaaaa    180
ggggttcagg aggtctctcg cacctgggga ttgcccatct ggcggggagc ctgggaaaag    240
gggtgcattg cactgagcgc tggacaccga ggggctaggt ttttctccc ggccccggc     300 ccggaggctc actcaccttc gacttctctt gtccccggct ctgcgagacg aagccggcca    360
ggagcaggga aagcaggcag gacgcctgca gcagccgggc catggcgggg tgggggcaca    420
ctcagggtcg cctgagccgc tgcctgatcc ctggccaccg tccgtctgag gtgtccggcg    480
ctcccagcca cctttcaagc cctcgggtgt gaccaatccg cggccaagcc gagacccttg    540
cagccaatcg                                                           550

<210> SEQ ID NO 133
<211> LENGTH: 550
<212> TYPE: DNA
<213> ORGANISM: Homo sapiens

<400> SEQUENCE: 133
aggggaactg gtatctccac agtaattact agagcagctc tggggaacgg agggttggct     60
aaggaagaaa agctcccca acccttgggg cgagggagcc ttctctcaat ggagccccc     120 caactcccct ccaccccca ccagtcttcc aggaaagagg aatacctac ccggcagggc    180 tgcgaaggaa gggaaatcc aaccagagcg aaagtcgcac gcggacagct ctgccagccc    240
ttggaggcat ccggcggtca cccacgggac aaagcgcggc tgcgggagcg cgcgcggggc    300
attccggacc cgcgtcgagc tccgctctag aggggcggc gggcggcgac aagccggaga    360
gaggaagggc caaggagcac ggccctcctg tcggcaccat cagcgggaga gtggcgagcg    420
gacgcctaga cggaggggcc ctactcagac cccatcgagc cagttcccaa gcttttccct    480
ccgacctgct ccctcccggg gcgcgtgagg gtgcgggtcg ggggtgaacc tggtgttggg    540
gaaagtgatt                                                           550

<210> SEQ ID NO 134
<211> LENGTH: 550
<212> TYPE: DNA
<213> ORGANISM: Homo sapiens
```

```
<400> SEQUENCE: 134
aatcactttc cccaacacca ggttcacccc cgacccgcac cctcacgcgc cccgggaggg    60
agcaggtcgg agggaaaagc ttgggaactg gctcgatggg gtctgagtag ggcccctccg   120
tctaggcgtc cgctcgccac tctcccgctg atggtgccga caggagggcc gtgctccttg   180
gcccttcctc tctccggctt gtcgccgccc gccgccccct ctagagcgga gctcgacgcg   240
ggtccggaat gccccgcgcg cgctcccgca gccgcgcttt gtcccgtggg tgaccgccgg   300
atgcctccaa gggctggcag agctgtccgc gtgcgacttt cgctctggtt ggatttcccc   360
ttccttcgca gccctgccgg gtagggtatt cctctttcct ggaagactgg tggggggtgg   420
aggggagttg gggggggctcc attgagagaa cgctccctcg ccccaagggt tgggggagct   480
tttcttcctt agccaaccct ccgttcccca gagctgctct agtaattact gtggagatac   540
cagttcccct                                                         550

<210> SEQ ID NO 135
<211> LENGTH: 2800
<212> TYPE: DNA
<213> ORGANISM: Homo sapiens

<400> SEQUENCE: 135
cgggcaaaaa tggagagcag gcagaggtca catcctcctc ctcttcctca cgctcccggg    60
ctgcgtgccc acaggggcac agccctgtgc gcggtgccac cgggggccat caggctgggt   120
tagaggaagg cccgacctcc gcgcagcaaa gaaaacaaac acagatgtgt ttggctggga   180
ccgggaggga gaaagtggcc cccttccccc gcccgcgcgc tccccgggc gtgaggctct   240 ccgggcggcg cggggcgcgg gcgaggctga cagtccccgg cggcccctcc tccccacgg   300 ggtgcgcgcc tggcccggcc cagccccctc tccgggtttt cccgggtgc tctcctcgct   360 ttctctttgt ctctgctgtt ctttctcggg ctcccgggtt cccacccgcc tgtgctctcc   420
ctctcgggcg tccgggccgg ttccctttaa cttcttctt tcccggggtg aaaactttgc   480
tcggagctgg cggcagctcg cggacgttat tggccggcgc cccgcccggc ggccccgccc   540
cccgcccccg cgctcccctc cgcccctcac tcccagcgcg agtggcggcg gcggcggagc   600 cttcggggc gagcgcgcgt gtgtgtgagt gcgcgccggc cagcgtgagt gtgtgtgcgc   660
cccgggcgcg ggcagggcag cactccgagc tcggcgggag cggcgggagc cgggcggccg   720
cgtagtcact cggcgagag aggcggcggc ggggccggga ccggggctgg ggctggggca   780
gcggcggccg cgccgggcat ggagctggca agcccgcgct gaggcgggac gcgcctgcta   840
gcagcgagcg agaggctctc cggcgaccgg cgcgcgggct cccccggaggg gccaggcaaa   900 cttttctttc tcttttgccc cctccagagg taaagtcccg aacgcggact ttccggcggg   960
gacgcgatcg gggggcatct gagagggacc ccgggctgcg agacgaaggg gcgcgggccg  1020
tgcagagtcg gggtcccccca gctctcctgc gcccgaaact tggggtgcga gggggctgg  1080 tcgcggacgg ggagaccggc tcaggcatgc ccctcgggcg gcgtgggggc ggcggtggcg  1140
gggaagcaga gcgttctccc gccggcgggg aagaagggg cgcgagcggt gcggacttgg  1200
agggccccgg cttcgccgcc cgcgggactt tggggagag aggcgggcag tcggctgcgg  1260
ggtgggtgcc caggaagccg ggcgttctcc cgcatctccg ctcgccaccc cgccgagagc  1320
tggagggcgc ggggcgggct ggctgagcgc agctcccttc tctccgcagg cgccttctgc  1380
ggcaggcgga cagatcctcg gcgcggcagg gccggggcaa gctggacgca gcatgatgcg  1440
cgcagtgtgg gaggcgctgg cggcgctggc ggcggtggcg tgcctggtgg gcgcggtgcg  1500
```

| | |
|---|---|
| cggcgggccc gggctcagca tgttcgcggg ccaggcggcg cagcccgatc cctgctcgga | 1560 |
| cgagaacggc cacccgcgcc gctgcatccc ggactttgtc aatgcggcct tcggcaagga | 1620 |
| cgtgcgcgtg tccagcacct gcggccggcc cccggcgcgc tactgcgtgg tgagcgagcg | 1680 |
| cggcgaggag cggctgcgct cgtgccacct ctgcaacgcg tccgacccca agaaggcgca | 1740 |
| cccgcccgcc ttcctcaccg acctcaacaa cccgcacaac ctgacgtgct ggcagtccga | 1800 |
| gaactacctg cagttcccgc acaacgtcac gctcacactg tccctcggca agaagttcga | 1860 |
| agtgacctac gtgagcctgc agttctgctc gccgcggccc gagtccatgg ccatctacaa | 1920 |
| gtccatggac tacgggcgca cgtgggtgcc cttccagttc tactccacgc agtgccgcaa | 1980 |
| gatgtacaac cggccgcacc gcgcgcccat caccaagcag aacgagcagg aggccgtgtg | 2040 |
| caccgactcg cacaccgaca tgcgcccgct ctcgggcggc ctcatcgcct tcagcacgct | 2100 |
| ggacgggcgg ccctcggcgc acgacttcga caactcgccc gtgctgcagg actgggtcac | 2160 |
| ggccacagac atccgcgtgg ccttcagccg cctgcacacg ttcggcgacg agaacgagga | 2220 |
| cgactcggag ctggcgcgcg actcgtactt ctacgcggtg tccgacctgc aggtgggcgg | 2280 |
| ccggtgcaag tgcaacggcc acgcggcccg ctgcgtgcgc gaccgcgacg acagcctggt | 2340 |
| gtgcgactgc aggcacaaca cggccggccc ggagtgcgac cgctgcaagc ccttccacta | 2400 |
| cgaccggccc tggcagcgcg ccacagcccg cgaagccaac gagtgcgtgg gtgagtgggg | 2460 |
| tgcggcggcg gagccggcgg cgggtggggc cgcgggcggg agctgctggg cctcgcagcg | 2520 |
| gcgagttcat aggagcgcgg gtcgagggaa cggcgggagg cgcgttcgcc gatgcccggg | 2580 |
| acccgggagg gctcagagca ggtccactcg ctcgcgtggc gctcgtggtg gacgcccgaa | 2640 |
| tttgcgccca gtgctctctg cgaagccaag aagcagcagg agaaatgttc ccgggagggg | 2700 |
| gtttggcaga acatttgcag ataggtctcc gctaaccctg gatccaaacg caaacattca | 2760 |
| ttgccttccc cctcgttggg ttggacgctg ggattcacct | 2800 |

<210> SEQ ID NO 136
<211> LENGTH: 2800
<212> TYPE: DNA
<213> ORGANISM: Homo sapiens

<400> SEQUENCE: 136

| | |
|---|---|
| aggtgaatcc cagcgtccaa cccaacgagg gggaaggcaa tgaatgtttg cgtttggatc | 60 |
| cagggttagc ggagacctat ctgcaaatgt tctgccaaac cccctcccgg gaacatttct | 120 |
| cctgctgctt cttggcttcg cagagagcac tgggcgcaaa ttcgggcgtc caccacgagc | 180 |
| gccacgcgag cgagtggacc tgctctgagc cctcccgggt cccgggcatc ggcgaacgcg | 240 |
| cctcccgccg ttccctcgac ccgcgctcct atgaactcgc cgctgcgagg cccagcagct | 300 |
| cccgcccgcg gccccacccg ccgccggctc cgccgccgca cccactcac ccacgcactc | 360 |
| gttggcttcg cgggctgtgg cgcgctgcca gggccggtcg tagtggaagg gcttgcagcg | 420 |
| gtcgcactcc gggccggccg tgttgtgcct gcagtcgcac accaggctgt cgtcgcggtc | 480 |
| gcgcacgcag cgggccgcgt ggccgttgca cttgcaccgg ccgcccacct gcaggtcgga | 540 |
| caccgcgtag aagtacgagt cgcgcgccag ctccgagtcg tcctcgttct cgtcgccgaa | 600 |
| cgtgtgcagg cggctgaagg ccacgcggat gtctgtggcc gtgacccagt cctgcagcac | 660 |
| gggcgagttg tcgaagtcgt gcgccgaggg ccgcccgtcc agcgtgctga aggcgatgag | 720 |
| gccgcccgag agcgggcgca tgtcggtgtg cgagtcggtg cacacggcct cctgctcgtt | 780 |
| ctgcttggtg atgggcgcgc ggtgcggccg gttgtacatc ttgcggcact gcgtggagta | 840 |

```
gaactggaag ggcacccacg tgcgcccgta gtccatggac ttgtagatgg ccatggactc      900
gggccgcggc gagcagaact gcaggctcac gtaggtcact tcgaacttct tgccgaggga      960
cagtgtgagc gtgacgttgt gcgggaactg caggtagttc tcggactgcc agcacgtcag     1020
gttgtgcggg ttgttgaggt cggtgaggaa ggcgggcggg tgcgccttct tggggtcgga     1080
cgcgttgcag aggtggcacg agcgcagccg ctcctcgccg cgctcgctca ccacgcagta     1140
gcgcgccggg ggccggccgc agtgctggac acgcgcacg tccttgccga aggccgcatt       1200
gacaaagtcc gggatgcagc ggcgcgggtg gccgttctcg tccgagcagg gatcgggctg     1260
cgccgcctgg cccgcgaaca tgctgagccc gggcccgccg cgcaccgcgc ccaccaggca     1320
cgccaccgcc gccagcgccc ccagcgcctc ccacactgcg cgcatcatgc tgcgtccagc     1380 ttgcccggc cctgccgcgc cgaggatctg tccgcctgcc gcagaaggcg cctgcggaga      1440
gaagggagct gcgctcagcc agcccgcccc gcgccctcca gctctcggcg gggtggcgag     1500
cggagatgcg ggagaacgcc cggcttcctg ggcacccacc ccgcagccga ctgcccgcct     1560
ctctccccca aagtcccgcg ggcggcgaag ccggggccct ccaagtccgc accgctcgcg     1620 cccttcttc cccgcccggc gggagaacgc tctgcttccc cgccaccgcc gccccacgc       1680 cgcccgaggg gcatgcctga gccggtctcc ccgtccgcga ccagccccccc tcgcacccca    1740 agtttcgggc gcaggagagc tggggacccc cgactctgca cggcccgcgc ccttcgtct      1800 cgcagcccgg ggtccctctc agatgccccc cgatcgcgtc cccgccggaa agtccgcgtt    1860
cgggacttta cctctggagg gggcaaaaga gaaagaaaag tttgcctggc ccctccgggg    1920
agcccgcgcg ccggtcgccg gagagcctct cgctcgctgc tagcaggcgc gtcccgcctc    1980
agcgcgggct tgccagctcc atgcccggcg cggccgccgc tgccccagcc ccagccccgg    2040
tcccggcccc gccgccgcct ctctcgcccg agtgactacg cggccgcccg gctcccgccg    2100
ctcccgccga gctcggagtg ctgccctgcc gcgcccgggg gcgcacacac actcacgctg   2160
gccggcgcgc actcacacac acgcgcgctc gcccccgaag gctccgccgc cgccgccact   2220
cgcgctggga gtgaggggcg gaggggagcg cggggcgggg gggcggggcc gccggcgggg   2280
gcgccggcca ataacgtccg cgagctgccg ccagctccga gcaaagtttt caccccggga    2340
aagaagaaag ttaaagggaa ccggcccgga cgcccgagag ggagagcaca ggcgggtggg    2400
aacccgggag cccgagaaag aacagcagag acaaagagaa agcgaggaga gcacccgggg    2460
aaaccccgga gagggggctg ggccgggcca ggcgcgcacc ccgtgggggga ggagggccg    2520 ccggggactg tcagcctcgc ccgcgccccg cgccgcccgg agagcctcac gcccggggga    2580
gcgcgcgggc gggggaaggg ggccactttc tccctcccgg tcccagccaa acacatctgt    2640
gtttgttttc tttgctgcgc ggaggtcggg ccttcctcta acccagcctg atggccccg     2700 gtggcaccgc gcacagggct gtgcccctgt gggcacgcag cccgggagcg tgaggaagag    2760
gaggaggatg tgacctctgc ctgctctcca ttttgcccg                            2800
```

<210> SEQ ID NO 137
<211> LENGTH: 1300
<212> TYPE: DNA
<213> ORGANISM: Homo sapiens

<400> SEQUENCE: 137

```
gcagtcctgt gtgactggtg agactcttgt aggggcgttt ctacaacgac gaaacccttc       60
ctaggcactc actccaacag aataacaagc ccattttatt agtatttcgt tttccatgta      120
aagttctgct catacgaata tatttataat tctgattttt ttacggcatt ggggagcaca      180
```

```
ccgacaggct gctgaacggt ggctggagat tcgagggaaa acgaagttcg ccgaggcggc    240
ctcgggcggg caggtcccgg gctccatcac agggcacacg cggctaccag ggacgcagcc    300
ccccaacaca cacacacaca cacacacaca cacacacaca cacacacaca ccctctccca    360
ctcatgcctg gcaacccagc agaaacttcg gactggggca aaacaagccc gggcccggc     420 ggcacgcggg gctaggcgcg ttcccgccag tacctggtcg cgaggccgct cgcggggtgc    480
cctgcgtgcc ccccactccc gcagcccgcg ccctgctcgc tcactgtggg ggcgcagcgg    540
ccaggcttct ctgtttgttg tttaaagaaa tcctagggcg ggcgagcggc ggcatctagg    600 ggaggggcg cagccagaat tcccttccag caagcgcgtg aggggcattc tcaacgcaaa     660
accagaccca gaaagtagtg accagccctc ctcggattac ccttcattgg ctcctcccct    720 gctccccca ccctccagat ttgcataaaa aaggccaaga aaactctggc tgtgccccag     780
caacggctca ttctgctccc ccgggtcgga gcccccgga gctgcgcgcg ggcttgcagc     840
gcctcgcccg cgctgtcctc ccggtgtccc gcttctccgc gccccagccg ccggctgcca    900
gcttttcggg gccccgagtc gcacccagcg aagagagcgg gcccgggaca agctcgaact    960
ccggccgcct cgcccttccc cggctccgct ccctctgccc cctcggggtc gcgcgcccac   1020
gatgctgcag ggccctggct cgctgctgct gctcttcctc gcctcgcact gctgcctggg   1080
ctcggcgcgc gggctcttcc tctttggcca gcccgacttc tcctacaagc gcagcaattg   1140
caagcccatc cctgccaacc tgcagctgtg ccacggcatc gaataccaga acatgcggct   1200
gcccaacctg ctgggccacg agaccatgaa ggaggtgctg gagcaggccg gcgcttggat   1260
cccgctggtc atgaagcagt gccacccgga caccaagaag                         1300

<210> SEQ ID NO 138
<211> LENGTH: 1300
<212> TYPE: DNA
<213> ORGANISM: Homo sapiens

<400> SEQUENCE: 138
cttcttggtg tccgggtggc actgcttcat gaccagcggg atccaagcgc cggcctgctc     60
cagcacctcc ttcatggtct cgtggcccag caggttgggc agccgcatgt tctggtattc    120
gatgccgtgg cacagctgca ggttggcagg gatgggcttg caattgctgc gcttgtagga    180
gaagtcgggc tggccaaaga ggaagagccc gcgcgccgag cccaggcagc agtgcgaggc    240
gaggaagagc agcagcagcg agccaggggcc ctgcagcatc gtgggcgcgc gaccccgagg    300
gggcagaggg agcggagccg gggaagggcg aggcggccgg agttcgagct tgtcccgggc    360
ccgctctctt cgctgggtgc gactcggggc cccgaaaagc tggcagccgg cggctggggc    420
gcggagaagc gggacaccgg gaggacacgc gggcgaggc gctgcaagcc cgcgcgcagc     480
tccggggggc tccgacccgg gggagcagaa tgagccgttg ctggggcaca gccagagttt    540
tcttggcctt ttttatgcaa atctggaggg tgggggagc aagggaggag ccaatgaagg     600
gtaatccgag gagggctggt cactactttc tgggtctggt tttgcgttga gaatgcccct    660
cacgcgcttg ctgaaggga attctggctg cgccccctcc cctagatgcc gccgctcgcc    720
cgccctagga tttcttaaa caacaaacag agaagcctgg ccgctgcgcc cccacagtga    780
gcgagcaggg cgcgggctgc gggagtgggg ggcacgcagg gcaccccgcg agcggcctcg    840
cgaccaggta ctggcgggaa cgcgcctagc cccgcgtgcc gccggggccc gggcttgttt    900
tgccccagtc cgaagtttct gctggggttgc caggcatgag tgggagaggg tgtgtgtgtg    960
tgtgtgtgtg tgtgtgtgtg tgtgtgtgtg tgtgttgggg ggctgcgtcc ctggtagccg   1020
```

| | |
|---|---|
| cgtgtgccct gtgatggagc ccgggacctg cccgcccgag gccgcctcgg cgaacttcgt | 1080 |
| tttccctcga atctccagcc accgttcagc agcctgtcgg tgtgctcccc aatgccgtaa | 1140 |
| aaaaatcaga attataaata tattcgtatg agcagaactt tacatggaaa acgaaatact | 1200 |
| aataaaatgg gcttgttatt ctgttggagt gagtgcctag gaagggtttc gtcgttgtag | 1260 |
| aaacgcccct acaagagtct caccagtcac acaggactgc | 1300 |

<210> SEQ ID NO 139
<211> LENGTH: 1034
<212> TYPE: DNA
<213> ORGANISM: Homo sapiens

<400> SEQUENCE: 139

| | |
|---|---|
| gctgcctttg ttctttgact actcagccaa ttcaggtctg agctgttctt cgacgccgcc | 60 |
| ctagatgcga tgatgaaggt caggtgcccg catcccaccc accgtcccct cgcaggggcc | 120 |
| ctaggaccca cccagatccc gcctgtctct ctccccgcgg caggttccgc tgcatcgtgc | 180 |
| acccttttccg cgagaagctg accctgcgga aggcgctcgt caccatcgcc gtcatctggg | 240 |
| ccctggcgct gctcatcatg tgtccctcgg ccgtcacgct gaccgtcacc cgtgaggagc | 300 |
| accacttcat ggtggacgcc cgcaaccgct cctacccgct ctactcctgc tgggaggcct | 360 |
| ggcccgagaa gggcatgcgc agggtctaca ccactgtgct cttctcgcac atctacctgg | 420 |
| cgccgctggc gctcatcgtg gtcatgtacg cccgcatcgc gcgcaagctc tgccaggccc | 480 |
| cgggcccggc cccggggggc gaggaggctg cggaccccgcg agcatcgcgg cgcagagcgc | 540 |
| gcgtggtgca catgctggtc atggtggcgc tgttcttcac gctgtcctgg ctgccgctct | 600 |
| gggcgctgct gctgctcatc gactacgggc agctcagcgc gccgcagctg cacctggtca | 660 |
| ccgtctacgc cttcccctttc gcgcactggc tggccttctt caacagcagc gccaacccca | 720 |
| tcatctacgg ctacttcaac gagaacttcc gccgcggctt ccaggccgcc ttccgcgccc | 780 |
| gcctctgccc gcgcccgtcg gggagccaca aggaggccta ctccgagcgg cccggcgggc | 840 |
| ttctgcacag gcgggtcttc gtggtggtgc ggcccagcga ctccgggctg ccctctgagt | 900 |
| cgggccctag cagtggggcc cccaggcccg gccgcctccc gctgcggaat gggcgggtgg | 960 |
| ctcaccacgg cttgcccagg gaagggcctg gctgctccca cctgcccctc accattccag | 1020 |
| cctgggatat ctga | 1034 |

<210> SEQ ID NO 140
<211> LENGTH: 1034
<212> TYPE: DNA
<213> ORGANISM: Homo sapiens

<400> SEQUENCE: 140

| | |
|---|---|
| tcagatatcc caggctggaa tggtgagggg caggtgggag cagccaggcc cttccctggg | 60 |
| caagccgtgg tgagccaccc gcccattccg cagcgggagg cggccgggcc tgggggcccc | 120 |
| actgctaggg cccgactcag agggcagccc ggagtcgctg gccgcacca ccacgaagac | 180 |
| ccgcctgtgc agaagcccgc cgggccgctc ggagtaggcc tccttgtggc tccccgacgg | 240 |
| gcgcgggcag aggcgggcgc ggaaggcggc ctggaagccg cggcggaagt tctcgttgaa | 300 |
| gtagccgtag atgatgggt tggcgctgct gttgaagaag gccagccagt gcgcgaaggg | 360 |
| gaaggcgtag acggtgacca ggtgcagctg cggcgcgctg agctgcccgt agtcgatgag | 420 |
| cagcagcagc gcccagagcg gcagccagga cagcgtgaag aacagcgcca ccatgaccag | 480 |
| catgtgcacc acgcgcgctc tgcgccgcga tgctcgcggg tccgcagcct cctcgccccc | 540 |

```
ggggccggg cccggggcct ggcagagctt gcgcgcgatg cgggcgtaca tgaccacgat    600
gagcgccagc ggcgccaggt agatgtgcga gaagagcaca gtggtgtaga ccctgcgcat    660
gcccttctcg ggccaggcct cccagcagga gtagagcggg taggagcggt tgcgggcgtc    720
caccatgaag tggtgctcct cacgggtgac ggtcagcgtg acggccgagg acacatgat    780 gagcagcgcc agggcccaga tgacggcgat ggtgacgagc gccttccgca gggtcagctt    840
ctcgcggaaa gggtgcacga tgcagcgaaa cctgccgcgg ggagagagac aggcgggatc    900
tgggtgggtc ctagggcccc tgcgagggga cggtgggtgg gatgcgggca cctgaccttc    960
atcatcgcat ctagggcggc gtcgaagaac agctcagacc tgaattggct gagtagtcaa   1020
agaacaaagg cagc                                                      1034

<210> SEQ ID NO 141
<211> LENGTH: 800
<212> TYPE: DNA
<213> ORGANISM: Homo sapiens

<400> SEQUENCE: 141
agaaaggtaa tatttggagg cctccgaggg acgggcaggg gaaagaggga tcctctgacc     60 cagcggggc tggaggatg gctgttttg ttttttccca cctagcctcg gaatcgcgga      120
ctgcgcccag tgacggactc aaacttaccc ttccctctga ccccgccgta ggatgacgcc    180
tcaaccctcg ggtgcgccca ctgtccaagt gacccgtgag acggagcggt ccttccccag    240
agcctcggaa gacgaagtga cctgcccac gtccgccccg cccagcccca ctcgcacacg    300
ggggaactgc gcagaggcgg aagagggagg ctgccgaggg gccccgagga agctccgggc    360
acggcgcggg ggacgcagcc ggcctaagag cgagttggca ctgagcaagc agcgacggag    420
tcggcgaaag aaggccaacg accgcgagcg caatcgaatg cacaacctca actcggcact    480
ggacgccctg cgcggtgtcc tgcccacctt cccagacgac gcgaagctca ccaagatcga    540
gacgctgcgc ttcgcccaca actacatctg ggcgctgact caaacgctgc gcatagcgga    600
ccacagcttg tacgcgctgg agccgccggc gccgcactgc ggggagctgg gcagcccagg    660
cggttccccc ggggactggg ggtccctcta ctccccagtc tcccaggctg gcagcctgag    720
tcccgccgcg tcgctggagg agcgacccgg gctgctgggg gccacctttt ccgcctgctt    780
gagcccaggc agtctggctt                                                800

<210> SEQ ID NO 142
<211> LENGTH: 800
<212> TYPE: DNA
<213> ORGANISM: Homo sapiens

<400> SEQUENCE: 142
aagccagact gcctgggctc aagcaggcgg aaaaggtggc cccagcagc ccgggtcgct      60 cctccagcga cgcggcggga ctcaggctgc cagcctggga gactgggggag tagagggacc    120 cccagtcccc gggggaaccg cctgggctgc ccagctcccc gcagtgcggc gccggcggct    180
ccagcgcgta caagctgtgg tccgctatgc gcagcgtttg agtcagcgcc cagatgtagt    240
tgtgggcgaa gcgcagcgtc tcgatcttgg tgagcttcgc gtcgtctggg aaggtgggca    300
ggacaccgcg cagggcgtcc agtgccgagt tgaggttgtg cattcgattg cgctcgcggt    360
cgttggcctt ctttcgccga ctccgtcgct gcttgctcag tgccaactcg ctcttaggcc    420
ggctgcgtcc cccgcgccgt gcccggagct tcctcggggc ccctcggcag cctccctctt    480
ccgcctctgc gcagttcccc cgtgtgcgag tggggctggg cggggcggac gtggggcagg    540
```

```
tcacttcgtc ttccgaggct ctggggaagg accgctccgt ctcacgggtc acttggacag      600
tgggcgcacc cgagggttga ggcgtcatcc tacggcgggg tcagagggaa gggtaagttt      660
gagtccgtca ctgggcgcag tccgcgattc cgaggctagg tgggaaaaaa caaaaacagc      720
catcctccca gccccgctg gtcagagga tccctctttc cctgcccgt ccctcggagg         780 cctccaaata ttacctttct                                                   800
```

<210> SEQ ID NO 143
<211> LENGTH: 1550
<212> TYPE: DNA
<213> ORGANISM: Homo sapiens

<400> SEQUENCE: 143

```
taaagcttcc ccagagggag gaaaggtggg ggcggggcgg ctgctgaggc ccaggatata       60
agggctggag gtgctgcttt caggcctggc cagcccacca tgcacgccca ctgcctgccc      120
ttccttctgc acgcctggtg ggccctactc caggcgggtg ctgcgacggt ggccactgcg      180
ctcctgcgta cgcgggggca gccctcgtcg ccatcccctc tggcgtacat gctgagcctc      240
taccgcgacc cgctgccgag ggcagacatc atccgcagcc tacaggcaga aggtaggcag      300
tgccgcgtgc cgcgccctgc tgggcacccc cggggcgcct ccgccgcgtc cagccagcgg      360
actcgggaag tgctgtgggt tggggctgc ggctccgagc cgggtttgca gccgcccggg       420
cgtcccgagc ccagggccta gctctgcggg tgtctccgcg tcagcaggct cggggtgcag      480
cgttggtggc tgggggcgta tccacggccg agtcgggaag ggattctagc gttcaggtg       540 tgtcctcgac ggggaccatt gtctctgggt tttggtttgg gattgcgcgg agcgcagcgc      600
ggaagggtgg gagcttctaa tctccagtct tgtgaagttg cttatcccgg agcctgggtc      660 tgccgcatctg taggataggt gtaataaata acacctcgcc tatcagactg tggaaagcgc     720
gagatgacaa tgcgcgcgaa acgctcagcg cagtacccgg cacagccaca gtcaacggtc     780
gttggtatta ctgtaatggt ttggtcttgg cgattttttt ttctttctgc gagtgagggt     840
gaatgggtcc cggggtgtga cgtcgggagt atcggcagct gagctggtaa catcggggat     900
tcgggctcac ggcccggaga tcaggatgg gctgtcccga agtcgcgaac tgtggcagcc      960
ttgggtcctc cagccgcgcc ggggaagtgt caagtgtctc gcttaacccc gggttcgggg    1020
ccatgatttg caggggagtg ggtgtcaagg acggcaggga tctgagggta tcgccctcga    1080
ggacctggca gcgcgttctg ggcacccagc gcggcgagca ggtgggtgct gcggagaggg    1140 agcccccttcc gcgcctcaat ccacattctg ccgcctgggc agccgcggcc gcccacgcct    1200
ccctccgcct gcgggggcca gacggccctc cctggggccg gggcgcaatc cacaaacgct    1260
aatctgatcc gacctgccgc ctgccgccc cttgtgacct ggtgccgggg gcccttcgct     1320
cccgcgcctg gggtcagaca gccggtgacc ctctccggaa gggtcatctg ggaccagcc     1380 agaccagggg acaccctcgg gggcggggca atgagaaatt tgctgagtg ctcggcccct    1440 caaccgaaaa gcggccgggg atgggagggg gcaaagaagg gagggagcgc ttttccagtt    1500
cactcccttc tggaaagttc gagatgtgtg cggtgatgga caggcatctg               1550
```

<210> SEQ ID NO 144
<211> LENGTH: 1550
<212> TYPE: DNA
<213> ORGANISM: Homo sapiens

<400> SEQUENCE: 144

```
cagatgcctg tccatcaccg cacacatctc gaactttcca gaagggagtg aactggaaaa       60
```

```
gcgctccctc ccttctttgc cccctcccat ccccggccgc ttttcggttg aggggccgag      120
cactccagca aatttctcat tgccccgccc ccgagggtgt ccctggtct ggctggtccc       180 cagatgaccc ttccggagag ggtcaccggc tgtctgaccc caggcgcggg agcgaagggc      240
ccccggcacc aggtcacaag gggcgggcag gcggcaggtc ggatcagatt agcgtttgtg     300
gattgcgccc cggccccagg gagggccgtc tggcccccgc aggcggaggg aggcgtgggc     360
ggccgcggct gcccaggcgg cagaatgtgg attgaggcgc ggaaggggct ccctctccgc     420
agcacccacc tgctcgccgc gctgggtgcc cagaacgcgc tgccaggtcc tcgagggcga    480
taccctcaga tccctgccgt ccttgacacc cactcccctg caaatcatgg ccccgaaccc     540
ggggttaagc gagacacttg acacttcccc ggcgcggctg gaggacccaa ggctgccaca     600
gttcgcgact tcgggacagc ccatcccctga tctccgggcc gtgagcccga atccccgatg   660
ttaccagctc agctgccgat actcccgacg tcacaccccg gacccattc accctcactc      720 gcagaaagaa aaaaaaatcg ccaagaccaa accattacag taataccaac gaccgttgac    780
tgtggctgtg ccgggtactg cgctgagcgt ttcgcgcgca ttgtcatctc gcgcttttcca  840 cagtctgata ggcgaggtgt tatttattac acctatccta cagatgcgca gacccaggct    900
ccgggataag caacttcaca agactggaga ttagaagctc ccaccttcc gcgctgcgct    960 ccgcgcaatc ccaaaccaaa acccagagac aatggtcccc gtcgaggaca cccctgaac   1020 gctagaatcc cttcccgact cggccgtgga tacgcccca gccaccaacg ctgcaccccg    1080
agcctgctga cgcggagaca cccgcagagc taggccctgg gctcgggacg cccggggcgc   1140
tgcaaacccg gctcggagcc gcagcccca acccacagca cttcccgagt ccgctggctg    1200
gacgcggcgg aggcgccccg ggggtgccca gcagggcgcg gcacgcggca ctgcctacct    1260
tctgcctgta ggctgcggat gatgtctgcc ctcggcagcg ggtcgcggta gaggctcagc   1320
atgtacgcca gaggggatgg cgacgagggc tgccccgcg tacgcaggag cgcagtggcc    1380
accgtcgcag cacccgcctg gagtagggcc caccaggcgt gcagaaggaa gggcaggcag   1440
tgggcgtgca tggtgggctg gccaggcctg aaagcagcac ctccagccct tatatcctgg   1500
gcctcagcag ccgccccgcc cccaccttc ctccctctgg ggaagcttta              1550

<210> SEQ ID NO 145
<211> LENGTH: 1050
<212> TYPE: DNA
<213> ORGANISM: Homo sapiens

<400> SEQUENCE: 145
accccggggc gtgggagaag cccctgcttg gggggaccgt ctgctgttta ggggctcccc      60
ttcgacacgt gggaggcaaa agtgcagagc gcaccatcat ccagctccgg ccgcactgca    120
cagcgaggcc ggcccggagc ccggatgctg ggctcggtcc cgccgaggct cggcctggct    180
gtaaagcaga gggggcgag ggaagccggg ccagcgggtg tcgcgggtag ccggcgtccg     240
ggacggggtg tggcgcccag agcgctgctg cctctcgcag ccaggaggct ggatgtcggg    300
tttgggtgtc ttccagaagg agccgcacta gcgacgaggg aagaggaact ggcttcccgg   360
gcagtctccc ccgccccaaa cttttcctcc tcgcggaggg tgggcgggcg agggaggaa    420 gcgcagccgg ggaacgtggc gcccgcgttc ctccgcccg ggggctgcgg ctgggctgag    480
tgtgtcttta aatctgagcc ccccgcccct cgcggtgggg ccgggactcg cggtccgggc   540
gggggcgggc gcggtgattg gcggccgggt cgggtccgcc cctcggcgtt gggtagcggg   600
gcgctgggga gcagcgcggc gcgcacgggc cggggcgcgc aggtcccgtc gccggtgagc   660
```

```
acgggctccc tctcgcgtgg cctcgccggg tccgcctggc ctgcccacct ccggagccac    720
ctctgccccc gcatgggctg gcgaagttgg gaggagcgag ctggagccag agcgcgcgcc    780
gggcgcgccc cgtcgctgcc tgactcggcg cccgcagttc gggcgcagca cgccggccgc    840
aggagcacgg atgccccccg gagccgcggg ctggcaggta ccgaagtgtc ctgccctggg    900
gctggcgagg ggagggcaaa tctggaatcc cccgggcacc cccagcccg aggctgctcc     960 agacaccaac tccccatcct ttggagaggt gaggtcctgg gccttcaccc cacacccgct   1020
caggattggt ccctgggagg caagagggac                                    1050

<210> SEQ ID NO 146
<211> LENGTH: 1050
<212> TYPE: DNA
<213> ORGANISM: Homo sapiens

<400> SEQUENCE: 146
gtccctcttg cctcccaggg accaatcctg agcgggtgtg gggtgaaggc ccaggacctc     60
acctctccaa aggatgggga gttggtgtct ggagcagcct cgggctgggg ggtgcccggg    120
ggattccaga tttgccctcc cctcgccagc cccaggcag gacacttcgg tacctgccag     180
cccgcggctc cggggggcat ccgtgctcct gcggccggcg tgctgcgccc gaactgcggg    240
cgccgagtca ggcagcgacg gggcgcgccc ggcgcgcgct ctggctccag ctcgctcctc    300
ccaacttcgc cagcccatgc gggggcagag gtggctccgg aggtgggcag gccaggcgga    360 ccggcgagg ccacgcgaga gggagcccgt gctcaccggc gacggaccct gcgcgccccg     420
gcccgtgcgc gccgcgctgc tccccagcgc cccgctaccc aacgccgagg ggcggacccg    480
acccggccgc caatcaccgc gcccgccccc gccggaccg cgagtccgg ccccaccgcg      540 aggggcgggg ggctcagatt taaagacaca ctcagcccag ccgcagcccc cgggcgggag    600
gaacgcgggc gccacgttcc ccggctgcgc ttcctccctc cgcccgccca ccctccgcga    660
ggaggaaaag tttgggcgg gggagactgc ccggaagcc agttcctctt ccctcgtcgc      720
tagtgcggct ccttctggaa gacacccaaa cccgacatcc agcctcctgg ctgcgagagg    780
cagcagcgct ctgggcgcca caccccgtcc cggacgccgg ctaccgcga cacccgctgg     840 cccggcttcc ctcgcccccc tctgctttac agccaggccg agcctcggcg ggaccgagcc    900
cagcatccgg gctccgggcc ggcctcgctg tgcagtgcgg ccggagctgg atgatggtgc    960
gctctgcact tttgcctccc acgtgtcgaa ggggagcccc taaacagcag acggtccccc   1020
caagcagggg cttctcccac gccccggggt                                    1050

<210> SEQ ID NO 147
<211> LENGTH: 550
<212> TYPE: DNA
<213> ORGANISM: Homo sapiens

<400> SEQUENCE: 147
ccgaaaggac ccgtcccagc gagccagggc ctggttttcc ttccgcagaa ggcggaggga     60
ccggagcggg cgcgggcacc cctgggctct gaggggcgcg ctctgaaggg cggcggactt    120
cagggccatg ctggctgtcc ccagaaagca ggagcccgaa accgcggggc caacgaacgc    180
ccacattctc tgctacaacc tcgccactcc cctgcgcctc tccccttgcc ccctgccccc    240
acaggtaacg cccagaacga gtgcttctcc cggtgggta ctgaggagcc tgggctgcag     300
ctgccgagcc gccacagcca cgctgagccc ggctggcct gcacactggc gccaccgct      360 ggcggggagc gggactgacg cgctcctctc cctctcctcc agcccagatc acggaggcgc    420
```

```
ggagctccat ctcctgccct gggcgagggg agtgagggag acaaagactt tgggcacaac    480
acccaccaca tagaacctat tctctagttg ggaaacaagt caaggcaaag gcgcacagag    540
tgaaagtcag                                                           550
```

<210> SEQ ID NO 148
<211> LENGTH: 550
<212> TYPE: DNA
<213> ORGANISM: Homo sapiens

<400> SEQUENCE: 148

```
ctgactttca ctctgtgcgc ctttgccttg acttgtttcc caactagaga ataggttcta     60
tgtggtgggt gttgtgccca aagtctttgt ctccctcact cccctcgccc agggcaggag    120
atggagctcc gcgcctccgt gatctgggct ggaggagagg gagaggagcg cgtcagtccc    180
gctccccgcc aggcggtggc gccagtgtgc aggccaggcc gggctcagcg tggctgtggc    240
ggctcggcag ctgcagccca ggctcctcag taccccaccg ggagaagcac tcgttctggg    300
cgttacctgt gggggcaggg gcaaggggga gaggcgcagg ggagtggcga ggttgtagca    360
gagaatgtgg gcgttcgttg gccccgcggt ttcgggctcc tgctttctgg ggacagccag    420
catggccctg aagtccgccg cccttcagag cgcgcccctc agagcccagg ggtgcccgcg    480
cccgctccgg tccctccgcc ttctgcggaa ggaaaaccag gccctggctc gctgggacgg    540
gtcctttcgg                                                           550
```

<210> SEQ ID NO 149
<211> LENGTH: 1550
<212> TYPE: DNA
<213> ORGANISM: Homo sapiens

<400> SEQUENCE: 149

```
ccctccagtt tgctggagtt gccggattac attgttcctc cccggtgtgc ggcgtgagct     60
tcccccaccc gagcgcccaa caagtctcct ttctccagcc tgcgcgctgc tgcgctgagg    120
ccgaatgaag cgcagcacgg tgcgggcagc ccgaggcccc gaggctgggc tctgtctgtc    180
tgggactgcg ccgtgcccag cctcggtccc ctctctgtgg gtaaggatgg ttgagtccag    240
cctccacggc agcggctcct tgtgccacta gcagcccttc ttctgcgctc tccgccttt     300 ctctctagac tggatctctc ctccccccg cgccccctc cccgcatctc ccactcgctg    360
gctctctctc cagctgcctc ctctccaggt ctctcctggc tgcgcgcgct cctctccccg    420
cttctccccc tcccgcagcc tcgccgcctt ggtgccttcc tgcccggctc ggccggcgct    480
cgtccccggc cccggccccg ccagcccggg tctccgcgct cggagcagct cagccctgca    540
gtggctcggg acccgatgct atgagaggga agcgagccgg gcgcccagac cttcaggagg    600
cgtcggatgc gcggcgggtc ttgggaccgg gctctctctc cggctcgcct tgccctcggg    660
tgattatttg gctccgctca tagccctgcc ttcctcggag gagccatcgg tgtcgcgtgc    720
gtgtggagta tctgcagaca tgactgcgtg gaggagattc cagtcgctgc tcctgcttct    780
cgggctgctg gtgctgtgcg cgaggctcct cactgcagcg aagggtaaga cggacttgct    840
cctggccggg gaggcggtag agccctcgga ggccccgtgt gcggacgcga gtgtgcgttt    900
tggggaccgc agggtacgga gtggccgcct ctgcccggcg ctgctccatc gccgaagctc    960
ggggaacgcg atgcacggga gggagcttcc atcgcgctct cccagccct cctgggcccc   1020 cgccccaccc cgccattcct tcccctctc ttgggctcac aggagagatc tctttttctc   1080
ggcagtacag ggtgtcaagg agaaaggaac ccaatacgag ttgggctgga actgtgctcc   1140
```

```
gccggggcgg tgttgcctcc tccgagacgt ggactccacg ggtcggggtg gctgaggggc   1200
agttcccagg actttctccc cggacccgac gcgcctggga aagcgtcccg ggtgaagccg   1260
gcctggaaag ttcgggctct ctacgggggt tttggtacca ataggcaaag gtctccgccg   1320
gcccggcctc ctcgcacccca tacacccccat tcctcctctc ctccttccct ctccaacgtc  1380
ctcagccggc gaggagtagc tgcctctaga aggtcgcccc cgctttcctc tcccccggac   1440
ttcgctcctt gcaagttgta aggtgttggc aaggtgcgtg aaacaggcta ggagttctgg   1500
accggcttcc aagtcagata cattcactgt gggcgcacgg gtatcctcct              1550

<210> SEQ ID NO 150
<211> LENGTH: 1550
<212> TYPE: DNA
<213> ORGANISM: Homo sapiens

<400> SEQUENCE: 150
aggaggatac ccgtgcgccc acagtgaatg tatctgactt ggaagccggt ccagaactcc     60
tagcctgttt cacgcacctt gccaacacct tacaacttgc aaggagcgaa gtccggggga   120
gaggaaagcg ggggcgacct tctagaggca gctactcctc gccggctgag gacgttggag   180
agggaaggag gagaggagga atggggtgta tgggtgcgag gaggccgggc cggcggagac   240 cttttgcctat tggtaccaaa accccgtag agagcccgaa cttccaggc cggcttcacc    300 cgggacgctt tcccaggcgc gtcgggtccg gggagaaagt cctgggaact gcccctcagc   360
caccccgacc cgtggagtcc acgtctcgga ggaggcaaca ccgccccggc ggagcacagt   420
tccagcccaa ctcgtattgg gttcctttct ccttgacacc ctgtactgcc gagaaaaaga   480
gatctctcct gtgagcccaa gagaggggga aggaatggcg gggtggggcg ggggcccagg   540
agggctgggg agagcgcgat ggaagctccc tcccgtgcat cgcgttcccc gagcttcggc   600
gatggagcag cgccgggcag aggcggccac tccgtaccct gcggtcccca aaacgcacac   660
tcgcgtccgc acacggggcc tccgagggct ctaccgcctc cccggccagg agcaagtccg   720 tcttacccctt cgctgcagtg aggagcctcg cgcacagcac cagcagcccg agaagcagga   780
gcagcgactg gaatctcctc cacgcagtca tgtctgcaga tactccacac gcacgcgaca   840
ccgatggctc ctccgaggaa ggcagggcta tgagcggagc caaataatca cccgagggca   900
aggcgagccg gagagagagc ccggtcccaa gacccgccgc gcatccgacg cctcctgaag   960
gtctgggcgc ccggctcgct tccctctcat agcatcgggt cccgagccac tgcagggctg   1020
agctgctccg agcgcggaga cccgggctgg cggggccggg gccggggacg agcgccggcc   1080
gagccgggca ggaaggcacc aaggcggcga ggctgcggga gggggagaag cggggagagg   1140
agcgcgcgca gccaggagag acctggagag gaggcagctg gagagagagc cagcgagtgg   1200
gagatgcggg gaggggggcg cggggggggag gagagatcca gtctagagag aaaaggcgga   1260
gagcgcagaa gaagggctgc tagtggcaca aggagccgct gccgtggagg ctggactcaa   1320
ccatccttac ccacagagag gggaccgagg ctgggcacgg cgcagtccca gacagacaga   1380
gcccagcctc ggggcctcgg gctgcccgca ccgtgctgcg cttcattcgg cctcagcgca   1440
gcagcgcgca ggctggagaa aggagacttg ttgggcgctc gggtggggga agctcacgcc   1500
gcacaccggg gaggaacaat gtaatccggc aactccagca aactggaggg              1550

<210> SEQ ID NO 151
<211> LENGTH: 1050
<212> TYPE: DNA
<213> ORGANISM: Homo sapiens
```

<400> SEQUENCE: 151

```
tcctccttga gcagggagac catcggggtg caacctggcc ggggcgggga ggaggtgcag      60
ggcattgcca gagcgggcct gtccatgggc aagggacagc gacctcctgg gccaggacat     120
gtgagagctg cgcaggcctg ggcccggcgt ggcggaggtg cgcagagcg gccagaagag      180
ggcgccagag agccaggcgc ggcccgcgga ggagcccgcg ccggcccta tacccagctc      240
cgcgccgcgc ggaccaccg agcccgcgct cagacgcccc agctccaccg agaggccgct      300
cgggccgtgt ccttcctctt ctccaggtgc aggcagagcc cccgagccat ggccagccct     360
tccggcagct ccgaagccac tggcaagccc cgaggcaggg atggccggcc caggagggag     420
gaggacgacg tccctcccga agagaagagg ctggggctgt agctggaggg gggaagcgca     480
cagcccgagg actgcgagaa cggggaggac gcgccgcggc caggcaggga ggagaccggc     540
acccagacag gtggcgaccg cagaggagta agtgacgcgg gcgctggggt ccggggggtgc    600
cggggggcgcc ggtaggggcg gcgggaggct ccgtggccgg ccccgggttg aagttggtat    660
tttagcggca actccgaagg gcgcggagtg acagcgcgtg acggcctccg agacgccagc    720
tgccgcttct cggctgtgtg gctttgactt cctgattctc ccacgacgtc gctggctggg    780
agacccactg gactctgcgg ctggccaaaa agagaggggc agccccgcgt cctggggggcc    840
cctagcaggg gaagtggcgg gtgttgcgct gggcatcctg tctggggcat ctgtctggga    900
ccctgttggt gcctctcacc tggcgagggg ccagtggtgg gggtaggggg gaagtccctg    960
gcgccaggct tggccaagcc ctgcttggct ggactgcggg ctggcggcgc tcacccagct   1020
cctcacctgt cccgcatctt cctgtttttc                                    1050
```

<210> SEQ ID NO 152
<211> LENGTH: 1050
<212> TYPE: DNA
<213> ORGANISM: Homo sapiens

<400> SEQUENCE: 152

```
gaaaaacagg aagatgcggg acaggtgagg agctgggtga gcgccgccag cccgcagtcc      60
agccaagcag ggcttggcca agcctggcgc cagggacttc cccctaccc ccaccactgg     120
cccctcgcca ggtgagaggc accaacaggg tcccagacag atgccccaga caggatgccc    180
agcgcaacac ccgccacttc ccctgctagg ggccccagg acgcggggct gccctctct      240
ttttggccag ccgcagagtc cagtgggtct cccagccagc gacgtcgtgg gagaatcagg    300
aagtcaaagc cacacagccg agaagcggca gctggcgtct cggaggccgt cacgcgctgt   360
cactccgcgc ccttcggagt tgccgctaaa ataccaactt caacccgggg ccggccacgg    420
agcctcccgc cgcccctacc ggcgcccccg gcaccccgg accccagcgc ccgcgtcact    480
tactcctctg cggtcgccac ctgtctgggt gccggtctcc tccctgcctg gccgcggcgc    540
gtcctccccg ttctcgcagt cctcgggctg tgcgcttccc ccctcagct acagcccag     600
cctcttctct tcgggaggga cgtcgtcctc ctccctcctg ggcggccat ccctgcctcg     660
gggcttgcca gtggcttcgg agctgccgga agggctggcc atggctcggg gctctgcct    720
gcacctggag aagaggaagg acacggcccg agcggcctct cggtggagct ggggcgtctg    780
agcgcgggct cggtgggtcc gcggcggcg gagctgggta taggggccgg gcggggctcc    840
tccgcgggcc gcgcctggct ctctggcgcc ctcttctggc cgctctcgcg cacctccgcc   900
acgccgggcc caggcctgcg cagctctcac atgtcctggc ccaggaggtc gctgtccctt   960
gcccatggac aggcccgctc tggcaatgcc ctgcacctcc tccccgcccc ggccaggttg  1020
```

```
caccccgatg gtctccctgc tcaaggagga                                      1050
```

<210> SEQ ID NO 153
<211> LENGTH: 1300
<212> TYPE: DNA
<213> ORGANISM: Homo sapiens

<400> SEQUENCE: 153

```
cccagtaagt caccaattaa gtctttacta cttaaaagca aaatccacct atgtcctgaa      60
cagtatccac tttacgagcc tcattatatg tacgagataa aattcagaaa taaataaata    120
tacatgtata cgtatacaaa tatatttcaa attaaaaaat acttttagat agtggtatgt    180
attacattta gaaattaata acgaagtaaa ttatgggatg tcatccacgc ctgtcccaaa    240
ggtaccgaat ttataaatca tctcaggtgc ggagcaggac aggttgaaaa taggaatgac    300
atgaacccgc gcggaacagc tgccggcgcg gtgtccaggg cggcaccccg cccggtcccg    360
gcccctccag ccctgggccc gaccctact acgcctctgc ctcgacgcga acgcggagcc    420
cgagcgcgcg tcacgccgtg tggggccgaa gaggctgcta cccagaggcg gagtgcgggc    480
tcgcgagggt ccccaccega ctctcgctcc cgccagcacc tacggactcg cgtcccccgcc   540
gcgcgccgac tcgggagcag caccgccccc ggcacaggag cctcacgcgc ctcttaccta    600
acaggaagtt gggtggaagc agcgcggacc cacggcacac cgaacgcact ccaacagaac    660
ccgacgcaga cacgcgcttt caaccggcgg agacactggc agggccagaa acgcgcgcag    720
cggggggcggg aggtcggtaa gctccccgcc cctgcccgag accccgcccc ggcccggccc    780
cgcctttttc tctgcctccc ctccctgcac gtacgggccc cgcccctcgc gcgacgtttt    840
ttgttgaccc ggaaacggat tctccggagc cgaggtccgc tcgggtgagt gccctccgct    900
ttttgtggcc aaacccagcc acgcagttcc cttcctgcgg cgtcctccac acccgggtc     960
tgctggtctc cgcggatgtc acaggctcgg caaccgccct cctgtcggcg gggagtcccg   1020
cgacgcccgg aaatgctccg aagcctgtcg cccagctgcc agatctgcgt ctgtgtccgg   1080
ttccgtcact gaggtcgccc ctgtccggcc cttccaccct agttctcttc accgtccgcc   1140
catcctatcg cgcgcggcct caggtcccga ttcggcatgt ggcttgtctt ccatcgtccc   1200
caccctcgcc cctcttggcc cctcagggca gccctgggat tcggcagacg ccagtcctcc   1260
ctgagatgct tccccatcct tccctccgcc aggccctacg                          1300
```

<210> SEQ ID NO 154
<211> LENGTH: 1300
<212> TYPE: DNA
<213> ORGANISM: Homo sapiens

<400> SEQUENCE: 154

```
cgtagggcct ggcggaggga aggatgggga agcatctcag ggaggactgg cgtctgccga     60
atcccagggc tgccctgagg ggccaagagg ggcgagggtg gggacgatgg aagacaagcc    120
acatgccgaa tcgggacctg aggccgcgcg cgataggatg ggcggacggt gaagagaact    180
agggtggaag ggccggacag gggcgacctc agtgacggaa ccggacacag acgcagatct    240
ggcagctggg cgacaggctt cggagcattt ccggcgtcg cggggactccc cgccgacagg    300
agggcggttg ccgagcctgt gacatccgcg gagaccagca gaccccgggt gtggaggacg    360
ccgcaggaag ggaactgcgt ggctgggttt ggccacaaaa agcggagggc actcacccga    420
gcggacctcg gctccggaga atccgttttcc gggtcaacaa aaaacgtcgc gcagggggcg   480
gggcccgtac gtgcagggag gggaggcaga gaaaaaggcg gggccgggcc ggggcggggt   540
```

```
ctcgggcagg ggcggggagc ttaccgacct cccgccccg ctgcgcgcgt ttctggccct      600
gccagtgtct ccgccggttg aaagcgcgtg tctgcgtcgg gttctgttgg agtgcgttcg      660
gtgtgccgtg ggtccgcgct gcttccaccc aacttcctgt taggtaagag gcgcgtgagg      720
ctcctgtgcc gggggcggtg ctgctcccga gtcggcgcgc ggcggggacg cgagtccgta      780
ggtgctggcg ggagcgagag tcgggtgggg accctcgcga gcccgcactc cgcctctggg      840
tagcagcctc ttcggcccca cacgcgtga cgcgcgctcg ggctccgcgt tcgcgtcgag      900
gcagaggcgt agtaggggtc gggcccaggg ctggagggc cgggaccggg cggggtgccg      960
ccctggacac cgcgccggca gctgttccgc gcgggttcat gtcattccta ttttcaacct     1020
gtcctgctcc gcacctgaga tgatttataa attcggtacc tttgggacag gcgtggatga     1080
catcccataa tttacttcgt tattaatttc taaatgtaat acataccact atctaaaagt     1140
atttttttaat ttgaaatata tttgtatacg tatacatgta tatttattta tttctgaatt    1200
ttatctcgta catataatga ggctcgtaaa gtggatactg ttcaggacat aggtggattt     1260
tgcttttaag tagtaaagac ttaattggtg acttactggg                           1300

<210> SEQ ID NO 155
<211> LENGTH: 1300
<212> TYPE: DNA
<213> ORGANISM: Homo sapiens

<400> SEQUENCE: 155
accggcgtcc cgctgggggc gcgcgagccc cacccccaga gatgctgact cagcaagtcg       60
ggaggggttg ggggtgggac ctgccaatct gcatttccaa ccggcgccca ggtgacgctg      120
actctgctgg tctaccgtct tggggtcac ctaatttttc agcgatgcct cccagctggg       180
gaggccaaga agtgcctcgc tcaaggtctt ccaacacccg acctccagac cctcaatcct      240
gggccagcta caccgcaaac cttttccagct gtctctcctg cgccctgcgt ttcttcccca     300
cgtcacttgc cagggagccg ctaaacagca agaccgcgcg ctctgcggct ccagagtgcg      360
gatttcggtc gcgtgcggct ctgaccgcgt cgccccatcc ctggcggggc cacgcacgga      420
cgccatggct ggcgccgcgg agccgggcga tgcgcgcgga ctctcccggg gccctgactg      480
tccctgagtc ctccctgcgg ggggcgtgcg cggcccgccc ccgcggcgc cacgcggccc      540
ctcctcggcc ggggattggt gcgccgggcg gggcggggcg gggcgggata aaggcgcggg      600
gtctggctgc gcggggtctg cgggcagctc caactctggg ttcgtagttt gcgctgggtg      660
cgcaggaagg tcagtgtggg ggtcgcccga catttccccc ccgcggaggt gggagccgag      720
ccacatcttg gagtggggac tggccgcgga gcgggttgcc cagggccggc cgaggtcggg      780
gcgagccctg cgcggcgctg gagactctgc attcccgggc gcgcgcaggg tccccggccg     840
tggtcgcaga gtcaggaggg gcggctccgg agcccggcgc ggggagggcc caggcgcagt      900
cggggttggc agggcgcgac actcgctccc ctccactttt gaaagggctt ccacgccga      960
gaagagggc gggcatggcc ggcccggcga aaccggtttg tacagacttt gggaagccat     1020
cgcctgcgca gggtgggacc ccacagcttg tccacctgcc caggctgaga cctcgtgtcc     1080
tagtcctgga tgccccacgg gtttctcgtc ccgggcagcg gcgcacggga ggagaagact     1140
cccggtctgc agtcagacct ccctctgaga ccctccctag ctcaggctta gagctttggg     1200
atttttctcg atcctttcta gctttcagat catccccacg taaagttcag actttaccag     1260
cccagagagt ttaaaaaaaa aaaaagagag agagagaaag                           1300

<210> SEQ ID NO 156
```

```
<211> LENGTH: 1300
<212> TYPE: DNA
<213> ORGANISM: Homo sapiens

<400> SEQUENCE: 156
ctttctctct ctctcttttt ttttttttaa actctctggg ctggtaaagt ctgaactttta      60 cgtggggatg atctgaaagc tagaaaggat cgagaaaaat cccaaagctc taagcctgag     120
ctagggaggg tctcagaggg aggtctgact gcagaccggg agtcttctcc tcccgtgcgc     180
cgctgcccgg gacgagaaac ccgtgggca tccaggacta ggacacgagg tctcagcctg      240
ggcaggtgga caagctgtgg ggtcccaccc tccgcaggcg atggcttccc aaagtctgta     300
caaaccggtt tcgccgggcc ggccatgccc gcccctcttc tcggcgtggg aagccctttc     360
aaaagtggag gggagcgagt gtcgcgccct gccaaccccg actgcgcctg ggccctcccc     420
gcgccgggct ccggagccgc ccctcctgac tctgcgacca cggccgggga ccctgcgcgc     480
gcccgggaat gcagagtctc cagcgccgcg cagggctcgc cccgacctcg gccggccctg     540
ggcaacccgc tccgcggcca gtccccactc caagatgtgg ctcggctccc acctccgcgg     600
gggggaaatg tcgggcgacc cccacactga ccttcctgcg cacccagcgc aaactacgaa     660
cccagagttg gagctgcccg cagacccccgc gcagccagac cccgcgcctt tatcccgccc     720
cgccccgccc cgcccggcgc accaatcccc ggccgaggag gggccgcgtg gcgccgcggg     780
gggcgggccg cgcacgcccc ccgcagggag gactcaggga cagtcagggc cccgggagag     840
tccgcgcgca tcgcccggct ccgcggcgcc agccatggcg tccgtgcgtg gccccgccag     900
ggatggggcg acgcggtcag agccgcacgc gaccgaaatc cgcactctgg agccgcagag     960
cgcgcggtct tgctgtttag cggctccctg gcaagtgacg tggggaagaa acgcagggcg    1020
caggagagac agctggaaag gtttgcggtg tagctggccc aggattgagg gtctggaggt    1080
cgggtgttgg aagaccttga gcgaggcact tcttggcctc cccagctggg aggcatcgct    1140
gaaaaattag gtgaccccca agacggtaga ccagcagagt cagcgtcacc tgggcgccgg    1200
ttggaaatgc agattggcag gtcccacccc caaccccctcc cgacttgctg agtcagcatc    1260
tctgggggtg gggctcgcgc gccccccagcg ggacgccggt                          1300

<210> SEQ ID NO 157
<211> LENGTH: 800
<212> TYPE: DNA
<213> ORGANISM: Homo sapiens

<400> SEQUENCE: 157
ctcatttcgg gccgcttttc tcagagggca aagatgggtc agggtgggat gttacattag      60
tgttgagact ctttggatcc gtttcgtggg taccgaggac gcctgggtac gcgggacagg     120
ctgcacccgc ctgctagagg cgccccatcg aggcgccacg ggtgaagctc ccggccccac     180
ctacggggcg gggctccggc tcggtccgac tattgcccgc ggtggggagg gggatggat     240 cacgccacgc gccaaaggcg atcgcgactc tccttctgca ggtagcctgg aaggctctct     300
ctctttctct acgccaccct tttcgtggca ctgaaaagcc ccgtcctctc ctcccagtcc     360
cgcctcctcc gagcgttccc cctactgcct ggaatggtgc ggtcccaggt cgcgggtcac     420
gcggcggagg gggcgtggcc tgccccggc ccagccggct cttctttgcc tctgctggag     480
tccggggagt ggcgttggct gctagagcga tgccgggccg gagttgcgtc gccttagtcc     540
tcctggctgc cgccgtcagc tgtgccgtcg cgcagcacgc gccgccggtg agtgagcttg     600
agccgaggcg cagagagggg cgtgcaggtg cgggcgcgga tggaggcgca ggtgtggcgg     660
```

```
cgcgagcggg tacaaggaac acctcgtgct gggcagcttc tttacggggg tctgtggttt    720
cgtgcacagg ggtgtgggtg cagagcgggc tggcgaaccc cgtcctcggt agattcggtg    780
ctacctgcaa ctagaactcc                                                800
```

<210> SEQ ID NO 158
<211> LENGTH: 800
<212> TYPE: DNA
<213> ORGANISM: Homo sapiens

<400> SEQUENCE: 158

```
ggagttctag ttgcaggtag caccgaatct accgaggacg gggttcgcca gcccgctctg     60
cacccacacc cctgtgcacg aaaccacaga ccccgtaaa gaagctgccc agcacgaggt    120
gttccttgta cccgctcgcg ccgccacacc tgcgcctcca tccgcgcccg cacctgcacg    180
cccctctctg cgcctcggct caagctcact caccggcggc gcgtgctgcg cgacggcaca    240
gctgacggcg gcagccagga ggactaaggc gacgcaactc cggcccggca tcgctctagc    300
agccaacgcc actccccgga ctccagcaga ggcaaagaag agccggctgg gccgggggca    360
ggccacgccc cctccgccgc gtgacccgcg acctgggacc gcaccattcc aggcagtagg    420
gggaacgctc ggaggaggcg ggactgggag gagaggacgg ggcttttcag tgccacgaaa    480
agggtggcgt agagaaagag agagagcctt ccaggctacc tgcagaagga gagtcgcgat    540
cgcctttggc gcgtggcgtg atccatcccc ctcccccacc gcgggcaata gtcggaccga    600
gccggagccc cgccccgtag gtggggccgg gagcttcacc cgtggcgcct cgatggggcg    660
cctctagcag gcgggtgcag cctgtcccgc gtacccaggc gtcctcggta cccacgaaac    720
ggatccaaag agtctcaaca ctaatgtaac atcccaccct gacccatctt tgccctctga    780
gaaaagcggc ccgaaatgag                                                800
```

<210> SEQ ID NO 159
<211> LENGTH: 800
<212> TYPE: DNA
<213> ORGANISM: Homo sapiens

<400> SEQUENCE: 159

```
ttctgcagag ccagcagccg gctcccacct acccaaggag agaagatcgc tccaagacag     60
tgagagcttc cctgccattt cagtgcaaag tccctccgga gcgacctcag aggagtaacc    120
gggccttaac ttttgcgct cgttttgcta taattttct ctatccacct ccatcccacc    180
cccacaacac tctttactgg gggtctttt tgtgttccgg atctccccct ccatggctcc    240
cttagccgaa gtcggggggct ttctgggcgg cctggagggc ttgggccagc aggtgggttc    300
gcatttcctg ttgcctcctg ccggggagcg ccgccgctg ctgggcgagc gcaggagcgc    360
ggcggagcgg agcgcgcgcg gcgggccggg ggctgcgcag ctggcgcacc tgcacggcat    420
cctgcgccgc cggcagctct attgccgcac cggcttccac ctgcagatcc tgcccgacgg    480
cagcgtgcag ggcacccggc aggaccacag cctcttcggt acgtactagc atcccgaccc    540
cacccccatc tgcgccccag ctcggctcct cgttccctcc ccttgcacct ccctctttgc    600
ctgccaaggg cgtcatcgcc gcgcggagcc cggagctccc ctggacccat ccggtgcaag    660
acgcaggctg gggctgaagg gctggccaga gcagccgcgg ggagaaattt tcctgctggt    720
ttgtcgccgc agcctctagc agggcagcag ctccagatgc tgggggcggg aggagaaagg    780
gtgggcgctt cgcaagctcc                                                800
```

<210> SEQ ID NO 160

```
<211> LENGTH: 800
<212> TYPE: DNA
<213> ORGANISM: Homo sapiens

<400> SEQUENCE: 160
ggagcttgcg aagcgcccac cctttctcct cccgccccca gcatctggag ctgctgccct      60
gctagaggct gcggcgacaa accagcagga aaatttctcc ccgcggctgc tctggccagc     120
ccttcagccc cagcctgcgt cttgcaccgg atgggtccag gggagctccg ggctccgcgc     180
ggcgatgacg cccttggcag gcaaagaggg aggtgcaagg ggagggaacg aggagccgag     240
ctggggcgca gatggggtg gggtcgggat gctagtacgt accgaagagg ctgtggtcct      300
gccgggtgcc ctgcacgctg ccgtcgggca ggatctgcag gtggaagccg gtgcggcaat     360
agagctgccg gcgcgcagg atgccgtgca ggtgcgccag ctgcgcagcc ccgccccgc       420 cgcgcgcgct ccgctccgcc gcgctcctgc gctcgcccag cagcggcggc cgctccccgg     480
caggaggcaa caggaaatgc gaacccacct gctggcccaa gccctccagg ccgcccagaa     540
agcccccgac ttcggctaag ggagccatgg agggggagat ccggaacaca aaagaccccc     600
ccagtaaaga gtgttgtggg ggtgggatgg aggtggatag agaaaaatta tagcaaaacg     660
agcgcaaaaa gttaaggccc ggttactcct ctgaggtcgc tccggaggga ctttgcactg     720
aaatggcagg gaagctctca ctgtcttgga gcgatcttct ctccttgggt aggtgggagc     780
cggctgctgg ctctgcagaa                                                  800

<210> SEQ ID NO 161
<211> LENGTH: 1300
<212> TYPE: DNA
<213> ORGANISM: Homo sapiens

<400> SEQUENCE: 161
cttaaccccc ccatctccag ttatcccaat gaaccgaccc cgaggggggca tttccgctga     60 agtccggggc tgtaaaaaat taagtgagaa gagccgcgct aaagccaagc gtcgtcgtca     120
cccaaggtac tgcgctgatg cgctgcgggc cgaccaggtg ctcccgccgg ggcgtcttct     180
cctacgcagg aagggccacg ccgagagagg caggcaacaa gggcacggct ggaggccgga     240
aggtcacccc gtccccggcg gggcgggcgc ggcccagcct cacttcccgg gcacgttcgg     300
gcggggcgat tgcagggaac ggggcgggga ggcgacagtc cccggctccg ccgcgcgcca     360
gcccgccttc gctgcccgga ggcgccgcag gcctgggttc ccggacagct gagcccgagc     420
gccgcctccc gaaaggtgaa ggcggcccgg ggaggcgggg acggtgacgg gggcggggc     480 cgcgggcggt ctcccgacgg ctgtcgcggg gccagcccaa agcccccgat ccccggtagc     540
tgcgcttccc gcgcggggcg ccggagtagg gcgggccaag ctggcctgcg gccgcggcgg     600
gaagaagggc tagcgaagca ccccgaccg ggcccaggcg ccgacgccg ggggcgcct       660 cgctgcaact tctctttgga agccccgaca cgagccccgg ccgcgcgcg cgctccccca     720 cggccacgcg cgcaccctgc cgcccgcacc cccgcgcgcc ctccgtctat ttttcctct     780 tcctttcatc ctcacactct aaaataggtc aagggggtgga agttacacct ggtgcagccc     840
tcggctctga tgcaaaagca gcttttgccc ctggctgcgg acagcgctg tgactactcg     900 caacgggaga gctgctgcca gtcgccacac cgtgcgaaa gcgccggcga ccggagcact     960
gacaatggtc tgcatagggg agcggagaga agcttctgtt gcgccctaga tccgctgcct    1020
cggcgcccgc ccgcagggag gaggggcgc gacaggtcgt ctagcgcgtg ccccggagcc    1080
cgcgcccggg tctggccgcc tgggtgagtt cctgctcgtc ccctgccttt ccagtagccc    1140
```

```
ggggtggctg tttaccttgc aaacagcctt gcaatacgat caaaacaggc gagacagcca   1200
tgcagtaagg gattgcggga tgtgctttgg gtgtgagatt ggataaatca gaattcagag   1260
ataaaggaca tgtctagtgc cttaaggggtt aaagtggatt                        1300
```

<210> SEQ ID NO 162
<211> LENGTH: 1300
<212> TYPE: DNA
<213> ORGANISM: Homo sapiens

<400> SEQUENCE: 162

```
aatccacttt aaccottaag gcactagaca tgtcctttat ctctgaattc tgatttatcc    60
aatctcacac ccaaagcaca tcccgcaatc ccttactgca tggctgtctc gcctgttttg   120
atcgtattgc aaggctgttt gcaaggtaaa cagccacccc gggctactgg aaaggcaggg   180
gacgagcagg aactcaccca ggcggccaga cccgggcgcg ggctccgggg cacgcgctag   240
acgacctgtc gcgccccctc ctccctgcgg cgggcgccg aggcagcgga tctagggcgc    300
aacagaagct tctctccgct cccctatgca gaccattgtc agtgctccgg tcgccggcgc   360
tttccgcacg gtgtggcgac tggcagcagc tctcccgttg cgagtagtca cagcgctgtc   420
ccgcagccag gggcaaaagc tgcttttgca tcagagccga gggctgcacc aggtgtaact   480
tccacccctt gacctatttt agagtgtgag gatgaaagga agaggaaaaa atagacggag   540
ggcgcgcggg ggtgcgggcg gcagggtgcg cgcgtggccg tggggagcg cgcgcgcggg    600 ccgggggctcg tgtcgggggct tccaaagaga agttgcagcg aggcgccccc cggcgtccgg  660
cgcctgggcc cggtcggggg tgcttcgcta gcccttcttc ccgccgcggc cgcaggccag   720 cttggccccgc cctactccgg cgcccgcgcg gggaagcgca gctaccgggg atcgggggct  780
ttgggctggc cccgcgacag ccgtcgggag accgcccgcg gcccccgccc ccgtcaccgt   840
ccccgcctcc ccgggccgcc ttcacctttc ggggaggcggc gctcgggctc agctgtccgg  900
gaacccaggc ctgcggcgcc tccgggcagc gaaggcgggc tggcgcgcgg cggagccggg   960
gactgtcgcc tccccgcccc gttccctgca atcgccccgc ccgaacgtgc ccggaagtg   1020 aggctgggcc gcgcccgccc cgccggggac ggggtgacct tccggcctcc agccgtgccc   1080
ttgttgcctg cctctctcgg cgtggcccctt cctgcgtagg agaagacgcc ccggcgggag  1140
cacctggtcg gcccgcagcg catcagcgca gtaccttggg tgacgacgac gcttggcttt   1200
agcgcggctc ttctcactta attttttaca gccccggact tcagcggaaa tgccccctcg   1260
gggtcggttc attgggataa ctggagatgg ggggggttaag                        1300
```

<210> SEQ ID NO 163
<211> LENGTH: 1800
<212> TYPE: DNA
<213> ORGANISM: Homo sapiens

<400> SEQUENCE: 163

```
ctagcattta ctggattcca gagtcttgtt atttaagaat gcatcttaaa cggtactatc    60
aaattcatgt tacgtgcagc ccagattgtt ttgggcagca cgaaaagttt ctgaggcgct   120
gcgtgtaccc caccccagga caccgtgtgt gcgcgccgag ctgagtgcga ggaacgtggc   180
gcgagggccg ggggatgccg ggctgcgtgg gtgtgagccc tcgcgcgacc gcgacccgc   240 gcctctcccg ctctcgccgg aacgtgaccg cagccgcacc tctcctccag ccctttccca   300
gccagacgct tccttttagg tccttctggg cgttttattgt aaattctgcg actaaaacac   360
gccggtgagc ccggccccacc gacagatgga tcaatcgccc ccttcccggc tagggggagga 420
```

-continued

| | | |
|---|---|---|
| ggaaccccc aaccccggag cctagggagc cgggagctgc ctcgggacga gctcctcgga | 480 | |
| gcccagccgg ctgcggagcc ccggcccggg tcggtctcgg ggccctcctg ccggggtggg | 540 | |
| gtgcgagccc ctgcccgatt cctctggggc ggttcaggca ggtttgccgg cctccgagga | 600 | |
| ggtggtcagg gcgccctggc ccagcaggct cttcccgag ccggggggag gggagaccgg | 660 | |
| ctggggaagg ggcatctcga aggggtggag gccggggcgg gcgggaggca agcgcgccgc | 720 | |
| gggcgtgagg gcaaagttcc cgaggtccgc gcggagagca cacgtgtatg tgcgcgcggg | 780 | |
| gctaggccgg ggccggcagg atgcgttggg ttcggggcg cgcggggccg gcgccgaagg | 840 | |
| ggataattcc tttccctggc accatcgggg agacgctttg tcggcctcgg ctcctgggcg | 900 | |
| cagggacgcc ttagcccacg gagggtggag ccccctcag acccgggcca ccggctgggg | 960 | |
| ttttctaac gccctgcccc ccgagccccc ggatggctcg ggcccacgg actccgcgcc | 1020 | |
| ctccagcctc agctcagctc cccaggcttc ccagacccag cggcgcaggg ggcgggggca | 1080 | |
| ggggcagtgg ggggttggagg gcgcagccgg tccccaggt ggggagagct gcgggggag | 1140 | |
| gaggaggagg gtgccgacgc ttgagtgggt tcgagcccga ccgtagccg gggagccag | 1200 | |
| tcagtttccg gccaaggcag caggtcagtc ccaggaaggg cgggcgattg agccgaggga | 1260 | |
| gccggcggct gggctctcct ctcggcccgc gatccccggc gccgccgccg ccgccaccgc | 1320 | |
| caccgccacc gccttcgcct tgtcgccgcc gccgctgcag agcatcgtag ctccgccgcg | 1380 | |
| ctcccgcgcc ccgcgccccg cgccgccagc cgcctgggag cccgagcgcc gagcccgggg | 1440 | |
| cggaggagag gggcgctggc gcgagagccc gggcgaggga gccgcgaagg gagaagggg | 1500 | |
| cgggcggagg gaggagcagg gagagtggga gaaggggag ggagagagga gagcgaggga | 1560 | |
| gagctggaga gagcgagagc aaagagcgag cgagggagag gagagagaga gagaggagag | 1620 | |
| agaaagacac acgcacgcag agacacacgg tcactggaat tccattagaa aaagtgagc | 1680 | |
| cgagcaaggg ttagcgggag aagatttttt tgaatcttgt cttcgtcttg gtgcgaaaga | 1740 | |
| agcgactcca gtctctcgtc ctcgaagctc cgactggatt gttcttgggc gctgacaccc | 1800 | |

<210> SEQ ID NO 164
<211> LENGTH: 1800
<212> TYPE: DNA
<213> ORGANISM: Homo sapiens

<400> SEQUENCE: 164

| | | |
|---|---|---|
| gggtgtcagc gcccaagaac aatccagtcg gagcttcgag gacgagagac tggagtcgct | 60 | |
| tctttcgcac caagacgaag acaagattca aaaaaatctt ctcccgctaa cccttgctcg | 120 | |
| gctcactttt ttctaatgga attccagtga ccgtgtgtct ctgcgtgcgt gtgtctttct | 180 | |
| ctctcctctc tctctctctc ctctccctcg ctcgctcttt gctctcgctc tctccagctc | 240 | |
| tccctcgctc tcctctctcc ctccccttc tcccactctc cctgctcctc cctccgcccg | 300 | |
| cccccttctc ccttcgcggc tccctcgccc gggctctcgc gccagcgccc ctctcctccg | 360 | |
| ccccgggctc ggcgctcggg ctcccaggcg gctggcggcg cggggcgcgg ggcgcgggag | 420 | |
| cgcggcggag ctacgatgct ctgcagcggc ggcggcgaca aggcgaaggc ggtgcggtg | 480 | |
| gcggtggcgg cggcggcggc gccggggatc gcgggccgag aggagagccc agccgccggc | 540 | |
| tccctcggct caatcgcccg ccttcctgg gactgacctg ctgccttggc cggaaactga | 600 | |
| ctggctcccc cggctacggc tcgggctcga acccactcaa gcgtcggcac cctcctcctc | 660 | |
| ctcccccgc agctctcccc accctgggga ccggctgcgc cctccaaccc ccactgcccg | 720 | |
| tgcccccgcc ccctgcgccg ctgggtctgg gaagcctggg gagctgagct gaggctggag | 780 | |

| | |
|---|---|
| ggcgcggagt ccgtggggcc cgagccatcc gggggctcgg ggggcagggc gttagaaaaa | 840 |
| ccccagccgg tgcccgggt ctgaggggg ctccaccctc cgtgggctaa ggcgtccctg | 900 |
| cgcccaggag ccgaggccga caaagcgtct ccccgatggt gccagggaaa ggaattatcc | 960 |
| ccttcggcgc cggccccgcg cgccccgaa cccaacgcat cctgccggcc ccggcctagc | 1020 |
| cccgcgcgca catacacgtg tgctctccgc gcggacctcg ggaactttgc cctcacgccc | 1080 |
| gcggcgcgct tgcctcccgc ccgccccggc ctccacccct tcgagatgcc ccttccccag | 1140 |
| ccggtctccc ctcccccggg ctcgggaaga agcctgctgg gccagggcgc cctgaccacc | 1200 |
| tcctcggagg ccggcaaacc tgcctgaacc gccccagagg aatcgggcag ggctcgcac | 1260 |
| cccacccccgg caggagggcc ccgagaccga cccgggccgg ggctccgcag ccggctgggc | 1320 |
| tccgaggagc tcgtcccgag gcagctcccg gctccctagg ctccggggtt gggggttcc | 1380 |
| tcctccccta gccgggaagg gggcgattga tccatctgtc ggtgggccgg gctcaccggc | 1440 |
| gtgttttagt cgcagaattt acaataaacg cccagaagga cctaaaagga agcgtctggc | 1500 |
| tgggaaaggg ctggaggaga ggtgcggctg cggtcacgtt ccggcgagag cgggagaggc | 1560 |
| gcggggtcgc ggtcgcgcga gggctcacac ccacgcagcc cggcatcccc cggccctcgc | 1620 |
| gccacgttcc tcgcactcag ctcggcgcgc acacacggtg tcctgggtg gggtacacgc | 1680 |
| agcgcctcag aaacttttcg tgctgcccaa acaatctgg gctgcacgta acatgaattt | 1740 |
| gatagtaccg tttaagatgc attcttaaat aacaagactc tggaatccag taaatgctag | 1800 |

<210> SEQ ID NO 165
<211> LENGTH: 1300
<212> TYPE: DNA
<213> ORGANISM: Homo sapiens

<400> SEQUENCE: 165

| | |
|---|---|
| aaacagcatt agccttctcc catcaaaagt ccggaagctg cccttcagtc gtcaaagtgt | 60 |
| ttgccttaat ttgcaatcgt tatgacttga gccaaatgct tataccctcat ttgtgtcgta | 120 |
| tatgtgaaga tacaattgca aatcgttcac gaccttgagt caagaccttg agtttcctga | 180 |
| ggtcaggaga ccgttaggga atgtgagtgt cccagacggg cgctgagccc agctcggaga | 240 |
| cccacccccgc ccgtagcagc ggcgcgggcc ccagagagcc ccgcactcgg ccgcgcctca | 300 |
| gttacgctga ctcggctgtg cccgcagtgt cgcgctgtcg cgtagccagg tgtcgccggg | 360 |
| ctggcgcggt tatttatgac tgcgtggttg ggctggggt tcggggccgg ggagcagccg | 420 |
| ggatccgccg cctcttccat gatcttcccg ggccgaacca cggaccgct acgctgaagg | 480 |
| tggcgtcgcg ggtccccggg gccgcgcgag tgtaggggtc gctctcggcc ggccgcgaag | 540 |
| ctcgcggcac cgacttctcg cgagatttcg gcgacccccc ccccgcccc cgcccctccg | 600 |
| ttctctgccc cctcccagct ctggtgtggg cggcctccgc tatggctgcg ctgcgaaggc | 660 |
| tcttgtggcc gccaccccgg gtgtctcctc cactctgcgc tcaccagccc ctccttgggc | 720 |
| cgtgggggcg gcctgcggtg accaccctgg gccttcctgg ccggcccttc tcctcccgag | 780 |
| aggatgagga gagggctgtg gcggaggcgg catggaggcg gcggcggcgc tgggggagc | 840 |
| tgagcgtggc ggcggcggcc ggcgggggc tggtcggcct ggtatgctac cagctgtacg | 900 |
| gggaccccag ggccggctcg ccggcgaccg gcgaccctc aaagagcgcg ccacggagc | 960 |
| ccgaggaccc gccccgcggc cggggatgc tgcccatccc agtggcggct gccaaggaga | 1020 |
| cggtgagtgc gcgagcgcgc gtcacacctg cgcgggggat gtgaccttcg tgccgggtac | 1080 |
| gcaggaccct ggaggctgtg gggacggtgc aagcgctgtg gccgcgggtg aggaacttcc | 1140 |

| | |
|---|---|
| cgtgagcgag gctgacacct aggccggaca gcctaggatc cggtcaccca cgtattggga | 1200 |
| agaccagtga tgctgtccct gatgcatcag gaccttaaag gtggctgcag ctaccaagta | 1260 |
| tcaatccaaa cccaaaacca acacccctcc ccctcttaca | 1300 |

<210> SEQ ID NO 166
<211> LENGTH: 1300
<212> TYPE: DNA
<213> ORGANISM: Homo sapiens

<400> SEQUENCE: 166

| | |
|---|---|
| tgtaagaggg ggaggggtgt tggttttggg tttggattga tacttggtag ctgcagccac | 60 |
| ctttaaggtc ctgatgcatc agggacagca tcactggtct tcccaatacg tgggtgaccg | 120 |
| gatcctaggc tgtccggcct aggtgtcagc ctcgctcacg ggaagttcct cacccgcggc | 180 |
| cacagcgctt gcaccgtccc cacagcctcc agggtcctgc gtacccggca cgaaggtcac | 240 |
| atccccgcg caggtgtgac gcgcgctcgc gcactcaccg tctccttggc agccgccact | 300 |
| gggatgggca gcatccccg gccgcggggc gggtcctcgg gctccgtggc cgcgctcttt | 360 |
| gagggtcgcc cggtcgccgg cgagccggcc ctggggtccc cgtacagctg gtagcatacc | 420 |
| aggccgacca gccccccgcc ggccgccgcc gccacgctca gctcccccca gcgccgccgc | 480 |
| cgcctccatg ccgcctccgc cacagccctc tcctcatcct ctcgggagga gaagggccgg | 540 |
| ccaggaaggc ccagggtggt caccgcaggc cgcccccacg gcccaaggag gggctggtga | 600 |
| gcgcagagtg gaggagacac ccggggtggc ggccacaaga gccttcgcag cgcagccata | 660 |
| gcggaggccg cccacaccag agctggggagg gggcagagaa cggaggggcg ggggcggggg | 720 |
| gggggtcgc cgaaatctcg cgagaagtcg gtgccgcgag cttcgcggcc ggccgagagc | 780 |
| gaccccctaca ctcgcgcggc cccggggacc ccgcgacgcca ccttcagcgt agcggtcccg | 840 |
| tggttcggcc cggaagatc atggaagagg cggcggatcc cggctgctcc ccggccccga | 900 |
| accccccagcc caaccacgca gtcataaata accgcgccag cccggcgaca cctggctacg | 960 |
| cgacagcgcg acactgcggg cacagccgag tcagcgtaac tgaggcgcgg ccgagtgcgg | 1020 |
| ggctctctgg ggcccgcgcc gctgctacgg gcggggtggg tctccgagct gggctcagcg | 1080 |
| cccgtctggg acactcacat tccctaacgg tctcctgacc tcaggaaact caaggtcttg | 1140 |
| actcaaggtc gtgaacgatt tgcaattgta tcttcacata tacgcacaa atgaggtata | 1200 |
| agcatttggc tcaagtcata acgattgcaa attaaggcaa acactttgac gactgaaggg | 1260 |
| cagcttccgg acttttgatg ggagaaggct aatgctgttt | 1300 |

<210> SEQ ID NO 167
<211> LENGTH: 1300
<212> TYPE: DNA
<213> ORGANISM: Homo sapiens

<400> SEQUENCE: 167

| | |
|---|---|
| cctggcgcgg acaggaccca gaaacaaacc acagcccggg gcgcagccgc cagggcgaag | 60 |
| gttagttccg gtcccttccc ctcccctccc cacttggacg cgcttgcgga ggattgcgtt | 120 |
| gacgagactc ttatttattg tcaccaacct gtggtggaat ttgcagttgc acattggatc | 180 |
| tgattcgccc cgccccgaat gacgcctgcc cggaggcagt gaaagtacag ccgcgccgcc | 240 |
| ccaagtcagc ctggacacat aaatcagcac gcggccggag aaccccgcaa tctctgcgcc | 300 |
| cacaaaatac accgacgatg cccgatctac tttaagggct gaaacccacg ggcctgagag | 360 |
| actataagag cgttccctac cgccatggaa caacggggac agaacgcccc ggccgcttcg | 420 |

```
ggggcccgga aaaggcacgg cccaggaccc agggaggcgc ggggagccag gcctgggccc      480
cgggtcccca agacccttgt gctcgttgtc gccgcggtcc tgctgttggt gagtccccgc      540
cgcggtccct ggctggggaa gagcgtgcct ggcgcctgga gagggcaggg agagagggg       600 acacggcggg ggtgcgtggc ccgggtcgcc tgccgccggg catgtccggg caagacgcac      660
cagtcgtcgg agtcggggga agagatgggt ccccgggttg ggcaggagcg acctgggccg      720
ccagggaaca gagcgcgcgc tccacttggt gtaaattccc gaatccagtg ggggagggcg      780
acaaggaggg aattcccgag taagctgcgt gaagccacgg agaggtcgtc ggactttgat      840
tttgttttct ttccttactt tctgtttctt tctcttttc tctttcttcc tttctttccc       900
tcccttcctt cctcgctcag ttcctgcctt aatttctttt tcttttgcgc cttcgaatga      960
attcctaaag gcgctcattg cagatcgctt tgaacctgcg gccggcgaag aactcccctg     1020
tggtcgctgc ggcccagtgg ttccgttccg tgcgcgggag tcgtcgcggg cgcagctgga     1080
gaggcccctt cccctcctta gcggctgcgc ccctacgcgt gcggggccgc tcatcgccaa     1140
tgccattgtt tggggttcct tgggaaaacg agatttagga aagggagtt gtggcacttg      1200 gggcctgacc tgcttgataa tagcagctgc attttggcct gggaagagcc tttcttgcca     1260
cctcttggca agtatccgtg ataatgggga agggacaaag                           1300

<210> SEQ ID NO 168
<211> LENGTH: 1300
<212> TYPE: DNA
<213> ORGANISM: Homo sapiens

<400> SEQUENCE: 168
ctttgtccct tccccattat cacggatact tgccaagagg tggcaagaaa ggctcttccc       60
aggccaaaat gcagctgcta ttatcaagca ggtcaggccc caagtgccac aactcccttc      120
tcctaaatct cgttttccca aggaacccca acaatggca ttggcgatga gcggccccgc       180
acgcgtaggg gcgcagccgc taaggagggg aaggggcctc tccagctgcg cccgcgacga      240
ctcccgcgca cggaacggaa ccactgggcc gcagcgacca caggggagtt cttcgccggc      300
cgcaggttca aagcgatctg caatgagcgc ctttaggaat tcattcgaag gcgcaaaaga      360
aaagaaaatt aaggcaggaa ctgagcgagg aaggaaggga gggaaagaaa ggaagaaaga      420
gaaaagagaa aagaaacaga aagtaaggaa agaaaacaaa atcaaagtcc gacgacctct      480
ccgtggcttc acgcagctta ctcgggaatt ccctccttgt cgccctcccc cactggattc      540
gggaatttac accaagtgga gcgcgcgctc tgttccctgg cggcccaggt cgctcctgcc      600
caacccgggg acccatctct tcccccgact ccgacgactg gtgcgtcttg cccggacatg      660
cccggccgca ggcgacccgg gccacgcacc cccgccgtgt cccctctctc cctgcccctc      720
tccaggcgcc aggcacgctc ttccccagcc agggaccgcg gcgggactc accaacagca       780 ggaccgcggc gacaacgagc acaagggtct tgggacccg gggcccaggc ctggctcccc       840
gcgcctccct gggtcctggg ccgtgccttt tccggccccc cgaagcggcc ggggcgttct      900
gtccccgttg ttccatggcg gtagggaacg ctcttatagt ctctcaggcc cgtgggtttc      960
agcccttaaa gtagatcggg catcgtcggt gtattttgtg ggcgcagaga ttgcggggtt     1020
ctccggccgc gtgctgattt atgtgtccag gctgacttgg ggcggcgcgg ctgtactttc     1080
actgcctccg ggcaggcgtc attcggggcg gggcgaatca gatccaatgt gcaactgcaa     1140
attccaccac aggttggtga caataaataa gagtctcgtc aacgcaatcc tccgcaagcg     1200
cgtccaagtg ggagggggag gggaagggac cggaactaac cttcgccctg gcggctgcgc     1260
```

```
cccgggctgt ggtttgtttc tgggtcctgt ccgcgccagg                       1300
```

<210> SEQ ID NO 169
<211> LENGTH: 800
<212> TYPE: DNA
<213> ORGANISM: Homo sapiens

<400> SEQUENCE: 169

```
tgccccttt  ctgagtgctt ggaagtgact gctgcaagtg acaagtgacc acgccttttc   60
ccccgcgggt ataaattcag aggcgctgcg ctccgattct ggcagtgcag ctgtgggaac  120
ctctccacgc gcacgaactc agccaacgat ttctgataga tttttgggag tttgaccaga  180
gatgcaaggg gtgaaggagc gcttcctacc gttagggaac tctggggaca gagcgccccg  240
gccgcctgat ggccgaggca gggtgcgacc caggacccag gacggcgtcg ggaaccatac  300
catggcccgg atccccaaga ccctaaagtt cgtcgtcgtc atcgtcgcgg tcctgctgcc  360
agtgagtccc ggccgcggtc cctggctggg gaagagcgca cctggcgccg ggaggggggca  420
gggagacggg gacacggcag ggatgcctgg ccctggtcac ctgcggccgg gcatgtccgg  480
gcaggacgaa ctcgccgtcg gagtcagggg aagaactggg tccccgggct gggcaggagg  540
gacccggccg cgagggagca gagaggcggt cccccctggct gccccgagcc cgcgaaggga  600
gggaagttcc agaatcgaga gagggaggga gtcaaggtgg aacccataga gtgagcctcc  660
tgaagacaca gagcggttgc ctctctcatt aattaattaa ttagttaata aaattacccc  720
catgtttaca ttcttaaacg tgttccttgg agatcggttt aaccaacagc cagtgaaaaa  780
actttcagc gctgtcttta                                              800
```

<210> SEQ ID NO 170
<211> LENGTH: 800
<212> TYPE: DNA
<213> ORGANISM: Homo sapiens

<400> SEQUENCE: 170

```
taaagacagc gctgaaaagt tttttcactg gctgttggtt aaaccgatct ccaaggaaca   60
cgtttaagaa tgtaaacatg gggttaattt tattaactaa ttaattaatt aatgagagag  120
gcaaccgctc tgtgtcttca ggaggctcac tctatgggtt ccaccttgac tccctccctc  180
tctcgattct ggaacttccc tcccttcgcg ggctcggggc agccaggggg accgcctctc  240
tgctcccctcg cggccgggtc cctcctgccc agcccgggga cccagttctt cccctgactc  300
cgacggcgag ttcgtcctgc ccggacatgc ccggccgcag gtgaccaggg ccaggcatcc  360
ctgccgtgtc cccgtctccc tgccccctcc cggcgccagg tgcgctcttc cccagccagg  420
gaccgcggcc gggactcact ggcagcagga ccgcgacgat gacgacgacg aactttaggg  480
tcttggggat ccgggccatg gtatggttcc cgacgccgtc ctgggtcctg ggtcgcaccc  540
tgcctcggcc atcaggcggc cgggcgctc tgtccccaga gttccctaac ggtaggaagc  600
gctccttcac cccttgcatc tctggtcaaa ctcccaaaaa tctatcagaa atcgttggct  660
gagttcgtgc gcgtggagag gttcccacag ctgcactgcc agaatcggag cgcagcgcct  720
ctgaatttat acccgcgggg gaaaaggcgt ggtcacttgt cacttgcagc agtcacttcc  780
aagcactcag aaaaggggca                                             800
```

<210> SEQ ID NO 171
<211> LENGTH: 1300
<212> TYPE: DNA
<213> ORGANISM: Homo sapiens

<400> SEQUENCE: 171

```
gaaataactt gagccaggga tcaaacacta agattggcag gaaatgagca ggaagaggta        60
gcggggtccc tgacgccatc tattcaattg tttttcagaa gaggtatcag ctcttgaagg       120
cttacttctc aatactggct gcgagagcaa gaatggtgtg taatttacaa aagccgtcat       180
tgctgtaggt aagttgtagc aaacgactcg cgcccgagca ttcccgcccc cgccttcgct       240
gcggccccgc ccacgacgac cctggggaac tacaagtccc gccatacagc ggggagcgcc       300
cggagctcgc gccggccccg ccccagccc ggtccccacc cccggctccg ccccggccc        360
cctcccgccg ggtcaacccc gaagagtcgc cggtggccgc ggcagacgga agccgaacga       420
gttcctcggc ggctgcagga tgggggactc caaagtgaaa gtggcggtgc ggatacgacc       480
catgaaccgg cgaggtgaga gccgagccct cctgggccgc cggggcggag cggcaggtg        540
cctggcgcgc ccttccctcg gccgccgtgg gggtccggc ggccccgccc ctatagtcag        600
cggcggggcg cgaggagggg cccggggacc ctgaaaccccg ctcccgcgct gagacgcccg      660
gctccctctt ctcccctccc ttcccccctg gccagccccg tccctggcgc cgtcgggccc      720
ctcgtgccgg ccccgctgcc ccttccgcct gcgcccgccc cgcccctgcg cccttttgcc      780
ctctcgtctc ccccggaggt tcccgagggc gccctcggcc ctcgcgccca gcctcgtcct      840
ggcccctcag cctcgctcct tccccgcccag ctgtcatcgt cgccccgcg cgcgggtcgc      900
cagcccctgc agcccgcctc gggaccgccc gggacccccc gggacccccgc gtctcgcccg    960
ggtcgcccaa gcctgcaccg ccttggcccg cggcgggaag aagggcaggg ggccaggcgg      1020
gtgccccgcg gcgagttcct tccacctggg cgtcctgaga ttggggtcag gtggaggaga      1080
tgcccttttc gttgttttg gacagttgag aaagttttgg ttttgcctga agtctcattc      1140
atcatctctc aataaatagc taagtgcca agattcttgt ggaattgtat ctttctgaca      1200
ttctcttaac tctgcaggga gtgtagagaa ggcagataaa ccgagtacat ttaaataatc      1260
tgtagacccg gggagtggag agaaccccaa aagtcagggg                               1300
```

<210> SEQ ID NO 172
<211> LENGTH: 1300
<212> TYPE: DNA
<213> ORGANISM: Homo sapiens

<400> SEQUENCE: 172

```
cccctgactt ttgggttct tccactccc cgggtctaca gattatttaa atgtactcgg        60
tttatctgcc ttctctacac tccctgcaga gttaagagaa tgtcagaaag atacaattcc       120
acaagaatct tggcacttta gctatttatt gagagatgat gaatgagact tcaggcaaaa       180
ccaaaacttt ctcaactgtc caaaaacaac gaaaaggca tctcctccac ctgaccccaa       240
tctcaggacg cccaggtgga aggaactcgc cgcggggcac ccgcctggcc ccctgccctt      300
cttcccgccg cgggccaagg cggtgcaggc ttgggcgacc cggcgagac gcgggtccc        360
gggggggtccc gggcggtccc gaggcgggct gcagggctg gcgacccgcg cgcggggcg       420
acgatgacag ctggcgggga aggagcgagg ctgaggggcc aggacgaggc tgggcgcgag       480
ggccgagggc gccctcggga acctccgggg gagacgagag ggcaaaaggg cgcaggggcg      540
gggcgggcgc aggcggaagg ggcagcgggg ccggcacgag gggcccgacg cgcgccaggga     600
cggggctggc cagggggggaa gggaggggag aagagggagc cgggcgtctc agcgcgggag    660
cgggtttcag ggtccccggg cccctcctcg cgccccgccg ctgactatag gggcggggcc      720
gccggacccc ccacggcggc cgagggaagg gcgcgccagg cacctgccgc ctccgccccg      780
```

-continued

| | |
|---|---|
| gcggcccagg agggctcggc tctcacctcg ccggttcatg ggtcgtatcc gcaccgccac | 840 |
| tttcactttg gagtccccca tcctgcagcc gccgaggaac tcgttcggct tccgtctgcc | 900 |
| gcggccaccg gcgactcttc ggggttgacc cggcgggagg gggccggggg cggagccggg | 960 |
| ggtgggacc gggctggggg cggggccggc gcgagctccg ggcgctcccc gctgtatggc | 1020 |
| gggacttgta gttccccagg gtcgtcgtgg gcggggccgc agcgaaggcg ggggcgggaa | 1080 |
| tgctcgggcg cgagtcgttt gctacaactt acctacagca atgacggctt ttgtaaatta | 1140 |
| cacaccattc ttgctctcgc agccagtatt gagaagtaag ccttcaagag ctgatacctc | 1200 |
| ttctgaaaaa caattgaata gatggcgtca gggaccccgc tacctcttcc tgctcatttc | 1260 |
| ctgccaatct tagtgtttga tccctggctc aagttatttc | 1300 |

<210> SEQ ID NO 173
<211> LENGTH: 1550
<212> TYPE: DNA
<213> ORGANISM: Homo sapiens

<400> SEQUENCE: 173

| | |
|---|---|
| accccctcct tccttctttc cctaccgccc cacgcgcgac ccggggatgg ctccgtggcc | 60 |
| tcacgagaac agctctcttg ccccatggcc ggacctcccc accctggcgc ccaataccgc | 120 |
| caacaccagt gggctgccag gggttccgtg ggaggcggcc ctagccgggg ccctgctggc | 180 |
| gctggcggtg ctggccaccg tgggaggcaa cctgctggtc atcgtggcca tcgcctggac | 240 |
| tccgagactc cagaccatga ccaacgtgtt cgtgacttcg ctggccgcag ccgacctggt | 300 |
| gatgggactc ctggtggtgc cgccggcggc caccttggcg ctgactggcc actggccgtt | 360 |
| gggcgccact ggctgcgagc tgtggaccct cgtggacgtg ctgtgtgtga ccgccagcat | 420 |
| cgaaaccctg tgcgccctgg ccgtggaccg ctacctggct gtgaccaacc cgctgcgtta | 480 |
| cggcgcactg gtcaccaagc gctgcgcccg gacagctgtg gtcctggtgt gggtcgtgtc | 540 |
| ggccgcggtg tcgtttgcgc ccatcatgag ccagtggtgg cgcgtagggg ccgacgccga | 600 |
| ggcgcagcgc tgccactcca acccgcgctg ctgtgccttc gcctccaaca tgccctacgt | 660 |
| gctgctgtcc tcctccgtct ccttctacct tcctcttctc gtgatgctct tcgtctacgc | 720 |
| gcgggttttc gtggtggcta cgcgccagct gcgcttgctg cgcggggagc tgggccgctt | 780 |
| tccgcccgag gagtctccgc cggcgccgtc gcgctctctg gccccggccc cggtggggac | 840 |
| gtgcgctccg cccgaagggg tgcccgcctg cggccggcgg cccgcgcgcc tcctgcctct | 900 |
| ccgggaacac cgggccctgt gcaccttggg tctcatcatg ggcaccttca ctctctgctg | 960 |
| gttgcccttc tttctggcca acgtgctgcg cgccctgggg ggccctctc tagtcccggg | 1020 |
| cccgcttttc cttgccctga actggctagg ttatgccaat tctgccttca accgctcat | 1080 |
| ctactgccgc agcccggact tcgcagcgc cttccgccgt cttctgtgcc gctgcggccg | 1140 |
| tcgcctgcct ccggagccct gcgccgccgc ccgcccggcc ctcttcccct cgggcgttcc | 1200 |
| tgcggcccgg agcagcccag cgcagcccag gctttgccaa cggctcgacg ggtaggtaac | 1260 |
| cggggcagag ggaccggcgg ctcagggtcg ggaagcatgc gatgtgtccg tgggtcaact | 1320 |
| ttttgagtgt ggagtttatt aagagaaggt gggatggctt tgcttggaga gaaaagggaa | 1380 |
| cgaggagtag cgaaccaaaa tgggaccccag ggtccttttc tttccggatc cagtcactag | 1440 |
| ggtagaagca aaggagggcg agcgggccgt cgttcctcac ccaaggaccc aaggtgcgcc | 1500 |
| accggaaagc gctgcggtgt cccgaggact ctcgcctcgc ctggtcggct | 1550 |

<210> SEQ ID NO 174

```
<211> LENGTH: 1550
<212> TYPE: DNA
<213> ORGANISM: Homo sapiens

<400> SEQUENCE: 174
agccgaccag gcgaggcgag agtcctcggg acaccgcagc gctttccggt ggcgcacctt      60
gggtccttgg gtgaggaacg acggcccgct cgccctcctt tgcttctacc ctagtgactg     120
gatccggaaa gaaaaggacc ctgggtccca ttttggttcg ctactcctcg ttcccttttc     180
tctccaagca aagccatccc accttctctt aataaactcc acactcaaaa agttgaccca     240
cggacacatc gcatgcttcc cgaccctgag ccgccggtcc ctctgccccg gttacctacc     300
cgtcgagccg ttggcaaagc ctgggctgcg ctgggctgct ccgggccgca ggaacgcccg     360
aggggaagag ggccgggcgg gcggcggcgc agggctccgg aggcaggcga cggccgcagc     420
ggcacagaag acggcggaag gcgctgcgaa agtccgggct gcggcagtag atgagcgggt     480
tgaaggcaga attggcataa cctagccagt tcagggcaag gaaagccggg cccgggacta     540
gagaggggcc cccagggcg cgcagcacgt tggccagaaa gagggcaac cagcagagag      600 tgaaggtgcc catgatgaga cccaaggtgc acagggcccg gtgttccgg agaggcagga     660 ggcgcgcggg ccgccggccg caggcgggca ccccttcggg cggagcgcac gtccccaccg     720
gggccggggc cagagagcgc gacggcgccg cggagactc ctcgggcgga aagcggccca     780
gctccccgcg cagcaagcgc agctggcgcg tagccaccac gaaaacccgc gcgtagacga     840
agagcatcac gagaagagga aggtagaagg agacggagga ggacagcagc acgtagggca     900
tgttggaggc gaaggcacag cagcgcgggt tggagtggca gcgctgcgcc tcggcgtcgg     960
cccctacgcg ccaccactgg ctcatgatgg gcgcaaacga caccgcggcc gacacgaccc     1020
acaccaggac cacagctgtc cgggcgcagc gcttggtgac cagtgcgccg taacgcagcg     1080
ggttggtcac agccaggtag cggtccacgg ccagggcgca cagggtttcg atgctggcgg     1140
tcacacacag cacgtccacc gaggtccaca gctcgcagcc agtggcgccc aacggccagt     1200
ggccagtcag cgccaaggtg gccgccggcg gcaccaccag gagtcccatc accaggtcgg     1260
ctgcggccag cgaagtcacg aacacgttgg tcatggtctg gagtctcgga gtccaggcga     1320
tggccacgat gaccagcagg ttgcctccca cggtggccag caccgccagc gccagcaggg     1380
ccccggctag ggccgcctcc cacggaaccc ctggcagccc actggtgttg gcggtattgg     1440
gcgccagggt ggggaggtcc ggccatgggg caagagagct gttctcgtga ggccacggag     1500
ccatccccgg gtcgcgcgtg gggcggtagg gaaagaagga aggaggggt                1550

<210> SEQ ID NO 175
<211> LENGTH: 1800
<212> TYPE: DNA
<213> ORGANISM: Homo sapiens

<400> SEQUENCE: 175
cgcagaccca gcaggagagc gcaacctagc atctttaagg ttcgcttagc ccttcctgtg      60
cacctggaag gaagccttat cttaaactcc cttccaccta gagtttattt tcgcctgcgt     120
gcgacagggc ttttgtactt aagtgagtta aggaatgaac cccgaactct tctgggaaag     180
ccaccaacgt tcccccgca cccctcccag ggttcctgac cacggagact ctgcttgggg     240
cacaggtgtg ggagtcgcaa acttttctct gcgccgtcct tttccgcgtg gaatgggacg     300
gagcagccct cccaggcgct gcctggctgc ggaggggagc gggcagcgag agcctcgggt     360
ctccgcctgg gttcccgggt ctccggggcg ctggcctcgg tctccgcgca gcgtccagcg     420
```

```
accccctgtcg ggggttcccg gcagccgcgc cgccaccccc cgcccggcca gcgcgggagg      480 aaaagggggct gcgcccggga gcgccgagcc caggctcctc ccggtggcgt gtccgcgcct      540
cggggtgggg gtgtggtggg gaagagggag ggggcgaggc caggggaggg tgcgaaggag      600
gcgcctgcct ccaacctgcg ggcgggaggt gggtggctgc ggggcaattg aaaaagagcc      660
ggcgaggagt tccccgaaac ttgttggaac tccgggctcg cgcggaggcc aggagctgag      720
cggcggcggc tgccggacga tgggagcgtg agcaggacgg tgataacctc tccccgatcg      780
ggttgcgagg gcgccgggca gaggccagga cgcgagccgc cagcggtggg acccatcgac      840 gacttccccgg ggcgacagga gcagcccga gagccagggc gagcgcccgt tccaggtggc      900
cggaccgccc gccgcgtccg cgccgcgctc cctgcaggca acgggagacg ccccgcgca      960 gcgcgagcgc ctcagcgcgg ccgctcgctc tcccccctcga gggacaaact tttcccaaac     1020
ccgatccgag cccttggacc aaactcgcct gcgccgagag ccgtccgcgt agagcgctcc     1080
gtctccggcg agatgtccga gcgcaaagaa ggcagaggca aagggaaggg caagaagaag     1140
gagcgaggct ccggcaagaa gccggagtcc ggcggcggca gccagagccc aggtgggtgc     1200
gcagcgcggc ccgggcccca cgatcctcct cctgctcctc ctactcctcc tcctcctcgg     1260
atgccgtggc ctctccctcc ccctctccct cgcccgtcct cttcgccctg cgctctgagc     1320
gcccgttgag tcgcgcggtg cttccctcc tggggccgc cgctcacctg ggcgccgagt      1380
cctaccgggc gcctacgccc agagctcagg gcaagggaca gcagtcccgg ccgcaccctc     1440
ccagagtccc gggagcgctt cgctccctgg cacggcccct ccccagcgcc ttagcggctg     1500
agcccagccc gggagtggga cctgggctat aggagtcgag gctgcgtgcg cgcgtgcccc     1560
gcgccataag cgctttgcac gggggccgtg tgccctctag cgggaaacgc tggaatgggc     1620
cgcctggagg gagagccggt cccctcggtg tgcctggcag cgcagaagtg ggtggtcgag     1680
caagaggccg cgtgggaagt tagcttcggc gttttggggc acagggcaag cgatgtagag     1740
tgcgcgccgg ttcatcttga ttcagtcctg tgctacggag actcaagagc agcggcaggg     1800
```

<210> SEQ ID NO 176
<211> LENGTH: 1800
<212> TYPE: DNA
<213> ORGANISM: Homo sapiens

<400> SEQUENCE: 176

```
ccctgccgct gctcttgagt ctccgtagca caggactgaa tcaagatgaa ccggcgcgca       60
ctctacatcg cttgccctgt gccccaaaac gccgaagcta acttcccacg cggcctcttg      120
ctcgaccacc cacttctgcg ctgccaggca caccgagggg accggctctc cctccaggcg      180
gcccattcca gcgtttcccg ctagagggca cacggccccc gtgcaaagcg cttatggcgc      240
ggggcacgcg cgcacgcagc ctcgactcct atagcccagg tcccactccc gggctgggct      300
cagccgctaa ggcgctgggg agggggccgtg ccagggagcc aagcgctccc gggactctgg     360
gagggtgcgg ccgggactgc tgtcccttgc cctgagctct gggcgtaggc gcccggtagg     420
actcggcgcc caggtgagcg gcggccccca ggagggaag caccgcgcga ctcaacgggc      480
gctcagagcg cagggcgaag aggacgggcg agggagaggg ggagggagag gccacggcat     540
ccgaggagga ggaggagtag gaggagcagg aggaggatcg tggggcccgg gccgcgctgc     600
gcacccacct gggctctggc tgcccgccgc ggactccggc ttcttgccgg agcctcgctc     660
cttcttcttg cccttccctt tgcctctgcc ttctttgcgc tcggacatct cgccggagac     720
ggagcgctct acgcggacgg ctctcggcgc aggcgagttt ggtccaaggg ctcggatcgg     780
```

```
gtttgggaaa agtttgtccc tcgaggggga gagcgagcgg ccgcgctgag gcgctcgcgc      840
tgcgcggggg cgtctcccgt tgcctgcagg gagcgcggcg cggacgcggc gggcggtccg      900
gccacctgga acgggcgctc gccctggctc tcggggctgc tcctgtcgcc ccgggaagtc      960
gtcgatgggt cccaccgctg gcggctcgcg tcctggcctc tgcccggcgc cctcgcaacc     1020
cgatcgggga gaggttatca ccgtcctgct cacgctccca tcgtccggca gccgccgccg     1080
ctcagctcct ggcctccgcg cgagcccgga gttccaacaa gtttcgggga actcctcgcc     1140
ggctcttttt caattgcccc gcagccaccc acctcccgcc cgcaggttgg aggcaggcgc     1200
ctccttcgca ccctcccctg gcctcgcccc tccctcttc cccaccacac ccccaccccg      1260
aggcgcggac acgccaccgg gaggagcctg ggctcggcgc tcccgggcgc agcccctttt     1320
cctcccgcgc tggccgggcg gggggtggcg gcgcggctgc cgggaacccc cgacaggggt     1380
cgctggacgc tgcgcggaga ccgaggccag cgccccggag acccgggaac ccaggcggag     1440
acccgaggct ctcgctgccc gctcccctcc gcagccaggc agcgcctggg agggctgctc     1500
cgtcccattc cacgcggaaa aggacggcgc agagaaaagt ttgcgactcc cacacctgtg     1560
ccccaagcag agtctccgtg gtcaggaacc ctgggagggg tgcgggggga acgttggtgg     1620
ctttcccaga agagttcggg gttcattcct taactcactt aagtacaaaa gccctgtcgc     1680
acgcaggcga aaataaactc taggtggaag ggagtttaag ataaggcttc cttccaggtg     1740
cacaggaagg gctaagcgaa ccttaaagat gctaggttgc gctctcctgc tgggtctgcg     1800

<210> SEQ ID NO 177
<211> LENGTH: 1550
<212> TYPE: DNA
<213> ORGANISM: Homo sapiens

<400> SEQUENCE: 177
gggagggtgg cctgcaaggc ggggccggtt gcggtcaagt tcaagtaggg tcagagcagg       60
agaacactgg cataaaaaat agccacatcc aaggaagcag tgaggtgtgg ggaccatcta      120
tttcggtggg ccttcccacc cccaggccgg ccttcccatc acgcgtgggt gtggggcac      180 tgccccccgct gcgcgcagga acagcgggga gagccaggag cggagcggct tcgggatgcc      240
agactgagca gtgggttcgt ctgcggccac ctctcaggga caagcttccc cccgcggag      300 actctgcttc ttttaaaagc cttcctgggt ttagtctagg gcgacaggac gacctccctt      360
gggaagggag agcctgccag tcccctccc attcgccagg cggtgcagcc cctcctcccg      420 cccgggggcgc gcgcacctca gcgtcgcggg cctagcgccc agcagccgcg ccccaggccg      480
ggcctcgggt tccgggagcc cgcaggcgcg cgcccggccg ggcgtgtcgg gagcgcgcgg      540
cggccggggg cggagcgcag ccagggctgc gcggcgcgcc ccggctcccg cccgctccca      600
gccgggcccc ccagcggtcg gcgggacggc tcccggctgc agtctgcccg cccgccccgc      660
gcgggggccg agtcgcgaag cgcgcctgcg accccggcgtc cgggcgcgct ggagaggacg      720
cgaggagcca tgaggcgcca gcctgcgaag gtggcggcgc tgctgctcgg gctgctcttg      780
gaggtagggg ccggggaccg ggtgctgccg gaggcgcggg gcccaccatg ctggcggctg      840
ggggcgcgca gttccgaggc gccccagagg accttgcctg ggagcgcaga cggtggagcg      900
acggggagcc acagccctgc gcgcctcccg gagctgggag gtgcgggacc ctggtgacgg      960
ggaggctccc gccccggtcc gcgccttccg tcgttccttc ggttttcgca ccccgccccc     1020
accctgcggg tgagcgcgtt tcccgcgccg accgcctccg ttagctcggg gtgacctttg     1080
tgcaccgtcc gccccctctc cccgccgcag agggccgagg atcggatgga cccggggttg     1140
```

```
ggcggggtg gtcctcgggc gcggcgcagg cgcggagagc ccgggcgcc gggcagtttg      1200 gggttaggaa aggatgggtg ccgagccggg gtgaggggag cgggcggagg ggactgtggg      1260
gaagtgtcgc gggagtgccg ggagttgtgg aggtgagcag cgggaggagg cgttcccgcg      1320
tgtgaaaatg aagtgcagcc tttaggtgcg gggaggaaat tctgcggaga gcctggctgg      1380 gtggggtgc ggagccgaag ccggcgggga acttgttgag cggcttccgg gtgcgagcgc      1440
ccgtgaccgc atcctggcg gggaccgcgg ctgctcctgg ctgtgaaatt gcatcctcgg      1500
atggggccac atacttctca ctaaagcagg ttccttaaaa tgcgaactag              1550
```

<210> SEQ ID NO 178
<211> LENGTH: 1550
<212> TYPE: DNA
<213> ORGANISM: Homo sapiens

<400> SEQUENCE: 178

```
ctagttcgca ttttaaggaa cctgctttag tgagaagtat gtggccccat ccgaggatgc        60
aatttcacag ccaggagcag ccgcggtccc cgccagggat gcggtcacgg gcgctcgcac       120
ccggaagccg ctcaacaagt tccccgccgg cttcggctcc gcaccccac ccagccaggc       180 tctccgcaga atttcctccc cgcacctaaa ggctgcactt cattttcaca cgcgggaacg       240
cctcctcccg ctgctcacct ccacaactcc cggcactccc gcgacacttc cccacagtcc       300
cctccgcccg ctcccctcac cccggctcgg caccatcct ttcctaaccc caaactgccc       360
ggcgccccgg gctctccgcg cctgcgccgc gcccgaggac caccccgcc caaccccggg       420 tccatccgat cctcggccct ctgcggcggg gagaggggc ggacggtgca caaaggtcac       480
cccgagctaa cggaggcggt cggcgcggga aacgcgctca cccgcagggt gggggcgggg      540
tgcgaaaacc gaaggaacga cggaaggcgc ggaccggggc gggagcctcc ccgtcaccag      600
ggtcccgcac ctcccagctc cgggaggcgc gcagggctgt ggctcccgt cgctccaccg      660 tctgcgctcc caggcaaggt cctctggggc gcctcggaac tgcgcgcccc cagccgccag      720
catggtgggc gccgcgcctc cggcagcacc cggtccccgg cccctacctc caagagcagc      780
ccgagcagca gcgccgccac cttcgcaggc tggcgcctca tggctcctcg cgtcctctcc      840
agcgcgcccg gacgccgggt cgcaggcgcg cttcgcgact cggccccgc gcggggcggg       900 cgggcagact gcagccggga gccgtccgc cgaccgctgg ggggcccggc tgggagcggg      960
cgggagccgg ggcgcgccgc gcagccctgg ctgcgctccg ccccggccg ccgcgcgctc       1020 ccgacacgcc cggccgggcg cgcgcctgcg ggctcccgga acccgaggcc cggcctgggg      1080
cgcggctgct gggcgctagg cccgcgacgc tgaggtgcgc gcgccccggg cgggaggagg      1140
ggctgcaccg cctggcgaat gggaggggga ctggcaggct ctcccttccc aagggaggtc      1200
gtcctgtcgc cctagactaa acccaggaag gcttttaaaa gaagcagagt ctccgcgggg      1260
ggaagcttgt tccctgagag gtggccgcag acgaacccac tgctcagtct ggcatcccga      1320
agccgctccg ctcctggctc tccccgctgt tcctgcgcgc agcggggca gtgcccccac      1380 acccacgcgt gatgggaagg ccggcctggg ggtgggaagg cccaccgaaa tagatggtcc      1440
ccacacctca ctgcttcctt ggatgtggct attttttatg ccagtgttct cctgctctga      1500
ccctacttga acttgaccgc aaccggcccc gccttgcagg ccaccctccc              1550
```

<210> SEQ ID NO 179
<211> LENGTH: 800
<212> TYPE: DNA
<213> ORGANISM: Homo sapiens -continued

```
<400> SEQUENCE: 179
tgctgggcaa tgcgtgcgtg gtggctgcca tcgccttgga gcgctccctg cagaacgtgg    60
ccaattatct tattggctct ttggcggtca ccgacctcat ggtgtcggtg ttggtgctgc   120
ccatggccgc gctgtatcag gtgctcaaca agtggacact gggccaggta acctgcgacc   180
tgttcatcgc cctcgacgtg ctgtgctgca cctcatccat cttgcacctg tgcgccatcg   240
cgctggacag gtactgggcc atcacggacc ccatcgacta cgtgaacaag gacgccc     300 ggcgcgccgc tgcgctcatc tcgctcactt ggcttattgg cttcctcatc tctatcccgc   360
ccatgctggg ctggcgcacc ccggaagacc gctcggaccc cgacgcatgc accattagca   420
aggatcatgg ctacactatc tattccacct ttggagcttt ctacatcccg ctgctgctca   480
tgctggttct ctatgggcgc atattccgag ctgcgcgctt ccgcatccgc aagacggtca   540 aaaggtgga gaagaccgga gcggacaccc gccatggagc atctcccgcc ccgcagccca   600
agaagagtgt gaatggagag tcggggagca ggaactggag gctgggcgtg gagagcaagg   660
ctgggggtgc tctgtgcgcc aatggcgcgg tgaggcaagg tgacgatggc gccgccctgg   720
aggtgatcga ggtgcaccga gtgggcaact ccaaagagca cttgcctctg cccagcgagg   780
ctggtcctac cccttgtgcc                                               800

<210> SEQ ID NO 180
<211> LENGTH: 800
<212> TYPE: DNA
<213> ORGANISM: Homo sapiens

<400> SEQUENCE: 180
ggcacaaggg gtaggaccag cctcgctggg cagaggcaag tgctctttgg agttgcccac    60
tcggtgcacc tcgatcacct ccagggcggc gccatcgtca ccttgcctca ccgcgccatt   120
ggcgcacaga gcaccccag ccttgctctc cacgcccagc ctccagttcc tgctccccga   180
ctctccattc acactcttct tgggctgcgg ggcgggagat gctccatggc gggtgtccgc   240
tccggtcttc tccacctttt tgaccgtctt gcggatgcgg aagcgcgcag ctcggaatat   300
gcgcccatag agaaccagca tgagcagcag cgggatgtag aaagctccaa aggtggaata   360
gatagtgtag ccatgatcct tgctaatggt gcatgcgtcg gggtccgagc ggtcttccgg   420
ggtgcgccag cccagcatgg gcgggataga gatgaggaag ccaataagcc aagtgagcga   480
gatgagcgca gcggcgcgcc ggggcgtcct cttgttcacg tagtcgatgg ggtccgtgat   540
ggcccagtac ctgtccagcg cgatggcgca caggtgcaag atggatgagg tgcagcacag   600
cacgtcgagg gcgatgaaca ggtcgcaggt tacctggccc agtgtccact tgttgagcac   660
ctgatacagc gcggccatgg gcagcaccaa caccgacacc atgaggtcgg tgaccgccaa   720
agagccaata agataattgg ccacgttctg cagggagcgc tccaaggcga tggcagccac   780
cacgcacgca ttgcccagca                                               800

<210> SEQ ID NO 181
<211> LENGTH: 550
<212> TYPE: DNA
<213> ORGANISM: Homo sapiens

<400> SEQUENCE: 181
tgacgcaagg tccagtccag attgccaggc ccggggcatg agagaggatc cttgtaggtt    60
tcggaggtgg gggggctgca ctccattgtt cactccgggc caatcagggt tggcccactt   120
cctcccagcc aatctcccctt cacccccagc ctccaaccca acccacccccg cccatcagcc   180
```

| | |
|---|---|
| cctggatccc catcacctcc cccgcatccc cggcagttct ggggaagctt cgtgacgcca | 240 |
| caggtcccgc ccccagctcc ggcccggggc tagtgcgtgt tgacgtcatg ctgcgtgcgg | 300 |
| gccggtgcgg aatcgctcct tcaactccgc ggggcagtag gagttagtta gcaaagagcc | 360 |
| gaggccgggc gcgcgaccct cgtccttctg ccctggccg cacactttgc gcacatctct | 420 |
| ttttctgcat ggtggatatt atttttcatt atccttttct gggtgctatg ggtgatcatt | 480 |
| ccaagagtaa gtatttctgt gtgtgtgtgg ggtggggtgt gtgtgtatgc ttaatatgca | 540 |
| aaatttctaa | 550 |

<210> SEQ ID NO 182
<211> LENGTH: 550
<212> TYPE: DNA
<213> ORGANISM: Homo sapiens

<400> SEQUENCE: 182

| | |
|---|---|
| ttagaaattt tgcatattaa gcatacacac acaccccacc ccacacacac acagaaatac | 60 |
| ttactcttgg aatgatcacc catagcaccc agaaaaggat aatgaaaaat aatatccacc | 120 |
| atgcagaaaa agagatgtgc gcaaagtgtg cggccagggg cagaaggacg agggtcgcgc | 180 |
| gcccggcctc ggctctttgc taactaactc ctactgcccc gcggagttga aggagcgatt | 240 |
| ccgcaccggc ccgcacgcag catgacgtca acacgcacta gccccgggcc ggagctgggg | 300 |
| gcgggacctg tggcgtcacg aagcttcccc agaactgccg gggatgcggg ggaggtgatg | 360 |
| gggatccagg ggctgatggg cggggtgggt tgggttggag gctggggggtg aagggagatt | 420 |
| ggctgggagg aagtgggcca accctgattg gcccggagtg aacaatggag tgcagccccc | 480 |
| ccacctccga aacctacaag gatcctctct catgccccgg gcctggcaat ctggactgga | 540 |
| ccttgcgtca | 550 |

<210> SEQ ID NO 183
<211> LENGTH: 1050
<212> TYPE: DNA
<213> ORGANISM: Homo sapiens

<400> SEQUENCE: 183

| | |
|---|---|
| cagggaacag acccagtagt tggcttggat ctcttaactc cagaaaaggc cgagtgagga | 60 |
| caagggagac cacagggata atttctgtgg ctctggtaag gggatgacaa gggagaaaaa | 120 |
| ctttcccacg gttccgtctg gcccgcggcg cttgtctgcc tgcgcggggt caaagcccgg | 180 |
| cgccgcccac gcgcggctcg ggtgggaacc cgcagacgtg gggcgagcag gccgctggc | 240 |
| tgtggcgggc gagcgccggg gcgccacgtc cgaggccgcg gggtcggggc tgcaggcaca | 300 |
| gctcgagcgc tttccgcggg gtttggctcc tgtcgcttcc cgtctcgccg aaccggcatc | 360 |
| gccgccgccg gagccgcagc gagtcctcag agcctggctg ctggcggccg ggagcgccgg | 420 |
| gacggggcgc gaagccggag gctccgggac gtggatacag gtaaaggccg gcgggtcgga | 480 |
| gtcgggcggg gcgcggcggc ggcgcctctc ggagggacct ggcctcggcc gggccctacc | 540 |
| cagccgcggt ggcccgggcc ccacgttggg cccaggcggg gacgtgccaa ggggctgggc | 600 |
| tagggttgcc gctggcctgg ccgcctctcg cccggcgggc ctcaggtgac gcggccgcgg | 660 |
| cttaactttc gcacctgagg ctctcggagc ggcctcgggg cgcgcccacc tggaggttgg | 720 |
| aattacacag ggtcgaaaaa gctgagtcct ggaggcgagg cgctgtaggt gtggcggagg | 780 |
| aggccgggga aggtggggtg ggtgccaggg gtccagtact gaaccctctc caggtctgag | 840 |
| gtggggaact gcgtcttgtt taatttcgga gcttgtgggg accacacagc cccttccacg | 900 |

| | |
|---|---:|
| gccgattccc tctgcacggt tccactttcc tttgtctagc ccatttcagt atcggcgtcg | 960 |
| cagtcgcttt tgttgcagcc ttgggtccgg agtgtacgac tttctgctag gcagaggtca | 1020 |
| taagctctga aatccatcgg gcggaggtgg | 1050 |

<210> SEQ ID NO 184
<211> LENGTH: 1050
<212> TYPE: DNA
<213> ORGANISM: Homo sapiens

<400> SEQUENCE: 184

| | |
|---|---:|
| ccacctccgc ccgatggatt tcagagctta tgacctctgc ctagcagaaa gtcgtacact | 60 |
| ccggacccaa ggctgcaaca aaagcgactg cgacgccgat actgaaatgg gctagacaaa | 120 |
| ggaaagtgga accgtgcaga gggaatcggc cgtggaaggg gctgtgtggt ccccacaagc | 180 |
| tccgaaatta aacaagacgc agttccccac ctcagacctg gagagggttc agtactggac | 240 |
| ccctggcacc caccccacct tccccggcct cctcgccac acctacagcg cctcgcctcc | 300 |
| aggactcagc ttttcgacc ctgtgtaatt ccaacctcca ggtgggcgcg ccccgaggcc | 360 |
| gctccgagag cctcaggtgc gaaagttaag ccgcggccgc gtcacctgag gcccgccggg | 420 |
| cgagaggcgg ccaggccagc ggcaacccta gcccagcccc ttggcacgtc cccgcctggg | 480 |
| ccaacgtggg ggcccgggcc accgcggctg ggtaggggccc ggccgaggcc aggtccctcc | 540 |
| gagaggcgcc gccgccgcgc cccgcccgac tccgacccgc cggcctttac ctgtatccac | 600 |
| gtccggagc ctccggcttc gcgcccgtc ccggcgctcc cggccgccag cagccaggct | 660 |
| ctgaggactc gctgcggctc cggcggcggc gatgccggtt cggcgagacg ggaagcgaca | 720 |
| ggagccaaac cccgcggaaa gcgctcgagc tgtgcctgca gccccgaccc cgcggcctcg | 780 |
| gacgtggcgc cccggcgctc gcccgccaca gccagcggcc ctgctcgccc cacgtctgcg | 840 |
| ggttcccacc cgagccgcgc gtgggcggcg ccgggctttg accccgcgca ggcagacaag | 900 |
| cgccgcgggc cagacggaac cgtgggaaag ttttctcccc ttgtcatccc cttaccagag | 960 |
| ccacagaaat tatccctgtg gtctcccttg tcctcactcg gccttttctg gagttaagag | 1020 |
| atccaagcca actactgggt ctgttccctg | 1050 |

<210> SEQ ID NO 185
<211> LENGTH: 1800
<212> TYPE: DNA
<213> ORGANISM: Homo sapiens

<400> SEQUENCE: 185

| | |
|---|---:|
| ggcagcagcc gctggcttct gcgcccacta ggagcttcgg atgcccgagt tagggctgcg | 60 |
| ccaaggcggc cggagcagag agggagacgg ggacggggac aggcagggac aaagtgcaag | 120 |
| aggcaaaact ggctgaaaag cagaagtgta ggagccgcca aggggcggga cgaacaggtc | 180 |
| cgtgggccgg gcggagccaa gggtgggggc cgggtccct ccaggtggca ctcgcggcgc | 240 |
| tagtcccag cctcctccct tcccccggcc ctgattggca ggcggcctgc gaccagccgc | 300 |
| gaacgccaca gcgccccggg cgcccaggag aacgcgaacg gccccccgcg ggagcgggcg | 360 |
| agtaggaggg ggcgccgggc tatatatata gcggctcggc ctcgggcggg cctggcgctc | 420 |
| agggaggcgc gcactgctcc tcagagtccc agctccagcc gcgcgctttc cgcccggctc | 480 |
| gccgctccat gcagccgggg tagagcccgg cgccggggg cccgtcgct tgcctcccgc | 540 |
| acctcctcgg ttgcgcactc ctgcccgagg tcggccgtgc gctcccgcgg gacgccacag | 600 |
| gcgcagctct gccccccagc ttcccggggcg cactgaccgc ctgaccgacg cacggccctc | 660 |

```
gggccgggat gtcggggccc gggacggccg cggtagcgct gctcccggcg gtcctgctgg      720
ccttgctggc gccctgggcg ggccgagggg gcgccgccgc acccactgca cccaacggca      780
cgctggaggc cgagctggag cgccgctggg agagcctggt ggcgctctcg ttggcgcgcc      840
tgccggtggc agcgcagccc aaggaggcgg ccgtccagag cggcgccggc gactacctgc      900
tgggcatcaa gcggctgcgg cggctctact gcaacgtggg catcggcttc cacctccagg      960
cgctccccga cggccgcatc ggcggcgcgc acgcggacac ccgcgacagt gagtggcgcg     1020
gccaggcgcg aaggggcggg ggcgggggc aacggccgcc gggccaaccc gctcagtcac     1080
actctgagac cctcggcggg cacctgctcg ggggccccgg gaaccggggc ggactcgggc     1140
tccggtccct tctgacgcgg ggctggggac gcagacactc ttggctccgg cagcccagcg     1200 caaccctga gtcgggcgc cgcctcccgc cttcagaaac tcgggctccg agcgccgaat      1260
tccagcgcct tcgcccgtgg gcacagggcg cgcggtgcag ccacagggg cccgagacac      1320 gcgcccggc ctggcccagg ctggggaacc gctggggtcg ggctcgcgtc tgaaggtccg      1380
ggactgggtg cggccgccgg gggtccccta cacaggcaag ctaatctgag ctagcgcagg     1440
cttgggctcc ggaggcccta gagggcagct tgggctctgg aggcccttgg gggcggctgc     1500
gccgggaacc ctggcccttt atccccaacc ccaccccaga aatagggtcc ccggaggcga     1560
acaagccgag gggcggagtg ggccagggat caccctgcccc gcaatgacct gcgccccgcc     1620
cccaggcctg ctggagctct cgcccgtgga gcggggcgtg gtgagcatct tcggcgtggc     1680
cagccggttc ttcgtggcca tgagcagcaa gggcaagctc tatggctcgg tgagtaccgc     1740
aggggtctgg ctaggcacct agttgggaac agcggacatg gctagcaggc tcgtggcttc     1800

<210> SEQ ID NO 186
<211> LENGTH: 1800
<212> TYPE: DNA
<213> ORGANISM: Homo sapiens

<400> SEQUENCE: 186
gaagccacga gcctgctagc catgtccgct gttcccaact aggtgcctag ccagacccct       60
gcggtactca ccgagccata gagccttgccc ttgctgctca tggccacgaa gaaccggctg      120
gccacgccga agatgctcac cacgccccgc tccacgggcg agagctccag caggcctggg      180
ggcggggcgc aggtcattgc ggggcaggtg atccctggcc cactccgccc ctcggcttgt      240
tcgcctccgg ggaccctatt tctggggtgg ggttgggat aaagggccag ggttcccggc      300
gcagccgccc ccaagggcct ccagagccca agctgccctc tagggcctcc ggagcccaag      360
cctgcgctag ctcagattag cttgcctgtg taggggaccc ccggcggccg cacccagtcc      420
cggaccttca gacgcgagcc cgaccccagc ggttccccag cctgggccag gccggggcgc      480
gtgtctcggg ccccctgtgg ctgcaccgcg cgccctgtgc ccacgggcga aggcgctgga     540
attcggcgct cggagcccga gtttctgaag gcggaggcg gcgcccgacc tcaggggttg      600
cgctgggctg ccggagccaa gagtgtctgc gtccccagcc ccgcgtcaga agggaccgga      660
gcccgagtcc gccccggttc ccggggcccc cgagcaggtg cccgccgagg gtctcagagt      720
gtgactgagc gggttggccc ggcggccgtt gccccccgcc ccgccccctt cgcgcctggc      780
cgcgccactc actgtcgcgg gtgtccgcgt gcgcgccgcc gatgcggccg tcggggagcg      840
cctggaggtg gaagccgatg cccacgttgc agtagagccg ccgcagccgc ttgatgccca     900
gcaggtagtc gccggcgccg ctctggacgg ccgcctcctt gggctgcgct gccaccggca      960
ggcgcgccaa cgagagcgcc accaggctct cccagcggcg ctccagctcg gcctccagcg     1020
```

| | |
|---|---:|
| tgccgttggg tgcagtgggt gcggcggcgc ccctcggcc cgcccagggc gccagcaagg | 1080 |
| ccagcaggac cgccgggagc agcgctaccg cggccgtccc gggccccgac atcccggccc | 1140 |
| gagggccgtg cgtcggtcag gcggtcagtg cgcccgggaa gctgggggc agagctgcgc | 1200 |
| ctgtggcgtc ccgcgggagc gcacggccga cctcggcag gagtgcgcaa ccaggaggt | 1260 |
| gcgggaggca agcgacgggg ccccgggcg ccgggctcta ccccggctgc atggagcggc | 1320 |
| gagccgggcg gaaagcgcgc ggctggagct gggactctga ggagcagtgc gcgcctccct | 1380 |
| gagcgccagg cccgcccgag gccgagccgc tatatatata gcccggcgcc ccctcctact | 1440 |
| cgcccgctcc cgcgggggc cgttcgcgtt ctcctgggcg cccggggcgc tgtggcgttc | 1500 |
| gcggctggtc gcaggccgcc tgccaatcag gccgggga agggaggagg ctggggacta | 1560 |
| gcgccgcgag tgccacctgg agggacccccg gcccccaccc ttggctccgc ccggcccacg | 1620 |
| gacctgttcg tcccgcccct tggcggctcc tacacttctg cttttcagcc agttttgcct | 1680 |
| cttgcacttt gtccctgcct gtccccgtcc ccgtctccct ctctgctccg gccgccttgg | 1740 |
| cgcagcccta actcgggcat ccgaagctcc tagtgggcgc agaagccagc ggctgctgcc | 1800 |

<210> SEQ ID NO 187
<211> LENGTH: 1300
<212> TYPE: DNA
<213> ORGANISM: Homo sapiens

<400> SEQUENCE: 187

| | |
|---|---:|
| tgaggtgagg ggccggagga gcaagggaca agaggagcag aggacaggtg atggaaatcc | 60 |
| tgcagcttta ggctccattc tgccatctac atcccagcgc agggtgaagc ctgagagccc | 120 |
| aaatggccaa ctccacaggg ctgaacgcct cagaagtcgc aggctcgttg ggttgatcc | 180 |
| tggcagctgt cgtggaggtg ggggcactgc tgggcaacgg cgcgctgctg gtcgtggtgc | 240 |
| tgcgcacgcc gggactgcgc gacgcgctct acctggcgca cctgtgcgtc gtggacctgc | 300 |
| tggcggccgc ctccatcatg ccgctgggcc tgctggccgc accgccgccc gggctgggcc | 360 |
| gcgtgcgcct gggccccgcg ccatgccgcg ccgctcgctt cctctccgcc gctctgctgc | 420 |
| cggcctgcac gctcggggtg gccgcacttg gcctggcacg ctaccgcctc atcgtgcacc | 480 |
| cgctgcggcc aggctcgcgg ccgccgcctg tgctcgtgct caccgccgtg tgggccgcgg | 540 |
| cgggactgct gggcgcgctc tccctgctcg gcacgccgcc cgcaccgccc cctgctcctg | 600 |
| ctcgctgctc ggtcctggct gggggcctcg ggcccttccg gccgctctgg gccctgctgg | 660 |
| ccttcgcgct gcccgccctc ctgctgctcg gcgcctacgg cggcatcttc gtggtggcgc | 720 |
| gtcgcgctgc cctgaggccc ccacggccgg cgcgcgggtc ccgactccac tcggactctc | 780 |
| tggatagccg cctttccatc ttgccgccgc tccggcctcg cctgcccggg gcaaggcgg | 840 |
| ccctggcccc agcgctggcc gtgggccaat ttgcagcctg ctggctgcct tatggctgcg | 900 |
| cgtgcctggc gcccgcagcg cgggccgcgg aagccgaagc ggctgtcacc tgggtcgcct | 960 |
| actcggcctt cgcggctcac cccttcctgt acgggctgct gcagcgcccc gtgcgcttgg | 1020 |
| cactgggccg cctctctcgc cgtgcactgc ctggacctgt gcgggcctgc actccgcaag | 1080 |
| cctggcaccc gcgggcactc ttgcaatgcc tccagagacc cccagagggc cctgccgtag | 1140 |
| gcccttctga ggctccagaa cagaccccg agttggcagg agggcggagc cccgcatacc | 1200 |
| aggggccacc tgagagttct ctctcctgag caggagaaag gagggtggtt tccgtggggg | 1260 |
| ctcatccaac ccctgcacag gtcacagcag gtgccctgct | 1300 |

<210> SEQ ID NO 188

```
<211> LENGTH: 1300
<212> TYPE: DNA
<213> ORGANISM: Homo sapiens

<400> SEQUENCE: 188
agcagggcac ctgctgtgac ctgtgcaggg gttggatgag cccccacgga aaccaccctc      60
ctttctcctg ctcaggagag agaactctca ggtggcccct ggtatgcggg gctccgccct     120
cctgccaact cggggtctg ttctggagcc tcagaagggc ctacggcagg gccctctggg      180
ggtctctgga ggcattgcaa gagtgcccgc gggtgccagg cttgcggagt gcaggcccgc     240
acaggtccag gcagtgcacg gcgagagagg cggcccagtg ccaagcgcac ggggcgctgc     300
agcagcccgt acaggaaggg gtgagccgcg aaggccgagt aggcgaccca ggtgacagcc     360
gcttcggctt ccgcggcccg cgctgcgggc gccaggcacg cgcagccata aggcagccag     420
caggctgcaa attggcccac ggccagcgct ggggccaggg ccgccttgcc cccgggcagg     480
cgaggccgga gcggcggcaa gatggaaagg cggctatcca gagagtccga gtggagtcgg     540
gacccgcgcg ccggccgtgg gggcctcagg gcagcgcgac gcgccaccac gaagatgccg     600
ccgtaggcgc cgagcagcag gagggcgggc agcgcgaagg ccagcagggc ccagagcggc     660
cggaagggcc cgaggccccc agccaggacc gagcagcgag caggagcagg gggcggtgcg     720
ggcggcgtgc cgagcaggga gagcgcgccc agcagtcccg ccgcggccca cacggcggtg     780
agcacgagca caggcggcgg ccgcgagcct ggccgcagcg ggtgcacgat gaggcggtag     840
cgtgccaggc caagtgcggc caccccgagc gtgcaggccg gcagcagagc ggcggagagg     900
aagcgagcgg cgcggcatgg cgcggggccc aggcgcacgc ggcccagccc gggcggcggt     960
gcggccagca ggcccagcgg catgatggag gcggccgcca gcaggtccac gacgcacagg    1020
tgcgccaggt agagcgcgtc gcgcagtccc ggcgtgcgca gcaccacgac cagcagcgcg    1080
ccgttgccca gcagtgcccc cacctccacg acagctgcca ggatcaaccc caacgagcct    1140
gcgacttctg aggcgttcag ccctgtggag ttggccattt gggctctcag gcttcaccct    1200
gcgctgggat gtagatggca gaatggagcc taaagctgca ggatttccat cacctgtcct    1260
ctgctcctct tgtcccttgc tcctccggcc cctcacctca                         1300

<210> SEQ ID NO 189
<211> LENGTH: 800
<212> TYPE: DNA
<213> ORGANISM: Homo sapiens

<400> SEQUENCE: 189
ccgcgacctt cgagaacccg catgctgttc tccaccaggt ctctcagtcc tccctgcccc      60
aatccccatg cccgcctccg cgaccctgtg atgcctccct tcttgcacag gagcagtgac     120
ctcagcactt acttaatcct ctcccggcgc cgagctcagt tggagaggct aggggtggta     180
gtgactggca ggaggccggg gcgggggaa cccccaagcc cggcgtctgg ggctgcgggt     240
ccgacccgag atccgccctc cctgcaagcc ccgagccgct ggccaggccc gctactgcgc     300
accagccgca tccgcgagcg ctggctctgc cggcctgagc tagggtgggt agggccggga     360
cccacggcgg aggtggggcc gggccgagca gcctcggggg atccccgaag ctacagcgcc     420
ttgcctccct gcacgctccg cgccccggc ctccgattgg ctgtcgggcc tagagcccgc      480
ccagaattgg accgttcgct tgtcgctcgg gtctggctcc accccagag ggagcctaga      540
acctggtcgc agtttttaga gactaccctc acccccgtggc ctgcgccgaa gttgggcgga    600
ggacagtggg tggccaggcc cttccgggcc agaactcggg acccctgcca gctacccgtg    660
```

```
ccaggacaga ctcaagcccc caaaacgcgg atggatgtac agaggagact ggggagagc     720 actggactgg gagtccttgg gcctgcactg aactctggct gactttgtga ccttgaagaa    780
actgcttttc ccttcctgaa                                                800
```

<210> SEQ ID NO 190
<211> LENGTH: 800
<212> TYPE: DNA
<213> ORGANISM: Homo sapiens

<400> SEQUENCE: 190

```
ttcaggaagg gaaaagcagt ttcttcaagg tcacaaagtc agccagagtt cagtgcaggc     60
ccaaggactc ccagtccagt gctctcccca gtctcctct gtacatccat ccgcgttttg     120
ggggcttgag tctgtcctgg cacgggtagc tggcaggggt cccgagttct ggcccggaag    180
ggcctggcca cccactgtcc tccgcccaac ttcggcgcag gccacggggt gagggtagtc    240
tctaaaaact gcgaccaggt tctaggctcc ctctgggggt ggagccagac ccgagcgaca    300
agcgaacggt ccaattctgg gcgggctcta ggcccgacag ccaatcggag gccggggcg    360 cggagcgtgc agggaggcaa ggcgctgtag cttcggggat ccccgaggc tgctcggccc     420 ggccccacct ccgccgtggg tcccggccct acccacccta gctcaggccg gcagagccag    480
cgctcgcgga tgcggctggt gcgcagtagc gggcctggcc agcggctcgg ggcttgcagg    540
gagggcggat ctcgggtcgg accgcagcc ccagacgccg ggcttggggg ttcccccgc     600 cccggcctcc tgccagtcac taccacccct agctctccca actgagctcg cgccgggag    660 aggattaagt aagtgctgag gtcactgctc ctgtgcaaga agggaggcat cacagggtcg    720
cggaggcggg catggggatt ggggcaggga ggactgagag acctggtgga gaacagcatg    780
cgggttctcg aaggtcgcgg                                                800
```

<210> SEQ ID NO 191
<211> LENGTH: 1050
<212> TYPE: DNA
<213> ORGANISM: Homo sapiens

<400> SEQUENCE: 191

```
ctgcagcagg acgtaagcac agtcatcgct gcaaactgca aactcgtaag cacagtcatc     60
gctgcaaact gcaaactcgt gctccgagcg ctgccctccc ctgtggagcg gaggagggga    120
ggcctggggc cgcggcggtg tgcgccccgc tctgaccgca gagccccctt cccgaggaaa    180
gcggctggcc cggtcccggc tggtgatcac gcggggcccc tgtctgcttg gtgcgcaggt    240
gagggtctgc ccttccgctg cgccccggac agcctggagg tgagcacgcg ctgggccctg    300
gaccgcgagc agcgggagaa gtacgagctg gtggccgtgt gcaccgtgca cgccggcgcg    360
cgcgaggagg tggtgatggt gcccttcccg gtgaccgtgt acgacgagga cgactcggcg    420
cccaccttcc ccgcgggcgt cgacaccgcc agcgccgtgg tggagttcaa gcggaaggag    480
gtgcttgtcc gcgcgtgctg tggtctaccc agtgtctgtc tccggccaca gttcgtttct    540
cggtcggttt agtgtccgtg tagccaccca accgtgtggc cgaccattcg cgctttcatt    600
tgtccttcgc ctccgtctgc gccgtctgtc ctaggggag gggaagggg agtcctgcca     660 gcacccagct gggccttgcc tcgggaggca aggaccagga cgaggcccga gggctcgcgt    720
ctggggcata cttgtgccgc tgcaggcggg cgcggcgcgc tgcccgggcg gggagcatct    780
gccgggaggg cactccctcc caccagcagt tagcccccaa cgggagggcc cttgagtgac    840
cacgagcaga gccggggatt ggagaaggac gggaaggcgg atcacctccg gcgccgcccg    900
```

| | |
|---|---|
| ccccgcccctt ctccggctcg cgctggtgga gcgcgaccgc cacctgctgg gcctcggcct | 960 |
| tcctgcagcc ggcccaccca gcaggggccg tgggagagtg ggcgtgggga ctgaggtagg | 1020 |
| tagtacgttg ccttgttccg cttctctggg | 1050 |

<210> SEQ ID NO 192
<211> LENGTH: 1050
<212> TYPE: DNA
<213> ORGANISM: Homo sapiens

<400> SEQUENCE: 192

| | |
|---|---|
| cccagagaag cggaacaagg caacgtacta cctacctcag tccccacgcc cactctccca | 60 |
| cggcccctgc tgggtgggcc ggctgcagga aggccgaggc ccagcaggtg gcggtcgcgc | 120 |
| tccaccagcg cgagccggag aagggcgggg cgggcggcgc cggaggtgat ccgccttccc | 180 |
| gtccttctcc aatccccggc tctgctcgtg gtcactcaag ggccctcccg ttgggggcta | 240 |
| actgctggtg ggagggagtg ccctcccggc agatgctccc cgcccgggca gcgcgccgcg | 300 |
| cccgcctgca gcggcacaag tatgccccag acgcgagccc tcgggcctcg tcctggtcct | 360 |
| tgcctcccga ggcaaggccc agctgggtgc tggcaggact ccccttccc ctcccctag | 420 |
| gacagacggc gcagacggag gcgaaggaca aatgaaagcg cgaatggtcg gccacacggt | 480 |
| tgggtggcta cacggacact aaaccgaccg agaaacgaac tgtggccgga gacagacact | 540 |
| gggtagacca cagcacgcgc ggacaagcac ctccttccgc ttgaactcca ccacggcgct | 600 |
| ggcggtgtcg acgcccgcgg ggaaggtggg cgccgagtcg tcctcgtcgt acacggtcac | 660 |
| cgggaagggc accatcacca cctcctcgcg cgcgccggcg tgcacggtgc acacggccac | 720 |
| cagctcgtac ttctcccgct gctcgcggtc cagggcccag cgcgtgctca cctccaggct | 780 |
| gtccggggcg cagcggaagg gcagaccctc acctgcgcac caagcagaca ggggcccccgc | 840 |
| gtgatcacca gccggaccg ggccagccgc tttcctcggg aagggggctc tgcggtcaga | 900 |
| gcggggcgca caccgccgcg gccccaggcc tcccctcctc cgctccacag gggagggcag | 960 |
| cgctcggagc acgagtttgc agtttgcagc gatgactgtg cttacgagtt tgcagtttgc | 1020 |
| agcgatgact gtgcttacgt cctgctgcag | 1050 |

<210> SEQ ID NO 193
<211> LENGTH: 800
<212> TYPE: DNA
<213> ORGANISM: Homo sapiens

<400> SEQUENCE: 193

| | |
|---|---|
| gcgccgacgg gggcgggtgg taggggatgt acgggtgtgt atatgcagag gtatgccagg | 60 |
| ctctgcccct taaagtttgg gggccggcgg aggcggcgcc gtggccggga gaaagtgtct | 120 |
| ctcatttagg agggtttgca ggtccagagt aaagtcactg aagagtggaa gcgaggaagg | 180 |
| aacaggatga ttagacctca gctgcggacc gcggggctgg gacgatgcct cctgccgggg | 240 |
| ctgctgctgc tcctggtgcc cgtcctctgg gccggggctg aaaagctaca tacccagccc | 300 |
| tcctgccccg cggtctgcca gcccacgcgc tgccccgcgc tgcccacctg cgcgctgggg | 360 |
| accacgccgg tgttcgacct gtgccgctgt tgccgcgtct ccccgcggc cgagcgtgaa | 420 |
| gtctgcggcg gggcgcaggg ccaaccgtgc gccccgggc tgcagtgcct ccagccgctg | 480 |
| cgccccgggt tccccagcac ctgcggttgc ccgacgctgg gaggggccgt gtgcggcagc | 540 |
| gacaggcgca cctaccccag catgtgcgcg ctccgggccg aaaaccgcgc cgcgcgccgc | 600 |
| ctgggcaagg tcccggccgt gcctgtgcag tgggggaact gcggggatac aggtgagccg | 660 |

```
cgggggcgcg cgccctcgga acactttcta actctggagg agcgtaaagg aacaagacct    720
cactgagacc gcacagttcg cgcctggtcc tcctgcgtca tttgcctcct ggattcgaca    780
cctctgtgtt cctgatttcc                                                800
```

<210> SEQ ID NO 194
<211> LENGTH: 800
<212> TYPE: DNA
<213> ORGANISM: Homo sapiens

<400> SEQUENCE: 194

```
ggaaatcagg aacacagagg tgtcgaatcc aggaggcaaa tgacgcagga ggaccaggcg     60
cgaactgtgc ggtctcagtg aggtcttgtt cctttacgct cctccagagt tagaaagtgt    120
tccgagggcg cgcgcccccg cggctcacct gtatccccgc agttccccca ctgcacaggc    180
acggccggga ccttgcccag gcggcgcgcg gcgcggtttt cggcccggag cgcgcacatg    240
ctggggtagg tgcgcctgtc gctgccgcac acggcccctc cagcgtcgg gcaaccgcag     300 gtgctgggga acccggggcg cagcggctgg aggcactgca gccccggggc gcacggttgg    360
ccctgcgccc cgccgcagac ttcacgctcg gccgcggggc agacgcggca acagcggcac    420
aggtcgaaca ccggcgtggt ccccagcgcg caggtgggca gcgcggggca gcgcgtgggc    480
tggcagaccg cggggcagga gggctgggta tgtagctttt cagccccggc ccagaggacg    540
ggcaccagga gcagcagcag ccccggcagg aggcatcgtc ccagccccgc ggtccgcagc    600
tgaggtctaa tcatcctgtt ccttcctcgc ttccactctt cagtgacttt actctggacc    660 tgcaaacccct cctaaatgag agacactttc tcccggccac ggcgccgcct ccgccggccc    720
ccaaacttta aggggcagag cctggcatac ctctgcatat acacacccgt acatccccta    780
ccacccgccc ccgtcggcgc                                                800
```

<210> SEQ ID NO 195
<211> LENGTH: 801
<212> TYPE: DNA
<213> ORGANISM: Homo sapiens

<400> SEQUENCE: 195

```
ttgtcttctc ccttccgacc tcccgtggcc ccagcgcggc cagctcacag taggtgctcg     60
ggcagcgttt cttcagggac ctagacggcc tggagaggaa gggccccagc ccagccgccc    120
gggcctctca cctggctctc ggggcgcccg gctcgcactt cctcccgccg ccccgcccct    180
tccacattcc tgccccgccg ggcctgcccc gcgcagtctg ggtctctgcg ccgcagccgc    240
ccgcccgccc gctcagcgcc cggccccggg atgacggcgg cccaggccgc gggtgaggag    300
gcgccaccag gcgtgcggtc cgtcaaggtg gtcctggtgg gcgacggcgg ctgcgggaag    360
acgtcgctgc tgatggtctt cgccgatggg gccttccccg aggtgagtgc cccgcgcctc    420
cgcctcgccc ggttccgctc gcgcgcccgg gtgtacaggt ccgtgccgga gcggcccagg    480
ctgtgcgcct aacccggcct ccgaggggtg tccagcgggg gcctggggtc cagggcagag    540
ttcttccgcc ccagccattg ggaatgaagg cctcagtgat gttatctgta aagccggagg    600
aatggcatcc accggggaga ggtgtcacaa ggactgagtg aggcgacctg ggtgcacaca    660
agatcctaag acagcacttg gccacacaat tccgctgagg gcctgagagc ttggaagcca    720
gactgccgag gttcaaatta tggctttgcc tcttatagct gtgtgccctt gggtaagtcc    780
cctaaccctg ctgtgcctgt g                                              801
```

<210> SEQ ID NO 196

```
<211> LENGTH: 1301
<212> TYPE: DNA
<213> ORGANISM: Homo sapiens

<400> SEQUENCE: 196
attgagagag agggagggcg aaaggaagga aggggagcca gaggtgggag tggaagaggc      60
agcctcgcct ggggctgatt ggctcccgag gccagggctc tccaagcggt ttataagagt     120
tggggctgcc gggcgccctg cccgctcgcc cgcgcgcccc aggacccaaa gccgggctcc     180
aagtcggcgc cccacgtcga ggctccgccg cagcctccgg agttggccgc agacaagaag     240
gggagggagc gggagaggga ggagagctcc gaagcgagag ggccgagcgc catgcgccgc     300
gccagcagag actacaccaa gtacctgcgt ggctcggagg agatgggcgg cggccccgga     360
gccccgcacg agggcccccT gcacgccccg ccgccgcctg cgccgcacca gccccctgcc     420
gcctcccgct ccatgttcgt ggccctcctg gggctggggc tgggccaggt tgtctgcagc     480
gtcgccctgt tcttctattt cagagcgcag gtgagtggcc accttcccag ggatcgcgg     540 ctgagagcgc ccatctcctt cccccgcact tggaaactga gtctggcggc agggctgggc     600
cacccagagc ttgcatattc cggaagggaa agtgactcca gaagggagag ggaagtgtt     660 gagtttgggg acaacctggc gcagggctgt cgggcgcacc ctgctctctc tccgcccacg     720 cacccccagct tctcggtgct ctgggggcgg actcccctgg ccggacgatg ggtttgaatc     780
tcaccccgtc ccttcgctgg gaaacaacac tggcctctca ccttttctgg tagtgattgc     840
atactttttc tccctgtcat ttctcacttg aagttaagaa tcaacttctg ttcacgtagg     900
aaaaaagatg agcgccttca cttgggcatc tacctttccc ttcccgccca ccacccggcg     960
ggtttcggtt cctgcgcctg gctgctctgc aggtgtgctg gggccacggt gctggagggc    1020
tgcgcggagc gggaggtcgc ggtgctcgtg cccaggtcgc ccaatgggtg ggcagaatga    1080
cacggcgcga ccagagaggc gcgggctcgg gatgggggct ctgcggctgt ggcgctgtcc    1140
tgtgggggtg aaggaagagg gacagcccca cgtgcctgct agggatgtgg gcggaggaag    1200
gaagcgaggt gagtgtgatg gcacagtgtt actacagtct agcaaataac caaccttcgg    1260 aaaagatgaag aggttttttg cacgacggct aggaactgca g                       1301

<210> SEQ ID NO 197
<211> LENGTH: 4301
<212> TYPE: DNA
<213> ORGANISM: Homo sapiens

<400> SEQUENCE: 197
gcaatttata gatgagagcg tggacggcag agagcattgt gtatgttgaa gtctctgcga      60 tatgggggtgt ccctgctgcc ccgctccagc ctttcacttc tgacctcctt cctctggctc     120
ttacgctaca ggatccaaaa ctactcggaa gacttgccgc gggcggtgat tgacgacgcc     180
tttgcccgcg ccttcgcact gtggagcgcg gtgacgccgc tcaccttcac tcgcgtgtac     240
agccgggacg cagacatcgt catccagttt ggtgtcgcgg gtgagaacgt gaggagggaa     300
aatccaagag acctgggcgg ggtcaggaa ggaggaccca cggagagcgt ggaggcagca     360
gtggcccagg cttcctcttg cctgcccgcg ctgccctggc ttatacggcc cctcctgcca     420
gacagtgcac agggccaggg cgccaggctg ggagagcttc gcgcaggcgg gatttcagcc     480
cgcacttatt tcggagccct tgccttgggc agcgcacaat ctgcgcagca gtactcggct     540
aaccctcttc ctctcgacct gtttcttcag agcacggaga cgggtatccc ttcgacggga     600
aggacgggct cctggcacac gcctttcctc ctggccccgg cattcaggga gacgcccatt     660
```

-continued

```
tcgacgatga cgagttgtgg tccctgggca agggcgtcgg tgagattctg agtcctcctg    720
gcccctgatt cccttcattc tctcccactc atcacccgcc gccctaactc cggtcccccc    780
tcctcctgca gtggttccaa ctcggtttgg aaacgcagat ggcgcggcct gccacttccc    840
cttcatcttc gagggccgct cctactctgc ctgcaccacc gacggtcgct ccgacggctt    900
gccctggtgc agtaccacgg ccaactacga caccgacgac cggtttggct tctgccccag    960
cgagagtgag tgaggggct cgccgagggc tgggggcgcc caccacccctt gatggtcctg   1020 ggttctaatt ccagctctgc cactagtgct gtgtggcctg caattcaccc tcccgcactc   1080
tgggcccaat tttctcatct gagaaatgat gagagatggg atgaactgca gaccatccat   1140
gggtcaaaga acaggacaca cttgggggtt ataatgtgct gtctccgcct tctcccctt    1200 tcccacatcc tcctcgcccc aggactctac acccaggacg gcaatgctga tgggaaaccc   1260
tgccagtttc cattcatctt ccaaggccaa tcctactccg cctgcaccac ggacggtcgc   1320
tccgacggct accgctggtg cgccaccacc gccaactacg accgggacaa gctcttcggc   1380
ttctgcccga cccgaggtac ctccaccctg tctaccaggt tcagcccgc cctctcatca   1440 tgtattggcc cccaaaacgc ggctcttccc tcccatcagt ttgtctttcc actctcattg   1500
gtcctcagga cgaccgtgac tccgcccacc tacaccacat ttccaccact atccctgact   1560
tccaatggcc ccgccccagc cactaaggtt cggccttttc tgcccagctg gccgcctctt   1620
ccttggtctg gtgtcccagg caccgcccac gggtctagcc tcttctcagg agtgctctac   1680
agcgccccct aggccaccaa gattgtttag ctccctgtcg ggtcggcccc tgactcctta   1740
ttggactcat ccatctggct catccaaggc cttgggtctc tccagctgac tcgacggtga   1800 tgggggggcaa ctcggcgggg gagctgtgcg tcttcccctt cactttcctg ggtaaggagt   1860
actcgacctg taccagcgag ggccgcggag atgggcgcct ctggtgcgct accacctcga   1920
actttgacag cgacaagaag tggggcttct gcccggacca aggtaggcgt ggtcccgcgg   1980
ctccggggct gggggttcccg gcagtggtgg tggtggggtg gccagggctg ggggctcggc   2040
ccggcgctca cgtctcaggc tccctctccc tccaggatac agtttgttcc tcgtggcggc   2100
gcatgagttc ggccacgcgc tgggcttaga tcattcctca gtgccggagg cgctcatgta   2160
ccctatgtac cgcttcactg agggggccccc cttgcataag gacgacgtga atggcatccg   2220
gcacctctat ggtgaggcag ggcagggat ggaggagga ggggaaaggg cgtggctgtg     2280
ccacagtacc aaagaattgg gggttgggga tcggggagg aacggggcgt gcaggagagg    2340
tgggacctca acgtctgtct ggaagcagag cctgggccca gtcgctgcca tgtcagtgct   2400
tagaggtggt gataaagaga ctctagagag agataggtgt gacttcaaaa gccagtctac   2460
tctgggcatg gtggctcacg cctctaatcc cagggctttg ggagacccaa ggcgggagga   2520
ttgcttaagc ccaggagttc cagaccagcc tcggcaacat agccagactc ccatctctac   2580
aaaaaataaa tgagcaaggc gtgaaggcac atgtctgtag tcctagctac tctggaggct   2640
gaggtgggag gatctcttga gcccaggagt tcgaggctgt agtgagctat gattgcacca   2700
ctgcattcca tcctgggcca tagaggatgt cgcttaaaac gaaaagaag aagaagaaag    2760 tcctgtggtt tgggaaggga ggctgagtga ggaggggcct gtgtgccaga ggaggcttca   2820
ctgagaagct tagggagca gatgttctag gggtacagag gtatgcagga ataggaagag    2880
tctcaccccg tgtctctttt taggtcctcg ccctgaacct gagccacggc tccaaccac    2940 caccacaccg cagcccacgg ctcccccgac ggtctgcccc accggacccc ccactgtcca   3000
cccctcagag cgccccacag ctggccccac aggtcccccc tcagctggcc ccacaggtcc   3060
```

```
cccactgct ggcccttcta cggccactac tgtgcctttg agtccggtgg acgatgcctg    3120
caacgtgaac atcttcgacg ccatcgcgga gattgggaac cagctgtatt tgttcaagga    3180
tgggtgagga ggcggggttg tgtggatgcg ggaggggget ttgcggaggg gctgcccgtc    3240
ccttcccgcc cactgcccct gtgtccaagg cttagagccc gtccttcccc tcctcgcttt    3300
ctcaggaagt actggcgatt ctctgagggc aggggagcc ggccgcaggg ccccttcctt    3360
atcgccgaca agtggcccgc gctgcccgc aagctggact cggtctttga ggagcggctc    3420
tccaagaagc ttttcttctt ctctggttag ttacctactt tccctccccc gcccggtcaa    3480
tccccatcag tcaaggaggc tcaagagacc atcgataacc cacgaaacgt cttgtgcgtt    3540
ttagaaaaat acgcccctg gcggacgcag tttagcaaac gtaggggcgg ctgagtttct    3600
gccccctcct ctccacgccc tcgcgtcgct ctacccagcg cctctgcccc tgggttgcag    3660
ggactgcggg cacgcgggct aggaaaggcc tcgccggaat ctccctcctc gcgttctagg    3720
agtacgtgct ccctctgcgc ccccaaaccg acgtgaccct cctcccctgc agggcgccag    3780
gtgtgggtgt acacaggcgc gtcggtgctg gcccgaggc gtctggacaa gctgggcctg    3840
ggagccgacg tggcccaggt gaccggggcc ctccggagtg caggggga atgctgctg    3900 ttcagcgggc ggcgcctctg gaggtgagcg ccgccgcggc cgccggcagg gggagcccgg    3960
gcgccgtcgg tccgtccgct agccggctca gcacctgtct cctccgcgcc tgcccgcagg    4020
ttcgacgtga aggcgcagat ggtggatccc cggagcgcca gcgaggtgga ccggatgttc    4080
cccggggtgc ctttggacac gcacgacgtc ttccagtacc gaggtgaggg ctgaggagga    4140
tcccttcgtg agacaccaca ctaagctcct cttagtgagt ggtcaaattc tgagcgagga    4200
agaaaaagcc cttggaaatg gaaacaaatg ccccagcaca gacaagatcc cagcagaggc    4260
agaggccttc tccaggtcat ttaggaagtc agggatgcaa c    4301

<210> SEQ ID NO 198
<211> LENGTH: 801
<212> TYPE: DNA
<213> ORGANISM: Homo sapiens

<400> SEQUENCE: 198
caggaacttt cgagatgagg tgcctttccc aaggtgacac taagtggagg agcccagcca      60
gagtccaggg gtccttacac aaccttcggt ggtctctctt tacctgtgaa gctgcagcct     120
gcttcccagc tcggggggcgt gtacaggaga ctggacctgg ggcagcctca gaatgcctgg     180
ctgcctggag ctctcctcgc gtgtccaggc ggcctgcttg gtctccctcc tctcccctct     240
taggtgccgg ggcgggcacc cggtgcaggg tgggcacggc gcctgccacc agcctcaggc     300
gctgggagaa gcgcaggttc ttctggataa ccgaagagac gtcaaaacag gctggggcaa     360
agtggtcaga gcagatgacc gagcggtcat tgcctccgta ccagtcggcg cggcaacccc     420
gcacgaagcg gtcccagagc agccgcacgg cccggtcctt gggaaagcgg aacagcgact     480
tcccagactt ggtggtgttg ccgcagtggg cggccacaca acgggccggc atggcggccg     540
tcttcggtgc gcgggagccg ggttccctgg accttcgccc ttgggcacgc tcctcgcagc     600
ggcctcggcg aggcaagtcc tcccctcctc acctgtccac tcgggtcgg gattgtttcc     660 ttccctacct ctggtcaccg gaagtggcga tctgggccc ccaatgggag ggctctttga     720
tatcttcctc ctcctcctcc ctgcgctgct ccccaggagc cagtggacac aagcagaggg     780
atacaaattt cgcgcgggca g                                                801

<210> SEQ ID NO 199
```

```
<211> LENGTH: 24
<212> TYPE: DNA
<213> ORGANISM: Artificial
<220> FEATURE:
<223> OTHER INFORMATION: Primer

<400> SEQUENCE: 199
tgatggtcgt attgcgggtt tatc                                          24

<210> SEQ ID NO 200
<211> LENGTH: 24
<212> TYPE: DNA
<213> ORGANISM: Artificial
<220> FEATURE:
<223> OTHER INFORMATION: Primer

<400> SEQUENCE: 200
atacctaaac ccaacgccga ctac                                          24

<210> SEQ ID NO 201
<211> LENGTH: 24
<212> TYPE: DNA
<213> ORGANISM: Artificial
<220> FEATURE:
<223> OTHER INFORMATION: Primer

<400> SEQUENCE: 201
cgcgatttga gtagttagcg tcgt                                          24

<210> SEQ ID NO 202
<211> LENGTH: 24
<212> TYPE: DNA
<213> ORGANISM: Artificial
<220> FEATURE:
<223> OTHER INFORMATION: Primer

<400> SEQUENCE: 202
aaccaacgcg acgacctaac taac                                          24

<210> SEQ ID NO 203
<211> LENGTH: 23
<212> TYPE: DNA
<213> ORGANISM: Artificial
<220> FEATURE:
<223> OTHER INFORMATION: Primer

<400> SEQUENCE: 203
tagatttcgg tgtttcgggc gtt                                           23

<210> SEQ ID NO 204
<211> LENGTH: 26
<212> TYPE: DNA
<213> ORGANISM: Artificial
<220> FEATURE:
<223> OTHER INFORMATION: Primer

<400> SEQUENCE: 204
ccgctaattc ccaatcgtac tactca                                        26

<210> SEQ ID NO 205
<211> LENGTH: 22
<212> TYPE: DNA
<213> ORGANISM: Artificial
<220> FEATURE:
<223> OTHER INFORMATION: Primer

<400> SEQUENCE: 205
```

```
ttcgtttcgt tcggtcgtga tt                                            22
```

<210> SEQ ID NO 206
<211> LENGTH: 24
<212> TYPE: DNA
<213> ORGANISM: Artificial
<220> FEATURE:
<223> OTHER INFORMATION: Primer

<400> SEQUENCE: 206

```
gactacgaac gcttcgaatt cctc                                          24
```

<210> SEQ ID NO 207
<211> LENGTH: 24
<212> TYPE: DNA
<213> ORGANISM: Artificial
<220> FEATURE:
<223> OTHER INFORMATION: Primer

<400> SEQUENCE: 207

```
gttgcgttgg tagcgattcg ttgt                                          24
```

<210> SEQ ID NO 208
<211> LENGTH: 23
<212> TYPE: DNA
<213> ORGANISM: Artificial
<220> FEATURE:
<223> OTHER INFORMATION: Primer

<400> SEQUENCE: 208

```
cccgaaccga atcctcgaaa tct                                           23
```

<210> SEQ ID NO 209
<211> LENGTH: 25
<212> TYPE: DNA
<213> ORGANISM: Artificial
<220> FEATURE:
<223> OTHER INFORMATION: Primer

<400> SEQUENCE: 209

```
gacgtagtat gatgcgcgta gtgtg                                         25
```

<210> SEQ ID NO 210
<211> LENGTH: 23
<212> TYPE: DNA
<213> ORGANISM: Artificial
<220> FEATURE:
<223> OTHER INFORMATION: Primer

<400> SEQUENCE: 210

```
gcgaacatac taaacccgaa ccc                                           23
```

<210> SEQ ID NO 211
<211> LENGTH: 24
<212> TYPE: DNA
<213> ORGANISM: Artificial
<220> FEATURE:
<223> OTHER INFORMATION: Primer

<400> SEQUENCE: 211

```
ggattacgtc ggtgttcgat ttgt                                          24
```

<210> SEQ ID NO 212
<211> LENGTH: 22
<212> TYPE: DNA
<213> ORGANISM: Artificial
<220> FEATURE:

```
<223> OTHER INFORMATION: Primer

<400> SEQUENCE: 212
aacgcacgat taaccctacg cc                                          22

<210> SEQ ID NO 213
<211> LENGTH: 24
<212> TYPE: DNA
<213> ORGANISM: Artificial
<220> FEATURE:
<223> OTHER INFORMATION: Primer

<400> SEQUENCE: 213
tcggattaag gtaggcgtgg tttc                                        24

<210> SEQ ID NO 214
<211> LENGTH: 21
<212> TYPE: DNA
<213> ORGANISM: Artificial
<220> FEATURE:
<223> OTHER INFORMATION: Primer

<400> SEQUENCE: 214
aacgtaaacg ccgaaccgaa c                                           21

<210> SEQ ID NO 215
<211> LENGTH: 24
<212> TYPE: DNA
<213> ORGANISM: Artificial
<220> FEATURE:
<223> OTHER INFORMATION: Primer

<400> SEQUENCE: 215
ggaagacgtc gttgttgatg gttt                                        24

<210> SEQ ID NO 216
<211> LENGTH: 23
<212> TYPE: DNA
<213> ORGANISM: Artificial
<220> FEATURE:
<223> OTHER INFORMATION: Primer

<400> SEQUENCE: 216
accgctccga cacgaaccta tac                                         23

<210> SEQ ID NO 217
<211> LENGTH: 23
<212> TYPE: DNA
<213> ORGANISM: Artificial
<220> FEATURE:
<223> OTHER INFORMATION: Primer

<400> SEQUENCE: 217
agcgttatgc gtcgcgttag tag                                         23

<210> SEQ ID NO 218
<211> LENGTH: 22
<212> TYPE: DNA
<213> ORGANISM: Artificial
<220> FEATURE:
<223> OTHER INFORMATION: Primer

<400> SEQUENCE: 218
gcaaacgacg acgaaacgta ca                                          22

<210> SEQ ID NO 219
```

```
<211> LENGTH: 23
<212> TYPE: DNA
<213> ORGANISM: Artificial
<220> FEATURE:
<223> OTHER INFORMATION: Primer

<400> SEQUENCE: 219
gaagagagcg ggttcgggat aag                                             23

<210> SEQ ID NO 220
<211> LENGTH: 23
<212> TYPE: DNA
<213> ORGANISM: Artificial
<220> FEATURE:
<223> OTHER INFORMATION: Primer

<400> SEQUENCE: 220
ctacaacatc gtaaacgcgc gac                                             23

<210> SEQ ID NO 221
<211> LENGTH: 22
<212> TYPE: DNA
<213> ORGANISM: Artificial
<220> FEATURE:
<223> OTHER INFORMATION: Primer

<400> SEQUENCE: 221
gagaagagga aggtagaagg ag                                              22

<210> SEQ ID NO 222
<211> LENGTH: 21
<212> TYPE: DNA
<213> ORGANISM: Artificial
<220> FEATURE:
<223> OTHER INFORMATION: Primer

<400> SEQUENCE: 222
ctacctaact ataaccaacc c                                               21

<210> SEQ ID NO 223
<211> LENGTH: 21
<212> TYPE: DNA
<213> ORGANISM: Artificial
<220> FEATURE:
<223> OTHER INFORMATION: Primer

<400> SEQUENCE: 223
acggaggagg atagtagtac g                                               21

<210> SEQ ID NO 224
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: "y" may be "c" or "t"

<400> SEQUENCE: 224
aggtaygttg tatttggtgg atttgg                                          26

<210> SEQ ID NO 225
<211> LENGTH: 21
<212> TYPE: DNA
<213> ORGANISM: Artificial
<220> FEATURE:
```

<223> OTHER INFORMATION: Primer

<400> SEQUENCE: 225
cccacctaca acaacaacac c                                        21

<210> SEQ ID NO 226
<211> LENGTH: 20
<212> TYPE: DNA
<213> ORGANISM: Artificial
<220> FEATURE:
<223> OTHER INFORMATION: Primer

<400> SEQUENCE: 226
gaacgcgtac ggaaggtagg                                          20

<210> SEQ ID NO 227
<211> LENGTH: 27
<212> TYPE: DNA
<213> ORGANISM: Artificial
<220> FEATURE:
<223> OTHER INFORMATION: Primer

<400> SEQUENCE: 227
gtgataggtt tgtagatttg atagttg                                  27

<210> SEQ ID NO 228
<211> LENGTH: 25
<212> TYPE: DNA
<213> ORGANISM: Artificial
<220> FEATURE:
<223> OTHER INFORMATION: Primer

<400> SEQUENCE: 228
aactaacctc cattttaact atttc                                    25

<210> SEQ ID NO 229
<211> LENGTH: 23
<212> TYPE: DNA
<213> ORGANISM: Artificial
<220> FEATURE:
<223> OTHER INFORMATION: Primer

<400> SEQUENCE: 229
gagagatgaa tttggatatt agt                                      23

<210> SEQ ID NO 230
<211> LENGTH: 24
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (14)..(14)
<223> OTHER INFORMATION: "y" may be "c" or "t"

<400> SEQUENCE: 230
ggtaaattgg tgtygttgga gaag                                     24

<210> SEQ ID NO 231
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (18)..(18)

```
<223> OTHER INFORMATION: "r" may be "a" or "g"

<400> SEQUENCE: 231
actaaacaat aatacccrac ctc                                              23

<210> SEQ ID NO 232
<211> LENGTH: 24
<212> TYPE: DNA
<213> ORGANISM: Artificial
<220> FEATURE:
<223> OTHER INFORMATION: Primer

<400> SEQUENCE: 232
gtcgttgggt tcggtttcgt tttg                                             24
```